(12) United States Patent
Nagai et al.

(10) Patent No.: US 8,987,473 B2
(45) Date of Patent: Mar. 24, 2015

(54) RING-FUSED COMPOUND

(75) Inventors: Keita Nagai, Matsudo (JP); Koh Nagasawa, Tokyo (JP); Hirobumi Takahashi, Ushiku (JP); Motoaki Baba, Kawasaki (JP); Shinichi Fujioka, Tokyo (JP); Eri Kondoh, Yokohama (JP); Kenichi Tanaka, Ushiku (JP); Yoshiki Itoh, Tsukuba (JP)

(73) Assignee: Sato Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/982,200

(22) PCT Filed: Jan. 30, 2012

(86) PCT No.: PCT/JP2012/052009
§ 371 (c)(1),
(2), (4) Date: Sep. 17, 2013

(87) PCT Pub. No.: WO2012/102405
PCT Pub. Date: Aug. 2, 2012

(65) Prior Publication Data
US 2014/0005221 A1    Jan. 2, 2014

(30) Foreign Application Priority Data
Jan. 28, 2011  (JP) .................. 2011-016950

(51) Int. Cl.
*C07D 471/04* (2006.01)
*C07D 413/06* (2006.01)
*C07D 409/06* (2006.01)
(Continued)

(52) U.S. Cl.
CPC ............ *C07D 209/08* (2013.01); *C07D 209/30* (2013.01); *C07D 231/56* (2013.01); *C07D 235/08* (2013.01); *C07D 235/10* (2013.01); *C07D 401/06* (2013.01); *C07D 405/06* (2013.01); *C07D 235/06* (2013.01); *C07D 403/04* (2013.01); *C07D 409/06* (2013.01); *C07D 413/06* (2013.01); *C07D 471/04* (2013.01)
USPC ...................... 548/454; 548/304.4; 548/361.1; 548/465; 548/254; 548/249; 548/144; 548/306.4

(58) Field of Classification Search
USPC ........... 548/454, 304.4, 361.1, 465, 254, 249, 548/144, 306.4
See application file for complete search history.

(56) References Cited

U.S. PATENT DOCUMENTS
5,877,199 A  *  3/1999  Birdsall et al. ............. 514/411
6,069,156 A     5/2000  Oku et al.
(Continued)

FOREIGN PATENT DOCUMENTS
JP      05-222000 A    8/1993
JP      10-503488 A    3/1998
(Continued)

OTHER PUBLICATIONS

By Sun et al., Organic Letters (2006), 8(4), 681-683.*
Christopher Hulme, et al., "Orally Active Indole N-Oxide PDE4 Inhibitors", Bioorganic & Medicinal Chemistry Letters, 1998, pp. 3053-3058, vol. 8, No. 21.
John N. Loeb, "The Influence of Temperature on the Solubility of Monosodium Urate", Arthritis and Rheumatism, Mar.-Apr. 1972, pp. 189-192, vol. 15, No. 2.
Hyon K. Choi, et al., "Pathogenesis of Gout", Ann. Intern. Med., 2005, pp. 499-516, vol. 43.
Yuki Taniguchi, et al., "Serum uric acid and the risk for hypertension and Type 2 diabetes in Japanese men: The Osaka Health Survey", Journal of Hypertension, 2001, pp. 1209-1215, vol. 19.
Johan Sundström, et al., "Relations of Serum Uric Acid to Longitudinal Blood Pressure Tracking and Hypertension Incidence", Hypertension, 2005, pp. 28-33, vol. 45.
Hyon K. Choi, et al., "Prevalence of the Metabolic Syndrome in Individuals with Hyperuricemia", The American Journal of Medicine, 2007, pp. 442-447, vol. 120.
(Continued)

*Primary Examiner* — Niloofar Rahmani
(74) *Attorney, Agent, or Firm* — Sughrue Mion, PLLC

(57) ABSTRACT

The present invention relates to a compound that has URAT1 inhibitory action, and a URAT1 inhibitor, a blood uric acid level-reducing agent and a pharmaceutical composition comprising the compound. More specifically, the present invention relates to a compound represented by Formula (I) below.

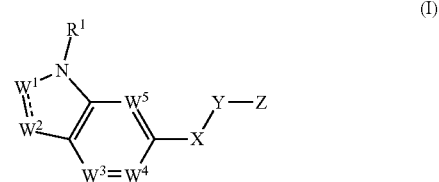

(I)

[in the formula,
$R^1$ is $-Q^1-A^1$ and the like; ---- is a double bond or a single bond; when ---- is a double bond, $W^1$ is a nitrogen atom or a group represented by the general formula: $=C(R^a)-$, and $W^2$ is a nitrogen atom or a group represented by the general formula: $=C(R^b)-$; when ---- is a single bond, $W^1$ is a group represented by the general formula: $-C(R^{aa})(R^{ab})-$ or a group represented by the general formula: $-(C=O)-$, and $W^2$ is a group represented by the general formula: $-C(R^{ba})(R^{bb})-$, a group represented by the general formula: $-(C=O)-$ or a group represented by the general formula: $-N(R^{bc})-$; $W^3$, $W^4$ and $W^5$ are each independently a nitrogen atom or a methine group and the like that may have a substituent; X is a single bond, an oxygen atom and the like; Y is a single bond or $(CR^{yi}R^{yi'})_n$; and Z is a hydroxyl group or $COOR^2$ and the like.

18 Claims, No Drawings

(51) Int. Cl.
*C07D 235/08* (2006.01)
*C07D 209/08* (2006.01)
*C07D 209/30* (2006.01)
*C07D 231/56* (2006.01)
*C07D 235/10* (2006.01)
*C07D 401/06* (2006.01)
*C07D 405/06* (2006.01)
*C07D 235/06* (2006.01)
*C07D 403/04* (2006.01)

(56) References Cited

U.S. PATENT DOCUMENTS

| | | |
|---|---|---|
| 6,166,219 A | 12/2000 | Yamasaki et al. |
| 6,348,474 B1 | 2/2002 | Kayakiri et al. |
| 6,420,409 B1 | 7/2002 | Yamasaki et al. |
| 6,869,950 B1 | 3/2005 | Yamasaki et al. |
| 2002/0143022 A1 | 10/2002 | Pamukcu et al. |
| 2005/0239797 A1 | 10/2005 | Gaster et al. |
| 2007/0010670 A1 | 1/2007 | Hirata et al. |
| 2007/0197512 A1 | 8/2007 | Inoue et al. |
| 2007/0281934 A1 | 12/2007 | Buggy et al. |
| 2009/0062363 A1 | 3/2009 | Kaku et al. |
| 2009/0181960 A1 | 7/2009 | Niimi et al. |
| 2010/0015093 A1 | 1/2010 | Einav et al. |
| 2011/0071146 A1 | 3/2011 | Niimi et al. |
| 2011/0081409 A1 | 4/2011 | Verner et al. |

FOREIGN PATENT DOCUMENTS

| | | | |
|---|---|---|---|
| JP | 11-503445 A | | 3/1999 |
| JP | 2003-513075 A | | 4/2003 |
| WO | 96/03377 A1 | | 2/1996 |
| WO | 97/24334 A1 | | 7/1997 |
| WO | 98/05327 A1 | | 2/1998 |
| WO | 9805327 | * | 2/1998 |
| WO | 98/15530 A1 | | 4/1998 |
| WO | 99/00372 A1 | | 1/1999 |
| WO | 99/00373 A1 | | 1/1999 |
| WO | 00/039099 A1 | | 7/2000 |
| WO | 2006/057460 A1 | | 6/2006 |
| WO | 2007/086504 A1 | | 8/2007 |
| WO | 2007/097197 A1 | | 8/2007 |
| WO | 2007/100066 A1 | | 9/2007 |
| WO | 2007/109178 A2 | | 9/2007 |
| WO | 2009/129335 A2 | | 10/2009 |
| WO | 2009/151695 A1 | | 12/2009 |
| WO | 2010/107739 A2 | | 9/2010 |

OTHER PUBLICATIONS

Nobukazu Ishizaka, et al., "Association Between Serum Uric Acid, Metabolic Syndrome, and Carotid Atherosclerosis in Japanese Individuals", Arterioscler Thromb Vasc Biol., 2005, pp. 1038-1044, vol. 25.

Domenic A. Sica, et al., "Renal Handling of Organic Anions and Cations: Excretion of Uric Acid", The Kidney Saubder, 1996, pp. 680-700, Philadelphia, PA.

Atsushi Enomoto, et al., "Molecular identification of a renal urate-anion exchanger that regulates blood urates levels", Nature, May 23, 2002, pp. 447-452, vol. 417.

Kimiyoshi Ichida, et al., "Clinical and Molecular Analysis of Patients with Renal Hypouricemia in Japan-Influence of URAT1 Gene on Urinary Urate Excretion", J. Am. Soc Nephrol, 2004, pp. 164-173, vol. 15.

Extended European Search Report dated Jun. 3, 2014, issued by the European Patent Office, in application No. 12739424.5.

"Recent Trend and Risk of Hyperuricemia/Gout," Japanese Society of Gout and Nucleic Acid Metabolism, the 2nd Edition of Guideline of Hyperuricemia or Gout Treatment, pp. 30-31 (2010).

Nakamura, "Treatment of Hyperuricemia and Gout—Pathogenesis and Pathophysiology of Hyperuricemia," Medical Review Co., Ltd., pp. 21-39 (2003).

Tomita et al., Gout and Nucleic Acid Metabolism, v. 30, No. 1, pp. 1-5 (2006).

Ohno, "Uricosuric agent," Japan Clinics, v. 66, No. 4, pp. 743-747 (2008).

* cited by examiner

RING-FUSED COMPOUND

CROSS REFERENCE TO RELATED APPLICATIONS

This application is a National Stage of International Application No. PCT/JP2012/052009 filed Jan. 30, 2012, claiming priority based on Japanese Patent Application No. 2011-016950 filed Jan. 28, 2011, the contents of all of which are incorporated herein by reference in their entirety.

TECHNICAL FIELD

The present invention relates to a ring-fused compound that is useful in the field of a medicine. Further specifically, the present invention relates to a ring-fused compound that has URAT1 inhibitory activity and is useful in the field of treatment of diseases associated with blood uric acid, and an URAT1 inhibitor, a blood uric acid level-reducing agent and a pharmaceutical composition containing the compound.

BACKGROUND ART

Uric acid is a final product of a purine metabolism in humans. The purine nucleotide is generated by degradation of a nucleic acid in the cell, ATP that is an energy source in a living body, and the like, or is absorbed from a meal. The purine nucleotide is metabolized to uric acid via hypoxanthine and xanthine. Uric acid is a final product of the purine metabolism in the higher primates including human as urate oxidase (uricase) is genetically silenced in these species. In many other mammals, uric acid is oxidized by uricase, and metabolized to allantoin.

About 98% of uric acid is present in the form of sodium urate in a body liquid (Non Patent Literature 1).

Since the solubility of sodium urate at physiological pH conditions is 6.4 mg/dL (Non Patent Literature 1), 7 mg/dL or more of the blood uric acid level beyond the solubility in the body liquid is defined as hyperuricemia (Non Patent Literature 2).

If the hyperuricemia persists, urate is crystallized and precipitated in the body liquid, which cause gout arthritis, gouty kidney, gouty node, urolithiasis, a renal function disorder and the like (Non Patent Literature 3).

In addition, in recent years, the hyperuricemia is known to be complicated with lifestyle diseases such as hypertension, hyperlipidaemia, impaired glucose tolerance and obesity in high rate (Non Patent Literatures 4, 5, 6 and 7), and such complications are known to increase the incidence rate of cardiovascular or cerebrovascular disorders.

The hyperuricemia is reported to be present in 20% or more of adult males in Japan, and tends to increase even now due to westernized lifestyle and the like (Non Patent Literature 8). As for the classification of hyperuricemia, the overproduction of uric acid is reported to be 12%, the decreased uric acid excretion to be 60% and the combined type to be 25% (Non Patent Literature 9). Thus, the decreased uric acid excretion is seen in 85% that is the sum of 60% of the decreased uric acid excretion and 25% of the combined type, which suggests the importance of the decreased uric acid excretion with respect to the cause of hyperuricemia.

Uric acid is mainly excreted from a kidney. In humans, about 70% is excreted from the kidney, and 30% is excreted from extra-renal pathway such as a bile or a saliva, a sweat and the like. The uric acid is filtered by 100% in a renal glomerulus, and then most part of it is re-absorbed in a proximal tubule, and about 10% is excreted in a terminal urine (Non Patent Literatures 3 and 10). Thus, it is suggested that uric acid excretion is strictly regulated by the re-absorption.

Since uric acid is present as an organic acid at physiological pH conditions, it was expected that a transporter responsible for re-absorption of uric acid has similar structural characteristics with an organic anion transporter family proteins. In recent years, URAT1 was identified as a transporter responsible for re-absorption of uric acid, which is present in the proximal tubule (Non Patent Literature 11). URAT1 is a 12-transmembrane transporter belonging to the SLC family. Northern blotting analysis showed that an expression of a URAT1 gene is localized in the kidney of an adult and fetus. It became clear from immunohistochemical analysis using anti-human URAT1 antibody that an URAT1 protein is present on a luminal surface of the proximal tubule. Furthermore, since uric acid is incorporated when URAT1 is expressed in a xenopus oocyte, it was confirmed that URAT1 can transport of uric acid (Non Patent Literature 11).

Further, it became clear that loss of function caused by mutations of the URAT1 gene leads to renal hypouricemia, and thus importance of URAT1 with respect to uric acid excretion came to the fore (Non Patent Literatures 11 and 12).

Currently used uricosuric agents, benzbromarone and probenecid have been shown to inhibit uric acid-transport activity of URAT1, and importance in the uric acid excretion of URAT1 has been cleared pharmacologically as well (Non Patent Literature 13).

From these, it is regarded that a drug inhibiting URAT1 can reduce the blood uric acid level by suppressing re-absorption of uric acid in the proximal tubule and by accelerating the uric acid excretion, and the drug inhibiting URAT1 is useful as an agent for treating or preventing pathological conditions associated with uric acid, specifically, hyperuricemia, gouty node, gout arthritis, gouty kidney, urolithiasis and renal function disorders. In addition, the drug inhibiting URAT1 is also useful as an agent for treating or preventing hypertension, hyperlipidaemia, abnormal glucose tolerance, obesity, a coronary artery diseases and cerebrovascular disorders, which are associated with hyperuricemia.

Incidentally, as a compound that has URAT1 inhibitory action, for example, Patent Literature 1 discloses a compound of the general formula described below.

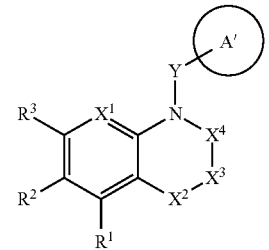

Patent Literature 2 discloses a compound of the general formula described below.

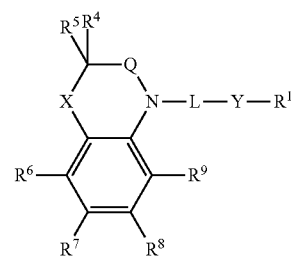

Patent Literature 3 discloses a compound of the general formula described below.

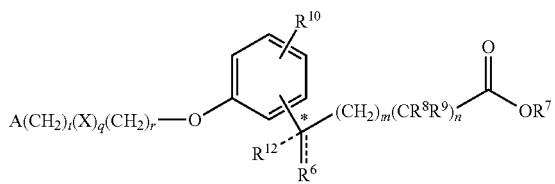

Patent Literature 4 discloses a compound of the general formula described below as a PDE5 (phosphodiesterase 5) inhibitor.

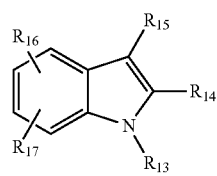

Patent Literature 5 discloses a compound of the general formula described below as a PDE5 inhibitor.

$R^1$—$SO_2NHCO$-A-$R^2$

Patent Literature 6 discloses a compound of the general formula described below as a 17β HSD (17β-hydroxysteroid dehydrogenase) type 5 inhibitor.

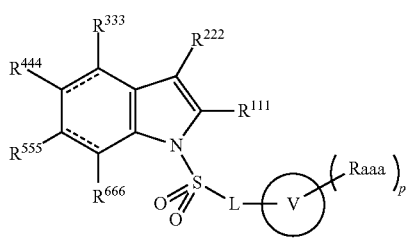

CITATION LIST

Patent Literatures

Patent Literature 1: WO 2006/057460 A
Patent Literature 2: WO 2007/086504 A
Patent Literature 3: WO 2009/151695 A
Patent Literature 4: WO 98/15530 A
Patent Literature 5: WO 99/00372 A
Patent Literature 6: WO 2007/100066 A Non Patent Literatures Non Patent Literature 1: Loeb J N., Arthritis Rhueum., 15, 189-192, 1972
Non Patent Literature 2: Japanese Society of Gout and Nucleic Acid Metabolism, the 2$^{nd}$ Edition of Guideline of Hyperuricemia or Gout Treatment, 30-31, 2010
Non Patent Literature 3: Choi H K. et al. Ann. Intern. Med., 43, 499-516, 2005
Non Patent Literature 4: Taniguchi Y. et al., J. Hypertension, 19, 1209-1215, 2001
Non Patent Literature 5: Sunderstrom J. et al., Hypertension, 45, 28-33, 2005
Non Patent Literature 6: Choi H K. et al., The Am. J. Med., 120, 442-447, 2007
Non Patent Literature 7: Ishizaka N. et al., Arterioscler. Thromb. Vasc. Biol., 25, 1038-1044, 2005
Non Patent Literature 8: TOMITA Masako, MIZUNO Shouichi, Gout and Nucleic Acid Metabolism, 30, 1-5, 2006
Non Patent Literature 9: NAKAMURA Toru, Treatment of Hyperuricemia and Gout, Medical Review Co., Ltd., 21-39, 2003
Non Patent Literature 10: Sica D A. and Schoolwerth A C., The Kidney, Saubder, Philadelphia Pa., 680-700, 1996
Non Patent Literature 11: Enomoto A. et al., Nature, 417, 447-452, 2002
Non Patent Literature 12: Ichida K. et al., J. Am. Soc. Nephrol. 15, 164-173, 2004
Non Patent Literature 13: OHNO Iwao, Japan Clinics, 66, 743-747, 2008

SUMMARY OF INVENTION

Technical Problem

The above-mentioned benzbromarone or probenecid was shown to inhibit a uric acid-transport activity of URAT1, but the URAT1 inhibitory action thereof was not sufficient. Furthermore, benzbromarone is known to lead to serious hepatic disorders and probenecid is known to lead to gastrointestinal tract disorders, and the like. In addition, both of the compounds are also known to cause drug interaction with other drugs. Therefore, a uric acid excretion facilitator that is safer and highly effective, is demanded.

Accordingly, it became problems to provide a novel compound that has excellent URAT1 inhibitory action, and an agent for treating or preventing a disease associated with blood uric acid.

Solution to Problem

The present inventors performed widely synthesis and investigation of novel ring-fused compounds to solve the problems, and as a result, found that a compound represented by General Formula (I) has excellent URAT1 inhibitory action, and completed the present invention.

Specifically, the present invention relates to a compound represented by Formula (I):

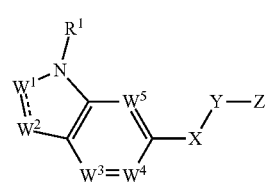

[in the formula, $R^1$ represents a lower alkyl group that may be substituted with a cycloalkyl group, a cycloalkyl group, a halo-lower alkyl group, a hydroxy-lower alkyl group, a lower alkoxy-lower alkyl group, a lower alkoxy-carbonyl group, a lower alkyl-sulfonyl group or a group represented by the general formula: -$Q^1$-$A^1$;

$Q^1$ represents a single bond or a lower alkylene group (herein 1 or 2, or more methylene groups constituting the lower alkylene group each independently may be substituted with a carbonyl group, a sulfinyl group or a sulfonyl group for the total methylene groups, and/or the hydrogen constituting the methylene group may be substituted with a lower alkyl group.);

$A^1$ represents an aryl group or a heteroaryl group, which may be substituted with one to three substituents selected from the <Substituent group L> described later (herein any two substituents adjacent to each other on the aryl group or the heteroaryl group may join together to form a lower alkylenedioxy group.);

---- represents a double bond or a single bond;

when ---- is a double bond, $W^1$ represents a nitrogen atom or a group represented by the general formula: $=C(R^a)-$, and $W^2$ represents a nitrogen atom or a group represented by the general formula: $=C(R^b)-$;

when ---- is a single bond, $W^1$ represents a group represented by the general formula: $-C(R^{aa})(R^{ab})-$ or a group represented by the general formula: $-(C=O)-$, and $W^2$ represents a group represented by the general formula: $-C(R^{ba})(R^{bb})-$, a group represented by the general formula: $-(C=O)-$ or a group represented by the general formula: $-N(R^{bc})-$;

$R^a$ and $R^b$ represent each independently a hydrogen atom, a substituent selected from the <Substituent group M> described later or a group represented by the general formula: $-Q^2-A^2$;

$R^{aa}$ and $R^{ab}$ represent each independently a hydrogen atom, a substituent selected from the <Substituent group N> described later or a group represented by the general formula: $-Q^2-A^2$, or $R^{aa}$ and $R^{ab}$ may join together to form a lower alkylene group (herein 1 to 2 or more methylene groups constituting the lower alkylene group each independently may be substituted with an oxygen atom, a carbonyl group, a vinylene group or a group represented by the general formula: $-N(R^c)-$ for the total methylene groups, and/or the hydrogen constituting the methylene group may be substituted with a hydroxyl group, a lower alkyl group or a halogen atom.);

$R^{ba}$ and $R^{bb}$ represent each independently a hydrogen atom, a halogen atom, an amino group, a lower alkyl-amino group, a di-lower alkyl-amino group, a hydroxy-lower alkyl-amino group, a lower alkyl-sulfonylamino group, a lower alkoxy-carbonylamino group, a substituent selected from the <Substituent group N> or a group represented by the general formula: $-Q^2-A^2$, or $R^{ba}$ and $R^{bb}$ may join together to form a lower alkylene group (herein 1 to 2 or more methylene groups constituting the lower alkylene group each independently may be substituted with an oxygen atom, a carbonyl group, a vinylene group or a group represented by the general formula: $-N(R^c)-$ for the total methylene groups, and/or the hydrogen constituting the methylene group may be substituted with a hydroxyl group, a lower alkyl group or a halogen atom.);

$R^{bc}$ represents a group selected from the group consisting of a hydrogen atom, a lower alkyl group, a cycloalkyl group, a halo-lower alkyl group, a lower alkoxy-carbonyl group, a carbamoyl group, a mono-lower alkyl-carbamoyl group, a di-lower alkyl-carbamoyl group and a lower alkanoyl group, or a group represented by the general formula: $-Q^2-A^2$;

$Q^2$ represents a single bond, a lower alkylene group or a lower alkenylene group (herein 1 or 2, or more methylene groups constituting the lower alkylene group each independently may be substituted with an oxygen atom, a nitrogen atom or a carbonyl group for the total methylene groups, and/or the hydrogen constituting the methylene group may be substituted with a halogen atom, a cyano group, a hydroxyl group or a lower alkyl group.);

$A^2$ represents a cycloalkyl group, an aliphatic heterocyclic group, an aryl group or a heteroaryl group, which may be substituted with one to three substituents selected from the <Substituent group L> (herein any two substituents adjacent to each other on the aryl group or the heteroaryl group may join together to form a lower alkylenedioxy group.);

$W^3$, $W^4$ and $W^5$ represent each independently a nitrogen atom, or a methine group that may have a substituent selected from the group consisting of a halogen atom, a hydroxyl group, a cyano group, a lower alkyl group, a cycloalkyl group, a halo-lower alkyl group, a lower alkoxy group and a halo lower alkoxy group; provided that zero to four of $W^1$, $W^2$, $W^3$, $W^4$ and $W^5$ are nitrogen atoms;

X represents a single bond, an oxygen atom, a sulfur atom, a sulfinyl group, a sulfonyl group, a carbonyl group, a lower alkenylene group, a lower alkynylene group or a group represented by the general formula: $-N(R^X)-$ (herein $R^X$ is a hydrogen atom or a lower alkyl group.);

Y is a single bond or $(CR^{Yi}R^{Yi'})_n$ (herein n is any integer of 1 to 6, i is any integer of 1 to n, and $(CR^{Yi}R^{Yi'})_n$ represents $(CR^{Y1}R^{Y1'})$ when n=1; represents $(CR^{Y1}R^{Y1'})-(CR^{Y2}R^{Y2'})$ when n=2; represents $(CR^{Y1}R^{Y1'})-(CR^{Y2}R^{Y2'})-(CR^{Y3}R^{Y3'})$ when n=3; represents $(CR^{Y1}R^{Y1'})-(CR^{Y2}R^{Y2'})-(CR^{Y3}R^{Y3'})-(CR^{4}R^{4'})$ when n=4; represents $(CR^{Y1}R^{Y1'})-(CR^{Y2}R^{Y2'})-(CR^{Y3}R^{Y3'})-(CR^{Y4}R^{Y4'})-(CR^{Y5}R^{Y5'})$ when n=5; and represents $(CR^{Y1}R^{Y1'})-(CR^{Y2}R^{Y2'})-(CR^{Y3}R^{Y3'})-(CR^{Y4}R^{Y4'})-(CR^{Y5}R^{Y5'})-(CR^{Y6}R^{Y6'})$ when n=6 (herein $R^{Y1}$, $R^{Y1'}$, $R^{Y2}$, $R^{Y2'}$, $R^{Y3}$, $R^{Y3'}$, $R^{Y4}$, $R^{Y4'}$, $R^{Y5}$, $R^{Y5'}$, $R^{Y6}$ and $R^{Y6'}$ are each independently a hydrogen atom, a halogen atom or a substituent selected from the <Substituent group N>, or in relation to $R^X$, $R^{Y1}$, $R^{Y1'}$, $R^{Y2}$, $R^{Y2'}$, $R^{Y3}$, $R^{Y3'}$, $R^{Y4}$, $R^{Y4'}$, $R^{Y5}$, $R^{Y5'}$, $R^{Y6}$ and $R^{Y6'}$, the combinations of the two groups below: "$R^{Y1}$ and $R^{Y1'}$", "$R^{Y2}$ and $R^{Y2'}$", "$R^{Y3}$ and $R^{Y3'}$", "$R^{Y4}$ and $R^{Y4'}$", "$R^{Y5}$ and $R^{Y5'}$", "$R^{Y6}$ and $R^{Y6'}$", "$R^X$ and $R^{Y1}$", "$R^X$ and $R^{Y2}$", "$R^X$ and $R^{Y3}$", "$R^{Y1}$ and $R^{Y2}$", "$R^{Y1}$ and $R^{Y3}$", "$R^{Y1}$ and $R^{Y4}$", "$R^{Y2}$ and $R^{Y3}$", "$R^{Y2}$ and $R^{Y4}$" or "$R^{Y2}$ and $R^{Y5}$", i.e., the two groups constituting the combinations may join together to form a lower alkylene group, wherein 1 or 2, or more methylene groups constituting the lower alkylene group each independently may be substituted with an oxygen atom, a carbonyl group, a vinylene group or the general formula: $-N(R^c)-$ for the total methylene groups, and/or the hydrogen constituting the methylene group may be substituted with a hydroxyl group, a lower alkyl group or a halogen atom.);

$R^c$ represents a hydrogen atom, a lower alkyl group, a halo-lower alkyl group or a lower alkanoyl group;

Z represents a hydroxyl group, $COOR^2$, $CONR^3R^4$, $SO_3R^2$, $SO_3NR^3R^4$, a 5-tetrazolyl group, a 5-oxo-1,2,4-oxadiazolyl group, a 2-oxo-1,3,4-oxadiazolyl group, a 5-imino-4,5-dihydro-1,3,4-oxadiazolyl group, a 2-thioxo-1,3,4-oxadiazolyl group or a 5-oxo-1,2,4-thiadiazolyl group;

wherein $R^2$, $R^3$ and $R^4$ represent each independently a hydrogen atom or a lower alkyl group; and the <Substituent group L>, the <Substituent group M> and the <Substituent group N> are defined as described below.

<Substituent Group L>:

a halogen atom, a hydroxyl group, a nitro group, a cyano group, a formyl group, an amino group, a carboxyl group, a lower alkyl group, and halo-lower alkyl group, a cycloalkyl group, a lower alkoxy group, a halo-lower alkoxy group, a hydroxy lower alkyl group, a lower alkoxy lower alkyl group, a lower alkoxycarbonyl group, a lower alkanoyl group, a lower alkylthio group and lower alkylsulfonyl group, a lower alkylamino group, a di-lower alkylamino group, a carbamoyl group, a mono-lower alkyl carbamoyl group, a di-lower alkyl carbamoyl group, a lower alkanoylamino group, a lower alkylsulfonylamino group, a lower alkoxycarbonylamino group, an aralkyl group, an aryloxy group, a heteroaryloxy group, and a lower alkenyl group <Substituent Group M>:

a halogen atom, a hydroxyl group, a nitro group, a cyano group, a formyl group, an amino group, a carboxyl group, lower alkyl group, and halo-lower alkyl group, a cycloalkyl group, a lower alkoxy group, a halo-lower alkoxy group, a hydroxy lower alkyl group, a lower alkoxy lower alkyl group, a lower alkoxycarbonyl group, a lower alkanoyl group, a lower alkylthio group, lower alkylsulfonyl group, a lower alkylamino group, a di-lower alkylamino group, a carbamoyl group, a mono-lower alkyl carbamoyl group, a di-lower alkyl carbamoyl group, a lower alkanoylamino group, a lower alkylsulfonylamino group, and a lower alkoxycarbonylamino group <Substituent Group N>:

a hydroxyl group, a cyano group, a formyl group, a carboxyl group, a lower alkyl group, a halo-lower alkyl group, a cycloalkyl group, a lower alkoxy group, a halo-lower alkoxy group, a hydroxy lower alkyl group, a lower alkoxy lower alkyl group, a lower alkoxycarbonyl group, a lower alkanoyl group, a carbamoyl group, a mono-lower alkyl carbamoyl group, and a di-lower alkyl carbamoyl group
or a pharmaceutically acceptable salt and ester of the compound.

Meanwhile, the compound represented by Formula (I) includes not only a racemic mixture of the compound, but also all enantiomers and diastereomers that is possibly present.

In addition, the present invention relates to a method of treating or preventing pathological conditions associated with the blood uric acid selected from the group consisting of hyperuricemia, gouty node, acute gout arthritis, chronic gout arthritis, gouty kidney, urolithiasis, a renal function disorder, a coronary artery disease and an ischemic heart disease in mammals (particularly, humans), which is characterized by administering a therapeutically effective dose of the compound of Formula (I) to the mammals.

Further, the present invention relates to a method of treating or preventing pathological conditions associated with the blood uric acid selected from the group consisting of hyperuricemia, gouty node, acute gout arthritis, chronic gout arthritis, gouty kidney, urolithiasis, a renal function disorder, a coronary artery disease and an ischemic heart disease in mammals (particularly, humans), which is characterized by administering a therapeutically effective dose of a URAT1 inhibitor, a blood uric acid level-reducing agent or a pharmaceutical composition containing the compound of Formula (I) to the mammals.

The present invention relates to a URAT1 inhibitor containing the compound of Formula (I) as an active ingredient.

Further, the present invention relates to a blood uric acid level-reducing agent containing the compound of Formula (I) as an active ingredient.

Further, the present invention relates to a treatment agent for treating or a pharmaceutical composition for preventing pathological conditions associated with the blood uric acid selected from the group consisting of hyperuricemia, gouty node, acute gout arthritis, chronic gout arthritis, gouty kidney, urolithiasis, a renal function disorder, a coronary artery disease and an ischemic heart disease, which is characterized by containing the compound of Formula (I) as an active ingredient.

Effect of Invention

A compound represented by Formula (I) of the present invention and a pharmaceutically acceptable salt and ester of the compound have excellent URAT1 inhibitory action as shown in Examples described below, and thus promote uric acid excretion. Accordingly, the compound represented by Formula (I) of the present invention and a pharmaceutically acceptable salt and ester of the compound can reduce the blood uric acid level, and are useful as an agent for treating or preventing pathological conditions associated with the blood uric acid such as hyperuricemia, gouty node, acute gout arthritis, chronic gout arthritis, gouty kidney, urolithiasis, a renal function disorder, a coronary artery disease or an ischemic heart disease.

DESCRIPTION OF EMBODIMENTS

Hereinafter, meanings of the terms used in the present invention will be described, and the present invention will be further described in detail.

Examples of the "halogen atom" in Formula (I) include a fluorine atom, a chlorine atom, a bromine atom, an iodine atom, and the like.

The "lower alkyl group" in Formula (I) means a $C_{1-6}$ straight or branched alkyl group, and examples thereof include a methyl group, an ethyl group, a propyl group, an isopropyl group, a butyl group, an isobutyl group, a sec-butyl group, a tert-butyl group, a pentyl group, an isopentyl group, an isoamyl group, a neopentyl group, a 1,1-dimethylpropyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,2,2-trimethylpropyl group, a 1-ethyl-3-methylpropyl group and the like.

The "cycloalkyl group" in Formula (I) means a 3-membered 5 to 8-membered aliphatic cyclic group and examples thereof include a cyclopropyl group, a cyclobutyl group, a cyclopentyl group, a cyclohexyl group, a cycloheptyl group, a cyclooctyl group and the like.

The "halo-lower alkyl group" in Formula (I) means the "lower alkyl group" in which any substitutable position is substituted with 1 or 2, or more, preferably 1 to 3 of the halogen atoms that are identical or different, and examples thereof include a fluoromethyl group, a difluoromethyl group, a trifluoromethyl group, a 2-fluoroethyl group, a 1,2-difluoroethyl group, a 2,2,2-trifluoroethyl group, a chloromethyl group, a 2-chloroethyl group, a 1,2-dichloroethyl group, a bromomethyl group, an iodomethyl group and the like.

The "lower alkoxy group" in Formula (I) means a group in which a hydrogen atom of a hydroxyl group is substituted with the "lower alkyl group", and examples thereof include a methoxy group, an ethoxy group, a propoxy group, an isopropoxy group, a butoxy group, a sec-butoxy group, a tert-butoxy group, a pentyloxy group, an isopentyloxy group, a hexyloxy group, an isohexyloxy group and the like.

The "halo lower alkoxy group" in Formula (I) means the "lower alkoxy group" in which any substitutable position is substituted with 1 or 2, or more, preferably 1 to 3 of the halogen atoms that are identical or different, and examples thereof include a fluoromethoxy group, a difluoromethoxy group, a trifluoromethoxy group, a 2-fluoroethoxy group, a 1,2-difluoroethoxy group, a 2,2,2-trifluoroethoxy group, a chloromethoxy group, a 2-chloroethoxy group, a 1,2-dichloroethoxy group, a bromomethoxy group, an iodomethoxy group and the like.

The "hydroxy-lower alkyl group" in Formula (I) means the "lower alkyl group" in which any substitutable position is substituted with 1 or 2, or more, preferably 1 or 2 hydroxyl groups, and examples thereof include a hydroxymethyl group, a 1-hydroxyethyl group, a 1-hydroxypropyl group, a 2-hydroxyethyl group, a 2-hydroxypropyl group, a 2-hydroxy-1-methyl ethyl group, a 1-hydroxy-1-methyl ethyl group, a 1,2-dihydroxyethyl group, a 3-hydroxypropyl group and the like.

The "lower alkoxy-lower alkyl group" in Formula (I) means the "lower alkyl group" in which any substitutable position is substituted with 1 or 2, or more, preferably 1 or 2 of the "lower alkoxy groups" that are identical or different, and examples thereof include a methoxymethyl group, an ethoxymethyl group, a 2-methoxyethyl group, a 2-ethoxyethyl group, a 1-methoxy-1-methylethyl group, a 1,2-dimethoxyethyl group, a 3-methoxypropyl group and the like.

The "lower alkoxy-carbonyl group" in Formula (I) means a group in which the "lower alkoxy group" and the carbonyl group are bonded to each other, and is specifically, a $C_{2-7}$ alkoxycarbonyl group, and examples thereof include a methoxycarbonyl group, an ethoxycarbonyl group, a propoxycarbonyl group, an isopropoxycarbonyl group, a butoxycarbonyl group, an isobutoxycarbonyl group, a tert-butoxycarbonyl group, a pentyloxycarbonyl group and the like.

The "lower alkanoyl group" in Formula (I) means a group in which the lower alkyl group and the carbonyl group are bonded to each other, and is specifically a $C_{2-7}$ alkanoyl group, and examples thereof include an acetyl group, a propionyl group, a butyryl group, an isobutyryl group, a valeryl group, an isovaleryl group, a pivaloyl group and the like.

The "lower alkylthio group" in Formula (I) means a group in which the "lower alkyl group" and a sulfur atom are bonded to each other, and is specifically a $C_{1-6}$ alkylthio group, and examples thereof include a methylthio group, an ethylthio group, a propylthio group, an isopropylthio group, a butylthio group, a sec-butylthio group, an isobutylthio group, a tert-butylthio group, a pentylthio group, an isopentylthio group, a hexylthio group, an isohexylthio group and the like.

The "lower alkyl-sulfonyl group" in Formula (I) means a group in which the "lower alkyl group" and a sulfonyl group are bonded to each other, and examples thereof include a methylsulfonyl group, an ethylsulfonyl group, a propylsulfonyl group, an isopropylsulfonyl group, a butylsulfonyl group, a sec-butylsulfonyl group, an isobutylsulfonyl group, a tert-butylsulfonyl group, a pentylsulfonyl group, an isopentylsulfonyl group, a hexylsulfonyl group, an isohexylsulfonyl group and the like.

The "lower alkyl-amino group" in Formula (I) means an N-mono-substituted amino group with the "lower alkyl group", and examples thereof include an N-methylamino group, an N-ethylamino group, an N-propylamino group, an N-isopropylamino group, an N-butylamino group, an N-sec-butylamino group, an N-tert-butylamino group and the like.

The "di-lower alkyl-amino group" in Formula (I) means a N,N-disubstituted amino group with the "lower alkyl groups" that are identical or different, and examples thereof include an N,N-dimethylamino group, an N,N-diethylamino group, an N,N-dipropylamino group, an N,N-diisopropylamino group, an N-methyl-N-ethylamino group, an N-methyl-N-propylamino group, an N-methyl-N-isopropylamino group and the like.

The "hydroxy-lower alkyl-amino group" in Formula (I) means an N-mono-substituted or N,N-disubstituted, preferably N-mono-substituted amino group with the "hydroxy-lower alkyl group", and examples thereof include a hydroxymethylamino group, a 2-hydroxyethylamino group, a 1-hydroxy-1-methylethylamino group, a 1,2-dihydroxyethylamino group, a 3-hydroxypropylamino group and the like.

The "mono-lower alkyl-carbamoyl group" in Formula (I) means a group in which a nitrogen atom of the carbamoyl group is N-mono-substituted with the "lower alkyl group", and examples thereof include an N-methylcarbamoyl group, an N-ethylcarbamoyl group, an N-propylcarbamoyl group, an N-isopropylcarbamoyl group, an N-butylcarbamoyl group, an N-sec-butylcarbamoyl group, an N-tert-butylcarbamoyl group and the like.

The "di-lower alkyl-carbamoyl group" in Formula (I) means a group in which the nitrogen atom of the carbamoyl group is N,N-disubstituted with the "lower alkyl groups" that are identical or different, and examples thereof include an N,N-dimethylcarbamoyl group, an N,N-diethylcarbamoyl group, an N-ethyl-N-methylcarbamoyl group, an N,N-dipropylcarbamoyl group, an N-methyl-N-propylcarbamoyl group, an N,N-diisopropylcarbamoyl group and the like.

In addition, the "di-lower alkyl-carbamoyl group" also includes a 5-membered to 8-membered monocycle formed by joining of the nitrogen atom constituting the carbamoyl group and the "lower alkyl groups" that are identical or different and bonded to the nitrogen atom, or a dicycle formed by condensation of the monocycle and a benzene ring or a pyridine ring, and examples thereof include groups represented by the formulae described below.

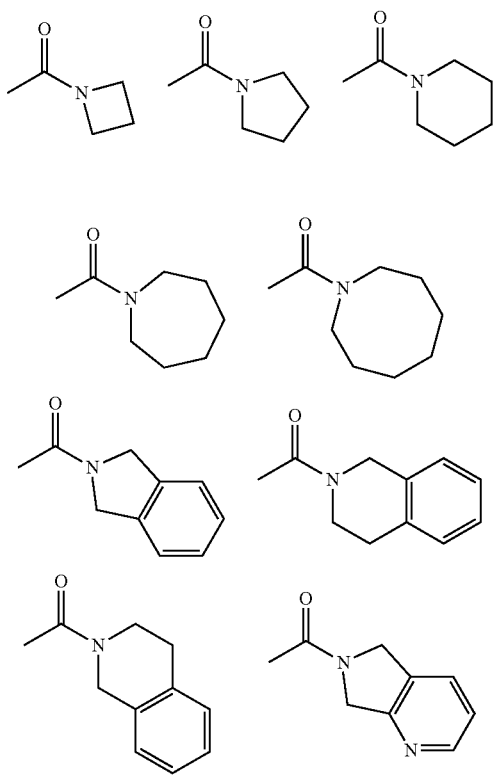

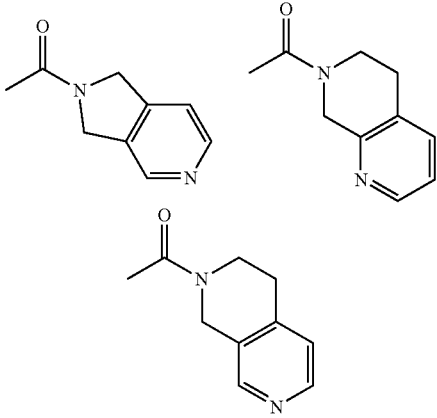

The "lower alkanoylamino group" in Formula (I) means a group in which the "lower alkanoyl group" and an amino group or the "lower alkyl-amino group" are bonded to each other, and examples thereof include an N-acetylamino group, an N-propanoylamino group, an N-butanoylamino group, an N-pentanoylamino group, an N-pivaloyl group, an N-methyl-N-acetylamino group, an N-methyl-N-propanoylamino group, an N-methyl-N-butanoylamino group, an N-methyl-N-pentanoylamino group, an N-ethyl-N-acetylamino group, an N-ethyl-N-propanoylamino group, an N-ethyl-N-butanoylamino group, an N-ethyl-N-pentanoylamino group and the like.

The "lower alkoxy-carbonylamino group" in Formula (I) means a group in which the "lower alkoxy-carbonyl group" is bonded to an amino group or the "lower alkyl-amino group", and examples thereof include a methoxycarbonylamino group, an ethoxycarbonylamino group, a propoxycarbonylamino group, an isopropoxycarbonylamino group, a butoxycarbonylamino group, an isobutoxycarbonylamino group, a sec-butoxycarbonylamino group, a tert-butoxycarbonylamino group, a pentyloxycarbonylamino group, a neopentyloxycarbonylamino group, a hexyloxycarbonylamino group, an isohexyloxycarbonylamino group, an N-methyl-methoxycarbonylamino group, an N-methyl-ethoxycarbonylamino group and the like.

The "lower alkyl-sulfonylamino group" in Formula (I) means a group in which the "lower alkyl-sulfonyl group" is bonded to an amino group or the "lower alkyl-amino group", and examples thereof include a methylsulfonylamino group, an ethylsulfonylamino group, a propylsulfonylamino group, an isopropylsulfonylamino group, a butylsulfonylamino group, a sec-butylsulfonylamino group, a tert-butylsulfonylamino group, an N-methyl-methylsulfonylamino group, an N-methyl-ethylsulfonylamino group, an N-methyl-propylsulfonylamino group, an N-methyl-isopropylsulfonylamino group, an N-methyl-butylsulfonylamino group, an N-methyl-sec-butylsulfonylamino group, an N-methyl-tert-butylsulfonylamino group, an N-ethyl-methylsulfonylamino group, an N-ethyl-ethylsulfonylamino group, an N-ethyl-propylsulfonylamino group, an N-ethyl-isopropylsulfonylamino group, an N-ethyl-butylsulfonylamino group, an N-ethyl-sec-butylsulfonylamino group, an N-ethyl-tert-butylsulfonylamino group and the like.

Examples of the "aryl group" in Formula (I) include a phenyl group, a naphthyl group, a biphenyl group, an anthryl group and the like.

The "heteroaryl group" in Formula (I) means a 5-membered or 6-membered monocycle containing 1 or 2, or more, preferably 1 to 4 heteroatoms that are identical or different and selected from the group consisting of an oxygen atom, a nitrogen atom and a sulfur atom, or means a dicycle obtained by condensation of the monocycle and a benzene ring or a pyridine ring, and examples thereof include a pyrrolyl group, a furyl group, a thienyl group, an imidazolyl group, a pyrazolyl group, a thiazolyl group, an isothiazolyl group, a oxazolyl group, an isoxazolyl group, a triazolyl group, a tetrazolyl group, a 1,2,3-oxadiazolyl group, a 1,2,4-oxadiazolyl group, a 1,3,4-oxadiazolyl group, a 1,2,5-oxadiazolyl group, a 1,2,3-thiadiazolyl group, a 1,2,4-thiadiazolyl group, a 1,3,4-thiadiazolyl group, a 1,2,5-thiadiazolyl group, a pyridyl group, a pyrazinyl group, a pyrimidinyl group, a pyridazinyl group, a 1,2,4-triazinyl group, a 1,3,5-triazinyl group, an indolyl group, an isoindolyl group, a benzofuranyl group, a benzothienyl group, a benzoimidazolyl group, a benzoxazolyl group, a benzoisoxazolyl group, a benzothiazolyl group, a benzoisothiazolyl group, an indazolyl group, an imidazopyridyl group, a purinyl group, a quinolyl group, a quinolizinyl group, an isoquinolyl group, aphthalenzinyl group, a naphthyridinyl group, a quinoxalinyl group, a quinazolinyl group, a cinnolinyl group, a pteridinyl group, a pyrido[3,2-b]pyridyl group and the like.

The "aliphatic heterocyclic group" in Formula (I) means a 5-membered or 6-membered monocycle containing 1 or 2, or more heteroatoms that are identical or different and selected from the group consisting of an oxygen atom, a nitrogen atom and a sulfur atom, or means a saturated or unsaturated aliphatic heterocyclic group that is a fused ring composed of two rings to three rings containing the heteroatoms, and examples thereof include an azetidinyl group, a pyrrolidinyl group, a piperidinyl group, a pyrazinyl group, a morpholino group, a tetrahydrofuranyl group, an imidazolidinyl group, a thiomorpholino group, a tetrahydroquinolyl group, a tetrahydroisoquinolyl group and the like.

The "aryloxy group" in Formula (I) means a group in which an oxygen atom is bonded to the "aryl group", and examples thereof include a phenoxy group, a Naphthalene-1-yloxy group, a Naphthalene-2-yloxy group and the like.

The "heteroaryloxy group" in Formula (I) means a group in which an oxygen atom is bonded to the "heteroaryl group", and examples thereof include a furan-2-yloxy group, a furan-3-yloxy group, a thiophene-2-yloxy group, a thiophene-3-yloxy group, a 1H-pyrrol-2-yloxy group, a 1H-pyrrol-3-yloxy group, a 1H-imidazole-2-yloxy group, a 1H-imidazole-4-yloxy group, a 3H-imidazole-4-yloxy group, a 4H-[1,3,4]triazole-3-yloxy group, a 2H-[1,2,4]triazole-3-yloxy group, a 1H-[1,2,4]triazole-3-yloxy group, a thiazole-2-yloxy group, a thiazole-4-yloxy group, a thiazole-5-yloxy group, a pyridin-2-yloxy group, a pyridin-3-yloxy group, a pyridin-4-yloxy group, a pyrimidin-2-yloxy group, a pyrimidin-4-yloxy group, a pyrimidin-5-yloxy group, a pyridazin-3-yloxy group, a pyridazin-4-yloxy group, a 2H-pyrazole-3-yloxy group, a 1H-pyrazole-4-yloxy group, a 1H-pyrazole-3-yloxy group, a pyrazinyloxy group, a quinoline-2-yloxy group, a quinoline-3-yloxy group, a quinoline-4-yloxy group, an isoquinoline-1-yloxy group, an isoquinoline-3-yloxy group, an isoquinoline-4-yloxy group, a quinazolin-2-yloxy group, a quinazolin-3-yloxy group, a quinoxalin-2-yloxy group, a quinoxalin-3-yloxy group, a cinnolin-3-yloxy group, a cinnolin-4-yloxy group, a 1H-benzoimidazole-2-yloxy group, a 1H-imidazo[4,5-b]pyridin-5-yloxy group, a 1H-imidazo[4,5-b]pyridin-6-yloxy group, a 1H-imidazo[4,5-b]pyridin-7-yloxy group, a benzo[d]isoxazole-4-yloxy group, a benzo[d]isoxazole-5-yloxy group, a benzo[d]

isoxazole-6-yloxy group, a benzoxazol-4-yloxy group, a benzoxazol-5-yloxy group, a benzoxazol-6-yloxy group and the like.

The "lower alkylene group" in Formula (I) means a $C_1$-straight or branched alkylene group, and examples thereof include a methylene group, an ethylene group, a trimethylene group, a tetramethylene group, a pentamethylene group, a hexamethylene group and the like.

The "lower alkenylene group" in Formula (I) means a divalent group formed by removing hydrogen atoms each from both ends of the chain of the "lower alkenyl group", and examples thereof include a vinylene group, a propenylene group and the like.

The "lower alkynylene group" in Formula (I) means a divalent group formed by removing hydrogen atoms each from both ends of the chain of the "lower alkynyl group", and examples thereof include an ethynylene group, a propynylene group and the like.

The "lower alkylenedioxy group" in Formula (I) means a group formed by respective bonding of the both ends of the "lower alkylene group" to an oxygen atom, and examples thereof include a methylenedioxy group, an ethylenedioxy group, a propylenedioxy group and the like.

The "lower alkenyl group" in Formula (I) means a $C_{2-6}$ straight or branched alkenyl group, and examples thereof include a vinyl group, a 1-propenyl group, an allyl group, an isopropenyl group, a 3-butenyl group, a 2-butenyl group, a 1-butenyl group, a 1-methyl-2-propenyl group, a 1-methyl-1-propenyl group, a 1-ethyl-1-ethenyl group, a 2-methyl-2-propenyl group, a 2-methyl-1-propenyl group, a 3-methyl-2-butenyl group, a 4-pentenyl group and the like.

The "lower alkynyl group" in Formula (I) means a $C_{2-6}$ straight or branched alkynyl group, and examples thereof include an ethynyl group, a 1-propynyl group, a 2-propynyl group, a 3-butynyl group, a 2-butynyl group, a 1-butynyl group, a 1-methyl-2-propynyl group, a 1-ethyl-2-propynyl group, a 1-methyl-2-butynyl group, a 4-pentynyl group and the like.

The "aralkyl group" in Formula (I) means the "lower alkyl group" in which any substitutable position is substituted with 1 or 2, or more, preferably 1 or 2 of the "aryl groups", and examples thereof include a benzyl group, a 1-phenylethyl group, a 2-phenylethyl group and 1-naphtylmethyl group, a 2-naphtylmethyl group and the like.

The "any substitutable position" used in this specification means a site of a substitutable hydrogen atom on a carbon atom, a nitrogen atom, an oxygen atom and/or a sulfur atom, wherein the substitution of the hydrogen atom is chemically accepted, and as a result, results in a stable compound.

Various symbols used in Formula (I) and the like will be further described in detail with preferable embodiments thereof in order to further specifically disclose the compound of the present invention.

$R^1$ in Formula (I) is a lower alkyl group that may be substituted with a cycloalkyl group, a cycloalkyl group, a halo-lower alkyl group, a hydroxy-lower alkyl group, a lower alkoxy-lower alkyl group, a lower alkoxy-carbonyl group, a lower alkyl-sulfonyl group or a group represented by the general formula: $-Q^1-A^1$.

$R^1$ is preferably, for example, a lower alkyl group that may be substituted with a cycloalkyl group, a cycloalkyl group, a lower alkyl-sulfonyl group, or a group represented by the general formula: $-Q^1-A^1$ and the like, more preferably a group represented by the general formula: $-Q^1-A^1$ and the like.

"A lower alkyl group that may be substituted with a cycloalkyl group" indicated by $R^1$ means an unsubstituted lower alkyl group, or a lower alkyl group in which any substitutable position is substituted with 1 or 2 or more, preferably 1 or 2 of the "cycloalkyl group" referred to in the above that are identical or different, and examples of the group preferably include a methyl group, an ethyl group, a propyl group, an isopropyl group, a butyl group, an isobutyl group, a sec-butyl group, a tert-butyl group, a pentyl group, an isopentyl group, an isoamyl group, a neopentyl group, a 1,1-dimethylpropyl group, a 1-methylbutyl group, a 2-methylbutyl group, a 1,2-dimethylpropyl group, a hexyl group, an isohexyl group, 1-methylpentyl group, 2-methylpentyl group, a 3-methylpentyl group, an 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,2,2-trimethyl propyl group, a 1-ethyl-3-methylpropyl group, a cyclopropylmethyl group, a cyclobutyl methyl group, a cyclopentyl methyl group, a cyclohexyl methyl group, a cycloheptyl methyl group, a 1-cyclopropylethyl group, a 1-cyclobutyl ethyl group, a 1-cyclopentyl ethyl group, a 1-cyclohexyl ethyl group, a 1-cycloheptyl ethyl group, a 2-cyclopropylethyl group, a 2-cyclobutyl ethyl group, a 2-cyclopentyl ethyl group, a 2-cyclohexyl ethyl group, a 2-cycloheptyl ethyl group, and the like, and more preferably an isopropyl group, an isobutyl group, a cyclopropylmethyl group, a cyclobutyl methyl group, a cyclopentyl methyl group, a cyclohexyl methyl group, and the like.

The cycloalkyl group of $R^1$ is preferably, for example, a cyclopropyl group, a cyclobutyl group, a cyclopentyl group, a cyclohexyl group and the like.

The halo-lower alkyl group of $R^1$ is preferably, for example, a fluoromethyl group, a difluoromethyl group, a trifluoromethyl group, a 2,2,2-trifluoroethyl group and the like.

The hydroxy-lower alkyl group of $R^1$ is preferably, for example, a hydroxymethyl group, a 2-hydroxyethyl group and the like.

The lower alkoxy-lower alkyl group of $R^1$ is preferably, for example, a methoxymethyl group, an ethoxymethyl group and the like.

The lower alkoxy-carbonyl group of $R^1$ is preferably, for example, a methoxycarbonyl group, an ethoxycarbonyl group, a propoxycarbonyl group, an isopropoxycarbonyl group, a butoxycarbonyl group, an isobutoxycarbonyl group, a tert-butoxycarbonyl group, a pentyloxycarbonyl group and the like.

The lower alkyl-sulfonyl group of $R^1$ is preferably, for example, a methanesulfonyl group, an ethanesulfonyl group and the like.

$Q^1$ represents a single bond or a lower alkylene group (herein 1 or 2, or more methylene groups constituting the lower alkylene group each independently may be substituted with a carbonyl group, a sulfinyl group or a sulfonyl group for the total methylene groups, and/or the hydrogen constituting the methylene group may be substituted with a lower alkyl group.).

The lower alkylene group of $Q^1$ is preferably, for example, a methylene group, an ethylene group, a trimethylene group and the like.

1 or 2, or more of the methylene groups constituting the lower alkylene group of $Q^1$ each independently may be substituted with a carbonyl group, a sulfinyl group or a sulfonyl group for the total methylene groups, and/or the hydrogen constituting the methylene group may be substituted with a lower alkyl group, and such substitutable or substituted group is preferably, for example, a group selected from the formulae described below.

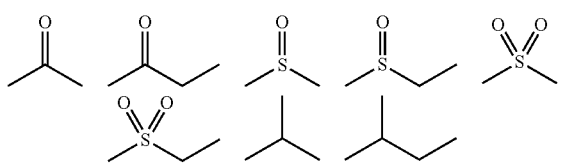

A¹ represents an aryl group or a heteroaryl group, which may be substituted with one to three substituents selected from the <Substituent group L> (herein any two substituents adjacent to each other on the aryl group or the heteroaryl group may join together to form a lower alkylenedioxy group.).

In this case, <Substituent group L> is the group consisting of a halogen atom, a hydroxyl group, a nitro group, a cyano group, a formyl group, an amino group, a carboxyl group, a lower alkyl group, a halo-lower alkyl group, a cycloalkyl group, a lower alkoxy group, a halo-lower alkoxy group, a hydroxy lower alkyl group, a lower alkoxy lower alkyl group, a lower alkoxycarbonyl group, a lower alkanoyl group, a lower alkylthio group, a lower alkylsulfonyl group, a lower alkylamino group, a di-lower alkylamino group, a carbamoyl group, a mono-lower alkyl carbamoyl group, a di-lower alkyl carbamoyl group, a lower alkanoylamino group, a lower alkylsulfonylamino group, a lower alkoxycarbonylamino group, an aralkyl group, an aryloxy group, a heteroaryloxy group, and a lower alkenyl group.

The aryl group indicated by A¹ is, preferably, for example, a phenyl group, a naphthyl group, a biphenyl group and the like.

The heteroaryl group of A¹ is, for example, an imidazolyl group, a furyl group, a thienyl group, a pyrazolyl group, a thiazolyl group, an isothiazolyl group, an oxazolyl group, an isoxazolyl group, a 1,2,4-oxadiazolyl group, a 1,3,4-oxadiazolyl group, a pyridyl group, a pyrazinyl group, a pyrimidinyl group, a benzofuranyl group, a quinolyl group, a benzothienyl group, and the like, more preferably, a pyridyl group, a quinolyl group, a thienyl group, a pyrazolyl group, a thiazolyl group, an isoxazolyl group, a benzothienyl group, and the like, and further preferably, a pyridyl group, an isoxazolyl group, a quinolyl group, and a benzothienyl group and the like.

The "any two substituents adjacent to each other on the aryl group or the heteroaryl group may join together to form a lower alkylenedioxy group" of A¹ refers to a lower alkylenedioxy group formed by joining of any two substituents adjacent to each other on the aryl group or the heteroaryl group, and is preferably, for example, a benzo[1,3]dioxolyl group, a 2,3-dihydro-benzo[1,4]dioxynyl group and the like.

Therefore, examples of A¹ include, for example, a phenyl group, a 2-fluorophenyl group, a 3-fluorophenyl group, a 4-fluorophenyl group, 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2-chlorophenyl group, a 3-chlorophenyl group, a 4-chlorophenyl group, a 2,3-dichlorophenyl group, a 2,4-dichlorophenyl group, a 2,5-dichlorophenyl group, a 2,6-dichlorophenyl group, a 2-bromophenyl group, a 3-bromophenyl group, a 4-bromophenyl group, a 2-chloro-3-fluorophenyl group, a 2-chloro-4-fluorophenyl group, a 2-chloro-5-fluorophenyl group, a 2-chloro-6-fluorophenyl group, a 2-bromo-3-fluorophenyl group, a 2-bromo-4-fluorophenyl group, a 2-bromo-5-fluorophenyl group, a 2-bromo-6-fluorophenyl group, a 2-methylphenyl group, a 3-methylphenyl group, a 4-methylphenyl group, a 2-ethylphenyl group, a 3-ethylphenyl group, a 4-ethylphenyl group, a 2-cyclopropylphenyl group, a 3-cyclopropylphenyl group, a 4-cyclopropylphenyl group, a 2-trifluoromethylphenyl group, a 3-trifluoromethylphenyl group, a 4-trifluoromethylphenyl group, a 2-methoxyphenyl group, a 3-methoxyphenyl group, a 4-methoxyphenyl group, a 2-difluoromethoxyphenyl group, a 3-difluoromethoxyphenyl group, a 4-difluoromethoxyphenyl group, a 2-trifluoro methoxyphenyl group, a 3-trifluoromethoxyphenyl group, a 4-trifluoromethoxyphenyl group, a 2-hydroxyphenyl group, a 3-hydroxyphenyl group, a 4-hydroxyphenyl group, a 2-hydroxy methylphenyl group, a 3-hydroxy methylphenyl group, a 4-hydroxy methylphenyl group, a 2,4-dimethylphenyl group, a 2,5-dimethylphenyl group, a 2,6-dimethylphenyl group, a 2,4,6-trimethylphenyl group, a 2-fluoro-6-trifluoro methylphenyl group, a 4-fluoro-2-trifluoro methylphenyl group, a benzo[1,3]dioxo-5-yl group, a 6-chlorobenzo[1,3]dioxo-5-yl group, a 1-naphthyl group, a 2-naphthyl group, a 2-biphenyl group, a 3-biphenyl group, a 4-biphenyl group, a 2-phenoxy group, a 3-phenoxy group, a 4-phenoxy group, a 2-imidazolyl group, a 2-furyl group, a 2-thienyl group, a 1,2,4-oxadiazol-5-yl group, a 1,3,4-oxadiazol-2-yl group, a 1,2,4-thiadiazole-5-yl group, a 1,3,4-thiadiazole-2-yl group, a 4-isoxazolyl group, a 3,5-dimethylisoxazolyl group, a 2-pyridyl group, a 3-pyridyl group, a 4-pyridyl group, a 2-fluoro-5-pyridyl group, a 3-fluoro-6-pyridyl group, a 2-chloro-3-pyridyl group, a 2-chloro-5-pyridyl group, a 2-methyl-3-pyridyl group, a 2-methyl-6-pyridyl group, a 2-pyrimidinyl group, a 4-benzo[b]furanyl group, a 7-benzo[b]furanyl group, a 2-quinolyl group, a 3-quinolyl group, a 4-quinolyl group, a 5-quinolyl group, a 6-quinolyl group, a 8-quinolyl group, a 5-chlorothiophene-2-yl group, a 2-benzo[b]thiophenyl group, a 3-benzo[b]thiophenyl group, a 4-benzo[b]thiophenyl group, a 5-benzo[b]thiophenyl group, a 6-benzo[b]thiophenyl group, a 7-benzo[b]thiophenyl group, a 5-chlorobenzo[b]thiophene-3-yl group, a 2-chloro-6-methylphenyl group, a 2-chloro-6-cyclopropyl phenyl group, a 2-chloro-6-cyanophenyl group, a 2,6-dicyclopropyl phenyl group, and the like, and among them, preferably, a 2-fluorophenyl group, a 3-fluorophenyl group, a 2,3-difluorophenyl group, a 2,4-difluorophenyl group, a 2,5-difluorophenyl group, a 2,6-difluorophenyl group, a 2-chlorophenyl group, a 2,3-dichlorophenyl group, a 2,6-dichlorophenyl group, a 2-bromophenyl group, a 2-chloro-3-fluorophenyl group, a 2-chloro-4-fluorophenyl group, a 2-chloro-5-fluorophenyl group, a 2-chloro-6-fluorophenyl group, a 2-bromo-3-fluorophenyl group, a 2-bromo-4-fluorophenyl group, a 2-bromo-5-fluorophenyl group, a 2-bromo-6-fluorophenyl group, a 2-methylphenyl group, a 2-trifluoro methylphenyl group, a 2-methoxyphenyl group, a 2-difluoromethoxyphenyl group, a 2-trifluoromethoxyphenyl group, a 2-hydroxyphenyl group, a 2-hydroxymethylphenyl group, a 2,4-dimethylphenyl group, a 2,5-dimethylphenyl group, a 2,6-dimethylphenyl group, a 2,4,6-trimethylphenyl group, a 2,3-dichlorophenyl group, a 2,6-dichlorophenyl group, a 2-fluoro-6-trifluoro methylphenyl group, a 2-trifluoro-4-fluorophenyl group, a 1-naphthyl group, a 8-quinolyl group, a 6-chlorobenzo[1,3]dioxo-5-yl group, a 5-chlorobenzo[b]thiophene-3-yl group, a 2-chloro-6-methylphenyl group, a 2-chloro-6-cyclopropylphenyl group, a 2-chloro-6-cyanophenyl group, and the like, and particularly preferably, a 2-chlorophenyl group, a 2,3-dichlorophenyl group, a 2,6-dichlorophenyl group, a 2-chloro-6-fluorophenyl group, a 2,5-dimethylphenyl group, a 2,6-dimethylphenyl group, a 2,4,6-trimethyl phenyl group, a 1-naphthyl group, a 8-quinolyl group, a 6-chlorobenzo[1,3]dioxo-5-yl group, a 5-chlorobenzo[b]thiophene-3-yl group, a 2-chloro-6-methylphenyl group, a 2-chloro-6-cyclopropyl phenyl group, and a 2-chloro-6-cyanophenyl group, and the like.

---- represents a double bond or a single bond, when ---- is a double bond, $W^1$ represents a nitrogen atom or a group represented by the general formula: =C($R^a$)—, and $W^2$ represents a nitrogen atom or a group represented by the general formula: =C($R^b$)—, when ---- is a single bond, $W^1$ represents a group represented by the general formula: —C($R^{aa}$)($R^{ab}$)—, or a group represented by the general formula: —(C=O)—, and $W^2$ represents a group represented by the general formula: —C($R^{ba}$)($R^{bb}$)—, a group represented by the general formula: —(C=O)— or a group represented by the general formula: —N($R^{bc}$)—.

Herein, the substructure of General Formula (I):

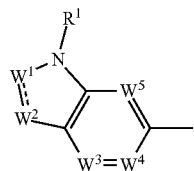

is exemplified as follows in relation to W ---- $W^2$.

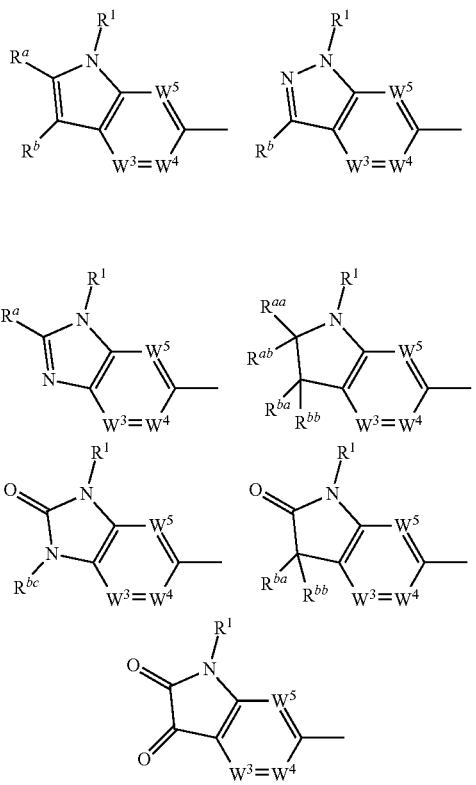

More preferably, the substructure of General Formula (I) is selected from the followings.

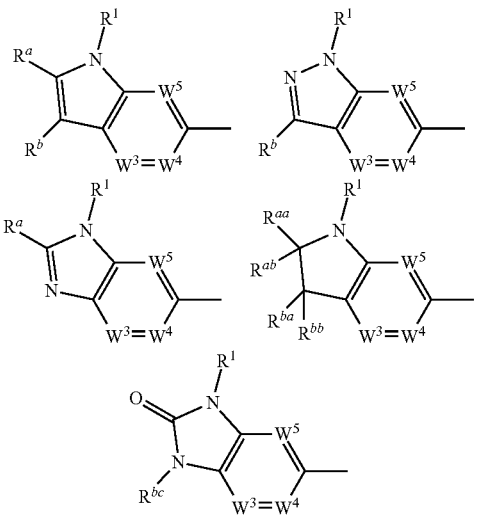

$R^a$ and $R^b$ represent each independently a hydrogen atom, a substituent selected from the <Substituent group M> or a group represented by the general formula: -$Q^2$-$A^2$.

Herein, <Substituent group M> is the group consisting of a halogen atom, a hydroxyl group, a nitro group, a cyano group, a formyl group, an amino group, a carboxyl group, a lower alkyl group, a halo-lower alkyl group, a cycloalkyl group, a lower alkoxy group, a halo-lower alkoxy group, a hydroxy lower alkyl group, a lower alkoxy lower alkyl group, a lower alkoxycarbonyl group, a lower alkanoyl group, a lower alkylthio group, a lower alkylsulfonyl group, a lower alkylamino group, a di-lower alkylamino group, a carbamoyl group, a mono-lower alkyl carbamoyl group, a di-lower alkyl carbamoyl group, a lower alkanoylamino group, a lower alkylsulfonylamino group, and a lower alkoxycarbonylamino group.

$R^a$ and $R^b$ are preferably, for example, a hydrogen atom, a halogen atom, a hydroxyl group, a cyano group, a formyl group, a carboxyl group, a lower alkyl group, a halo-lower alkyl group, a cycloalkyl group, a hydroxy-lower alkyl group, a lower alkoxy-lower alkyl group, a lower alkoxy-carbonyl group, a lower alkanoyl group and a group represented by the general formula: -$Q^2$-$A^2$ and the like, and more preferably, a hydrogen atom, a halogen atom, a cyano group, a lower alkyl group, a halo-lower alkyl group, a cycloalkyl group, a lower alkanoyl group and a group represented by the general formula: -$Q^2$-$A^2$ and the like.

$R^{aa}$ and $R^{ab}$ are each independently a hydrogen atom, a substituent selected from the <Substituent group N> or a group represented by the general formula: -$Q^2$-$A^2$.

<Substituent group N> is the group consisting of a hydroxyl group, a cyano group, a formyl group, a carboxyl group, a lower alkyl group, a halo-lower alkyl group, a cycloalkyl group, a lower alkoxy group, a halo-lower alkoxy group, a hydroxy lower alkyl group, a lower alkoxy lower alkyl group, a lower alkoxycarbonyl group, a lower alkanoyl group, a carbamoyl group, a mono-lower alkyl carbamoyl group, and a di-lower alkyl carbamoyl group.

Alternatively, $R^{aa}$ and $R^{ab}$ may join together to form a lower alkylene group (herein 1 to 2 or more methylene groups constituting the lower alkylene group each independently may be substituted with an oxygen atom, a carbonyl group, a vinylene group or a group represented by the general formula: —N($R^c$)— for the total methylene groups, and/or the hydrogen constituting the methylene group may be substituted with a hydroxyl group, a lower alkyl group or a halogen atom.).

The "$R^{aa}$ and $R^{ab}$ may join together to form a lower alkylene group" refers that the carbon atoms substituted with $R^{aa}$ and $R^{ab}$ are bonded to each other via the lower alkylene group, whereby to form a saturated 3-membered to 7-membered, cyclocarbocyclic ring. Herein, 1 to 2 or more methylene groups constituting the lower alkylene group each independently may be substituted with an oxygen atom, a carbonyl group, a vinylene group or a group represented by the general formula: —N($R^c$)— for the total methylene groups, and/or the hydrogen constituting the methylene group may be substituted with a hydroxyl group, a lower alkyl group or a halogen atom. For example, a cyclopropyl group, a cyclobutyl group, a cyclopentyl group, a cyclohexyl group and the like are preferable.

$R^{aa}$ and $R^{ab}$ are preferably, for example, a hydrogen atom, a lower alkyl group, a halo-lower alkyl group, a cycloalkyl group, a lower alkoxy group and a group represented by the general formula: -$Q^2$-$A^2$ and the like.

$R^{ba}$ and $R^{bb}$ represent each independently a hydrogen atom, a halogen atom, an amino group, a lower alkyl-amino group, a di-lower alkyl-amino group, a hydroxy-lower alkyl-amino group, a lower alkyl-sulfonylamino group, a lower alkoxy-carbonylamino group, a substituent selected from the <Substituent group N> or a group represented by the general formula: -$Q^2$-$A^2$.

Alternatively, $R^{ba}$ and $R^{bb}$ may join together to form a lower alkylene group (herein 1 to 2 or more methylene groups constituting the lower alkylene group each independently may be substituted with an oxygen atom, a carbonyl group, a vinylene group or a group represented by the general formula: —N($R^c$)— for the total methylene groups, and/or the hydrogen constituting the methylene group may be substituted with a hydroxyl group, a lower alkyl group or a halogen atom).

The "$R^{ba}$ and $R^{bb}$ may join together to form a lower alkylene group" refers that the carbon atoms substituted with $R^{ba}$ and $R^{bb}$ are bonded to each other via the lower alkylene group, whereby to form a saturated 3-membered to 7-membered, cyclocarbocyclic ring. Herein, 1 to 2 or more methylene groups constituting the lower alkylene group each independently may be substituted with an oxygen atom, a carbonyl group, a vinylene group or a group represented by the general formula: —N($R^c$)— for the total methylene groups, and/or the hydrogen constituting the methylene group may be substituted with a hydroxyl group, a lower alkyl group or a halogen atom. For example, a cyclopropyl group, a cyclobutyl group, a cyclopentyl group, a cyclohexyl group and the like are preferable.

$R^{ba}$ and $R^{bb}$ are preferably, for example, a hydrogen atom, a halogen atom, a lower alkyl-amino group, a di-lower alkyl-amino group, a lower alkyl group, a halo-lower alkyl group, a cycloalkyl group, a lower alkoxy group, a lower alkoxy-carbonyl group, a lower alkanoyl group, a carbamoyl group, a mono-lower alkyl-carbamoyl group and a di-lower alkyl-carbamoyl group and a group represented by the general formula: -$Q^2$-$A^2$ and the like.

$R^{bc}$ represents a substituent selected from the group consisting of a hydrogen atom, a lower alkyl group, a cycloalkyl group, a halo-lower alkyl group, a lower alkoxy-carbonyl group, a carbamoyl group, a mono-lower alkyl-carbamoyl group, a di-lower alkyl-carbamoyl group and a lower alkanoyl group or a group represented by the general formula: -$Q^2$-$A^2$.

$R^{bc}$ is preferably, for example, a hydrogen atom, a lower alkyl group, a halo-lower alkyl group, a lower alkanoyl group and a group represented by the general formula: -$Q^2$-$A^2$ and the like.

$Q^2$ represents a single bond, a lower alkylene group or a lower alkenylene group, wherein 1 or 2, or more methylene groups constituting the lower alkylene group each independently may be substituted with an oxygen atom, a nitrogen atom or a carbonyl group for the total methylene groups, and/or the hydrogen constituting the methylene group may be substituted with a halogen atom, a cyano group, a hydroxyl group or a lower alkyl group.

The lower alkylene group of $Q^2$ is preferably, for example, a methylene group, an ethylene group, a trimethylene group and the like.

1 or 2, or more of the methylene groups constituting the lower alkylene group of $Q^2$ each independently may be substituted with an oxygen atom, a nitrogen atom or a carbonyl group for the total methylene groups, and/or the hydrogen constituting the methylene group may be substituted with a halogen atom, a cyano group, a hydroxyl group or a lower alkyl group. Such substitutable or substituted group is preferably, for example, a group selected from the formulae described below.

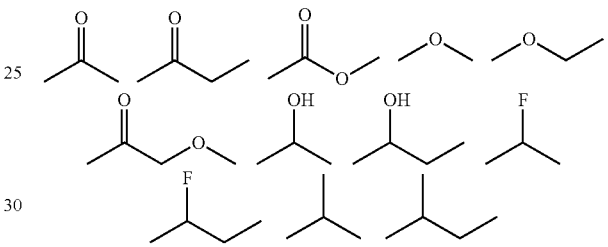

$Q^2$ is more preferably a single bond, a methylene group and a group selected from those described below and the like.

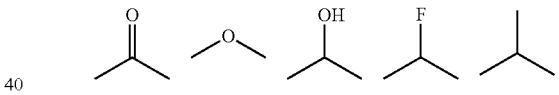

$A^2$ represents a cycloalkyl group, an aliphatic heterocyclic group, an aryl group or a heteroaryl group, which may be substituted with one to three substituents selected from the <Substituent group L> (herein any two substituents adjacent to each other on the aryl group or the heteroaryl group may join together to form a lower alkylenedioxy group.).

The aryl group of $A^2$ is preferably, for example, a phenyl group, a naphthyl group, a biphenyl group and the like.

The heteroaryl group of $A^2$ is preferably, for example, imidazolyl group, a furyl group, a thienyl group, a pyrazolyl group, a thiazolyl group, an isothiazolyl group, a oxazolyl group, an isoxazolyl group, a 1,2,4-oxadiazolyl group, a 1,3,4-oxadiazolyl group, a pyridyl group, a pyrazinyl group, a pyrimidinyl group, a benzofuranyl group, a quinolyl group and the like, more preferably, a pyridyl group, a quinolyl group and the like, and further preferably a pyridyl group and the like.

The "any two substituents adjacent to each other on the aryl group or the heteroaryl group may join together to form a lower alkylenedioxy group" of $A^2$ refers that any two substituents adjacent to each other on the aryl group or the heteroaryl group join to form a lower alkylenedioxy group. For example, a benzo[1,3]dioxolyl group, a 2,3-dihydro-benzo[1,4]dioxynyl group and the like are preferable.

Therefore, $A^2$ is, preferably, a phenyl group, a 2-fluorophenyl group, a 3-fluorophenyl group, a 4-fluorophenyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2-chlorophenyl group, a 3-chlorophenyl group, a 4-chlorophenyl group, a 2-bromophenyl group, a 3-bromophenyl group, a 4-bromophenyl group, a 2-chloro-3-fluorophenyl group, a 2-chloro-4-fluorophenyl group, a 2-chloro-5-fluorophenyl group, a 2-chloro-6-fluorophenyl group, a 2-bromo-3-fluorophenyl group, a 2-bromo-4-fluorophenyl group, a 2-bromo-5-fluorophenyl group, a 2-bromo-6-fluorophenyl group, a 2-methylphenyl group, a 3-methylphenyl group, a 4-methylphenyl group, a 2-trifluoromethylphenyl group, a 3-trifluoromethylphenyl group, a 4-trifluoromethylphenyl group, a 2-methoxyphenyl group, a 3-methoxyphenyl group, a 4-methoxyphenyl group, a 2-difluoromethoxyphenyl group, a 3-difluoromethoxyphenyl group, a 4-difluoromethoxyphenyl group, a 2-trifluoromethoxyphenyl group, a 3-trifluoromethoxyphenyl group, a 4-trifluoromethoxyphenyl group, a 2-hydroxyphenyl group, a 3-hydroxyphenyl group, a 4-hydroxyphenyl group, a 2-hydroxymethylphenyl group, a 3-hydroxymethylphenyl group, a 4-hydroxymethylphenyl group, a 2,6-dimethylphenyl group, a 2,3-dichlorophenyl group, a 2,6-dichlorophenyl group, a 2-fluoro-6-trifluoro methylphenyl group, a 2-trifluoro-4-fluorophenyl group, a 2-imidazolyl group, a 2-furyl group, a 2-thienyl group, a 1,2,4-oxadiazol-5-yl group, a 1,3,4-oxadiazol-2-yl group, a 1,2,4-thiadiazole-5-yl group, a 1,3,4-thiadiazole-2-yl group, a 2-pyridyl group, a 3-pyridyl group, a 4-pyridyl group, a 2-fluoro-5-pyridyl group, a 3-fluoro-6-pyridyl group, a 2-pyrimidinyl group, a 4-benzo[b]furanyl group, a 7-benzo[b]furanyl group, a 2-quinolyl group, a 3-quinolyl group, a 4-quinolyl group, a 5-quinolyl group, a 6-quinolyl group, and a 8-quinolyl group, and the like.

$W^3$, $W^4$ and $W^5$ represent each independently a nitrogen atom, or a methine group that may have a substituent selected from the group consisting of a halogen atom, a hydroxyl group, a cyano group, a lower alkyl group, a cycloalkyl group, a halo-lower alkyl group, a lower alkoxy group and a halo lower alkoxy group.

The "methine group that may have a substituent selected from the group consisting of halogen atom, a hydroxyl group, a cyano group, a lower alkyl group, a cycloalkyl group, a halo-lower alkyl group, a lower alkoxy group and a halo lower alkoxy group" means an unsubstituted methine group or a methine group that has a substituent. The substituent can be selected from the group consisting of a halogen atom, a hydroxyl group, a cyano group, a lower alkyl group, a cycloalkyl group, a halo-lower alkyl group, a lower alkoxy group and a halo lower alkoxy group.

The halogen atom of the substituent is preferably, for example, a fluorine atom, a chlorine atom and the like.

The lower alkyl group of the substituent is preferably, for example, a methyl group, an ethyl group and the like.

The cycloalkyl group of the substituent is preferably, for example, a cyclopropyl group and the like.

The halo-lower alkyl group of the substituent is preferably, for example, a fluoromethyl group, a difluoromethyl group, a trifluoromethyl group and the like.

The lower alkoxy group of the substituent is preferably, for example, a methoxy group, an ethoxy group and the like.

The halo lower alkoxy group of the substituent is preferably, for example, a difluoromethoxy group, a trifluoromethoxy group and the like.

$W^1$, $W^2$, $W^3$, $W^4$ and $W^5$ are such that 0 to 4, preferably 0 to 3, particularly preferably 0 to 2 of $W^1$, $W^2$, $W^3$, $W^4$ and $W^5$ are nitrogen atoms.

X is a single bond, an oxygen atom, a sulfur atom, a sulfinyl group, a sulfonyl group, a carbonyl group, a lower alkenylene group, a lower alkynylene group or a group represented by the general formula: —N($R^X$)— (herein $R^X$ is a hydrogen atom or a lower alkyl group.).

The lower alkenylene group of X is preferably, for example, a vinylene group and the like.

The lower alkynylene group of X is preferably, for example, an ethynylene group and the like.

X is preferably, for example, a single bond, an oxygen atom, a carbonyl group, a vinylene group and a group represented by the general formula: —N($R^X$)— and the like.

The lower alkyl group of $R^X$ is preferably, for example, a methyl group, an ethyl group, a propyl group and the like, more preferably a methyl group and the like.

Y is a single bond or $(CR^{Yi}R^{Yi'})_n$ (herein n is any integer of 1 to 6, i is any integer of 1 to n, and $(CR^{Yi}R^{Yi'})_n$ represents $(CR^{Y1}R^{Y1'})$ when n=1; represents $(CR^{Y1}R^{Y1'})—(CR^{Y2}R^{Y2'})$ when n=2; represents $(CR^{Y1}R^{Y1'})—(CR^{Y2}R^{Y2'})—(CR^{Y3}R^{Y3'})$ when n=3; represents $(CR^{Y1}R^{Y1'})—(CR^{Y2}R^{Y2'})—(CR^{Y3}R^{Y3'})—(CR^{4}R^{4'})$ when n=4; represents $(CR^{Y1}R^{Y1'})—(CR^{Y2}R^{Y2'})—(CR^{Y3}R^{Y3'})—(CR^{4}R^{4'})—(CR^{Y5}R^{Y5'})$ when n=5, and represents $(CR^{Y1}R^{Y1'})—(CR^{Y2}R^{Y2'})—(CR^{Y3}R^{Y3'})—(CR^{Y4}R^{Y4'})—(CR^{Y5}R^{Y5'})—(CR^{Y6}R^{Y6'})$ when n=6.).

Y is preferably, for example, a single bond and $(CR^{Y1}R^{Y1'})_n$ (herein n is any integer of 1 to 3, i is any integer of 1 to n, and $(CR^{Y1}R^{Y1'})_n$ represents $(CR^{Y1}R^{Y1'})$ when n=1; represents $(CR^{Y1}R^{Y1'})—(CR^{Y2}R^{Y2'})$ when n=2, and represents $(CR^{Y1}R^{Y1'})—(CR^{Y2}R^{Y2'})—(CR^{Y3}R^{Y3'})$ when n=3.).

$R^{Y1}$, $R^{Y1'}$, $R^{Y2}$, $R^{Y2'}$, $R^{Y3}$, $R^{Y3'}$, $R^{Y4}$, $R^{Y4'}$, $R^{Y5}$, $R^{Y5'}$, $R^{Y6}$ and $R^{Y6'}$ are each independently a hydrogen atom, a halogen atom or a substituent selected from the <Substituent group N>.

$R^{Y1}$, $R^{Y1'}$, $R^{Y2}$, $R^{Y2'}$, $R^{Y3}$, $R^{Y3'}$, $R^{Y4}$, $R^{Y4'}$, $R^{Y5}$, $R^{Y5'}$, $R^{Y6}$ and $R^{Y6'}$ are preferably each independently, for example, a hydrogen atom, a halogen atom, a hydroxyl group, a cyano group, a lower alkyl group, a lower alkoxy group and the like.

The lower alkyl group of the substituent is preferably, for example, a methyl group, an ethyl group and the like.

The lower alkoxy group of the substituent is preferably, for example, a methoxy group, an ethoxy group and the like.

In relation to $R^X$, $R^{Y1}$, $R^{Y1'}$, $R^{Y2}$, $R^{Y2'}$, $R^{Y3}$, $R^{Y3'}$, $R^{Y4}$, $R^{Y4'}$, $R^{Y5}$, $R^{Y5'}$, $R^{Y6}$ and $R^{Y6'}$, the combinations of the two groups below: (i) $R^{Y1}$ and $R^{Y1'}$, (ii) $R^{Y2}$ and $R^{Y2'}$, (iii) $R^{Y3}$ and $R^{Y3'}$, (iv) $R^{Y4}$ and $R^{Y4'}$, (v) $R^{Y5}$ and $R^{Y5'}$, (vi) $R^{Y6}$ and $R^{Y6'}$, (vii) $R^X$ and $R^{Y1}$, (viii) $R^X$ and $R^{Y2}$, (ix) $R^X$ and $R^{Y3}$, (x) $R^{Y1}$ and $R^{Y2}$, (xi) $R^{Y1}$ and $R^{Y3}$, (xii) $R^{Y1}$ and $R^{Y4}$, (xiii) $R^{Y2}$ and $R^{Y3}$, (xiv) $R^{Y2}$ and $R^{Y4}$ or (xv) $R^{Y2}$ and $R^{Y5}$, i.e., the two groups constituting the combinations may join together to form a lower alkylene group, wherein 1 or 2, or more methylene groups constituting the lower alkylene group each independently may be substituted with an oxygen atom, a carbonyl group, a vinylene group or the general formula —N($R^c$)— for the total methylene groups, and/or the hydrogen constituting the methylene group may be substituted with a hydroxyl group, a lower alkyl group or a halogen atom.

(i) The "$R^{Y1}$ and $R^{Y1'}$ join to form a lower alkylene group" refers that the carbon atoms substituted with $R^{Y1}$ and $R^{Y1'}$ are bonded to each other via the lower alkylene group, whereby to form a saturated 3-membered to 7-membered, cyclocarbocyclic ring. For example, examples thereof include a cyclopropyl group, a cyclobutyl group, a cyclopentyl group, a cyclohexyl group and the like, and preferably a cyclopropyl group and the like.

(ii) The "$R^{Y2}$ and $R^{Y2'}$ join to form a lower alkylene group" refers that the carbon atoms substituted with $R^{Y2}$ and $R^{Y2'}$ are bonded to each other via the lower alkylene group, whereby to form a saturated 3-membered to 7-membered, cyclocarbocyclic ring. For example, examples thereof include a cyclopropyl group, a cyclobutyl group, a cyclopentyl group, a cyclohexyl group and the like, and preferably a cyclopropyl group and the like.

(iii) The "$R^{Y3}$ and $R^{Y3'}$ join to form a lower alkylene group" refers that the carbon atoms substituted with $R^{Y3}$ and $R^{Y3'}$ are bonded to each other via the lower alkylene group, whereby to form a saturated 3-membered to 7-membered, cyclocarbocyclic ring. For example, examples thereof include a cyclopropyl group, a cyclobutyl group, a cyclopentyl group, a cyclohexyl group, and the like, and preferably a cyclopropyl group and the like.

(iv) The "$R^{Y4}$ and $R^{Y4'}$ join to form a lower alkylene group" refers that the carbon atoms substituted with $R^{Y4}$ and $R^{Y4'}$ are bonded to each other via the lower alkylene group, whereby to form a saturated 3-membered to 7-membered, cyclocarbocyclic ring. For example, examples thereof include a cyclopropyl group, a cyclobutyl group, a cyclopentyl group, a cyclohexyl group, and the like, and preferably a cyclopropyl group and the like.

(v) The "$R^{Y5}$ and $R^{Y5'}$ join to form a lower alkylene group" refers that the carbon atoms substituted with $R^{Y5}$ and $R^{Y5'}$ are bonded to each other via the lower alkylene group, whereby to form a saturated 3-membered to 7-membered, cyclocarbocyclic ring. For example, examples thereof include a cyclopropyl group, a cyclobutyl group, a cyclopentyl group, a cyclohexyl group, and the like, and preferably a cyclopropyl group and the like.

(vi) The "$R^{Y6}$ and $R^{Y6'}$ join to form a lower alkylene group" refers that the carbon atoms substituted with $R^{Y6}$ and $R^{Y6'}$ are bonded to each other via the lower alkylene group, whereby to form a saturated 3-membered to 7-membered, cyclocarbocyclic ring. For example, examples thereof include a cyclopropyl group, a cyclobutyl group, a cyclopentyl group, a cyclohexyl group, and the like, and preferably a cyclopropyl group and the like.

(vii) The "$R^{X}$ and $R^{Y1}$ join to form a lower alkylene group" refers that $R^{X}$ and $R^{Y1}$ are bonded to each other via the lower alkylene group, whereby to form a saturated 3-membered to 7-membered, cyclocarbocyclic ring. For example, it is represented by the formula described below.

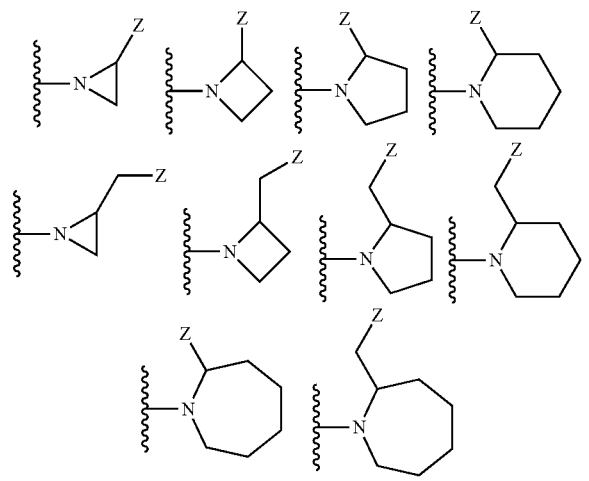

(viii) The "$R^{X}$ and $R^{Y2}$ join to form a lower alkylene group" refers that $R^{X}$ and $R^{Y2}$ are bonded to each other via the lower alkylene group, whereby to form a saturated 3-membered to 7-membered, cyclocarbocyclic ring. For example, it is represented by the formula described below.

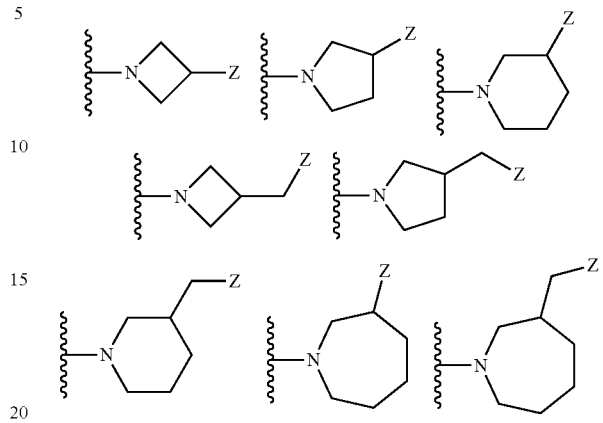

(ix) The "$R^{X}$ and $R^{Y3}$ join to form a lower alkylene group" refers that $R^{X}$ and $R^{Y3}$ are bonded to each other via the lower alkylene group, whereby to form a saturated 3-membered to 7-membered, cyclocarbocyclic ring. For example, it is represented by the formula described below.

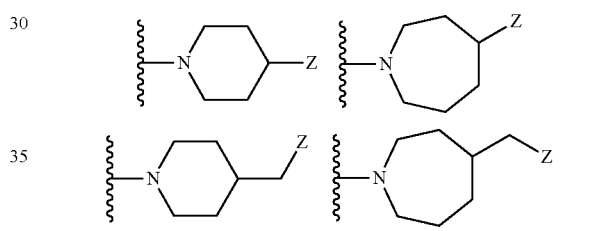

(x) The "$R^{Y1}$ and $R^{Y2}$ join to form a lower alkylene group" refers that $R^{Y1}$ and $R^{Y2}$ are bonded to each other via the lower alkylene group, whereby to form a saturated 3-membered to 7-membered, cyclocarbocyclic ring. For example, it is represented by the formula described below.

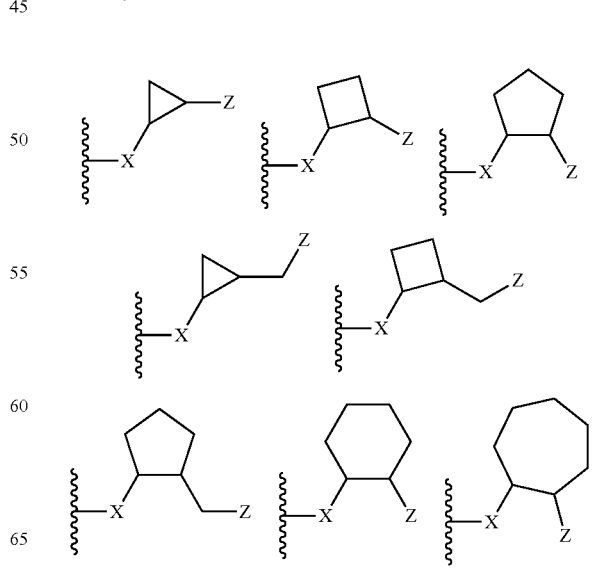

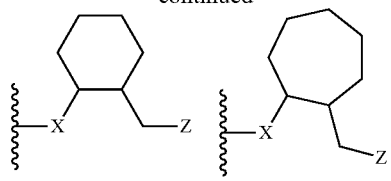

(xi) The "$R^{Y1}$ and $R^{Y3}$ join to form a lower alkylene group" refers that $R^{Y1}$ and $R^{Y3}$ are bonded to each other via the lower alkylene group, whereby to form a saturated 3-membered to 7-membered, cyclocarbocyclic ring. For example, it is represented by the formula described below.

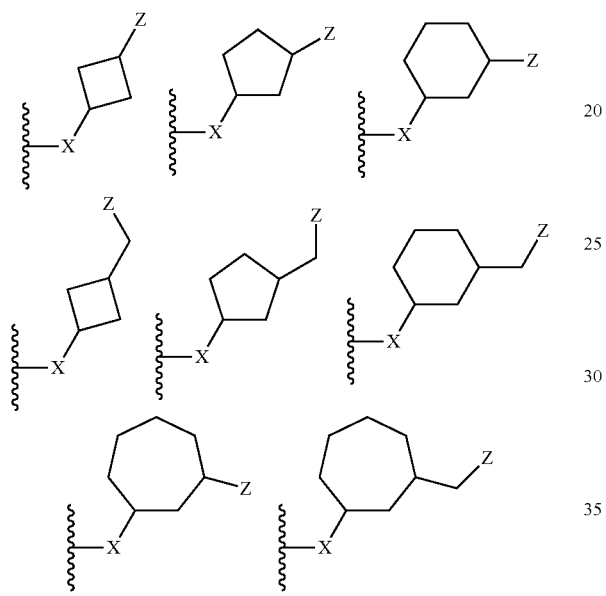

(xii) The "$R^{Y1}$ and $R^{Y4}$ join to form a lower alkylene group" refers that $R^{Y1}$ and $R^{Y4}$ are bonded to each other via the lower alkylene group, whereby to form a saturated 3-membered to 7-membered, cyclocarbocyclic ring. For example, it is represented by the formula described below.

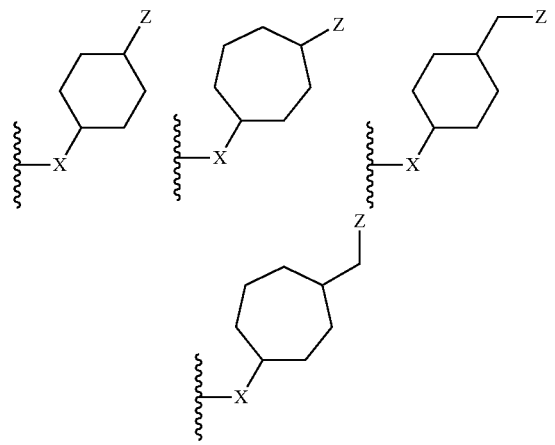

(xiii) The "$R^{Y2}$ and $R^{Y3}$ join to form a lower alkylene group" refers that $R^{Y2}$ and $R^{Y3}$ are bonded to each other via the lower alkylene group, whereby to form a saturated 3-membered to 7-membered, cyclocarbocyclic ring. For example, it is represented by the formula described below.

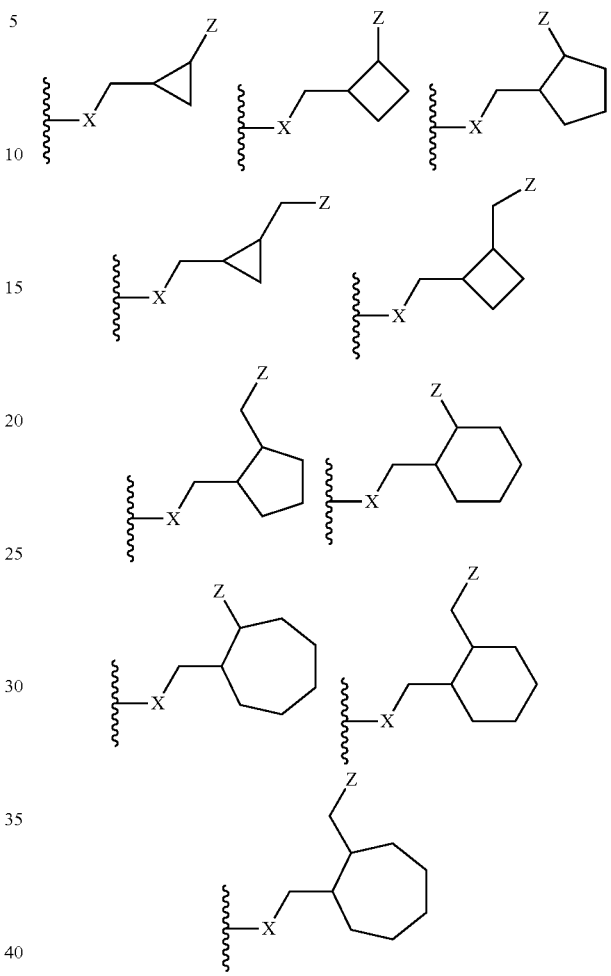

(xiv) The "$R^{Y2}$ and $R^{Y4}$ join to form a lower alkylene group" refers that $R^{Y2}$ and $R^{Y4}$ are bonded to each other via the lower alkylene group, whereby to form a saturated 3-membered to 7-membered, cyclocarbocyclic ring. For example, it is represented by the formula described below.

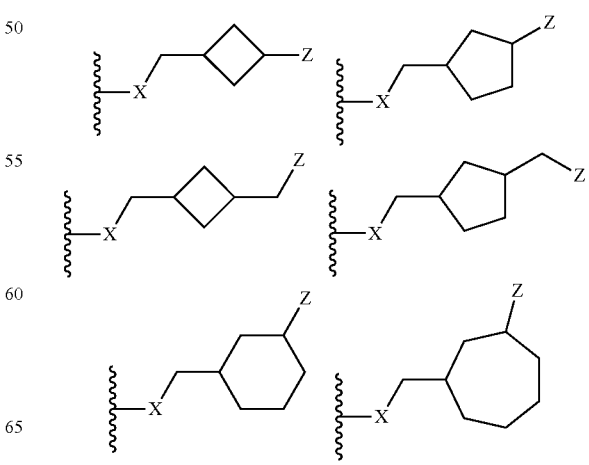

-continued

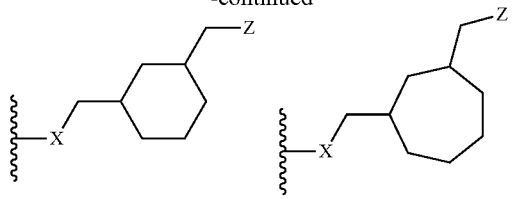

(xv) The "$R^{Y2}$ and $R^{Y5}$ join to form a lower alkylene group" refers that $R^{Y2}$ and $R^{Y5}$ are bonded to each other via the lower alkylene group, whereby to form a saturated 3-membered to 7-membered, cyclocarbocyclic ring. For example, it is represented by the formula described below.

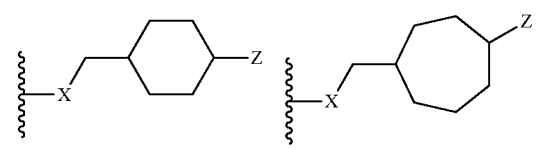

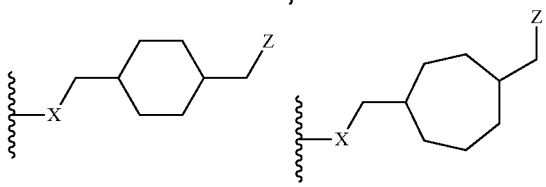

1 or 2 or more of the methylene groups constituting the lower alkylene group forming the (i) to (xv) each independently may be substituted with an oxygen atom, a carbonyl group, a vinylene group or the general formula: —N($R^c$)— for the total methylene groups, and/or the hydrogen constituting the methylene group may be substituted with a hydroxyl group, a lower alkyl group or a halogen atom.

$R^c$ is a hydrogen atom, a lower alkyl group, a halo-lower alkyl group or a lower alkanoyl group.

Accordingly, the combination of —X—Y— in General Formula (I) is exemplified as follows:

(1) when X is a single bond and Y is a single bond, General Formula (I) is represented by the formula described below.

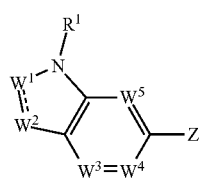

(2) when X is a single bond and Y is $(CR^{Yi}R^{Yi'})_n$, General Formula (I) is represented by the formula described below.

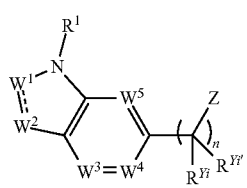

(3) when X is an oxygen atom and Y is $(CR^{Yi}R^{Yi'})_n$, General Formula (I) is represented by the formula described below.

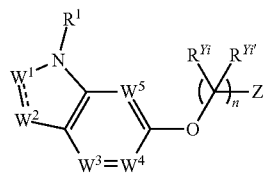

(4) when X is a carbonyl group and Y is $(CR^{Yi}R^{Yi'})_n$, General Formula (I) is represented by the formula described below.

(5) when X is a vinylene group and Y is a single bond, General Formula (I) is represented by the formula described below.

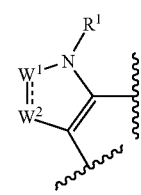

Z is a hydroxyl group, $COOR^2$, $CONR^3R^4$, $SO_3R^2$, $SO_3NR^3R^4$, a 5-tetrazolyl group, a 5-oxo-1,2,4-oxadiazolyl group, a 2-oxo-1,3,4-oxadiazolyl group, a 5-imino-4,5-dihydro-1,3,4-oxadiazolyl group, a 2-thioxo-1,3,4-oxadiazolyl group, or a 5-oxo-1,2,4-thiadiazolyl group.

$R^2$, $R^3$, and $R^4$ are each independently a hydrogen atom or a lower alkyl group.

Preferable embodiments of the present invention can also be expressed as (1) to (9) described below.

(1) The compound of Formula (I), wherein the substructure described below:

is selected from the followings:

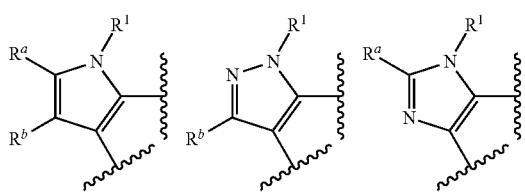

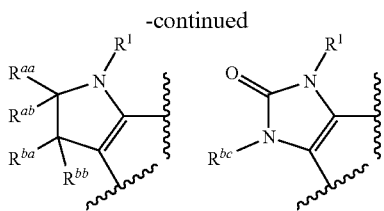

or a pharmaceutically acceptable salt or ester of the compound.

(2) The compound or a pharmaceutically acceptable salt or ester of the compound as described in the (1), wherein $W^3$, $W^4$, and $W^5$ are each independently a nitrogen atom, or a methine group that may have a substituent selected from the group consisting of a halogen atom and a lower alkyl group.

(3) The compound or a pharmaceutically acceptable salt or ester of the compound as described in the (2), wherein X is a single bond, an oxygen atom, a carbonyl group, a vinylene group or a group represented by the general formula: —N($R^X$)—.

(4) The compound or a pharmaceutically acceptable salt or ester of the compound as described in the (3), wherein $R^1$ is a group represented by the general formula: -$Q^1$-$A^1$.

(5) The compound or a pharmaceutically acceptable salt or ester of the compound as described in the (4), wherein $Q^1$ is a single bond or a lower alkylene group that may be substituted with a lower alkyl group.

(6) The compound or a pharmaceutically acceptable salt or ester of the compound as described in the (5), wherein Y is a single bond or $(CR^{Yi}R^{Yi'})_n$ (herein n is any integer of 1 to 6, i is any integer of 1 to n, and $(CR^{Yi}R^{Yi'})_n$ represents $(CR^{Y1}R^{Y1'})$ when n=1; represents $(CR^{Y1}R^{Y1'})$—$(CR^{Y2}R^{Y2'})$ when n=2; represents $(CR^{Y1}R^{Y1'})$—$(CR^{Y2}R^{Y2'})$—$(CR^{Y3}R^{Y3'})$ when n=3; represents $(CR^{Y1}R^{Y1'})$—$(CR^{Y2}R^{Y2'})$—$(CR^{Y3}R^{Y3'})$—$(CR^{Y4}R^{Y4'})$ when n=4; represents $(CR^{Y1}R^{Y1'})$—$(CR^{Y2}R^{Y2'})$—$(CR^{Y3}R^{Y3'})$—$(CR^{Y4}R^{Y4'})$—$(CR^{Y5}R^{Y5'})$ when n=5; and represents $(CR^{Y1}R^{Y1'})$—$(CR^{Y2}R^{Y2'})$—$(CR^{Y3}R^{Y3'})$—$(CR^{Y4}R^{Y4'})$—$(CR^{Y5}R^{Y5'})$—$(CR^{Y6}R^{Y6'})$ when n=6, wherein $R^{Y1}$, $R^{Y1'}$, $R^{Y2}$, $R^{Y2'}$, $R^{Y3}$, $R^{Y3'}$, $R^{Y4}$, $R^{Y4'}$, $R^{Y5}$, $R^{Y5'}$, $R^{Y6}$ and $R^{Y6'}$ are each independently a hydrogen atom, a halogen atom or a substituent selected from the <Substituent group N>.

(7) The compound or a pharmaceutically acceptable salt or ester of the compound as described in the (6), wherein $Q^1$ is a methylene group.

(8) The compound or a pharmaceutically acceptable salt or ester of the compound as described in the (7), wherein the aryl group or the heteroaryl group of $A^1$ is a phenyl group, a naphthyl group, a pyridyl group, a pyridazinyl group, a pyrazinyl group, a pyrimidinyl group, a quinolyl group, an isoquinolyl group, or a benzothienyl group.

(9) The compound or a pharmaceutically acceptable salt or ester of the compound as described in the (8), wherein the <Substituent group L> is the group consisting of a hydroxyl group, a halogen atom, a cyano group, a methyl group, an ethyl group, a cyclopropyl group, a trifluoromethyl group, a hydroxymethyl group, a methoxy group, and a trifluoromethoxy group.

A compound shown by the above-mentioned Formula (I) or pharmaceutically acceptable salt or ester includes, for example, a compound given in an example, or a pharmaceutically acceptable salt or ester of the compound. Among them, compounds (a)-(s) provided below and a pharmaceutically acceptable salt or ester of the compound are more preferable:

(a) 1-(2,6-dimethylbenzyl)-3-methyl-1H-indole-6-carboxylic acid (Example 61)

(b) 2-[1-(2,6-dimethylbenzyl)-3-methyl-1H-indole-6-yl]acetic acid (Example 64)

(c) 2-[1-(2,6-dimethylbenzyl)-3-methyl-1H-indazole-6-yl]acetic acid (Example 66)

(d) 2-[3-chloro-1-(2,6-dimethylbenzyl)-1H-indole-6-yl]acetic acid (Example 68)

(e) 2-[1-(2,6-dimethylbenzyl)-2,3-dihydro-1H-indole-6-yl]acetic acid (Example 75)

(f) (3-RS)-2-[1-(2,6-dimethylbenzyl)-2,3-dihydro-3-methyl-1H-indole-6-yl]acetic acid (Example 78)

(g) 2-[1-(2,6-dimethylbenzyl)-2,3-dihydro-3,3-dimethyl-1H-indole-6-yl]acetic acid (Example 80)

(h) 2-[1-(2,6-dichlorobenzyl)-3-methyl-1H-indole-6-yl]acetic acid (Example 82)

(i) 2-[1-(2,6-dichlorobenzyl)-3-methyl-1H-indazole-6-yl]acetic acid (Example 97)

(j) 2-[1-(2-chloro-6-methylbenzyl)-3-methyl-1H-indazole-6-yl]acetic acid (Example 102)

(k) 3-[1-(2,6-dichlorobenzyl)-3-methyl-1H-indazole-6-yl]propionic acid (Example 122)

(l) 1-(2,6-dichlorobenzyl)-3-methyl-6-(1H-tetrazole-5-ylmethyl)-1H-indazole (Example 134)

(m) 2-[1-(2,6-dichlorobenzyl)-3-ethyl-1H-indazole-6-yl]acetic acid (Example 140)

(n) 1-(2-chloro-6-methylbenzyl)-3-methyl-6-(1H-tetrazole-5-yl)-1H-pyrazolo[4,3-b]pyridine (Example 160)

(o) 1-(2-chloro-6-cyclopropylbenzyl)-3-methyl-6-(1H-tetrazole-5-yl)-1H-pyrazolo[4,3-b]pyridine (Example 164)

(p) 3-chloro-1-(2,6-dichlorobenzyl)-1H-pyrazolo[4,3-b]pyridine-6-carboxylic acid (Example 172)

(q) 3-chloro-1-(2-chloro-6-methylbenzyl)-1H-pyrazolo[4,3-b]pyridine-6-carboxylic acid (Example 174)

(r) 3-chloro-1-(2-chloro-6-methylbenzyl)-6-(1H-tetrazole-5-yl)-1H-pyrazolo[4,3-b]pyridine (Example 177)

(s) [1-(2,6-dichlorobenzyl)-3-methyl-1H-indazole-6-yl]difluoroacetic acid (Example 183).

The compound of the present invention may have an asymmetrical center, a chiral axis, and a chiral plane.

The compound of the present invention may occur as a racemate, a racemic mixture, and an individual diastereomer.

In addition, all possible isomers including optical isomers, and mixtures thereof are all included in the present invention.

Further, the compound disclosed in the present specification may be present as a tautomer, and although the compound is depicted as only one tautomer structure, both tautomer types are intended to be encompassed by the scope of the present invention.

The substitution in, for example, an oxygen atom, a carbonyl group, a vinylene group or a group represented by the general formula: —N($R^c$)— of the methylene group constituting the lower alkylene group in the present invention is accepted when the substitution is chemically accepted, and as a result, results in a stable compound.

In addition, the present invention also encompasses N-oxide of the compound represented by Formula (I) in the scope thereof. Generally, the N-oxide may be formed on any available nitrogen atom. The N-oxide may be formed by an ordinary means, for example, reaction of the compound of Formula (I) with oxone in the presence of wet alumina.

Next, the aforementioned "pharmaceutically acceptable salt or ester" will be described.

The "salt" of the compound of the present invention means pharmaceutically acceptable conventional ones. For example, examples of thereof include base addition salts in a carboxyl group, a hydroxyl group or an acidic heteroaryl group when the salt has the carboxyl group, the hydroxyl group or an acidic heteroaryl group such as a tetrazolyl group, and acid addition salts in an amino group or a basic heteroaryl group when the salt has the amino group or the basic heteroaryl group.

Examples of the base addition salt include alkali metal salts such as a sodium salt and a potassium salt; alkali earth metal salts such as a calcium salt and a magnesium salt; an ammonium salt; organic amine salts such as a trimethylamine salt, atriethylamine salt, adicyclohexylamine salt, an ethanolamine salt, a diethanolamine salt, a triethanolamine salt, a procaine salt, an N,N'-dibenzylethylenediamine salt, and the like.

Examples of the acid addition salt include inorganic acid salts such as a hydrochloric acid salt, a sulfuric acid salt, a nitric acid salt, a phosphoric acid salt, and a perchloric acid salt; organic acid salts such as a maleic acid salt, a fumaric acid salt, a tartaric acid salt, a citric acid salt, an ascorbic acid salt, and a trifluoroacetic acid salt; sulfonic acid salts such as a methane sulfonic acid salt, an isethionic acid salt, a benzene sulfonic acid salt, and a p-toluene sulfonic acid salt and the like.

The "ester" of the compound of the present invention means pharmaceutically acceptable conventional ones, where a carboxyl group is included, for example, in the carboxyl group. Examples of the ester include ester with lower alkyl groups, such as a methyl group, an ethyl group, a propyl group, an isopropyl group, a butyl group, a sec-butyl group, a tert-butyl group, a pentyl group, an isopentyl group, and a neopentyl group, ester with a cycloalkyl group, such as a cyclopropyl group, a cyclobutyl group, and a cyclopentyl group, ester with an aralkyl group, such as a benzyl group and a phenethyl group, ester with a lower alkenyl group, such as an allyl group and a 2-butenyl group, ester with lower alkoxy lower alkyl groups, such as a methoxymethyl group, a 2-methoxyethyl group, and a 2-ethoxyethyl group, ester with a lower alkanoloxy lower alkyl group, such as an acetoxy methyl group, a pivaloyloxymethyl group, and a 1-pivaloyloxyethyl group, ester with a lower alkoxycarbonyl lower alkyl group, such as a methoxycarbonylmethyl group and an isopropoxycarbonylmethyl group, ester with a carboxy lower alkyl group, such as a carboxymethyl group, ester with a lower alkoxycarbonyloxy lower alkyl group, such as a 1-(ethoxycarbonyloxy)ethyl group, and a 1-(cyclohexyloxy carbonyloxy)ethyl group, ester with a carbamoyloxy lower alkyl group, such as a carbamoyl oxymethyl group, ester with a phthalidyl group, ester with a (5-substituted-2-oxo-1,3-dioxole-4-yl)methyl group, such as a (5-methyl-2-oxo-1,3-dioxole-4-yl)methyl group, and the like.

A method of manufacturing a pharmaceutically acceptable salt of the compound of the present invention can be performed by appropriately combining methods that are ordinarily used in the field of organic synthesis chemistry. Specifically, examples of the method include a method of neutralizing and titrating a solution of a free-form compound of the present invention with an alkali solution or acidic solution, and the like.

A method of manufacturing the ester of the compound of the present invention can be performed by appropriately combining methods that are ordinarily used in the field of organic synthesis chemistry. Specifically, the ester of the compound of the present invention can be manufactured by esterification of a free carboxyl group in accordance with an ordinary method.

The "pharmaceutically acceptable salt" of the present invention also includes a solvate with a pharmaceutically acceptable solvent such as water or ethanol.

Next, a method of manufacturing the compound of the present invention will be specifically described. However, the present invention is not limited to these methods of manufacturing. When the compound of the present invention is manufactured, the order of the reactions may be appropriately changed. The reaction may be performed from a process or site that is regarded rational.

In addition, a process of converting a substituent (conversion or further modification of the substituent) may be appropriately inserted between respective processes. When there is a reactive functional group, protection or de-protection may be appropriately performed. In addition, in order to promote the progress of the reaction, a reagent besides the exemplified reagent may be used appropriately. In heating each reaction, microwave irradiation may be used as necessary. In addition, a raw material compound not described for a method of manufacturing is a commercial compound, or a compound that can be easily prepared by combination of known synthesis reactions.

The compound obtained in each process can be isolated and purified with an ordinary method conventionally used such as crystallization, re-crystallization, column chromatography, and preparative HPLC, or may proceed to the next process without isolation and purification as the case may be.

The "room temperature" in the methods of manufacturing below means 1 to 40° C.

Schemes 1 to 8 below are general synthesis methods of the compound of Formula (I).

Scheme 1: Method of manufacturing compound of Formula (I) from compound of Formula (II)

Scheme 1

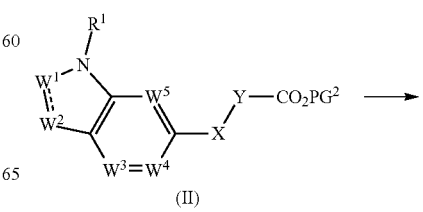

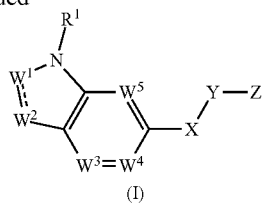

(I)

The compound of Formula (I) [in the formula, $R^1$, $W^1$, $W^2$, $W^3$, $W^4$, $W^5$, X, and Y are as described above, and Z is COOH.] can be obtained by removing the protective group $PG^2$ of the compound represented by Formula (II) [in the formula, $R^1$, $W^1$, $W^2$, $W^3$, $W^4$, $W^5$, X, and Y are as described above, and $PG^2$ is a protective group.].

Herein, the protective group $PG^2$ of Formula (II) is not particularly limited as long as it has the function thereof, but examples thereof include a lower alkyl group such as a methyl group, an ethyl group, a propyl group, an isopropyl group, and a tert-butyl group; a halo-lower alkyl group such as a 2,2,2-trichloroethyl group; a lower alkenyl group such as an allyl group; and an aralkyl group such as a benzyl group, a p-methoxybenzyl group, a p-nitrobenzyl group, a benzhydryl group, and a trityl group, particularly preferably, a methyl group, an ethyl group, a tert-butyl group, an allyl group, a benzyl group, a p-methoxybenzyl group, a benzhydryl group, and the like.

A method for removal of the protective group varies depending on the kind of protective group and the stability of the object compound (I) and the like, but is performed by, for example, in accordance with the method described in the document [see Protective Groups in Organic Synthesis, 3rd Edition, by T. W. Greene, John Wiley & Sons (1999)] or a similar method thereto, for example, solvolysis using an acid or base, specifically, for example, a method of reacting 0.01 mole to a large excess of an acid, preferably trifluoroacetic acid, formic acid, hydrochloric acid, and the like, or equal mole to a large excess of a base, preferably potassium hydroxide, calcium hydroxide, and the like; chemical reduction using a metal hydride complex and the like; or catalytic reduction using a palladium-carbon catalyst, a Raney nickel catalyst, and the like; and the like.

Scheme 2: Method of manufacturing compound of Formula (II) from compound of Formula (III)

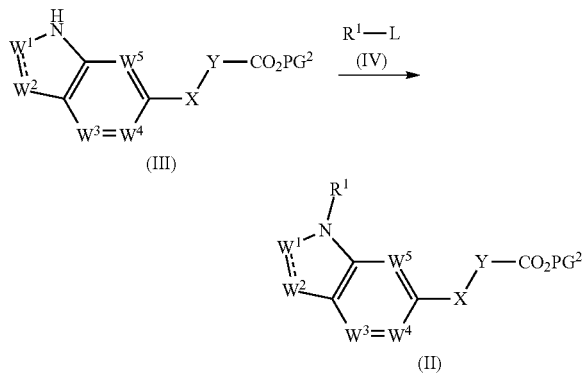

The compound of Formula (II) [in the formula, $R^1$, $W^1$, $W^2$, $W^3$, $W^4$, $W^5$, X, and Y are as described above, and $PG^2$ is a protective group.] can be obtained by alkylation reaction of the compound represented by Formula (III) [in the formula, $W^1$, $W^2$, $W^3$, $W^4$, W, X, and Y are as described above, and $PG^2$ is a protective group.] and the compound of Formula (IV) [in the formula, $R^1$ is as described above, and L represents a leaving group.].

The leaving group L of Formula (IV) is not particularly limited as long as it produces the compound (II) by elimination by reaction with the compound (II), and examples of the leaving group include a halogen atom (a chlorine atom, a bromine atom, and the like), a p-toluenesulfonyl group, a methanesulfonyl group, and the like, and preferably a bromine atom, a chlorine atom, a p-toluenesulfonyl group, and the like.

The amount of the compound (IV) with respect to 1 mole of the used compound (III) is ordinarily 1 to 10 mole, and preferably 1 to 3 mole.

Examples of the used base include sodium carbonate, potassium carbonate, a sodium hydrogen carbonate, a sodium hydride, a potassium hydroxide, and the like, and preferably a potassium carbonate, a sodium hydride, a potassium hydroxide, and the like.

The amount of the base is ordinarily 1 to 10 mole, and preferably 1 to 5 mole with respect to 1 mole of the compound (III).

The reaction temperature is ordinarily 0° C. to 160° C., and preferably 25° C. to 100° C.

The reaction time is ordinarily 1 hour to 24 hours, and preferably 1 hour to 12 hours.

The reaction solvent is not particularly limited as long as it has no adverse effect on the reaction, but is preferably a solvent such as dimethylformamide, N-methyl-2-pyrrolidone, tetrahydrofuran, 1,4-dioxane, acetone, methylethylketone, and acetonitrile.

Scheme 3: Method of manufacturing compound of Formula (III) from compound of Formula (V)

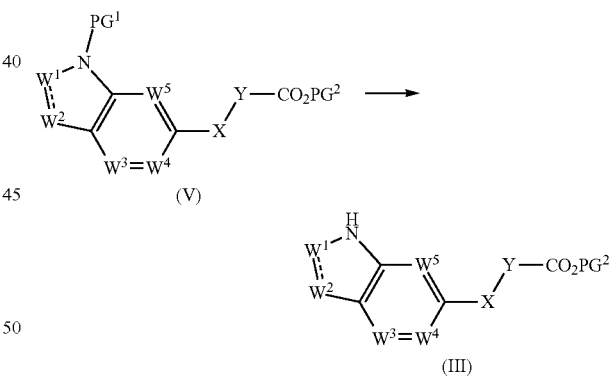

The compound of Formula (III) [in the formula, $W^1$, $W^2$, $W^3$, $W^4$, $W^5$, X, and Y are as described above, and $PG^2$ represents a protective group.] can be obtained by removing the protective group $PG^1$ of the compound represented by Formula (V) [in the formula, $W^1$, $W^2$, $W^3$, $W^4$, $W^5$, X, and Y are as described above, and $PG^1$ and $PG^2$ represent a protective group.].

Herein, the protective group $PG^1$ of the above-mentioned Formula (V) is not particularly limited if it has the function, but examples of the group include: an aralkyl group, such as a benzyl group, a p-methoxybenzyl group, a 3,4-dimethoxybenzyl group, an o-nitrobenzyl group, a p-nitrobenzyl group, a benzhydryl group, and a trityl group; a lower alkanoyl group such as a formyl group, an acetyl group, a propionyl group, a butyryl group and a pivaloyl group; a benzoyl group; an aryl alkanoyl group such as a phenylacetyl group and a phenoxyacetyl group; a lower alkoxycarbonyl group such as a methoxycarbonyl group, an ethoxycarbonyl group, a propyloxycarbonyl group, and a tert-butoxycarbonyl group; an aralkyloxycarbonyl group such as a benzyloxycarbonyl group, a p-nitrobenzyloxycarbonyl group and a phenethyloxycarbonyl group; a lower alkyl silyl group such as a trimethylsilyl group and a tert-butyldimethylsilyl group; a tetrahydropyranyl group; a trimethylsilylethoxymethyl group; a lower alkylsulfonyl group such as a methylsulfonyl group and an ethylsulfonyl group; and an arylsulfonyl group such as a benzenesulfonyl group and a p-toluenesulfonyl group, and particularly preferably, a tert-butoxycarbonyl group, a methylsulfonyl group, a p-toluenesulfonyl group and the like.

A method for removal of the protective group varies depending on the kind of protective group and the stability of the object compound (III) and the like, but is performed by, for example, in accordance with the method described in the document [see Protective Groups in Organic Synthesis, 3rd Edition, by T. W. Greene, John Wiley & Sons (1999)] or a similar method thereto, for example, solvolysis using an acid or base, specifically, for example, method of reacting 0.01 mole to a large excess of an acid, preferably trifluoroacetic acid, formic acid, hydrochloric acid, and the like; equal mole to a large excess of a base, preferably potassium hydroxide, calcium hydroxide, and the like; chemical reduction using a metal hydride complex, and the like; or catalytic reduction using a palladium-carbon catalyst, a Raney nickel catalyst and the like; and the like.

Scheme 4: Method of manufacturing compound of Formula (V) from compound of Formula (VI)

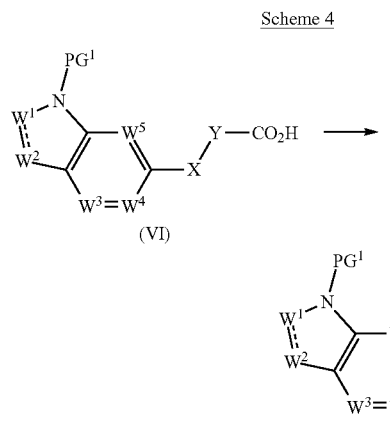

The compound of Formula (V) [in the formula, $W^1$, $W^2$, $W^3$, $W^4$, $W^5$, X, and Y are as described above, and $PG^1$ and $PG^2$ represent a protective group.] can be obtained by esterification of the compound represented by Formula (VI) [in the formula, $W^1$, $W^2$, $W^3$, $W^4$, $W^5$, X, and Y are as described above, and $PG^1$ represents a protective group.].

Herein, the protective group $PG^2$ of Formula (V) is not particularly limited as long as it has the function thereof, but examples thereof include a lower alkyl group such as a methyl group, an ethyl group, a propyl group, an isopropyl group, and a tert-butyl group; a halo-lower alkyl group such as a 2,2,2-trichloroethyl group; a lower alkenyl group such as an allyl group; and an aralkyl group such as a benzyl group, a p-methoxybenzyl group, a p-nitrobenzyl group, a benzhydryl group, and a trityl group, and particularly preferably, a methyl group, an ethyl group, a tert-butyl group, an allyl group, a benzyl group, a p-methoxybenzyl group, a benzhydryl group, and the like.

A method for introduction of the protective group varies depending on the kind of protective group and the stability of the compound and the like, but the protective group can be synthesized, for example, in accordance with the method described in the document [see Protective Groups in Organic Synthesis, 3rd Edition, by T. W. Greene, John Wiley & Sons (1999)] or a similar method thereto.

Scheme 5: Method of manufacturing compound of Formula (VI) from compound of Formula (VII)

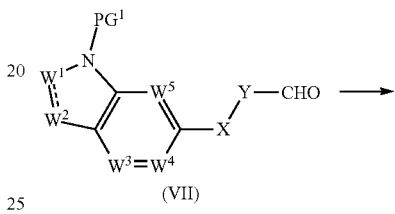

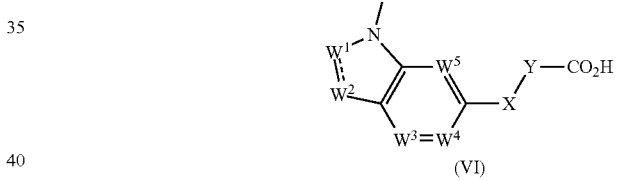

The compound of Formula (VI) [in the formula, $W^1$, $W^2$, $W^3$, $W^4$, $W^5$, X, and Y are as described above, and $PG^1$ represents a protective group.] can be obtained by oxidization reaction of the compound represented by Formula (VII) [in the formula, $W^1$, $W^2$, $W^3$, $W^4$, $W^5$, X, and Y are as described above, and $PG^1$ represents a protective group.]. For example, the compound of Formula (VI) can be synthesized by reacting sodium chlorite in the presence of 2-methyl-2-butene and sodium dihydrogen phosphate in a mixed solvent of tert-butanol-water.

In the reaction, ordinarily 1 to 20 mole, and preferably 1 to 10 mole of 2-methyl-2-butene, ordinarily 1 to 5 mole, and preferably 1 to 3 mole of sodium dihydrogen phosphate, and ordinarily 1 to 10 mole, and preferably 1 to 5 mole of sodium chlorite are used with respect to 1 mole of the compound (VII).

The reaction temperature is ordinarily 0° C. to 100° C., and preferably 0° C. to 40° C.

The reaction time is ordinarily 1 hour to 24 hours, and preferably 1 hour to for 6 hours.

The reaction solvent is not particularly limited as long as it has no adverse effect on the reaction, but is preferably water or a mixed solvent of water and a water-soluble solvent such as tert-butanol or acetonitrile.

Scheme 6: Method of manufacturing compound of Formula (VII) from compound of Formula (VIII)

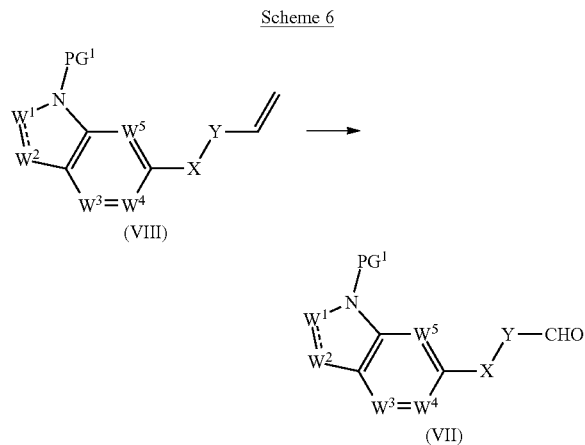

(VIII)

(VII)

The compound of Formula (VII) [in the formula, $W^1$, $W^2$, $W^3$, $W^4$, $W^5$, X, and Y are as described above, and $PG^1$ represents a protective group.] can be obtained by oxidization reaction of the compound represented by Formula (VIII) [in the formula, $W^1$, $W^2$, $W^3$, $W^4$, $W^5$, X, and Y are as described above, and $PG^1$ represents a protective group.]. For example, the compound of Formula (VII) can be synthesized by reacting osmium tetraoxide and sodium periodate in a mixed solvent of tert-butanol-water.

In the reaction, ordinarily 0.0001 to 1 mole, and preferably 0.01 to 1 mole of osmium tetraoxide, and ordinarily 1 to 10 mole, and preferably 1 to 5 mole of sodium periodate are used with respect to 1 mole of the compound (VIII).

The reaction temperature is ordinarily 0° C. to 100° C., and preferably 0° C. to 40° C.

The reaction time is ordinarily 1 hour to 24 hours, and preferably 1 hour to 12 hours.

The reaction solvent is not particularly limited as long as it has no adverse effect on the reaction, but is preferably a mixed solvent of water and a water-soluble solvent such as tert-butanol, dioxane or acetone.

Scheme 7: Method of manufacturing compound of Formula (VIII) from compound of Formula (IX)

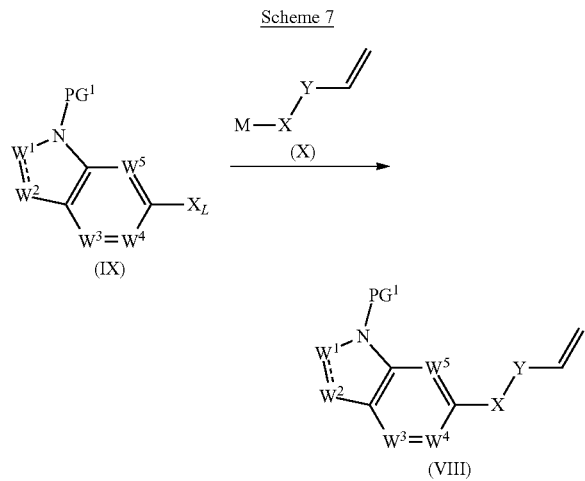

(IX)

(VIII)

The compound of Formula (VIII) [in the formula, $W^1$, $W^2$, $W^3$, $W^4$, $W^5$, X, and Y are as described above, and $PG^1$ represents a protective group.] can be obtained by coupling reaction of the compound represented by Formula (IX) [in the formula, $W^1$, $W^2$, $W^3$, $W^4$, and $W^5$ are as described above, and $PG^1$ represents a protective group, and $X_L$ is a halogen atom.] and Formula (X) [in the formula, X and Y are as described above, and M is boron, tin and the like.]. More specifically, the compound (VIII) can be obtained by reacting the compound (IX) that has a halogen atom and $(HO)_2B$—X—Y—CH=$CH_2$ or $(n-Bu)_3Sn$—X—Y—CH=$CH_2$ in the presence of a base and a palladium catalyst (further a phosphine ligand as necessary).

In the reaction, ordinarily 1 to 10 mole, and preferably 1 to 3 mole of the compound (X) is used with respect to 1 mole of the compound (IX).

Examples of the compound (X) include tributylvinyl tin, tributylallyl tin and the like.

Examples of the used base include sodium carbonate, potassium carbonate, cesium carbonate, cesium fluoride, potassium fluoride, sodium fluoride, lithium chloride, and the like.

The amount of the used base is ordinarily 1 to 10 mole, and preferably 1 to 3 mole with respect to 1 mole of the compound (IX).

Examples of the used palladium catalyst include $Pd(PPh_3)_4$, $Pd(OAc)_2$, $Pd_2(dba)_3$, $PdCl_2(PPh_3)_2$, and the like.

The amount of the used palladium catalyst is ordinarily 0.01 to 0.5 mole, and preferably 0.05 to 0.2 mole with respect to 1 mole of the compound (IX).

Examples of the used phosphine ligand include $PPh_3$, P(o-tol)$_3$, P(tert-Bu)$_3$, 2-[di(tert-butyl)phosphino]-1,1'-biphenyl, 2-[di(tert-butyl)phosphino]-2'-dimethylamino-1,1'-biphenyl, 2-[dicyclohexylphosphino]-1,1'-biphenyl, 2-[dicyclohexylphosphino]-2'-dimethylamino-1,1'-biphenyl and the like.

The reaction temperature is ordinarily 0° C. to 200° C., and preferably 25° C. to 130° C.

The reaction solvent is not particularly limited as long as it has no adverse effect on the reaction, but is preferably a solvent such as dimethylformamide, tetrahydrofuran, 1,4-dioxane, acetonitrile, and toluene.

Scheme 8: Method of manufacturing compound of Formula (IX) from compound of Formula (XI)

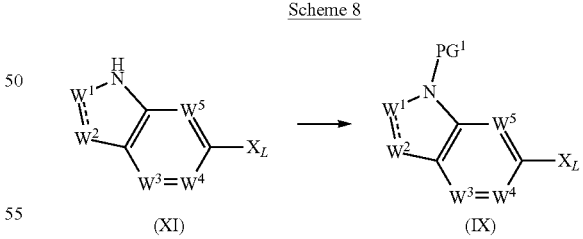

(XI)

(IX)

The compound of Formula (IX) [in the formula, $W^1$, $W^2$, $W^3$, $W^4$, and $W^5$ are as described above, and $PG^1$ represents a protective group, and $X_L$ is a halogen atom.] can be obtained by protecting the compound represented by Formula (XI) [in the formula, $W^1$, $W^2$, $W^3$, $W^4$, and $W^5$ are as described above, and $X_L$ is a halogen atom.] with the protective group $PG^1$.

The compound (XI) is a commercially available compound or a compound known in a document and the like.

Herein, the protective group $PG^1$ of the above-mentioned Formula (IX) is not particularly limited as long as it has the function thereof, examples of the group include an aralkyl group such as a benzyl group, a p-methoxybenzyl group, a 3,4-dimethoxybenzyl group, an o-nitrobenzyl group, a p-nitrobenzyl group, a benzhydryl group, and a trityl group; a lower alkanoyl group such as a formyl group, an acetyl group, a propionyl group, a butyryl group, and a pivaloyl group; a benzoyl group; an aryl alkanoyl group, such as a phenylacetyl group and a phenoxyacetyl group; a lower alkoxycarbonyl group, such as a methoxycarbonyl group, an ethoxycarbonyl group, a propyloxy carbonyl group, and a tert-butoxycarbonyl group; an aralkyloxy carbonyl group such as a benzyloxycarbonyl group, a p-nitrobenzyloxycarbonyl group, and a phenethyloxycarbonyl group; a lower alkyl silyl group such as a trimethylsilyl group and a tert-butyldimethylsilyl group; a tetrahydropyranyl group; a trimethylsilylethoxymethyl group; a lower alkylsulfonyl group, such as a methylsulfonyl group and an ethylsulfonyl group; an arylsulfonyl group such as a benzenesulfonyl group and a p-toluenesulfonyl group, and in particular, a tert-butoxycarbonyl group, a methylsulfonyl group, a p-toluenesulfonyl group, and the like, are preferable.

A method for introduction of the protective group varies depending on the kind of protective group and the stability of the compound and the like, but the protective group can be synthesized, for example, in accordance with the method described in the document [see Protective Groups in Organic Synthesis, 3rd Edition, by T. W. Greene, John Wiley & Sons (1999)] or a similar method thereto.

Schemes 9 to 10 below are synthesis methods of the compound of Formula (XV) wherein ---- is a double bond, and the substituent $R^b$ is a halogen atom or the general formula: $-Q^2-A^2$ in Formula (I).

Scheme 9: Method of manufacturing compound of Formula (XIII) from compound of Formula (XII)

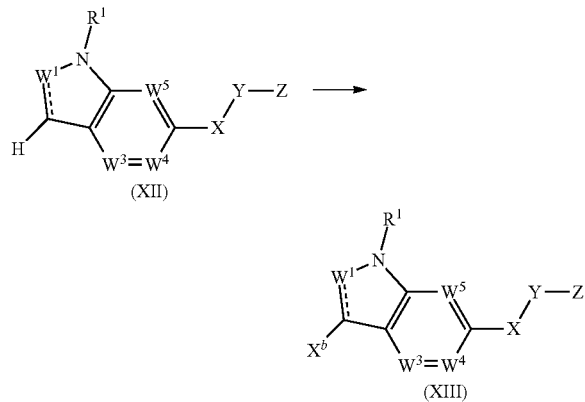

The compound of Formula (XIII) [in the formula, $R^1$, $W^1$, $W^3$, $W^4$, $W^5$, X, Y, and Z are as described above, and $X^b$ is a halogen atom.] can be obtained by halogenation of the compound represented by Formula (XII) [in the formula, $R^1$, $W^1$, $W^3$, $W^4$, $W^5$, X, Y, and Z are as described above.]. More specifically, the compound (XIII) can be obtained by reacting the compound of Formula (XII) and N-chlorosuccinamide or N-bromosuccinamide, and the like.

In the reaction, ordinarily 1 to 10 mole, and preferably 1 to 3 mole of the halogenating agent is used with respect to 1 mole of the compound (XII).

Examples of the halogenating agent include N-chlorosuccinamide, N-bromosuccinamide and the like.

The reaction temperature is ordinarily 0° C. to 100° C., and preferably 0° C. to 25° C.

The reaction solvent is not particularly limited as long as it has no adverse effect on the reaction, but is preferably a solvent such as tetrahydrofuran, 1,4-dioxane, chloroform, and acetonitrile.

Scheme 10: Method of manufacturing compound of Formula (XV) from compound of Formula (XIII)

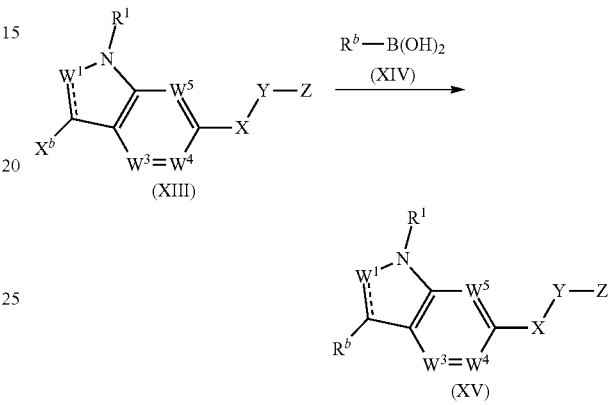

The compound of Formula (XV) [in the formula, $R^1$, $R^b$, $W^1$, $W^3$, $W^4$, $W^5$, X, Y, and Z are as described above.] can be obtained by coupling reaction of the compound represented by Formula (XIII) [in the formula, $R^1$, $W^1$, $W^3$, $W^4$, $W^5$, X, Y, and Z are as described above, and $X^b$ is a halogen atom.] and the compound represented by Formula (XIV) [in the formula, $R^b$ is an aryl group, a heteroaryl group, a lower alkyl group, a cyclo-lower alkyl group, a lower alkenyl group, or the like.]. More specifically, the compound (XV) can be obtained by reacting the compound (XIII) that has a halogen atom, and $R^b$—B $(OH)_2$ and the like in the presence of a base and a palladium catalyst (further a phosphine ligand as necessary).

In the reaction, ordinarily 1 to 10 mole, and preferably 1 to 3 mole of $R^b$—B $(OH)_2$ is used with respect to 1 mole of the compound (XIII).

As the $R^b$—B $(OH)_2$, for example, a commercial aryl boron derivative, a heteroaryl boron derivative, a vinyl boron derivative, an allyl boron derivative, a lower alkyl boron derivative, and a cyclo-lower alkyl boron derivative such as phenyl boronic acid, phenyl boronic acid ester, and dialkyl phenyl borane may be used. In addition, the intended boron derivative can be manufactured by a known method, a similar method thereto, or a combination thereof with an ordinary method.

Examples of the used base include sodium carbonate, potassium carbonate, cesium carbonate, cesium fluoride, potassium fluoride, sodium fluoride, and the like.

The amount of the used base is ordinarily 1 to 10 mole, and preferably 1 to 3 mole with respect to 1 mole of the compound (XIII).

Examples of the used palladium catalyst include $Pd(PPh_3)_4$, $Pd(OAc)_2$, $Pd_2(dba)_3$, $PdCl_2(PPh_3)_2$, and the like.

The amount of the used palladium catalyst is ordinarily 0.01 to 0.5 mole, and preferably 0.05 to 0.2 mole with respect to 1 mole of the compound (XIII).

Examples of the used phosphine ligand include $PPh_3$, P(o-tol)$_3$, P(tert-Bu)$_3$, 2-[di(tert-butyl)phosphino]-1,1'-biphenyl, 2-[di(tert-butyl)phosphino]-2'-dimethylamino-1,1'-biphenyl, 2-[dicyclohexylphosphino]-1,1'-biphenyl, 2-[dicyclohexylphosphino]-2'-dimethylamino-1,1'-biphenyl and the like.

The reaction temperature is ordinarily 0° C. to 200° C., and preferably 25° C. to 130° C.

The reaction solvent is not particularly limited as long as it has no adverse effect on the reaction, but is preferably a solvent such as dimethylformamide, tetrahydrofuran, 1,4-dioxane, acetonitrile, and toluene.

Schemes 11 to 16 below are other synthesis methods of the compound represented by Formula (III-I) wherein X is a single bond and Y is a methylene group in the compound of Formula (III)

Scheme 11: Method of manufacturing compound of Formula (III-1) from compound of Formula (XVI)

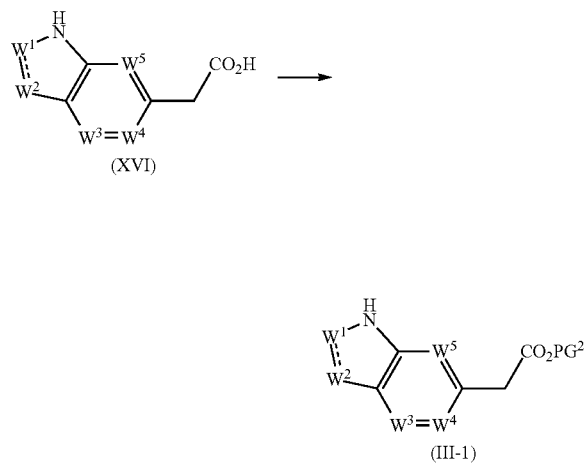

The compound of Formula (III-1) [in the formula, $W^1$, $W^2$, $W^3$, $W^4$, and $W^5$ are as described above, and $PG^2$ represents a protective group.] can be obtained by esterification of the compound represented by Formula (XVI) [in the formula, $W^1$, $W^2$, $W^3$, $W^4$, and $W^5$ are as described above.].

Herein, the protective group $PG^2$ of the above-mentioned Formula (III-1) is not particularly limited as long as it has the function thereof, but examples of the group include: a lower alkyl group such as a methyl group, an ethyl group, a propyl group, an isopropyl group and a tert-butyl group; a halo-lower alkyl group such as a 2,2,2-trichloroethyl group; a lower alkenyl group such as an allyl group; and an aralkyl group such as a benzyl group, a p-methoxybenzyl group, a p-nitrobenzyl group, a benzhydryl group, and a trityl group, and the like, and particularly preferably, a methyl group, an ethyl group, a tert-butyl group, an allyl group, a benzyl group, p-methoxybenzyl group, and a benzhydryl group, and the like.

A method for introduction of the protective group varies depending on the kind of protective group and the stability of the compound and the like, but the protective group can be synthesized, for example, in accordance with the method described in the document [see Protective Groups in Organic Synthesis, 3rd Edition, by T. W. Greene, John Wiley & Sons (1999)] or a similar method thereto.

Scheme 12: Method of manufacturing compound of Formula (XVI) from compound of Formula (XVII)

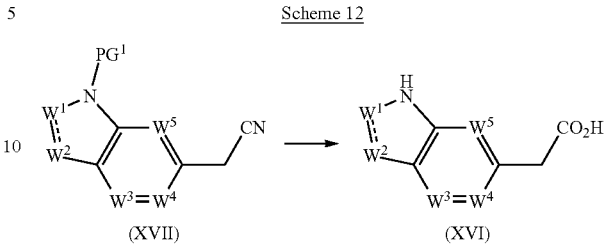

The compound of Formula (XVI) [in the formula, $W^1$, $W^2$, $W^3$, $W^4$, and $W^5$ are as described above.] can be obtained by hydrolysis of the compound represented by Formula (XVII) [in the formula, $W^1$, $W^2$, $W^3$, $W^4$, and $W^5$ are as described above, and $PG^1$ is a protective group.]. More specifically, the compound of Formula (XVI) can be obtained by de-protection of the protective group $PG^1$ along with hydrolysis of the cyano group of the compound of Formula (XVII).

Herein, the protective group $PG^1$ of a compound denoted by the above-mentioned Formula (XVII) is not particularly limited as long as it has the function thereof, but examples of the group include: a lower alkanoyl group such as a formyl group, an acetyl group, a propionyl group, a butyryl group, and a pivaloyl group; a benzoyl group; an aryl alkanoyl group such as a phenylacetyl group, phenoxyacetyl group; a lower alkoxycarbonyl group such as a methoxycarbonyl group, an ethoxycarbonyl group, a propyloxycarbonyl group, and a tert-butoxycarbonyl group; an aralkyloxycarbonyl group such as a benzyloxycarbonyl group, a p-nitrobenzyloxycarbonyl group, and a phenethyl oxycarbonyl group; a lower alkylsilyl group such as a trimethylsilyl group and a tert-butyldimethylsilyl group; a lower alkylsulfonyl group such as a methylsulfonyl group and an ethyl sulfonyl group; and an arylsulfonyl group such as a benzenesulfonyl group and a p-toluenesulfonyl group, and the like, and particularly preferably, a tert-butoxycarbonyl group, a methylsulfonyl group, and a p-toluenesulfonyl group and the like.

This hydrolysis reaction is performed by using acid or base hydrolysis, specifically, for example, a method of reacting 0.01 mole to a large excess of an acid, preferably acetic acid, formic acid, sulfuric acid, phthalic acid, hydrochloric acid and the like, or 0.01 mole to a large excess of a base, preferably sodium hydroxide, potassium hydroxide and the like.

The reaction temperature is ordinarily 0° C. to 200° C., and preferably 0° C. to 160° C.

The reaction solvent is not particularly limited as long as it has no adverse effect on the reaction, but is preferably a solvent such as methanol, ethanol, 1-propanol, 2-propanol, 1-butanol, 2-butanol, tert-butanol, tetrahydrofuran, 1,4-dioxane, cyclohexane, 1,3-dimethylbenzene, and toluene.

Scheme 13: Method of manufacturing compound of Formula (XVII) from compound of Formula (XVIII)

Scheme 13

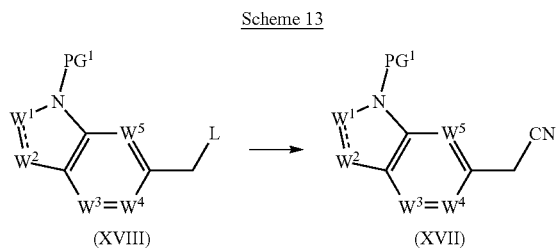

The compound of Formula (XVII) [in the formula, $W^1$, $W^2$, $W^3$, $W^4$, and $W^5$ are as described above, and $PG^1$ is a protective group.] can be obtained by cyanation of the compound represented by Formula (XVIII) [in the formula, $W^1$, $W^2$, $W^3$, $W^4$, and $W^5$ are as described above, and $PG^1$ is a protective group, and L is a leaving group.].

The leaving group L of Formula (XVIII) is not particularly limited as long as it has the function thereof, but examples thereof include a halogen atom (a chlorine atom, a bromine atom, and the like), a p-toluenesulfonyloxy group, a benzenesulfonyloxy group, a methanesulfonyloxy group, ethanesulfonyloxy, and the like, and preferably a bromine atom, a chlorine atom, a p-toluenesulfonyloxy group, a methanesulfonyloxy group, and the like.

In the reaction, ordinarily 1 mole to 10 mole, and preferably 1 mole to 3 mole of the cyanide is used with respect to 1 mole of the compound (XVIII).

Examples of the used cyanide include lithium cyanide, sodium cyanide, potassium cyanide, tetraethyl cyanide, trimethylsilyl cyanide, tetrabutyl cyanide, and the like.

The reaction temperature is ordinarily 0° C. to 200° C., and preferably 0° C. to 160° C.

The reaction solvent is not particularly limited as long as it has no adverse effect on the reaction, but is preferably a solvent such as N,N-dimethylformamide, N,N-dimethylacetoamide, dimethylsulfoxide, methanol, ethanol, 1-propanol, 2-propanol, 1-butanol, 2-butanol, tert-butanol, tetrahydrofuran, dimethoxyethane, 1,4-dioxane, cyclohexane, 1,3-dimethylbenzene, and toluene.

Scheme 14: Method of manufacturing compound of Formula (XVIII) from compound of Formula (XIX)

Scheme 14

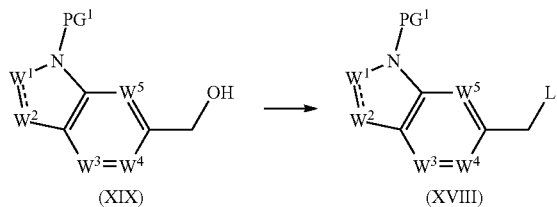

The compound of Formula (XVIII) [in the formula, $W^1$, $W^2$, $W^3$, $W^4$, and $W^5$ are as described above, and $PG^1$ is a protective group, and L is a leaving group.] can be obtained by conversion of the hydroxyl group of the compound represented by Formula (XIX) [in the formula, $W^1$, $W^2$, $W^3$, $W^4$, and $W^5$ are as described above, and $PG^1$ is a protective group.] to a leaving group such as a chlorine atom, a bromine atom, an iodine atom, a methanesulfonyloxy group, and a p-toluenesulfonyloxy group in the presence of a base.

The leaving group L of Formula (XVIII) is not particularly limited as long as it has the function thereof, but examples thereof include a halogen atom (a chlorine atom, a bromine atom and the like), a p-toluenesulfonyloxy group, a benzenesulfonyloxy group, a methanesulfonyloxy group, ethanesulfonyloxy, and the like, and preferably a bromine atom, a chlorine atom, a p-toluenesulfonyloxy group, a methanesulfonyloxy group, and the like.

In the reaction, as the compound leading to a leaving group, for example, ordinarily 1 mole to 10 mole, and preferably 1 mole to 3 mole of sulfonic acid chloride is used with respect to 1 mole of the compound (XIX).

Examples of the used sulfonic acid chloride include methane sulfonyl chloride, ethanesulfonyl chloride, p-toluene sulfonyl chloride, phenylsulfonyl chloride, and the like.

Examples of the used base include triethylamine, diisopropylethylamine, and the like.

The reaction temperature is ordinarily 0° C. to 200° C., and preferably 0° C. to 25° C.

The reaction solvent is not particularly limited as long as it has no adverse effect on the reaction, but is preferably a solvent such as chloroform, dichloromethane, tetrahydrofuran, dimethoxyethane, 1,4-dioxane, cyclohexane, 1,3-dimethyl benzene, and toluene.

In addition, the compound of Formula (XVIII) can be also obtained by Appel reaction in which the compound represented by Formula (XIX) is reacted with a halogenating agent such as carbon tetrabromide and carbon tetrachloride, and triphenyl phosphine.

In the reaction, ordinarily 1 mole to 10 mole, and preferably 1 mole to 3 mole of the halogenating agent is used with respect to 1 mole of the compound (XIX).

Examples of the used halogenating agent include carbon tetrabromide, carbon tetrachloride, hexachloroacetone, hexabromoacetone, triphosgene, lithium bromide, methane iodide, bromine, iodine, and the like.

In the reaction, ordinarily 1 mole to 10 mole, and preferably 1 mole to 3 mole of triphenylphosphine is used with respect to 1 mole of the compound (XIX).

The reaction temperature is ordinarily 0° C. to 200° C., and preferably 0° C. to 25° C.

The reaction solvent is not particularly limited as long as it has no adverse effect on the reaction, but is preferably a solvent such as chloroform, dichloromethane, tetrahydrofuran, dimethoxyethane, 1,4-dioxane, cyclohexane, 1,3-dimethylbenzene, acetonitrile, and toluene.

Scheme 15: Method of manufacturing compound of Formula (XIX) from compound of Formula (XX)

Scheme 15

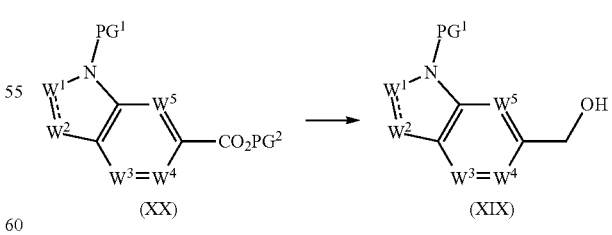

The compound of Formula (XIX) [in the formula, $W^1$, $W^2$, $W^3$, $W^4$, and $W^5$ are as described above, and PG is a protective group.] can be obtained by reduction of the compound represented by Formula (XX) [in the formula, $W^1$, $W^2$, $W^3$, $W^4$, and $W^5$ are as described above, and $PG^1$ and $PG^2$ are protective groups.]. More specifically, the compound of Formula (XIX) can be obtained by reacting the compound of Formula (XX) that has an ester, with a reducing agent such as lithium aluminum hydride.

Herein, the protective group $PG^2$ of the above-mentioned Formula (XX) is not particularly limited as long as it has the function thereof, but examples of the group include: a lower alkyl group such as a methyl group, an ethyl group, a propyl group, an isopropyl group, and a tert-butyl group; a halo-lower alkyl group, such as 2,2,2-trichloroethyl group; a lower alkenyl group, such as an allyl group; an aralkyl group such as a benzyl group, a p-methoxybenzyl group, a p-nitrobenzyl group, a benzhydryl group, and a trityl group, and the like, and particularly preferably, a methyl group, an ethyl group, a tert-butyl group, an allyl group, a benzyl group, a p-methoxybenzyl group, and a benzhydryl group.

In the reaction, ordinarily 1 mole to 10 mole, and preferably 1 mole to 3 mole of the reducing agent is used with respect to 1 mole of the compound (XX).

Examples of the used reducing agent include lithium aluminum hydride, diisobutylaluminum hydride, triethyl boron lithium hydride, bis(2-methoxyethoxy) aluminum sodium hydride, boron hydride, and the like.

The reaction temperature is ordinarily −100° C. to 200° C., and preferably 0° C. to 25° C.

The reaction solvent is not particularly limited as long as it has no adverse effect on the reaction, but is preferably a solvent such as diethyl ether, tetrahydrofuran, 1,4-dioxane, dimethoxyethane, cyclohexane, 1,3-dimethylbenzene, toluene, methanol, ethanol, 1-propanol, and 2-propanol.

Scheme 16: Method of manufacturing compound of Formula (XX) from compound of Formula (XXI)

Scheme 16

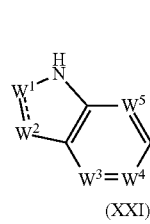

(XXI)

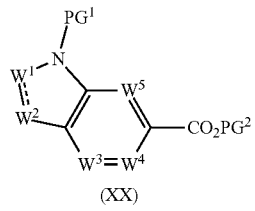

(XX)

The compound of Formula (XX) [in the formula, $W^1$, $W^2$, $W^3$, $W^4$, and $W^5$ are as described above, and $PG^1$ and $PG^2$ are protective groups.] can be obtained by protecting the compound represented by Formula (XXI) [in the formula, $W^1$, $W^2$, $W^3$, $W^4$, and $W^5$ are as described above, and $PG^2$ is a protective group.] with the protective group $PG^1$.

Herein, the protective group $PG^1$ of the above-mentioned Formula (XX) is not particularly limited as long as the function thereof, but examples of the group includes: an aralkyl group such as a benzyl group, a p-methoxybenzyl group, a 3,4-dimethoxybenzyl group, an o-nitrobenzyl group, a p-nitrobenzyl group, a benzhydryl group, and a trityl group; a lower alkanoyl group such as a formyl group, an acetyl group, a propionyl group, a butyryl group and a pivaloyl group; a benzoyl group; an aryl alkanoyl group such as a phenylacetyl group, and a phenoxyacetyl group; a lower alkoxycarbonyl group, such as a methoxycarbonyl group, an ethoxycarbonyl group, a propyloxycarbonyl group, and a tert-butoxycarbonyl group; an aralkyloxy carbonyl group such as a benzyloxycarbonyl group, p-nitrobenzyloxycarbonyl group, and a phenethyloxycarbonyl group; a lower alkyl silyl group, such as a trimethylsilyl group and a tert-butyldimethylsilyl group; tetrahydropyranyl group; a trimethylsilylethoxymethyl group; a lower alkylsulfonyl group, such as a methylsulfonyl group and an ethyl sulfonyl group; and an arylsulfonyl group such as a benzenesulfonyl group and a p-toluenesulfonyl group, and the like, and particularly preferably, a tert-butoxycarbonyl group, a methylsulfonyl group, and a p-toluenesulfonyl group and the like.

A method for introduction of the protective group varies depending on the kind of protective group and the stability of the compound and the like, but the protective group can be synthesized, for example, in accordance with the method described in the document [see Protective Groups in Organic Synthesis, 3rd Edition, by T. W. Greene, John Wiley & Sons (1999)] or a similar method thereto.

Meanwhile, examples of the compound of Formula (XXI) include, for example, methyl lindole-6-carboxylate, ethyl indole-6-carboxylate, benzyl indole-6-carboxylate, tert-butyl indole-6-carboxylate, methyl 3-methyl-1H-lindole-6-carboxylate, ethyl 3-methyl-1H-indole-6-carboxylate, methyl 3-ethyl-1H-indole-6-carboxylate, methyl 3-isopropyl-1H-indole-6-carboxylate, methyl 1H-pyrrolo[3,2-b]pyridin-6-carboxylate, methyl lindazole-6-carboxylate, ethyl indazole-6-carboxylate, methyl 3-methylindazole-6-carboxylate, and the like. The compound of Formula (XXI) may use a commercial product, or may be manufactured by appropriately combining known methods or the methods described in Examples, or a similar method thereto as necessary.

Schemes 17 to 18 below are other synthesis methods of the compound represented by Formula (II-1) wherein the group represented by X is a single bond, and the group represented by Y is an a group represented by $CR^{Y1}R^{Y1'}$ in the compound represented by Formula (II).

Scheme 17: Method of manufacturing compound of Formula (II-1) from compound of Formula (XXII)

Scheme 17

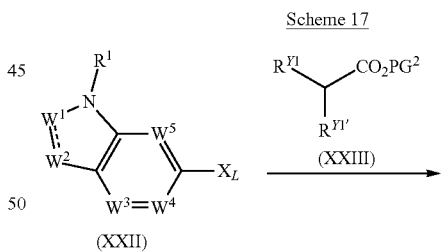

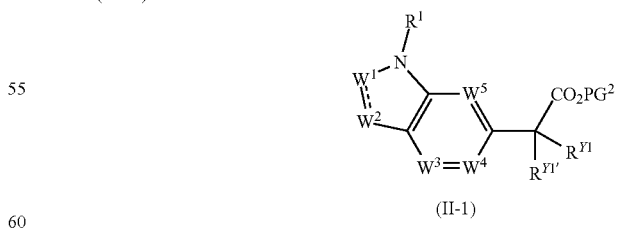

(II-1)

The compound of Formula (II-1) [in the formula, $R^1$, $R^{Y1}$, $R^{Y1', W1}$, $W^2$, $W^3$, $W^4$, and $W^5$ are as described above, and $PG^2$ represents a protective group.] can be obtained by coupling reaction of the compound represented by Formula (XXII) [in the formula, $R^1$, $W^1$, $W^2$, $W^3$, $W^4$, and W are as described above, and XL is a halogen atom.] and Formula (XXIII) [in the formula, $R^{Y1}$, $R^{Y1}$ are as described above, and $PG^2$ represents a protective group.]. More specifically, the compound (II-1) can be obtained by reacting the compound (XXII) that has a halogen atom with the compound (XXIII), in the presence of a base and a palladium catalyst (further a phosphine ligand as necessary).

In the reaction, ordinarily 1 to 10 mole, and preferably 1 to 3 mole of the compound (XXIII) is used with respect to 1 mole of the compound (XXII).

Examples of the compound (XXIII) include methyl acetate, ethyl acetate, tert-butyl acetate, methyl propionate, ethyl propionate, tert-butyl propionate, methyl isobutyrate, and the like.

Examples of the used base include lithium dicyclohexylamide, sodium dicyclohexylamide, lithium hexamethyldisilazide, sodium hexamethyldisilazide, potassium hexamethyldisilazide, lithium diisopropylamide, and the like.

The amount of the used base is ordinarily 1 to 10 mole, and preferably 1 to 3 mole with respect to 1 mole of the compound (XXII).

Examples of the used palladium catalyst include $Pd(PPh_3)_4$, $Pd(OAc)_2$, $Pd(dba)_2$, $Pd_2(dba)_3$, $PdCl_2(PPh_3)_2$, and the like.

The amount of the used palladium catalyst is ordinarily 0.01 to 0.5 mole, and preferably 0.05 to 0.2 mole with respect to 1 mole of the compound (XXII).

Examples of the used phosphine ligand include $PPh_3$, $P(o\text{-}tol)_3$, $P(\text{tert-Bu})_3$, 2-[di(tert-butyl)phosphino]-1,1'-biphenyl, 2-[di(tert-butyl)phosphino]-2'-dimethylamino-1,1'-biphenyl, 1,2,3,4,5-pentaphenyl-1'-[di(tert-butyl)phosphino]ferrocene, 2-[dicyclohexylphosphino]-1,1'-biphenyl, 2-[dicyclohexylphosphino]-2'-dimethylamino-1,1'-biphenyl, and the like.

The reaction temperature is ordinarily 0° C. to 80° C., and preferably 0° C. to 25° C.

The reaction solvent is not particularly limited as long as it has no adverse effect on the reaction, but is preferably a solvent such as N,N-dimethylformamide, tetrahydrofuran, 1,4-dioxane, cyclohexane, 1,3-dimethylbenzene, acetonitrile, and toluene.

Scheme 18: Method of manufacturing compound of Formula (XXII) from Formula (XXIV)

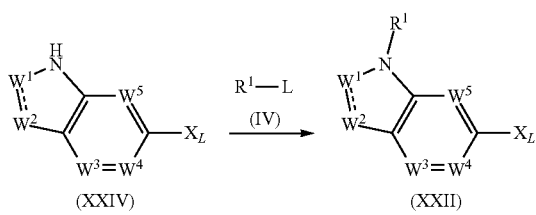

(XXIV)                              (XXII)

The compound of Formula (XXII) [in the formula, $R^1$, $W^1$, $W^2$, $W^3$, $W^4$, and $W^5$ are as described above, and $X_L$ is a halogen atom.] can be obtained by alkylation reaction of the compound represented by Formula (XXIV) [in the formula, $W^1$, $W^2$, $W^3$, $W^4$, and $W^5$ are as described above, and $X_L$ is a halogen atom.] and the compound of Formula (IV) [in the formula, $R^1$ is as described above, and L represents a leaving group.] in the presence of a base.

The leaving group L of Formula (IV) is not particularly limited as long as it is eliminated by the reaction with the compound (IV) to produce the compound (XXII), and examples of the leaving group include a halogen atom (a chlorine atom, a bromine atom, and the like), a p-toluenesulfonyloxy group, a benzenesulfonyloxy group, an ethanesulfonyloxy group, a methanesulfonyloxy group, and the like, and preferably a bromine atom, a chlorine atom, a p-toluenesulfonyloxy group, and the like.

The amount of the used compound (IV) is ordinarily 1 to 10 mole, and preferably 1 to 3 mole with respect to 1 mole of the compound (XXIV).

Examples of the used base include sodium carbonate, potassium carbonate, cesium carbonate, sodium hydrogen carbonate, cesium fluoride, sodium hydride, potassium hydroxide, and the like, and preferably potassium carbonate, sodium hydride, potassium hydroxide, and the like.

The amount of the base is ordinarily 1 to 10 mole, and preferably 1 to 5 mole with respect to 1 mole of the compound (XXIV).

The reaction temperature is ordinarily 0° C. to 160° C., and preferably 25° C. to 100° C.

The reaction time is ordinarily 1 hour to 24 hours, and preferably 1 hour to 12 hours.

The reaction solvent is not particularly limited as long as it has no adverse effect on the reaction, but is preferably a solvent such as N,N-dimethylformamide, N,N-dimethylacetoamide, N-methyl-2-pyrrolidone, chloroform, dichloromethane, tetrahydrofuran, 1,4-dioxane, acetone, methylethylketone, and acetonitrile.

Examples of the compound of Formula (XXIV) include 6-bromoindole, 6-bromo-3-methylindole, 6-bromo-3-ethylindole, 6-bromoindazole, 6-bromo-2,3-dihydro-1H-indole, 6-bromo-2,3-dihydro-3-methyl-1H-indole-2-one, 6-bromo-2,3-dihydro-3-methyl-1H-indole, 6-bromo-2,3-dihydro-3,3-dimethyl-1H-indole-2-one, 6-bromo-2,3-dihydro-3,3-dimethyl-1H-indole, 6-bromo-3-methyl-1H-indazole, 6-bromo-3-ethyl-1H-indazole, 6-bromo-3-propyl-1H-indazole, 6-bromo-3-isopropyl-1H-indazole, 6-bromo-3-cyclopropyl-1H-indazole, 6-bromo-1H-indazole-3-carbonitrile, 6-chloro-3-methyl-1H-pyrazolo[3,4-b]pyridine, 6-bromo-3-methyl-1H-pyrazolo[4,3-b]pyridine, 6-bromo-3-ethyl-1H-pyrazolo[4,3-b]pyridine, 6-bromo-3-propyl-1H-pyrazolo[4,3-b]pyridine, 6-bromo-3-cyclopropyl-1H-pyrazolo[4,3-b]pyridine, 6-bromo-3-chloro-1H-pyrazolo[4,3-b]pyridine, and 6-chloro-5-methoxy-3-methyl-1H-indazole and the like. The compound of Formula (XXIV) may use a commercial product, or can be manufactured by a suitable combination of known methods or the methods described in Example or a similar method thereto as necessary.

Scheme 19 to 20 below are synthesis methods of the compound represented by Formula (III-2) wherein the group represented by X is a single bond, and the group represented by Y is $-(CH_2)_2-(CH_2)_m-$ (herein m is any integer of 0 to 4) in the compound represented by Formula (III).

Scheme 19: Method of manufacturing compound of Formula (III-2) from compound of Formula (III-3)

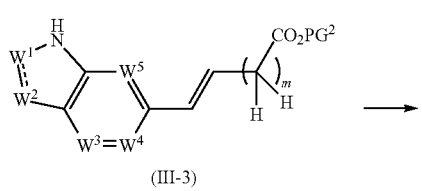

(III-3)

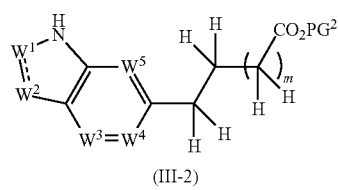

(III-2)

The compound of Formula (III-2) [in the formula, $W^1$, $W^2$, $W^3$, $W^4$, and $W^5$ are as described above, m is any integer of 0 to 4, and $PG^2$ represents a protective group.] can be obtained by reduction reaction of the compound represented by Formula (III-3) [in the formula, $W^1$, $W^2$, $W^3$, $W^4$, and $W^5$ are as described above, m is any integer of 0 to 4, and $PG^2$ represents a protective group.]. More specifically, the compound (III-2) can be obtained by reacting the compound (III-3) that has an alkene group in the presence of a reduction catalyst such as palladium on carbon under hydrogen atmosphere.

Examples of the used catalyst include 5% palladium on carbon, 10% palladium on carbon, 20% palladium hydroxide, Raney nickel, platinum, platinum oxide, and the like.

The amount of the used catalyst is ordinarily 0.01 to 1 mole, and preferably 0.05 to 0.2 mole with respect to 1 mole of the compound (III-3).

The reaction temperature is ordinarily 0° C. to 200° C., and preferably 25° C. to 80° C.

The reaction solvent is not particularly limited as long as it has no adverse effect on the reaction, but is preferably a solvent such as methanol, ethanol, 1-propanol, 2-propanol, ethyl acetate, dimethylformamide, dimethylacetoamide, tetrahydrofuran, 1,4-dioxane, and toluene.

Scheme 20: Method of manufacturing compound of Formula (III-3) from compound of Formula (XXIV)

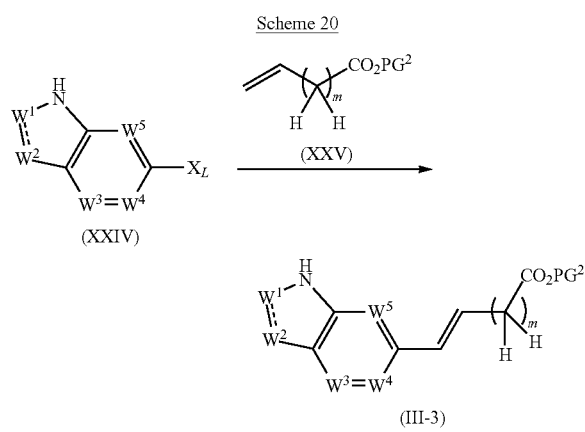

The compound of Formula (III-3) [in the formula, $W^1$, $W^2$, $W^3$, $W^4$, and $W^5$ are as described above, m is any integer of 0 to 4, and $PG^2$ represents a protective group.] can be obtained by coupling reaction of the compound represented by Formula (XXIV) [in the formula, $W^1$, $W^2$, $W^3$, $W^4$, and $W^5$ are as described above, and $X_L$ is a halogen atom.] and Formula (XXV) [in the formula, m is any integer of 0 to 4, and $PG^2$ represents a protective group.]. More specifically, the compound (III-3) can be obtained by reacting the compound (XXIV) that has a halogen atom with the compound (XXV) in the presence of a base and a palladium catalyst (further a phosphine ligand as necessary).

In the reaction, ordinarily 1 to 10 mole, and preferably 1 to 3 mole of the compound (XXV) is used with respect to 1 mole of the compound (XXIV).

Examples of the compound (XXV) include methyl acrylate, ethyl acrylate, propyl acrylate, tert-butyl acrylate, methyl 2-butenoate, methyl 3-butenoate, acrylic acid, 2-butenoic acid, 3-butenoic acid, and the like.

Examples of the used base include triethyl amine, sodium acetate, potassium acetate, sodium hydrogen carbonate, sodium carbonate, cesium fluoride, potassium fluoride, potassium carbonate, and the like.

The amount of the used base is ordinarily 1 to 10 mole, and preferably 1 to 3 mole with respect to 1 mole of the compound (XXIV).

Examples of the used palladium catalyst include $Pd(PPh_3)_4$, $Pd(OAc)_2$, $Pd_2(dba)_3$, $PdCl_2(PPh_3)_2$, and the like.

The amount of the used palladium catalyst is ordinarily 0.01 to 0.5 mole, and preferably 0.05 to 0.2 mole with respect to 1 mole of the compound (XXIV).

Examples of the used phosphine ligand include $PPh_3$, $P(o\text{-}tol)_3$, $P(2\text{-}furyl)_3$, $P(tert\text{-}Bu)_3$, 2-[di(tert-butyl)phosphino]-1,1'-biphenyl, 2-[di(tert-butyl)phosphino]-2'-dimethylamino-1,1'-biphenyl, 2-[dicyclohexylphosphino]-1,1'-biphenyl, 2-[dicyclohexylphosphino]-2'-dimethylamino-1,1'-biphenyl, and the like.

The reaction temperature is ordinarily 0° C. to 200° C., and preferably 25° C. to 160° C.

The reaction solvent is not particularly limited as long as it has no adverse effect on the reaction, but is preferably a solvent such as N,N-dimethylformamide, N,N-dimethylacetoamide, chloroform, dichloromethane, tetrahydrofuran, 1,4-dioxane, acetonitrile, and toluene.

Examples of a compound of Formula (XXIV), include 6-bromoindole, 6-bromo-3-methylindole, 6-bromo-3-ethylindole, 6-bromoindazole, 6-bromo-2,3-dihydro-1H-indole, 6-bromo-2,3-dihydro-3-methyl-1H-indole-2-one, 6-bromo-2,3-dihydro-3-methyl-1H-indole, 6-bromo-2,3-dihydro-3,3-dimethyl-1H-indole-2-one, 6-bromo-2,3-dihydro-3,3-dimethyl-1H-indole, 6-bromo-3-methyl-1H-indazole, 6-bromo-3-ethyl-1H-indazole, 6-bromo-3-propyl-1H-indazole, 6-bromo-3-isopropyl-1H-indazole, 6-bromo-3-cyclopropyl-1H-indazole, 6-bromo-1H-indazole-3-carbonitrile, 6-chloro-3-methyl-1H-pyrazolo[3,4-b]pyridine, 6-bromo-3-methyl-1H-pyrazolo[4,3-b]pyridine, 6-bromo-3-ethyl-1H-pyrazolo[4,3-b]pyridine, 6-bromo-3-propyl-1H-pyrazolo[4,3-b]pyridine, 6-bromo-3-cyclopropyl-1H-pyrazolo[4,3-b]pyridine, 6-bromo-3-chloro-1H-pyrazolo[4,3-b]pyridine, 6-chloro-5-methoxy-3-methyl-1H-indazole, and the like. The compound of Formula (XXIV) may use a commercial product, or can be manufactured by a suitable combination of known methods or the methods described in Example or a similar method thereto as necessary.

Schemes 21 to 23 are synthesis methods of the compound represented by Formula (I-1) wherein Z is a 5-tetrazolyl group in the compound of Formula (I).

Scheme 21: Method of manufacturing compound of Formula (I-1) from compound of Formula (XXVI)

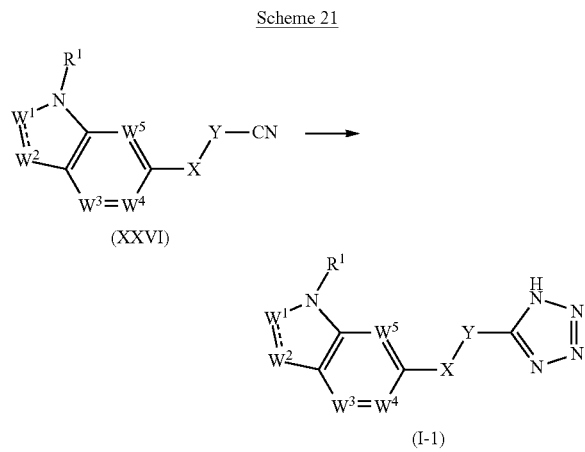

(XXVI)

(I-1)

The compound of Formula (I-1) [in the formula, $R^1$, $W^1$, $W^2$, $W^3$, $W^4$, $W^5$, X, and Y are as described above.] can be obtained by the reaction of the compound represented by Formula (XXVI) [in the formula, $R^1$, $W^1$, $W^2$, $W^3$, $W^4$, $W^5$, X, and Y are as described above.] and azide. More specifically, the compound (I-1) can be obtained by reacting the compound (XXVI) that has a cyano group with an azide such as sodium azide, in the presence of a salt such as ammonium chloride.

In the reaction, ordinarily 1 to 10 mole, and preferably 1 to 3 mole of the azide is used with respect to 1 mole of the compound (XXVI).

Examples of the azide include alkali metal azides such as lithium azide, sodium azide, and potassium azide, trialkyl tin azides such as trioctyl tin azide or hydrazoic acid and the like.

Examples of the used salt include ammonium chloride, zinc chloride, zinc bromide, aluminum chloride, and the like.

The amount of the used salt is ordinarily 1 to 10 mole, and preferably 1 to 3 mole with respect to 1 mole of the compound (XXVI).

The reaction temperature is ordinarily 0° C. to 200° C., and preferably 100° C. to 170° C.

The reaction solvent is not particularly limited as long as it has no adverse effect on the reaction, but is preferably a solvent such as dimethylformamide, water, dimethylacetoamide, N-methyl-2-pyrrolidone, tetrahydrofuran, 1,4-dioxane, and toluene.

Scheme 22: Method of manufacturing compound of Formula (XXVI) from compound of Formula (XXVII)

Scheme 22

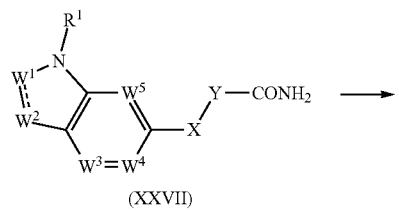

(XXVII)

-continued

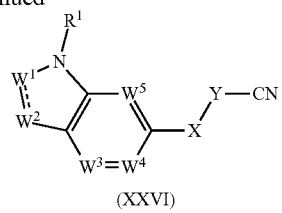

(XXVI)

The compound of Formula (XXVI) [in the formula, $R^1$, $W^1$, $W^2$, $W^3$, $W^4$, $W^5$, X, and Y are as described above.] can be obtained by dehydration reaction of the compound represented by Formula (XXVII) [in the formula, $R^1$, $W^1$, $W^2$, $W^3$, $W^4$, $W^5$, X, and Y are as described above.]. More specifically, the compound (XXVI) can be obtained by reacting the compound (XXVII) that has an amide group in the presence of a dehydrating agent such as thionyl chloride.

In the reaction, ordinarily 1 to 10 mole, and preferably 1 to 3 mole of the dehydrating agent is used with respect to 1 mole of the compound (XXVII).

Examples of the dehydrating agent include thionyl chloride, oxalyl chloride, cyanuric acid chloride, phosphorus pentaoxide, phosphorus pentachloride, acetic anhydride, phosphorus oxychloride, and the like.

The reaction temperature is ordinarily 0° C. to 200° C., and preferably 0° C. to 25° C.

The reaction solvent is not particularly limited as long as it has no adverse effect on the reaction, but is preferably a solvent such as dichloromethane, chloroform, tetrahydrofuran, 1,4-dioxane, acetonitrile, and toluene.

Scheme 23: Method of manufacturing compound of Formula (XXVII) from compound of Formula (I) (in the formula, Z is COOH)

Scheme 23

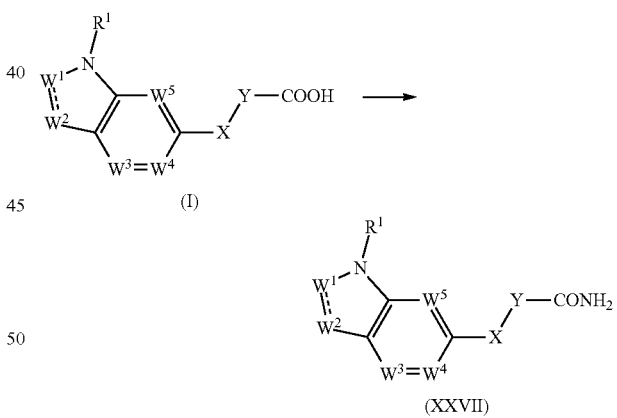

The compound of Formula (XXVII) [in the formula, $R^1$, $W^1$, $W^2$, $W^3$, $W^4$, $W^5$, X, and Y are as described above.] can be obtained by amidation reaction of the compound represented by Formula (I) [in the formula, $R^1$, W, $W^2$, $W^3$, $W^4$, $W^5$, X, and Y are as described above.]. More specifically, the compound (XXVII) that has an amide group can be obtained by reacting the compound represented by Formula (I) with a halogenating agent such as thionyl chloride and oxalyl chloride, whereby to produce corresponding acid chloride, and reacting the acid chloride with ammonia water.

In the reaction, ordinarily 1 to 10 mole, and preferably 1 to 3 mole of the halogenating agent is used with respect to 1 mole of the compound (1).

Examples of the halogenating agent include thionyl chloride, oxalyl chloride, phosphorus trichloride, phosphorus pentachloride, sulfuryl chloride, and the like.

The reaction temperature is ordinarily 0° C. to 200° C., and preferably 0° C. to 25° C.

The reaction solvent is not particularly limited as long as it has no adverse effect on the reaction, but is preferably a solvent such as dichloromethane, chloroform, tetrahydrofuran, 1,3-dimethylbenzene, 1,4-dioxane, and toluene.

Scheme 24 below is a synthesis method of the compound represented by Formula (XXVI-1) wherein X is a single bond and Y is a single bond in the compound of Formula (XXVI).

Scheme 24: Method of manufacturing compound of Formula (XXVI-1) from compound of Formula (XXII)

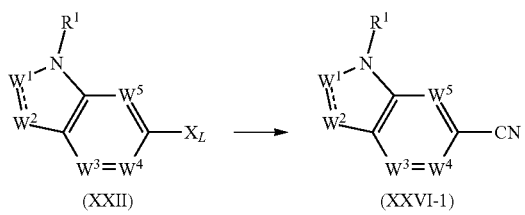

The compound of Formula (XXVI-1) [in the formula, $R^1$ is as described above, and $W^1$, $W^2$, $W^3$, $W^4$, and $W^5$ are as described above.] can be obtained by coupling reaction of the compound represented by Formula (XXII) [in the formula, $R^1$ is as described above, and $W^1$, $W^2$, $W^3$, $W^4$, and $W^5$ are as described above, and XL is a halogen atom.] and a cyanide such as zinc cyanide. More specifically, the compound (XXVI-1) can be obtained by reacting the compound (XXII) that has a halogen atom with a cyanide in the presence of a palladium catalyst (further a phosphine ligand as necessary).

In the reaction, ordinarily 1 to 10 mole, and preferably 1 to 3 mole of the cyanide is used with respect to 1 mole of the compound (XXII).

Examples of the cyanide include zinc cyanide, sodium cyanide, potassium cyanide, and the like.

Examples of the used palladium catalyst include $Pd(PPh_3)_4$, $Pd(OAc)_2$, $Pd(dba)_2$, $Pd_2(dba)_3$, $PdCl_2(PPh_3)_2$, and the like.

The amount of the used palladium catalyst is ordinarily 0.01 to 0.5 mole, and preferably 0.05 to 0.2 mole with respect to 1 mole of the compound (XXII).

Examples of the used phosphine ligand include $PPh_3$, P(o-tol)$_3$, P (tert-Bu)$_3$, 2-[di(tert-butyl)phosphino]-1,1'-biphenyl, 2-[di(tert-butyl)phosphino]-2'-dimethylamino-1,1'-biphenyl, 2-[dicyclohexylphosphino]-1,1'-biphenyl, 2-[dicyclohexylphosphino]-2'-dimethylamino-1,1'-biphenyl, and the like.

A reducing agent such as zinc may be added as necessary in this reaction.

The reaction temperature is ordinarily 0° C. to 200° C., and preferably 25° C. to 130° C.

The reaction solvent is not particularly limited as long as it has no adverse effect on the reaction, but is preferably a solvent such as dimethylformamide, tetrahydrofuran, dimethoxyethane, 1,4-dioxane, acetonitrile, and toluene.

Scheme 25 below is another synthesis method of the compound of Formula (I).

Scheme 25: Method of manufacturing of compound of Formula (I) from Formula (XXVI)

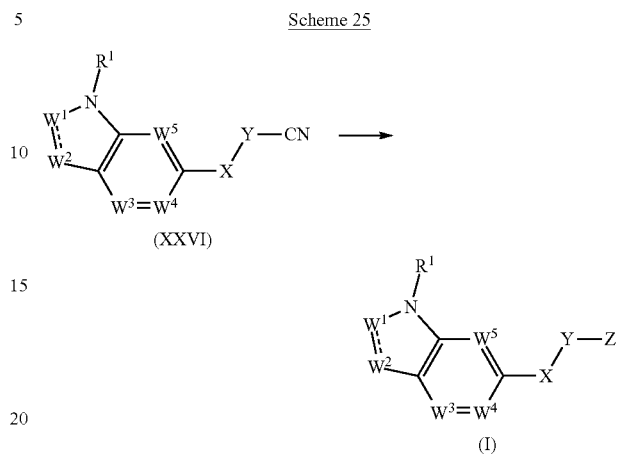

The compound of Formula (I) [in the formula, $R^1$, $W^1$, $W^2$, $W^3$, $W^4$, $W^5$, X, and Y are as described above, and Z is COOH.] can be obtained by hydrolysis reaction of the compound represented by Formula (XXVI) [in the formula, $R^1$, $W^1$, $W^2$, $W^3$, $W^4$, W, X, and Y are as described above.]. More specifically, the compound (I) can be obtained by solvolysis using an acid or a base, specifically, for example, a method of reacting 0.01 mole to a large excess of an acid, preferably acetic acid, hydrochloric acid, sulfuric acid, trifluoroacetic acid, phthalic acid and the like, or 0.01 mole to a large excess of a base, preferably potassium hydroxide, sodium hydroxide, calcium hydroxide and the like in the presence of an alcoholic solvent.

The reaction temperature is ordinarily 0° C. to 200° C., and preferably 0° C. to 160° C.

The reaction solvent is not particularly limited as long as it has no adverse effect on the reaction, but is preferably a solvent such as methanol, ethanol, 1-propanol, 2-propanol, 1-butanol, 2-butanol, tert-butanol, tetrahydrofuran, 1,4-dioxane, cyclohexane, 1,3-dimethylbenzene, and toluene.

The alcoholic solvent used in the solvolysis using the base is not particularly limited as long as it has no adverse effect on the reaction, but is preferably methanol, ethanol, 1-propanol, 2-propanol, 1-butanol, 2-butanol, tert-butanol, and the like.

Scheme 26 below is a general method of manufacturing the compound of Formula (II-2) wherein X is a carbonyl group in the compound of Formula (II).

Scheme 26: Method of manufacturing compound of Formula (II-2) from Formula (XXVIII)

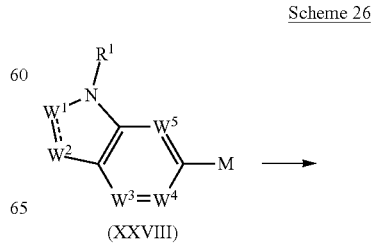

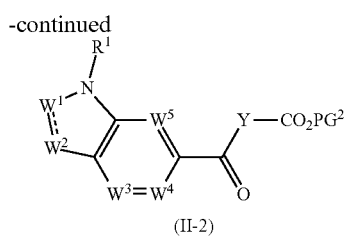

(II-2)

The compound of Formula (II-2) [in the formula, $R^1$, $W^1$, $W^2$, $W^3$, $W^4$, $W^5$, and Y are as described above, and $PG^2$ represents a protective group.] can be obtained by coupling reaction of the compound represented by Formula (XXVIII) [in the formula, $R^1$, $W^1$, $W^2$, $W^3$, $W^4$, and $W^5$ are as described above, and M is boron, tin, and the like.] and an acid chloride. More specifically, the compound (II-2) can be obtained by reacting the compound (XXVIII) with an acid chloride in the presence of a palladium catalyst (further a phosphine ligand as necessary and a base).

In the reaction, ordinarily 1 to 10 mole, and preferably 1 to 3 mole of the acid chloride is used with respect to 1 mole of the compound (XXVIII).

Examples of the acid chloride include methyl 3-chlorocarbonylpropionate, ethyl 3-chlorocarbonylpropionate, ethyl chloroglyoxylate, and the like.

$PG^2$ in Formula (II-2) is a group derived from the acid chloride, and examples thereof include a methyl group, an ethyl group, and the like.

Examples of the used base include triethyl amine, diisopropylethyl amine, and the like.

The amount of the used base is ordinarily 1 to 10 mole, and preferably 1 to 3 mole with respect to 1 mole of the compound (XXVIII).

Examples of the used palladium catalyst include $Pd(PPh_3)_4$, $Pd(OAc)_2$, $Pd(dba)_2$, $Pd_2(dba)_3$, $PdCl_2(PPh_3)_2$, and the like.

The amount of the used palladium catalyst is ordinarily 0.01 to 0.5 mole, and preferably 0.05 to 0.2 mole with respect to 1 mole of the compound (XXVIII).

Examples of the used phosphine ligand include $PPh_3$, P(o-tol)$_3$, P(tert-Bu)$_3$, 2-[di(tert-butyl)phosphino]-1,1'-biphenyl, 2-[di(tert-butyl)phosphino]-2'-dimethylamino-1,1'-biphenyl, 2-[dicyclohexylphosphino]-1,1'-biphenyl, 2-[dicyclohexylphosphino]-2'-dimethylamino-1,1'-biphenyl, and the like.

The reaction temperature is ordinarily 0° C. to 200° C., and preferably 25° C. to 130° C.

The reaction solvent is not particularly limited as long as it has no adverse effect on the reaction, but is preferably a solvent such as dimethylformamide, tetrahydrofuran, 1,4-dioxane, acetonitrile, and toluene.

Scheme 27: Method of manufacturing compound of Formula (XXVIII) from Formula (XXII)

Scheme 27

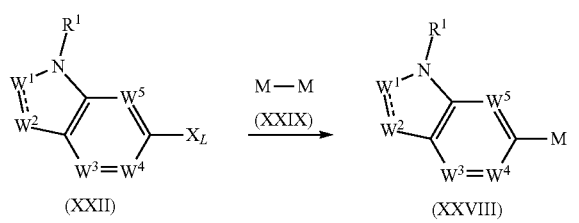

The compound of Formula (XXVIII) [in the formula, $R^1$, $W^1$, $W^2$, $W^3$, $W^4$, and $W^5$ are as described above, and M is boron, tin, and the like.] can be obtained by coupling reaction of the compound represented by Formula (XXII) [in the formula, $R^1$, $W^1$, $W^2$, $W^3$, $W^4$, and $W^5$ are as described above, and XL is a halogen atom.] and Formula (XXIX) [in the formula, M is boron, tin, and the like.]. More specifically, the compound (XXVIII) can be obtained by reacting the compound (XXII) that has a halogen atom with the compound (XXIX) in the presence of a palladium catalyst (further a phosphine ligand as necessary and a base).

In the reaction, the ordinarily 1 to 10 mole, and preferably 1 to 3 mole of the compound (XXIX) is used with respect to 1 mole of the compound (XXII).

Examples of the compound (XXIX) include bis(trimethyl tin), bis(triethyl tin), bis(tributyl tin), bis(pinacolato) diboron, and the like.

Examples of the used base include potassium acetate, trimethyl amine, and the like.

The amount of the used base is ordinarily 1 to 10 mole, and preferably 1 to 3 mole with respect to 1 mole of the compound (XXII).

Examples of the used palladium catalyst include $Pd(PPh_3)_4$, $Pd(OAc)_2$, $Pd_2(dba)_3$, $PdCl_2(PPh_3)_2$, and the like.

The amount of the used palladium catalyst is ordinarily 0.01 to 0.5 mole, and preferably 0.05 to 0.2 mole with respect to 1 mole of the compound (XXII).

Examples of the used phosphine ligand include $PPh_3$, P(o-tol)$_3$, P(tert-Bu)$_3$, 2-[di(tert-butyl)phosphino]-1,1'-biphenyl, 2-[di(tert-butyl)phosphino]-2'-dimethylamino-1,1'-biphenyl, 2-[dicyclohexylphosphino]-1,1'-biphenyl, 2-[dicyclohexylphosphino]-2'-dimethylamino-1,1'-biphenyl, and the like.

The reaction temperature is ordinarily 0° C. to 200° C., and preferably 25° C. to 130° C.

The reaction solvent is not particularly limited as long as it has no adverse effect on the reaction, but is preferably a solvent such as dimethylformamide, tetrahydrofuran, dimethoxyethane, 1,4-dioxane, acetonitrile, and toluene.

Scheme 28 below is a synthesis method of the compound represented by Formula (II-3) wherein X is a single bond and Y is —$CF_2$—$(CH_2)_p$— (herein p is any integer of 0 to 5) in the compound of Formula (II).

Scheme 28: Method of manufacturing compound of Formula (II-3) from Formula (II-2)

Scheme 28

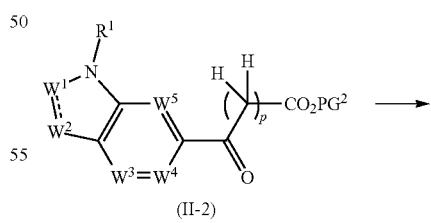

The compound of Formula (II-3) [in the formula, $R^1$, $W^1$, $W^2$, $W^3$, $W^4$, and $W^5$ are as described above, and p is any integer of 0 to 5, and $PG^2$ is a protective group.] can be obtained by fluorination of the compound represented by Formula (II-2) [in the formula, $R^1$, $W^1$, $W^2$, $W^3$, $W^4$, and $W^5$ are as described above, and p is any integer of 0 to 5, and $PG^2$ is a protective group.]. More specifically, the compound (II-3) can be obtained by reacting the compound (II-2) with a fluorinating agent such as diethyl aminosulfur trifluoride (DAST).

In the reaction, ordinarily 1 to 10 mole, and preferably 1 to 3 mole of the fluorinating agent is used with respect to 1 mole of the compound (II-2).

Examples of the fluorinating agent include diethyl aminosulfur trifluoride (DAST), bis(2-methoxyethyl)aminosulfur trifluoride, 1,1,2,2-tetrafluoroethyl-N,N-dimethylamine, diethyl aminodifluorosulfinium tetrafluoroborate, morpholinodifluorosulfinium tetrafluoroborate, 4-tert-butyl-2,6-dimethylphenylsulfur trifluoride, and the like.

The reaction temperature is ordinarily 0° C. to 200° C., and preferably 25° C. to 130° C.

The reaction solvent is not particularly limited as long as it has no adverse effect on the reaction, but is preferably a solvent such as dichloromethane, tetrahydrofuran, 1,4-dioxane, 1,2-dimethoxyethane, acetonitrile, and toluene.

Next, the URAT1 inhibitor, the blood uric acid level-reducing agent, and the pharmaceutical composition for treating or preventing pathological conditions associated with the blood uric acid of the present invention will be described.

The "URAT1" used in this specification represents the uric acid transporter 1 (Uric acid transporter 1).

The "inhibiting URAT1" used in this specification means inhibiting the function as the uric acid transporter of URAT1 to cause the activity thereof to disappear or to be reduced, and, for example, it means specifically inhibiting the function of URAT1 based on the conditions of Example 187 described below.

The "URAT1 inhibitor" used in this specification means a drug that contains the compound of Formula (I) (containing the form of a pharmaceutically acceptable salt or an ester of the compound), and inhibits the function as the uric acid transporter of URAT1 whereby to cause the activity thereof to disappear or to be reduced.

The "blood uric acid level-reducing agent" used in this specification means a drug that contains the compound of Formula (I) (containing the form of a pharmaceutically acceptable salt or an ester of the compound), and inhibits URAT1, whereby to reduce the blood uric acid level.

The "reducing the blood uric acid level" used in this specification means reducing the uric acid (containing urate) in the blood (containing the serum or the plasma) by inhibiting the function of URAT1 as the uric acid transporter, preferably reducing high serum uric acid level, more preferably reducing the serum uric acid level to less than 8 mg/dL (preferably less than 7 mg/dL, and further preferably less than 6 mg/dL as the serum uric acid level).

The "high blood uric acid level" used in this specification means that the serum uric acid level is 6 mg/dL or more, preferably 7 mg/dL or more, and more preferably 8 mg/dL or more.

The "pharmaceutical composition for treating or preventing pathological conditions associated with the blood uric acid" used in this specification means a pharmaceutical composition that contains the compound of Formula (I) (containing the form of a pharmaceutically acceptable salt or an ester of the compound), and inhibits URAT1, whereby to treat or prevent pathological conditions associated with the blood uric acid.

The "pathological conditions associated with the blood uric acid" used in this specification refers to pathological conditions associated with the above-mentioned "high blood uric acid level", and examples thereof include hyperuricemia, gouty node, acute gout arthritis, chronic gout arthritis, gouty kidney, urolithiasis, a renal function disorder, a coronary artery disease, an ischemic heart disease, and the like.

Any one of the URAT1 inhibitor, the blood uric acid level-reducing agent and the pharmaceutical composition for treating or preventing pathological conditions associated with the blood uric acid can be provided as a formulation.

The "formulation" encompasses oral formulations and parenteral formulations. The oral formulation is, for example, a tablet, a capsule, a powder, a granule, and the like, and the parenteral formulation is, for example, a sterilized liquid formulation such as a solution or a suspension, specifically, an injection, a drop, and the like, and preferably, an intravenous injection or an intravenous infusion.

The "formulation" of the present invention may contain ordinarily, a therapeutically effective dose of the compound of the present invention along with a pharmaceutically acceptable carrier or diluent. This formulation technique is regarded as a technique of common knowledge to one of ordinarily skill in the art, and is well known. Preferably, the formulation may be performed for an oral formulation, an intravenous infusion or an injection with a lot of methods well known to one of ordinarily skill in the art together with a pharmaceutically acceptable carrier or diluent.

Examples of the "pharmaceutically acceptable carrier or diluent" include an excipient (for example, fat, beeswax, polyol of semi-solid and liquid, natural or hardened oil and the like); water (for example, distilled water, particularly, distilled water for injection, and the like), physiological saline, alcohol (for example, ethanol), glycerol, polyol, an aqueous solution of glucose, mannitol, vegetable oil, and the like; additives (for example, a filler, a disintegrant, a binder, a lubricant, a wetting agent, a stabilizer, an emulsifier, a dispersing agent, a preservative, a sweetener, a colorant, a seasoning agent or an aromatic substance, a thickening agent, a diluent, a buffering agent, a solvent or a solubilizer, an agent for accomplishing the storage effect, a salt for changing the osmotic pressure, a coating agent, or an anti-oxidant) and the like.

The formulation of the present invention may select various forms. Examples thereof include oral formulations such as, for example, a tablet, a capsule, a powder, a granule or a solution, sterilized-liquid parenteral formulations such as a solution or a suspension, a suppository, an ointment, and the like.

The formulation of the present invention may be a solid formulation, or a liquid formulation.

The solid formulation may be manufactured as it is as a form of a tablet, a capsule, a granule or a powder, or may be manufactured using a proper carrier (additive). Examples of such a carrier (additive) include: saccharides such as lactose or glucose; starches of corn, wheat, rice, and the like; a fatty acid such as a stearic acid; an inorganic salt such as magnesium aluminometasilicate or phosphoric anhydride calcium; synthetic macromolecules such as a polyvinylpyrrolidone or a polyalkylene glycol; a fatty acid salt such as calcium stearate or a magnesium stearate; alcohols such as a stearyl alcohol or benzyl alcohol; synthetic cellulosic derivatives such as methylcellulose, carboxymethyl cellulose, ethyl cellulose, or hydroxypropyl methylcellulose; and other additives for general use such as gelatin, talc, vegetable oil, and gum arabic, and the like.

Such solid formulation such as a tablet, a capsule, a granule and a powder may generally contain, for example, 0.1 to 100% by mass, preferably 5 to 98% by mass of the compound represented by Formula (I) based on the total mass of the formulation as an active ingredient.

The liquid formulation is manufactured as a form such as a suspension, a syrup, an injection, and a drop (intravenous infusion solution) by using proper additives that are ordinarily used in the liquid formulation such as water, alcohols and a vegetable-derived oil such as soybean oil, peanut oil and sesame oil.

Particularly, examples of the proper solvent or diluent when administered in a form of parenteral intramuscular injection, intravenous injection or subcutaneous injection include, for example, distilled water for injection, an aqueous solution of lidocaine hydrochloride (for intramuscular injection), physiological saline, an aqueous solution of glucose, ethanol, polyethylene glycol, propylene glycol, a liquid for intravenous injection (for example, an aqueous solution of citric acid, sodium citrate, and the like), an electrolytic solution (for intravenous infusion and for intravenous injection) and the like, and a mixed solution thereof.

These injections may be in a form that is dissolved at the time of use as a powder of the active ingredient as it is or a powder of the active ingredient added with a proper carrier (additive), in addition to a form in which the active ingredient is preliminarily dissolved. These injection liquids may contain, for example, 0.1 to 10% by mass of the active ingredient based on the total mass of the formulation.

In addition, a solution for oral administration such as a suspension and a syrup may contain, respectively, for example, 0.1 to 10% by mass of the active ingredient based on the total mass of the formulation.

The compound of the present invention, the URAT1 inhibitor, the blood uric acid level-reducing agent, and the pharmaceutical composition for treating or preventing pathological conditions associated with uric acid of the present invention may be used in combination with another pharmaceutical composition or drug (hereinafter, also referred to as the combination drug).

The "combination" means combination use of multiple drugs as an active ingredient. For example, examples of the "combination use" include use as a combination preparation, use as a kit, use in combination which is characterized by separate, respective administration through identical or different administration route, and the like.

The administration time of the compound of the present invention, the URAT1 inhibitor, and the blood uric acid level-reducing agent and the pharmaceutical composition for treating or preventing pathological conditions associated with the blood uric acid of the present invention, and the combination drug is not limited, and they may be administered simultaneously, or may be administered at staggered time to an administration subject. The dose of the combination drug may be in accordance to a dose that is clinically used, and may be appropriately selected depending on a subject to be administered, the age and the weight of the subject to be administered, the symptom, the administration time, the formulation, the administering method, the combination and the like. The administration form of the combination drug is not limited, as long as the URAT1 inhibitor, the blood uric acid level-reducing agent or the pharmaceutical composition for treatment of pathological conditions associated with the blood uric acid of the present invention is combined with a combination drug at the time of the administration.

Examples of the combination drug include "an agent for treating and/or preventing hyperuricemia", "an agent for treating and/or preventing gout arthritis", "an agent for treating and/or preventing gouty kidney", "an agent for treating and/or preventing urolithiasis", "an agent for treating and/or preventing hypertension or hypertension complication", "an agent for treating and/or preventing hyperlipidaemia or hyperlipidaemia complication", "an agent for treating and/or preventing diabetes or diabetic complication", "an agent for treating and/or preventing obesity or obesity complication", "an agent for treating and/or preventing a primary disease that causes secondary hyperuricemia", "an agent for treating and/or preventing renal failure, a cardiovascular disorder or a cerebrovascular disorder caused by hyperuricemia" and "a nucleic acid metabolism antagonist". One to three of these combination drugs may be used in combination with the URAT1 inhibitor, the blood uric acid level-reducing agent and the pharmaceutical composition for treating or preventing pathological conditions associated with the blood uric acid of the present invention.

Examples of the "agent for treating and/or preventing hyperuricemia" include an agent for suppressing production of uric acid such as an xanthine oxidase inhibitor, an uric acid excretion facilitator and the like. Specifically, the examples include allopurinol, probenecid, bucolome, febuxostat, FYX-051 (4-(5-pyridin-4-yl-1H-[1,2,4]triazole-3-yl)pyridin-2-carbonitrile), benzbromarone, oxypurinol, and the like.

Examples of the "agent for treating and/or preventing gout arthritis" include non-steroidal anti-inflammatory agents such as indometacin, naproxen, fenbufen, pranoprofen, and oxaprozin; colchicine; an adrenocortical steroid, and the like.

Examples of the "agent for treating and/or preventing gouty kidney" include an agent for suppressing production of uric acid such as an xanthine oxidase inhibitor; an uric acid excretion facilitator; a citric acid formulation; an uric alkalifying agent such as sodium bicarbonate, and the like. Specifically, the examples include allopurinol, probenecid, bucolome, febuxostat, FYX-051 (4-(5-pyridin-4-yl-1H-[1,2,4]triazole-3-yl)pyridin-2-carbon itrile), benzbromarone, oxypurinol, and the like.

Examples of the "agent for treating and/or preventing urolithiasis" include a citric acid formulation; an uric alkalifying agent such as sodium bicarbonate, and the like.

Examples of the "agent for treating and/or preventing hypertension or hypertension complication" include a loop diuretic agent, an angiotensin conversion enzyme inhibitor, an angiotensin II receptor antagonist, a Ca antagonist, a β blocker, a α, β blocker, a α blocker, and the like. More specifically, for example, a furosemide sustained release drug, captopril, a captopril sustained release drug, enalapril maleate, alacepril, delapril hydrochloride, cilazapril, lisinopril, benazepril hydrochloride, imidapril hydrochloride, temocapril hydrochloride, quinapril hydrochloride, trandolapril, perindopril erbumine, losartan potassium, candesartan cilexetil, nicardipine hydrochloride, nicardipine hydrochloride sustained release drug, nilvadipine, nifedipine, nifedipine sustained release drug, benidipine hydrochloride, diltiazem hydrochloride, diltiazem hydrochloride sustained release drug, nisoldipine, nitrendipine, manidipine hydrochloride, barnidipine hydrochloride, efonidipine hydrochloride, amlodipine besylate, felodipine, cilnidipine, aranidipine, propranolol hydrochloride, propranolol hydrochloride sustained release drug, pindolol, a pindolol sustained release drug, indenolol hydrochloride, carteolol hydrochloride, a carteolol hydrochloride sustained release drug, bunitrolol hydrochloride, a bunitrolol hydrochloride sustained release drug, atenolol, acebutolol hydrochloride, metoprolol tartrate, a metoprolol tartrate sustained release drug, nipradilol, penbutolol sulfate, tilisolol hydrochloride, carvedilol, bisoprolol fumarate, betaxolol hydrochloride, celiprolol hydrochloride, bopindolol malonate, bevantolol hydrochloride, labetalol hydrochloride, arotinolol hydrochloride, amosulalol hydrochloride, prazosin hydrochloride, terazosin hydrochloride, doxazosin mesilate, bunazosin hydrochloride, a bunazosin hydrochloride sustained release drug, urapidil, phentolamine mesilate, and the like are included.

Examples of the "agent for treating and/or preventing hyperlipidaemia or hyperlipidaemia complication" include a HMG-CoA reduction enzyme inhibitor, an anion exchange resin, probucol, a nicotinic acid formulation, a fibrate-based drug, an eicosapentaenoic acid formulation, and the like. More specifically, for example, lovastatin, simvastatin, pravastatin, fluvastatin, atorvastatin, cerivastatin, colestimide, cholestyramine, niceritrol, nicomol, fenofibrate, bezafibrate, clinofibrate, clofibrate, ethyl icosapentate, and the like are included.

Examples of the "agent for treating and/or preventing diabetes or diabetic complication" include an insulin formulation, a sulfonyl urea agent, an insulin secretion facilitator, a sulfone amide agent, a biguanide agent, an a glucosidase inhibitor, an insulin resistance-improving agent, a dipeptidyl peptidase IV inhibitor, an angiotensin conversion enzyme inhibitor, an aldose reduction enzyme inhibitor, an anti-arrhythmia agent, and the like. More specifically, for example, insulin, chlorpropamide, glibenclamide, glipizide, tolbutamide, glyclopyramide, acetohexamide, glimepiride, tolazamide, gliclazide, nateglinide, glybuzole, metformin hydrochloride, buformin hydrochloride, voglibose, acarbose, pioglitazone hydrochloride, sitagliptin phosphate, vildagliptin, allogliputin mexiletine benzoic acid, epalrestat, and the like are included.

Examples of the "agent for treating and/or preventing obesity or obesity complication" include mazindole, acarbose, voglibose, epalrestat, and the like.

Examples of the "agent for treating and/or preventing a primary disease that causes uric acid excretion reduction type secondary hyperuricemia" include, for example, an agent for treating or preventing a chronic renal disease, polycystic kidney, toxemia of pregnancy, lead nephropathy, hyperlacticacidemia, Down's syndrome, sarcoidosis, Type I glycogenosis (via hyperlacticacidemia), dehydration, and the like.

Examples of the "agent for treating and/or preventing renal failure, a cardiovascular disorder or a cerebrovascular disorder caused by hyperuricemia" include a loop diuretic agent (for example, furosemide), a citric acid formulation, sodium bicarbonate, a cationic exchange resin, aluminum hydroxide, alfacalcidol, a β-blocker (for example, propranolol hydrochloride), an angiotensin conversion enzyme inhibitor (for example, captopril), a cardiotonic agent (for example, digoxin), an agent for treating angina pectoris (for example, isosorbide nitrate), a Ca antagonist (for example, diltiazem hydrochloride), an agent for suppressing production of uric acid (for example, allopurinol), an amino acid formulation, a hyperammonemia-improving agent, an agent for treating arrhythmia (for example, mexiletine), an agent for treating anemia (for example, mepitiostane, erythropoietin), and in addition, the "agent for treating and/or preventing hypertension or hypertension complication", the "agent for treating and/or preventing hyperlipidaemia or hyperlipidaemia complication", the "agent for treating and/or preventing diabetes or diabetic complication", the "agent for treating and/or preventing obesity or obesity complication", and the like.

Examples of the "nucleic acid metabolism antagonist" include azathiopurine, mizoribine, mycophenolic acid, and the like.

In addition, any one of the compound of the present invention, the URAT1 inhibitor, the blood uric acid level-reducing agent, and the pharmaceutical composition for treating or preventing pathological conditions associated with uric acid of the present invention, can reduce the blood uric acid level in combination use with a drug that leads to increase of the blood uric acid level.

Examples of the "drug that leads to increase of the blood uric acid level" include a nucleic acid metabolism antagonist, a hypotensive diuretic agent (for example, furosemide and a thiazide-based diuretic agent), an anti-tuberculosis agent (for example, pyrazinamide and ethambutol), an anti-inflammatory analgesic agent (for example, salicylic acid), a hyperlipidaemia agent (for example, nicotinic acid), an agent for treating asthma (for example, theophylline), an immunosuppressive agent (for example, cyclosporine), an agent for treating type C hepatitis (for example, ribavirin), ethanol, and the like.

EXAMPLE

The present invention will be further specifically described with Examples below, but the present invention is not limited to these Examples. For various reagents used in Examples, commercial products were used unless stated otherwise. For the thin layer chromatography in Examples, Silica gel$_{60}$ F$_{254}$ manufactured by MERCK KGaA was used as the plate, and a UV detector was used as the detection method. For the silica gel column chromatography, Biotage (registered trademark) SNAP Cartridge KP-Sil silica gel prepacked column manufactured by Biotage, or Chromatorex (registered trademark) Q-PACK COOH silica gel prepacked column manufactured by FUJI SILYSIA CHEMICAL LTD. was used. For the reverse phase preparative liquid chromatography, CombiPrep Pro C18 manufactured by YMC CO., LTD. was used as the column, and 0.1% trifluoroacetic acid in water and 0.1% trifluoroacetic acid in acetonitrile were used as the mobile phase.

For $^1$H-NMR, AL400 (400 MHz) manufactured by JEOL Ltd. was used, and $^1$H-NMR was measured using tetramethyl silane as a standard substance. The mass spectrum was measured with electrospray ionization (ESI) using ACQUITY (registered trademark) SQD manufactured by WATERS. The microwave reaction was performed using Initiator (registered trademark) manufactured by Biotage.

The meanings of the symbols are as described below.
s: Singlet
d: Doublet
t: Triplet
q: Quartet
dd: Double Doublet
dt: Double Triplet
td: Triple Doublet
tt: Triple Triplet
ddd: Double Double Doublet
ddt: Double Double Triplet
dtd: Double Triple Doublet
tdd: Triple Double Doublet
tq: Triple Quartet
m: Multiplet
br: Broad
DMSO-d$_6$: Deuterated dimethyl sulfoxide
CDCl$_3$: Deuterated chloroform CD₃OD: Deuterated methanol
tBu: tert-butyl group

Example 1

Synthesis of 1-benzyl-1H-indole-6-carboxylic acid [1] (Hereinafter Referred to as "a Compound [1]")

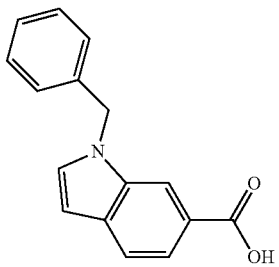 [SMILES: O=C(O)c1ccc2ccn(Cc3ccccc3)c2c1]

(1) Synthesis of methyl 1-benzyl-1H-indole-6-carboxylate [1-1] (Hereinafter Referred to as a Compound [1-1])

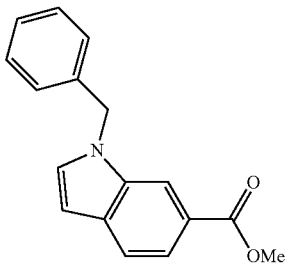 [SMILES: COC(=O)c1ccc2ccn(Cc3ccccc3)c2c1]

To a solution of methyl indole-6-carboxylate (1.0 g) in N,N-dimethylformamide (10 mL), potassium carbonate (1.2 g) and benzyl chloride (1.4 g) were added at room temperature, and then the reaction mixture was stirred at 60° C. for 3 hours. After cooling to room temperature, the reaction mixture was quenched with water, and the mixture was extracted with chloroform. The obtained organic layer was dried over anhydrous sodium sulfate, filtered, and the filtrate was concentrated under reduced pressure. The obtained residue was purified by silica gel column chromatography to give the titled compound (681 mg) as a colorless oil.

¹H-NMR (400 MHz, CDCl₃) δ: 8.09 (1H, s), 7.81 (1H, dd, J=8.3, 1.5 Hz), 7.66 (1H, d, J=8.3 Hz), 7.33-7.25 (4H, m), 7.12-7.09 (2H, m), 6.59 (1H, dd, J=3.2, 0.7 Hz), 5.38 (2H, s), 3.91 (3H, s).

(2) Synthesis of 1-benzyl-1H-indole-6-carboxylic acid [1]

To a solution of the compound [1-1] obtained in the process (1) (681 mg) in ethanol (30 mL), anaqueous solution of 1 N-sodium hydroxide (10 mL) was added, and then the reaction mixture was stirred at 50° C. for 18 hours. After cooling to room temperature, to the reaction mixture was added 1 N-hydrochloric acid for acidification, and extracted with chloroform. The obtained organic layer was dried over anhydrous sodium sulfate, filtered, and the filtrate was concentrated under reduced pressure. The obtained residue was purified by silica gel column chromatography to give the titled compound (453 mg) as a white solid.

¹H-NMR (400 MHz, CDCl₃) δ: 8.17 (1H, s), 7.87 (1H, dd, J=8.3, 1.5 Hz), 7.69 (1H, d, J=8.5 Hz), 7.35-7.24 (3H, m), 7.26 (1H, d, J=0.5 Hz), 7.13 (2H, d, J=7.1 Hz), 6.61 (1H, d, J=3.2 Hz), 5.41 (2H, s).

Example 2

Synthesis of 1-(2,6-dimethylbenzyl)-1H-indole-6-carboxylic acid [2] (Hereinafter Referred to as the Compound [2])

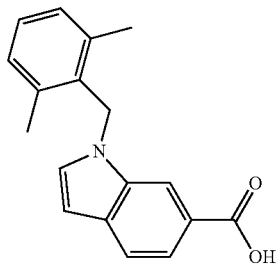 [SMILES: Cc1cccc(C)c1Cn1ccc2ccc(C(=O)O)cc21]

(1) Synthesis of methyl 1-(2,6-dimethylbenzyl)-1H-indole-6-carboxylate [2-1] (Hereinafter Referred to as the Compound [2-1])

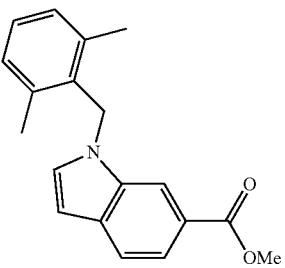 [SMILES: COC(=O)c1ccc2ccn(Cc3c(C)cccc3C)c2c1]

The titled compound (7.4 g) as a white solid was prepared from methyl indole-6-carboxylate (5.0 g) and 2,6-dimethylbenzyl chloride (5.3 g) according to the method of the process (1) of Example 1.

¹H-NMR (400 MHz, CDCl₃) δ: 8.30 (1H, s), 7.84 (1H, dd, J=8.3, 1.5 Hz), 7.65 (1H, d, J=8.3 Hz), 7.23 (1H, dd, J=8.4, 6.8 Hz), 7.14 (2H, d, J=7.6 Hz), 6.74 (1H, d, J=3.2 Hz), 6.44 (1H, dd, J=3.2, 1.0 Hz), 5.32 (2H, s), 3.98 (3H, s), 2.26 (6H, s).

(2) Synthesis of 1-(2,6-dimethylbenzyl)-1H-indole-6-carboxylic acid [2]

The titled compound (883 mg) as a white solid was prepared from the compound [2-1] obtained in the process (1) (1.0 g) according to the method of the process (2) of Example 1.

¹H-NMR (400 MHz, CDCl₃) δ: 8.37 (1H, s), 7.91 (1H, dd, J=8.4, 1.3 Hz), 7.68 (1H, d, J=8.3 Hz), 7.22 (1H, dd, J=8.4, 7.2 Hz), 7.14 (2H, d, J=7.6 Hz), 6.78 (1H, d, J=3.2 Hz), 6.47 (1H, dd, J=3.0, 0.9 Hz), 5.34 (2H, s), 2.27 (6H, s).

Example 3

Synthesis of 1-(2,4,6-trimethylbenzyl)-1H-indole-6-carboxylic acid [3](Hereinafter Referred to as the Compound [3])

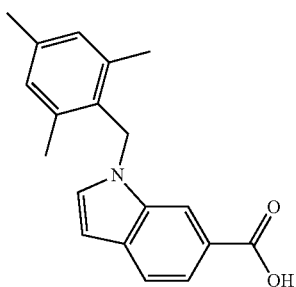 [SMILES: Cc1cc(C)c(Cn2ccc3ccc(C(=O)O)cc32)c(C)c1]

The titled compound (790 mg) as a pale yellow solid was prepared from methyl indole-6-carboxylate (1.0 g) and 2,4,6-trimethylbenzyl chloride (1.2 g) according to the method of Example 1.
$^1$H-NMR (400 MHz, CDCl$_3$) δ: 8.38 (1H, s), 7.92 (1H, dd, J=8.4, 1.3 Hz), 7.68 (1H, d, J=8.3 Hz), 6.96 (2H, s), 6.80 (1H, d, J=3.2 Hz), 6.46 (1H, dd, J=3.0, 0.6 Hz), 5.30 (2H, s), 2.33 (3H, s), 2.23 (6H, s).

Example 4

Synthesis of 2-(1-benzyl-1H-indole-6-yl)acetic acid [4](Hereinafter Referred to as a Compound [4])

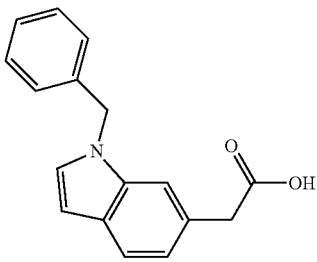

(1) Synthesis of methyl 1-tosyl-1H-indole-6-carboxylate [4-1] (Hereinafter Referred to as a Compound [4-1])

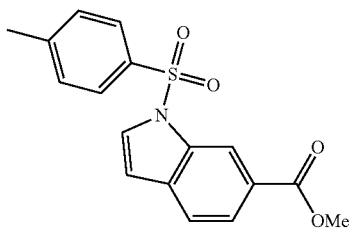 [SMILES: COC(=O)c1ccc2ccn(S(=O)(=O)c3ccc(C)cc3)c2c1]

To a solution of methyl indole-6-carboxylate (2.1 g) of 2-pentanone (40 mL), potassium carbonate (6.5 g) and 4-methylbenzenesulfonyl chloride (4.4 g) were added at room temperature, and then the reaction mixture was stirred at 80° C. for 16 hours. After cooling to room temperature, the insoluble materials were filtered, and the filtrate was concentrated under reduced pressure. To the obtained residue, a mixed solvent of ethyl acetate-hexane was added, and the obtained solid was filtered, and washed with hexane to give the titled compound (3.6 g) as a white solid.
$^1$H-NMR (400 MHz, CDCl$_3$) δ: 8.69 (1H, s), 7.93 (1H, dd, J=8.2, 1.3 Hz), 7.80 (2H, d, J=8.3 Hz), 7.71 (1H, d, J=3.7 Hz), 7.56 (1H, d, J=8.3 Hz), 7.24 (2H, d, J=8.3 Hz), 6.69 (1H, d, J=3.4 Hz), 3.97 (3H, s), 2.35 (3H, s).

(2) Synthesis of (1-tosyl-1H-indole-6-yl)methanol [4-2](Hereinafter Referred to as a Compound [4-2])

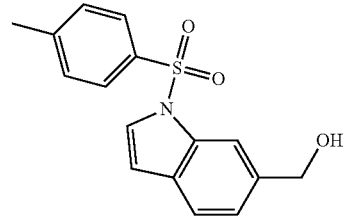

Lithium aluminum hydride (505 mg) was added to tetrahydrofuran (70 mL). To the suspension was dropped a solution of the compound [4-1] obtained in the process (1) (3.5 g) in tetrahydrofuran (70 mL) at 0° C., and then the reaction mixture was stirred at 0° C. for 3 hours. To the reaction mixture was added sodium sulfate 10 hydrate, filtered through a pad of celite, and the filtrate was concentrated under reduced pressure to give the titled compound (3.4 g) as a brown oil.
$^1$H-NMR (400 MHz, CDCl$_3$) δ: 7.99 (1H, s), 7.77 (2H, d, J=10.0 Hz), 7.57 (1H, d, J=2.9 Hz), 7.51 (1H, d, J=8.1 Hz), 7.25-7.20 (3H, m), 6.64 (1H, d, J=3.4 Hz), 4.79 (2H, s), 2.34 (3H, s), 1.80-1.70 (1H, brs).

(3) Synthesis of 6-(chloromethyl)-1-tosyl-1H-indole [4-3](Hereinafter Referred to as a Compound [4-3])

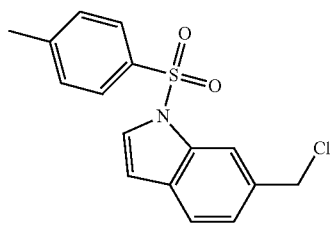 [SMILES: Cc1ccc(S(=O)(=O)n2ccc3ccc(CCl)cc32)cc1]

To a solution of the compound [4-2] obtained in the process (2) (3.3 g) in chloroform (40 mL) were added triethylamine (2.4 mL) and methanesulfonyl chloride (1.1 mL) at 0° C., and then the reaction mixture was stirred at room temperature for 27 hours. To the reaction mixture was added a saturated aqueous solution of sodium hydrogen carbonate, and extracted with chloroform. The obtained organic layer was dried over anhydrous sodium sulfate, filtered, and the filtrate was concentrated under reduced pressure to give the titled compound (3.8 g) as a brown solid.

$^1$H-NMR (400 MHz, CDCl$_3$) δ: 8.03 (1H, s), 7.77 (2H, d, J=8.5 Hz), 7.58 (1H, d, J=3.7 Hz), 7.51 (1H, d, J=8.1 Hz), 7.26 (1H, dd, J=8.1, 1.5 Hz), 7.23 (2H, d, J=8.8 Hz), 6.64 (1H, d, J=3.7 Hz), 4.73 (2H, s), 2.35 (3H, s).

(4) Synthesis of 2-(1-tosyl-1H-indole-6-yl)acetonitrile [4-4] (Hereinafter Referred to as a Compound [4-4])

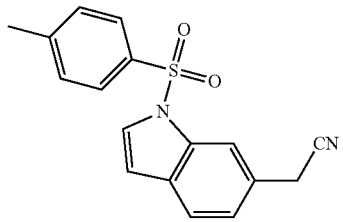 [SMILES: Cc1ccc(S(=O)(=O)n2ccc3ccc(CC#N)cc32)cc1]

To a solution of the compound [4-3] obtained in the process (3) (3.8 g) in dimethyl sulfoxide (40 mL) was added sodium cyanide (652 mg) at room temperature, and then the reaction mixture was stirred at room temperature for 48 hours. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (2.4 g) as a colorless oil.

$^1$H-NMR (400 MHz, CDCl$_3$) δ: 7.95 (1H, s), 7.77 (2H, d, J=8.3 Hz), 7.59 (1H, d, J=3.7 Hz), 7.53 (1H, d, J=8.1 Hz), 7.25 (2H, d, J=7.8 Hz), 7.20 (1H, dd, J=7.9, 1.8 Hz), 6.65 (1H, d, J=3.7 Hz), 3.87 (2H, s), 2.35 (3H, s).

(5) Synthesis of 2-(1H-indole-6-yl)acetic acid [4-5] (Hereinafter Referred to as a Compound [4-5])

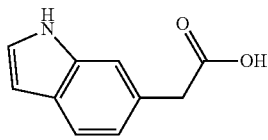 [SMILES: O=C(O)Cc1ccc2cc[nH]c2c1]

To a solution of the compound [4-4] obtained in the process (4) (2.4 g) in ethanol (12 mL) was added an aqueous solution of 5 N-sodium hydroxide (12 mL) at room temperature, and then heated at reflux for 6 hours. After cooling to room temperature, the ethanol was concentrated under reduced pressure, and then the obtained aqueous phase was washed with diethylether. Then, concentrated hydrochloric acid (5 mL) was dropped at 0° C. for acidification, and the precipitate was filtered. The obtained solid was dissolved in a mixed solvent of chloroform-methanol, dried over anhydrous sodium sulfate, filtered, and the filtrate was concentrated under reduced pressure to give the titled compound (980 mg) as a colorless oil.

$^1$H-NMR (400 MHz, CD$_3$OD) δ: 10.40 (1H, s), 7.47 (1H, d, J=7.3 Hz), 7.30 (1H, s), 7.20-7.15 (1H, m), 6.93 (1H, dd, J=8.2, 2.1 Hz), 6.39 (1H, s), 3.65 (2H, s).

(6) Synthesis of methyl 2-(1H-indole-6-yl)acetate [4-6] (Hereinafter Referred to as a Compound [4-6])

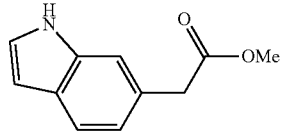 [SMILES: COC(=O)Cc1ccc2cc[nH]c2c1]

To a solution of the compound [4-5] obtained in the process (5) (497 mg) in N,N-dimethylformamide (10 mL) were added potassium carbonate (511 mg) and methyl iodide (0.12 mL) at 0° C., and then the reaction mixture was stirred at room temperature for 13 hours. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (512 mg) as a white solid.

$^1$H-NMR (400 MHz, CD$_3$OD) δ: 8.25-8.00 (1H, br), 7.59 (1H, d, J=8.1 Hz), 7.33 (1H, d, J=0.7 Hz), 7.19 (1H, t, J=2.8 Hz), 7.04 (1H, dd, J=8.1, 1.2 Hz), 6.53 (1H, s), 3.73 (2H, s), 3.69 (3H, s).

(7) Synthesis of 2-(1-benzyl-1H-indole-6-yl)acetic acid [4]

To a solution of the compound [4-6] obtained in the process (6) (49 mg) in acetonitrile (2 mL) were added powdered potassium hydroxide (19 mg) and benzyl chloride (0.033 mL) at room temperature, and then the reaction mixture was subjected to microwave irradiation at 140° C. for 20 minutes. To this reaction mixture were added methanol (1 mL) and an aqueous solution of 1 N-sodium hydroxide (1 mL), and the reaction mixture was subjected to microwave irradiation at 140° C. for 10 minutes. To the reaction mixture was added 4 N-hydrochloric acid for acidification, and then the reaction mixture was extracted with ethyl acetate. The obtained organic layer was dried over anhydrous sodium sulfate, filtered, and the filtrate was concentrated under reduced pressure. The obtained residue was purified by silica gel column chromatography to give the titled compound (42 mg) as a white solid.

$^1$H-NMR (400 MHz, CD$_3$OD) δ: 7.44 (1H, d, J=8.3 Hz), 7.31 (1H, s), 7.28-7.10 (6H, m), 7.03 (1H, dd, J=8.3, 1.5 Hz), 6.41 (1H, dd, J=3.2, 1.0 Hz), 5.36 (2H, s), 3.53 (2H, s).

ESI-MS found: 266 [M+H]$^+$

Example 5

Synthesis of 2-[1-(2,6-dimethylbenzyl)-1H-indole-6-yl]acetic acid [5] (Hereinafter Referred to as a Compound [5])

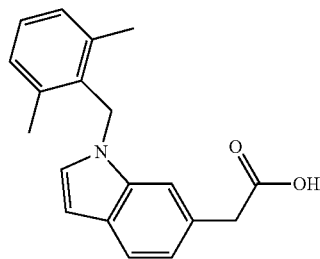 [SMILES: Cc1cccc(C)c1Cn1ccc2ccc(CC(=O)O)cc21]

The titled compound (81 mg) was prepared from the compound [4-6] obtained in the process (6) of Example 4 (97 mg) and 2,6-dimethylbenzyl chloride (79 mg) according to the method of the process (7) of Example 4.

$^1$H-NMR (400 MHz, CD$_3$OD) δ: 7.52-7.44 (2H, m), 7.21-7.14 (1H, m), 7.10 (2H, d, J=7.6 Hz), 7.00 (1H, dd, J=8.2, 1.1 Hz), 6.56 (1H, d, J=3.2 Hz), 6.32 (1H, d, J=3.2 Hz), 5.29 (2H, s), 3.72 (2H, s), 2.24 (6H, s).

ESI-MS found: 294 [M+H]$^+$

Example 6

Synthesis of 2-[1-(2-methylbenzyl)-1H-indole-6-yl]acetic acid [6] (Hereinafter Referred to as a Compound [6])

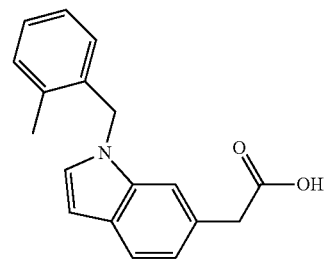 [SMILES: Cc1ccccc1Cn1ccc2ccc(CC(=O)O)cc21]

The titled compound (39 mg) as a white solid was prepared from the compound [4-6] obtained in the process (6) of Example 4 (50 mg) and 2-methylbenzyl chloride (44 μL) according to the method of the process (7) of Example 4.

$^1$H-NMR (400 MHz, CD$_3$OD) δ: 7.51 (1H, d, J=8.1 Hz), 7.23 (1H, s), 7.21-7.12 (2H, m), 7.08-7.02 (2H, m), 6.98 (1H, dd, J=8.3, 1.7 Hz), 6.68 (1H, d, J=7.8 Hz), 6.45 (1H, dd, J=3.2, 0.7 Hz), 5.34 (2H, s), 3.64 (2H, s), 2.29 (3H, s).

ESI-MS found: 280 [M+H]$^+$

Example 7

Synthesis of 2-[1-(2-chlorobenzyl)-1H-indole-6-yl]acetic acid [7] (Hereinafter Referred to as a Compound [7])

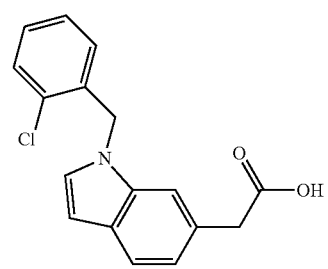 [SMILES: O=C(O)Cc1ccc2ccn(Cc3ccccc3Cl)c2c1]

The titled compound (39 mg) as a white solid was prepared from the compound [4-6] obtained in the process (6) of Example 4 (49 mg) and 2-chlorobenzyl chloride (42 μL) according to the method of the process (7) of Example 4.

$^1$H-NMR (400 MHz, CD$_3$OD) δ: 7.53 (1H, d, J=8.1 Hz), 7.43 (1H, dd, J=8.1, 1.2 Hz), 7.26-7.20 (3H, m), 7.12 (1H, td, J=7.5, 1.1 Hz), 7.00 (1H, dd, J=8.2, 1.3 Hz), 6.62 (1H, dd, J=7.7, 1.1 Hz), 6.50 (1H, dd, J=3.2, 0.7 Hz), 5.47 (2H, s), 3.63 (2H, s).

ESI-MS found: 300 [M+H]$^+$

Example 8

Synthesis of 2-{1-[2-(trifluoromethyl)benzyl]-1H-indole-6-yl}acetic acid [8] (Hereinafter Referred to as a Compound [8])

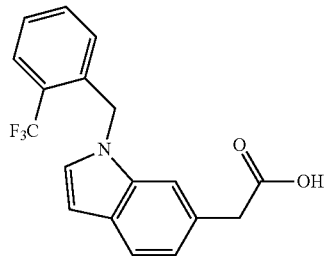 [SMILES: O=C(O)Cc1ccc2ccn(Cc3ccccc3C(F)(F)F)c2c1]

The titled compound (50 mg) as a white solid was prepared from the compound [4-6] obtained in the process (6) of Example 4 (50 mg) and 2-(trifluoromethyl)benzyl bromide (53 mg) according to the method of the process (7) of Example 4.

$^1$H-NMR (400 MHz, CD$_3$OD) δ: 7.73 (1H, d, J=6.1 Hz), 7.50 (1H, d, J=7.8 Hz), 7.42-7.30 (2H, m), 7.20-7.10 (2H, m), 7.08 (1H, d, J=7.6 Hz), 6.60-6.48 (2H, m), 5.59 (2H, s), 3.50 (2H, s)

ESI-MS found: 334 [M+H]$^+$

Example 9

Synthesis of 2-[1-(2-fluorobenzyl)-1H-indole-6-yl]acetic acid [9] (Hereinafter Referred to as a Compound [9])

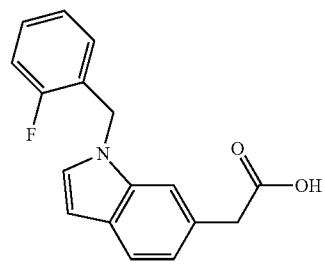 [SMILES: O=C(O)Cc1ccc2ccn(Cc3ccccc3F)c2c1]

The titled compound (22 mg) as a white solid was prepared from the compound [4-6] obtained in the process (6) of Example 4 (100 mg) and 2-fluorobenzyl chloride according to the method of the process (7) of Example 4.

ESI-MS found: 284 [M+H]$^+$

Example 10

Synthesis of 2-[1-(3-fluorobenzyl)-1H-indole-6-yl]acetic acid [10] (Hereinafter Referred to as a Compound [10])

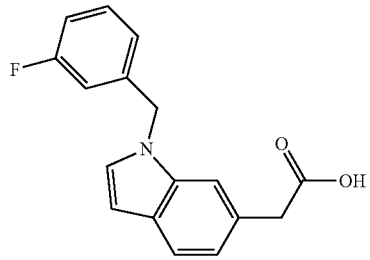

The titled compound (47 mg) as a white solid was prepared from the compound [4-6] obtained in the process (6) of Example 4 (100 mg) and 3-fluorobenzyl chloride according to the method of the process (7) of Example 4.
ESI-MS found: 284 [M+H]$^+$ Example 11

Synthesis of 2-[1-(4-fluorobenzyl)-1H-indole-6-yl]acetic acid [11] (Hereinafter Referred to as a Compound [11])

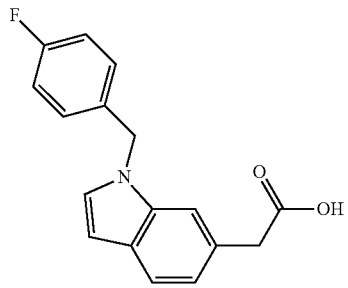 [SMILES: O=C(O)Cc1ccc2ccn(Cc3ccc(F)cc3)c2c1]

The titled compound (36 mg) as a white solid was prepared from the compound [4-6] obtained in the process (6) of Example 4 (100 mg) and 4-fluorobenzyl chloride according to the method of the process (7) of Example 4.
ESI-MS found: 284 [M+H]$^+$ Example 12

Synthesis of 2-[1-(2-chloro-6-fluorobenzyl)-1H-indole-6-yl]acetic acid [12] (Hereinafter Referred to as a Compound [12])

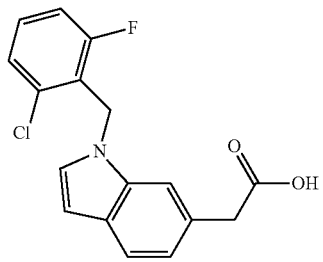 [SMILES: O=C(O)Cc1ccc2ccn(Cc3c(F)cccc3Cl)c2c1]

The titled compound (40 mg) as a white solid was prepared from the compound [4-6] obtained in the process (6) of Example 4 (100 mg) and 2-chloro-6-fluorobenzyl chloride according to the method of the process (7) of Example 4.
ESI-MS found: 318 [M+H]$^+$ [M+H]$^+$ Example 13

Synthesis of 2-[1-(2-chloro-4-fluorobenzyl)-1H-indole-6-yl]acetic acid [13] (Hereinafter Referred to as a Compound [13])

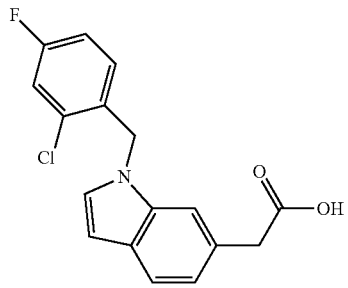 [SMILES: O=C(O)Cc1ccc2ccn(Cc3ccc(F)cc3Cl)c2c1]

The titled compound (38 mg) as a white solid was prepared from the compound [4-6] obtained in the process (6) of Example 4 (100 mg) and 2-chloro-4-fluorobenzyl chloride according to the method of the process (7) of Example 4.
ESI-MS found: 318 [M+H]$^+$ Example 14

Synthesis of 2-[1-(2-chloro-5-fluorobenzyl)-1H-indole-6-yl]acetic acid [14] (Hereinafter Referred to as a Compound [14])

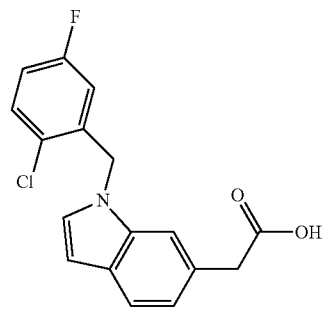 [SMILES: O=C(O)Cc1ccc2ccn(Cc3cc(F)ccc3Cl)c2c1]

The titled compound (24 mg) as a white solid was prepared from the compound [4-6] obtained in the process (6) of Example 4 (100 mg) and 2-chloro-5-fluorobenzyl bromide according to the method of the process (7) of Example 4.
ESI-MS found: 318 [M+H]$^+$ Example 15

Synthesis of 2-[1-(3-chlorobenzyl)-1H-indole-6-yl]acetic acid [15] (Hereinafter Referred to as a Compound [15])

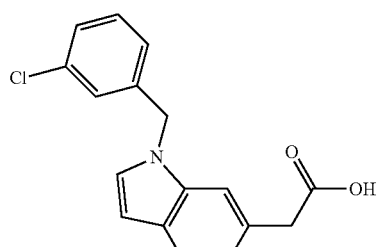

The titled compound (20 mg) as a white solid was prepared from the compound [4-6] obtained in the process (6) of Example 4 (100 mg) and 3-chlorobenzyl chloride according to the method of the process (7) of Example 4.
ESI-MS found: 300 [M+H]$^+$

Example 16

Synthesis of 2-[1-(4-chlorobenzyl)-1H-indole-6-yl]acetic acid [16] (Hereinafter Referred to as a Compound [16])

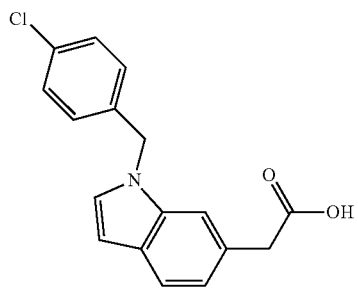 [SMILES: O=C(O)Cc1ccc2ccn(Cc3ccc(Cl)cc3)c2c1]

The titled compound (17 mg) as a light brown solid was prepared from the compound [4-6] obtained in the process (6) of Example 4 (100 mg) and 4-chlorobenzyl chloride according to the method of the process (7) of Example 4.
ESI-MS found: 300 [M+H]$^+$

Example 17

Synthesis of 2-[1-(2,6-dichlorobenzyl)-1H-indole-6-yl]acetic acid [17] (Hereinafter Referred to as a Compound [17])

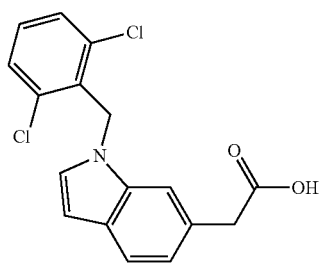 [SMILES: O=C(O)Cc1ccc2ccn(Cc3c(Cl)cccc3Cl)c2c1]

The titled compound (65 mg) as a white solid was prepared from the compound [4-6] obtained in the process (6) of Example 4 (100 mg) and 2,6-dichlorobenzyl chloride according to the method of the process (7) of Example 4.
ESI-MS found: 334 [M+H]$^+$

Example 18

Synthesis of 2-[1-(2,3-dichlorobenzyl)-1H-indole-6-yl]acetic acid [18] (Hereinafter Referred to as a Compound [18])

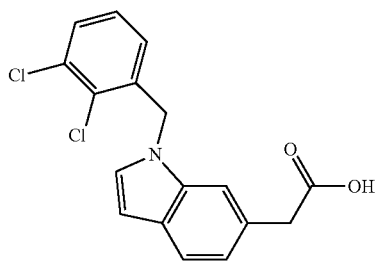 [SMILES: O=C(O)Cc1ccc2ccn(Cc3cccc(Cl)c3Cl)c2c1]

The titled compound (13 mg) as a white solid was prepared from the compound [4-6] obtained in the process (6) of Example 4 (100 mg) and 2,3-dichlorobenzyl chloride according to the method of the process (7) of Example 4.
ESI-MS found: 334 [M+H]$^+$

Example 19

Synthesis of 2-{1-[(6-chlorobenzo[d][1,3]dioxol-5-yl)methyl]-1H-indole-6-yl}acetic acid [19] (Hereinafter Referred to as a Compound [19])

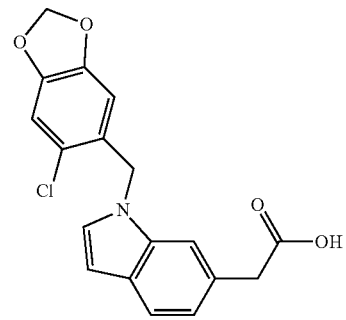 [SMILES: O=C(O)Cc1ccc2ccn(Cc3cc4c(cc3Cl)OCO4)c2c1]

The titled compound (46 mg) as a white solid was prepared from the compound [4-6] obtained in the process (6) of Example 4 (100 mg) and 6-chloropiperonyl chloride according to the method of the process (7) of Example 4.
ESI-MS found: 344 [M+H]$^+$

Example 20

Synthesis of 2-[1-(2,4-dichlorobenzyl)-1H-indole-6-yl]acetic acid [20] (Hereinafter Referred to as a Compound [20])

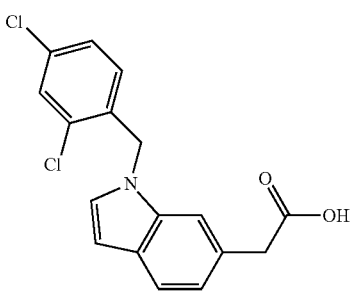 [SMILES: O=C(O)Cc1ccc2ccn(Cc3ccc(Cl)cc3Cl)c2c1]

The titled compound (29 mg) as a white solid was prepared from the compound [4-6] obtained in the process (6) of Example 4 (100 mg) and 2,4-dichlorobenzyl chloride according to the method of the process (7) of Example 4.
ESI-MS found: 334 [M+H]$^+$

Example 21

Synthesis of 2-[1-(2,5-dichlorobenzyl)-1H-indole-6-yl]acetic acid [21] (Hereinafter Referred to as a Compound [21])

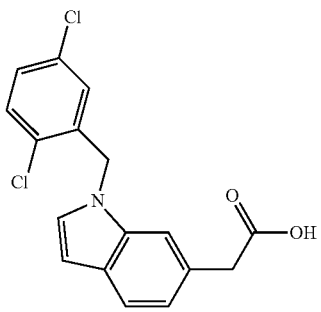 [SMILES: O=C(O)Cc1ccc2ccn(Cc3cc(Cl)ccc3Cl)c2c1]

The titled compound (17 mg) as a white solid was prepared from the compound [4-6] obtained in the process (6) of Example 4 (100 mg) and 2,5-dichlorobenzyl bromide according to the method of the process (7) of Example 4.

ESI-MS found: 334 [M+H]$^+$

Example 22

Synthesis of 2-{1-[2-fluoro-6-(trifluoromethyl)benzyl]-1H-indole-6-yl}acetic acid [22] (Hereinafter Referred to as a Compound [22])

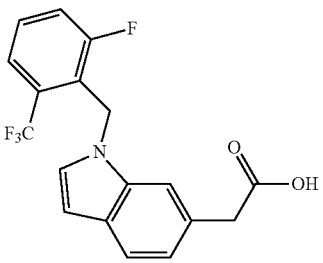 [SMILES: O=C(O)Cc1ccc2ccn(Cc3c(F)cccc3C(F)(F)F)c2c1]

The titled compound (16 mg) as a white solid was prepared from the compound [4-6] obtained in the process (6) of Example 4 (100 mg) and 2-fluoro-6-(trifluoromethyl)benzyl bromide according to the method of the process (7) of Example 4.

ESI-MS found: 352 [M+H]$^+$

Example 23

Synthesis of 2-{1-[4-fluoro-2-(trifluoromethyl)benzyl]-1H-indole-6-yl}acetic acid [23] (Hereinafter Referred to as a Compound [23])

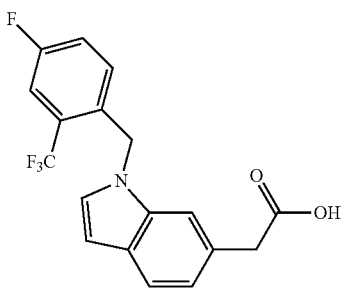 [SMILES: O=C(O)Cc1ccc2ccn(Cc3ccc(F)cc3C(F)(F)F)c2c1]

The titled compound (36 mg) as a reddish brown solid was prepared from the compound [4-6] obtained in the process (6) of Example 4 (100 mg) and 4-fluoro-2-(trifluoromethyl)benzyl bromide according to the method of the process (7) of Example 204.

ESI-MS found: 352 [M+H]$^+$

Example 24

Synthesis of 2-[1-(4-ethylbenzyl)-1H-indole-6-yl]acetic acid [24] (Hereinafter Referred to as a Compound [24])

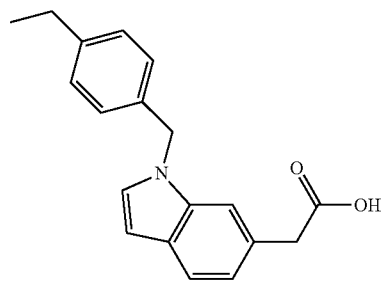 [SMILES: CCc1ccc(Cn2ccc3ccc(CC(=O)O)cc32)cc1]

The titled compound (24 mg) as a reddish brown solid was prepared from the compound [4-6] obtained in the process (6) of Example 4 (100 mg) and 4-ethylbenzyl chloride according to the method of the process (7) of Example 4.

ESI-MS found: 294 [M+H]$^+$

Example 25

Synthesis of 2-[1-(2,4-difluorobenzyl)-1H-indole-6-yl]acetic acid [25] (Hereinafter Referred to as a Compound [25])

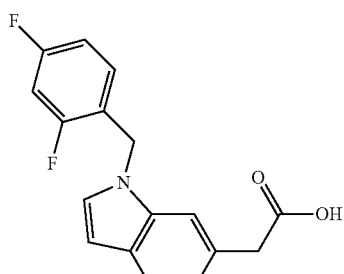

The titled compound (35 mg) as a white solid was prepared from the compound [4-6] obtained in the process (6) of Example 4 (100 mg) and 2,4-difluorobenzyl chloride according to the method of the process (7) of Example 4.

ESI-MS found: 302 [M+H]$^+$

Example 26

Synthesis of 2-[1-(2,6-difluorobenzyl)-1H-indole-6-yl]acetic acid [26] (Hereinafter Referred to as a Compound [26])

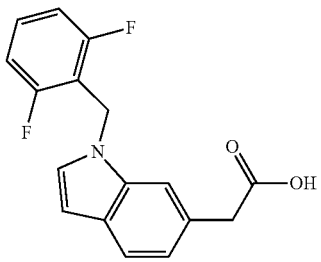

The titled compound (20 mg) as a white solid was prepared from the compound [4-6] obtained in the process (6) of Example 4 (100 mg) and 2,6-difluorobenzyl chloride according to the method of the process (7) of Example 4.
ESI-MS found: 302 [M+H]$^+$

Example 27

Synthesis of 2-[1-(2,5-difluorobenzyl)-1H-indole-6-yl]acetic acid [27] (Hereinafter Referred to as a Compound [27])

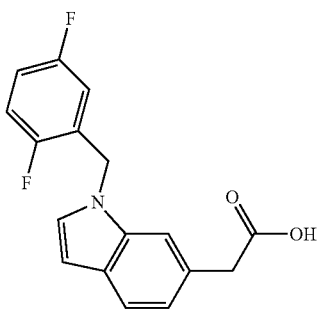 [SMILES: O=C(O)Cc1ccc2ccn(Cc3cc(F)ccc3F)c2c1]

The titled compound (18 mg) as a white solid was prepared from the compound [4-6] obtained in the process (6) of Example 4 (100 mg) and 2,5-difluorobenzyl bromide according to the method of the process (7) of Example 4.
ESI-MS found: 302 [M+H]$^+$

Example 28

Synthesis of 2-[1-(2,3-difluorobenzyl)-1H-indole-6-yl]acetic acid [28] (Hereinafter Referred to as a Compound [28])

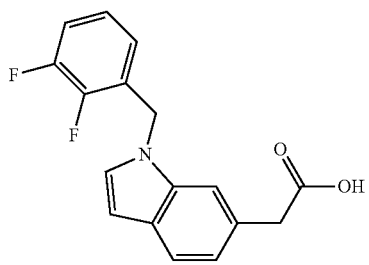 [SMILES: O=C(O)Cc1ccc2ccn(Cc3cccc(F)c3F)c2c1]

The titled compound (14 mg) as a white solid was prepared from the compound [4-6] obtained in the process (6) of Example 4 (100 mg) and 2,3-difluorobenzyl bromide according to the method of the process (7) of Example 4.
ESI-MS found: 302 [M+H]$^+$

Example 29

Synthesis of 2-{1-[3-(trifluoromethyl)benzyl]-1H-indole-6-yl}acetic acid [29] (Hereinafter Referred to as a Compound [29])

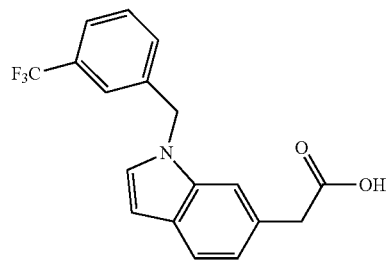 [SMILES: O=C(O)Cc1ccc2ccn(Cc3cccc(C(F)(F)F)c3)c2c1]

The titled compound (38 mg) as a white solid was prepared from the compound [4-6] obtained in the process (6) of Example 4 (100 mg) and 3-(trifluoromethyl)benzyl chloride according to the method of the process (7) of Example 4.
ESI-MS found: 334 [M+H]$^+$

Example 30

Synthesis of 2-{1-[4-(trifluoromethyl)benzyl]-1H-indole-6-yl}acetic acid [30] (Hereinafter Referred to as a Compound [30])

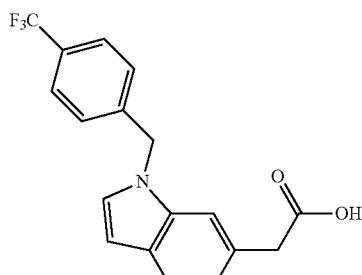

The titled compound (33 mg) as a white solid was prepared from the compound [4-6] obtained in the process (6) of Example 4 (100 mg) and 4-(trifluoromethyl)benzyl chloride according to the method of the process (7) of Example 4.
ESI-MS found: 334 [M+H]$^+$

Example 31

Synthesis of 2-[1-(2,4-dimethylbenzyl)-1H-indole-6-yl]acetic acid [31] (Hereinafter Referred to as a Compound [31])

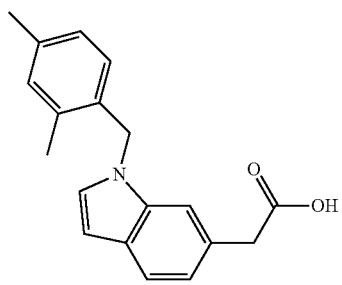 [SMILES: Cc1ccc(Cn2ccc3ccc(CC(=O)O)cc32)c(C)c1]

The titled compound (22 mg) as a white solid was prepared from the compound [4-6] obtained in the process (6) of Example 4 (100 mg) and 2,4-dimethylbenzyl chloride according to the method of the process (7) of Example 4.
ESI-MS found: 294 [M+H]$^+$

Example 32

Synthesis of 2-[1-(2,5-dimethylbenzyl)-1H-indole-6-yl]acetic acid [32] (Hereinafter Referred to as a Compound [32])

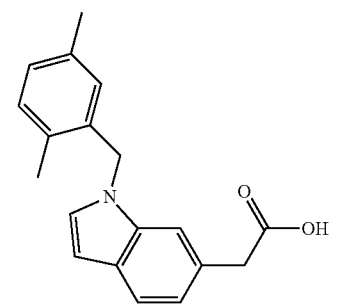 [SMILES: Cc1ccc(C)c(Cn2ccc3ccc(CC(=O)O)cc32)c1]

The titled compound (26 mg) as a white solid was prepared from the compound [4-6] obtained in the process (6) of Example 4 (100 mg) and 2,5-dimethylbenzyl chloride according to the method of the process (7) of Example 4.
ESI-MS found: 294 [M+H]$^+$

Example 33

Synthesis of 2-[1-(3-methylbenzyl)-1H-indole-6-yl]acetic acid [33] (Hereinafter Referred to as a Compound [33])

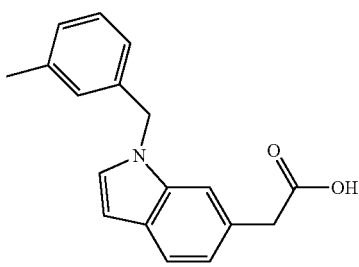 [SMILES: Cc1cccc(Cn2ccc3ccc(CC(=O)O)cc32)c1]

The titled compound (43 mg) as a reddish brown solid was prepared from the compound [4-6] obtained in the process (6) of Example 4 (100 mg) and 3-methylbenzyl chloride according to the method of the process (7) of Example 4.
ESI-MS found: 280 [M+H]$^+$

Example 34

Synthesis of 2-[1-(4-methylbenzyl)-1H-indole-6-yl]acetic acid [34] (Hereinafter Referred to as a Compound [34])

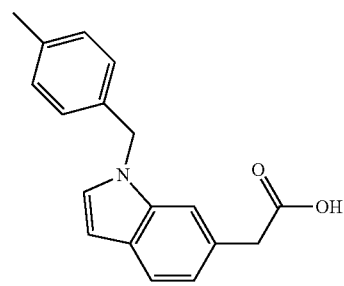 [SMILES: Cc1ccc(Cn2ccc3ccc(CC(=O)O)cc32)cc1]

The titled compound (21 mg) as a reddish brown solid was prepared from the compound [4-6] obtained in the process (6) of Example 4 (100 mg) and 4-methylbenzyl chloride according to the method of the process (7) of Example 4.
ESI-MS found: 280 [M+H]$^+$

Example 35

Synthesis of 2-[1-(pyridine-4-ylmethyl)-1H-indole-6-yl]acetic acid [35](Hereinafter Referred to as a Compound [35])

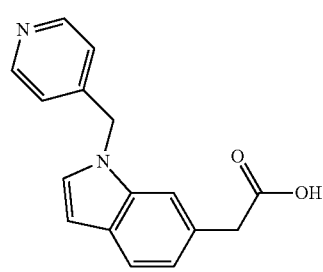 [SMILES: O=C(O)Cc1ccc2ccn(Cc3ccncc3)c2c1]

The titled compound (12 mg) as a yellow solid was prepared from the compound [4-6] obtained in the process (6) of Example 4 (100 mg) and 4-(chloromethyl)pyridine according to the method of the process (7) of Example 4.
ESI-MS found: 267 [M+H]$^+$

Example 36

Synthesis of 2-[1-(2-methoxybenzyl)-1H-indole-6-yl]acetic acid [36] (Hereinafter Referred to as a Compound [36])

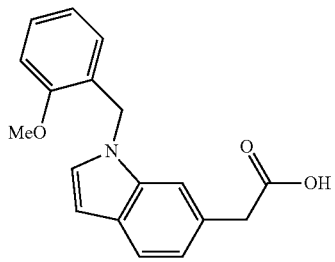 [SMILES: COc1ccccc1Cn1ccc2ccc(CC(=O)O)cc21]

The titled compound (29 mg) as a white solid was prepared from the compound [4-6] obtained in the process (6) of Example 4 (100 mg) and 2-methoxybenzyl chloride according to the method of the process (7) of Example 4.
ESI-MS found: 296 [M+H]$^+$

Example 37

Synthesis of 2-[1-(3-methoxybenzyl)-1H-indole-6-yl]acetic acid [37] (Hereinafter Referred to as a Compound [37])

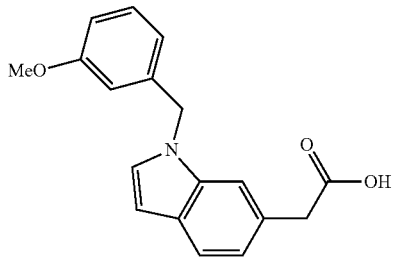 [SMILES: COc1cccc(Cn2ccc3ccc(CC(=O)O)cc32)c1]

The titled compound (55 mg) as a white solid was prepared from the compound [4-6] obtained in the process (6) of Example 4 (100 mg) and 3-methoxybenzyl chloride according to the method of the process (7) of Example 4.
ESI-MS found: 296 [M+H]$^+$

Example 38

Synthesis of 2-[1-(4-methoxybenzyl)-1H-indole-6-yl]acetic acid [38] (Hereinafter Referred to as a Compound [38])

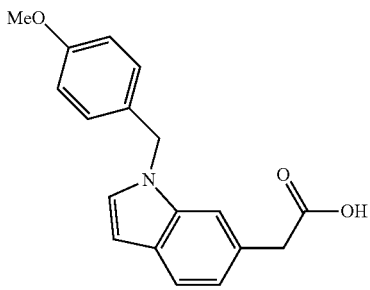 [SMILES: COc1ccc(Cn2ccc3ccc(CC(=O)O)cc32)cc1]

The titled compound (44 mg) as a light brown solid was prepared from the compound [4-6] obtained in the process (6) of Example 4 (100 mg) and 4-methoxybenzyl chloride according to the method of the process (7) of Example 4.
ESI-MS found: 296 [M+H]$^+$

Example 39

Synthesis of 2-[1-(Naphthalene-1-ylmethyl)-1H-indole-6-yl]acetic acid [39] (Hereinafter Referred to as a Compound [39])

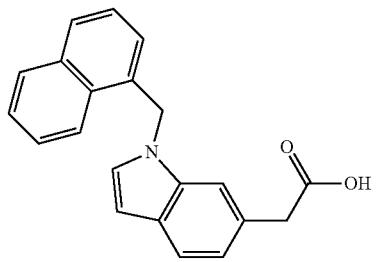 [SMILES: O=C(O)Cc1ccc2ccn(Cc3cccc4ccccc34)c2c1]

The titled compound (30 mg) as a white solid was prepared from the compound [4-6] obtained in the process (6) of Example 4 (100 mg) and 1-(chloromethyl)naphthalene according to the method of the process (7) of Example 4.
ESI-MS found: 316 [M+H]$^+$

Example 40

Synthesis of 2-[1-(Naphthalene-2-ylmethyl)-1H-indole-6-yl]acetic acid [40] (Hereinafter Referred to as a Compound [40])

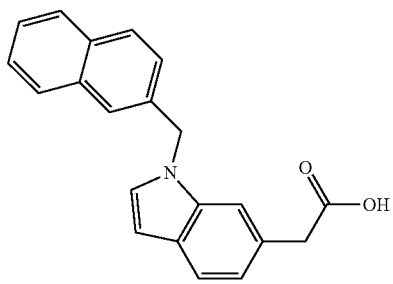 [SMILES: O=C(O)Cc1ccc2ccn(Cc3ccc4ccccc4c3)c2c1]

The titled compound (31 mg) as a white solid was prepared from the compound [4-6] obtained in the process (6) of Example 4 (100 mg) and 2-(chloromethyl)naphthalene according to the method of the process (7) of Example 4.

ESI-MS found: 316 [M+H]$^+$

Example 41

Synthesis of 2-{1-[(6-chloropyridine-3-yl)methyl]-1H-indole-6-yl}acetic acid [41] (Hereinafter Referred to as a Compound [41])

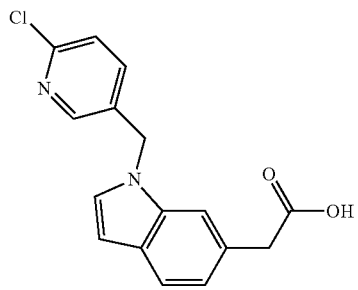

The titled compound (26 mg) as a white solid was prepared from the compound [4-6] obtained in the process (6) of Example 4 (100 mg) and 2-chloro-5-(chloromethyl)pyridine according to the method of the process (7) of Example 4.
ESI-MS found: 301 [M+H]$^+$

Example 42

Synthesis of 2-{1-[(6-methylpyridine-2-yl)methyl]-1H-indole-6-yl}acetic acid [42] (Hereinafter Referred to as a Compound [42])

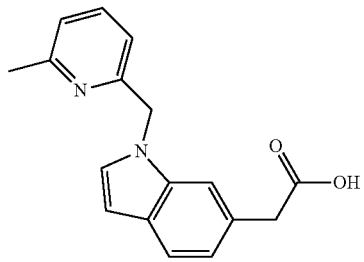

The titled compound (26 mg) as a white solid was prepared from the compound [4-6] obtained in the process (6) of Example 4 (100 mg) and 2-(bromomethyl)-6-methylpyridine according to the method of the process (7) of Example 4.
ESI-MS found: 281 [M+H]$^+$

Example 43

Synthesis of 2-[1-(biphenyl-2-ylmethyl)-1H-indole-6-yl]acetic acid [43](Hereinafter Referred to as a Compound [43])

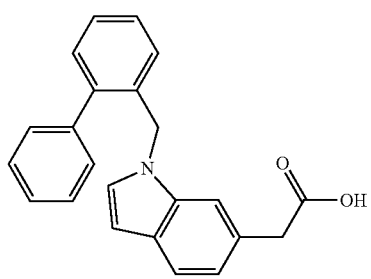 [SMILES: O=C(O)Cc1ccc2ccn(Cc3ccccc3-c3ccccc3)c2c1]

The titled compound (41 mg) as a white solid was prepared from the compound [4-6] obtained in the process (6) of Example 4 (100 mg) and 2-phenylbenzyl bromide according to the method of the process (7) of Example 4.
ESI-MS found: 342 [M+H]$^+$

Example 44

Synthesis of 2-[1-(biphenyl-3-ylmethyl)-1H-indole-6-yl]acetic acid [44](Hereinafter Referred to as a Compound [44])

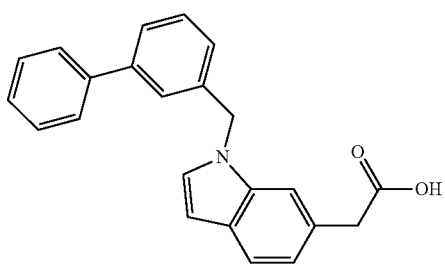 [SMILES: O=C(O)Cc1ccc2ccn(Cc3cccc(-c4ccccc4)c3)c2c1]

The titled compound (46 mg) as an amorphous was prepared from the compound [4-6] obtained in the process (6) of Example 4 (100 mg) and 3-phenylbenzyl bromide according to the method of the process (7) of Example 4.
ESI-MS found: 342 [M+H]$^+$

Example 45

Synthesis of 2-[1-(biphenyl-4-ylmethyl)-1H-indole-6-yl]acetic acid [45](Hereinafter Referred to as a Compound [45])

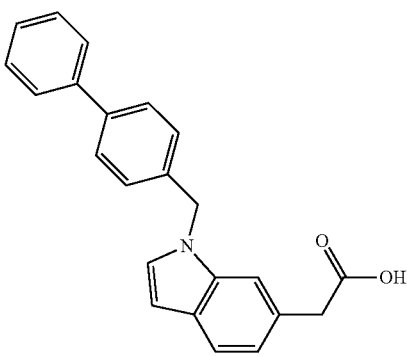 [SMILES: O=C(O)Cc1ccc2ccn(Cc3ccc(-c4ccccc4)cc3)c2c1]

The titled compound (22 mg) as a light brown solid was prepared from the compound [4-6] obtained in the process (6) of Example 4 (100 mg) and 4-phenylbenzyl chloride according to the method of the process (7) of Example 4.
ESI-MS found: 342 [M+H]$^+$

Example 46

Synthesis of 2-[1-(3-phenoxybenzyl)-1H-indole-6-yl]acetic acid [46] (Hereinafter Referred to as a Compound [46])

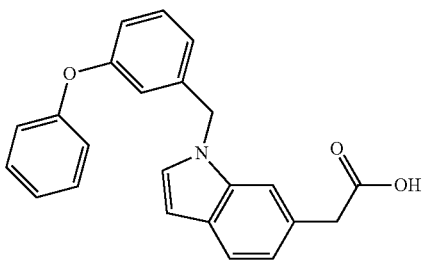 [SMILES: O=C(O)Cc1ccc2ccn(Cc3cccc(Oc4ccccc4)c3)c2c1]

The titled compound (44 mg) as an amorphous substance was prepared from the compound [4-6] obtained in the process (6) of Example 4 (100 mg) and 3-phenoxybenzyl chloride according to the method of the process (7) of Example 4.
ESI-MS found: 358 [M+H]$^+$

Example 47

Synthesis of 2-[1-(3-phenylpropyl)-1H-indole-6-yl]acetic acid [47] (Hereinafter Referred to as a Compound [47])

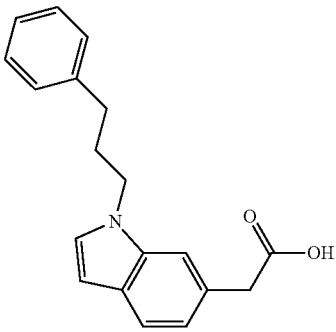 [SMILES: O=C(O)Cc1ccc2ccn(CCCc3ccccc3)c2c1]

The titled compound (44 mg) as a white solid was prepared from the compound [4-6] obtained in the process (6) of Example 4 (100 mg) and 3-phenylpropyl chloride according to the method of the process (7) of Example 4.
ESI-MS found: 294 [M+H]$^+$

Example 48

Synthesis of 2-(1-isopropyl-1H-indole-6-yl)acetic acid [48] (Hereinafter Referred to as a Compound [48])

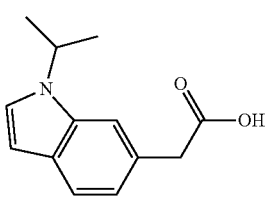 [SMILES: CC(C)n1ccc2ccc(CC(=O)O)cc21]

The titled compound (12 mg) as an amorphous was prepared from the compound [4-6] obtained in the process (6) of Example 4 (100 mg) and isopropyl chloride according to the method of the process (7) of Example 4.
ESI-MS found: 218 [M+H]$^+$

Example 49

Synthesis of 2-(1-isobutyl-1H-indole-6-yl)acetic acid [49] (Hereinafter Referred to as a Compound [49])

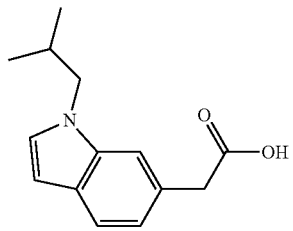 [SMILES: CC(C)Cn1ccc2ccc(CC(=O)O)cc21]

The titled compound (10 mg) as a white solid was prepared from the compound [4-6] obtained in the process (6) of Example 4 (100 mg) and isobutyl chloride according to the method of the process (7) of Example 4.
ESI-MS found: 232 [M+H]$^+$

Example 50

Synthesis of 2-[1-(cyclohexylmethyl)-1H-indole-6-yl]acetic acid [50] (Hereinafter Referred to as a Compound [50])

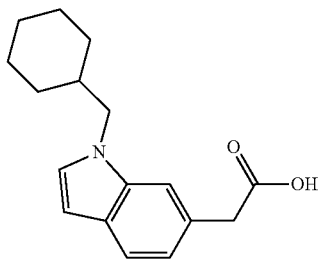 [SMILES: O=C(O)Cc1ccc2ccn(CC3CCCCC3)c2c1]

The titled compound (69 mg) as a white solid was prepared from the compound [4-6] obtained in the process (6) of Example 4 (100 mg) and cyclohexylmethyl bromide according to the method of the process (7) of Example 4.
ESI-MS found: 272 [M+H]$^+$

Example 51

Synthesis of 1-(2,6-dimethylbenzyl)-1H-benzimidazole-6-carboxylic acid [51] (Hereinafter Referred to as a Compound [51])

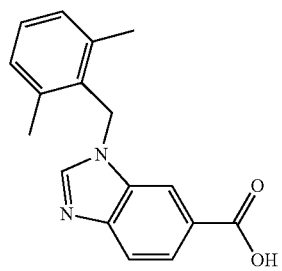

(1) Synthesis of 2,6-dimethylbenzyl 1-(2,6-dimethylbenzyl)-1H-benzimidazole-6-carboxylate [51-1] (Hereinafter Referred to as a Compound [51-1])

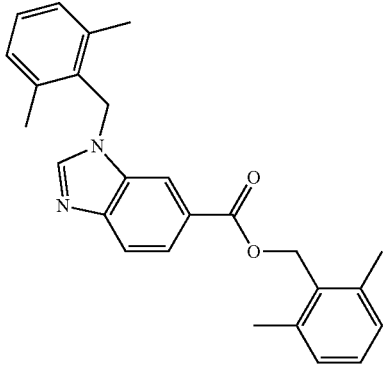 [SMILES: Cc1cccc(C)c1COC(=O)c1ccc2ncn(Cc3c(C)cccc3C)c2c1]

To a solution of 5-benzoimidazole carboxylic acid (1.1 g) in N,N-dimethylformamide (15 mL) were added potassium carbonate (2.7 g) and 2,6-dimethylbenzyl chloride (2.3 g) at room temperature, and then the reaction mixture was stirred at room temperature for 2 days. The reaction mixture was quenched with water, and extracted with chloroform. The obtained organic layer was dried over anhydrous sodium sulfate, filtered, and the filtrate was concentrated under reduced pressure. The obtained residue was purified by silica gel column chromatography to give the titled compound (1.1 g) as a white solid.
$^1$H-NMR (400 MHz, CDCl$_3$) δ: 8.19 (1H, d, J=2.2 Hz), 8.01 (1H, dd, J=8.5, 1.7 Hz), 7.80 (1H, d, J=8.5 Hz), 7.52 (1H, s), 7.24-7.22 (2H, m), 7.13-7.11 (4H, m), 5.49 (2H, s), 5.31 (2H, s), 2.48 (6H, s), 2.26 (6H, s).

(2) Synthesis of 1-(2,6-dimethylbenzyl)-1H-benzimidazole-6-carboxylic acid

To a solution of the compound [51-1] obtained in the process (1) (49 mg) in methanol (3 mL) was added an aqueous solution of 1 N-sodium hydroxide (3 mL) at room temperature, and then the reaction mixture was stirred at 60° C. for 18 hours. After cooling to room temperature, to the reaction mixture was added 1N-hydrochloric acid for acidification, and the precipitated solid was filtered to give the titled compound (30 mg) as a white solid.
$^1$H-NMR (400 MHz, DMSO-d$_6$) δ: 8.16 (1H, d, J=1.2 Hz), 7.92 (1H, s), 7.83 (1H, dd, J=8.5, 1.5 Hz), 7.71 (1H, d, J=8.5 Hz), 7.22 (1H, dd, J=8.3, 6.8 Hz), 7.14 (2H, d, J=7.6 Hz), 5.52 (2H, s), 2.26 (6H, s).

Example 52

Synthesis of 2-[1-(2,6-dimethylbenzyl)-1H-benzimidazole-6-yl]acetic acid [52] (Hereinafter Referred to as a Compound [52])

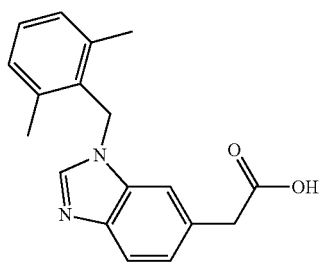

(1) Synthesis of [1-(2,6-dimethylbenzyl)-1H-benzimidazole-6-yl]methanol [52-1] (Hereinafter Referred to as a Compound [52-1])

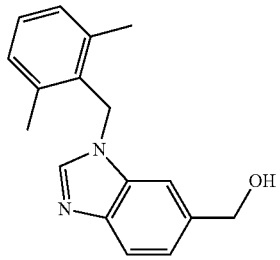

The titled compound (456 mg) as a white solid was prepared from the compound [51-1] obtained in the process (1) of Example 51 (1.1 g) and lithium aluminum hydride (197 mg) according to the method of the process (2) of Example 4.
$^1$H-NMR (400 MHz, CDCl$_3$) δ: 7.78 (1H, d, J=8.3 Hz), 7.55 (1H, s), 7.38 (1H, s), 7.29-7.26 (2H, m), 7.15 (2H, d, J=7.3 Hz), 5.28 (2H, s), 4.88 (2H, d, J=4.9 Hz), 2.29 (6H, s), 1.95 (1H, s).

(2) Synthesis of 2-[1-(2,6-dimethylbenzyl)-1H-benzimidazole-6-yl]acetonitrile [52-2] (Hereinafter Referred to as a Compound [52-2])

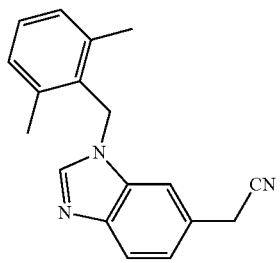 [SMILES: Cc1cccc(C)c1Cn1cnc2ccc(CC#N)cc21]

To a solution of the compound [52-1] obtained in the process (1) (408 mg) in dichloromethane (10 mL) were added carbon tetrabromide (669 mg) and triphenylphosphine (525 mg) at room temperature, and then the reaction mixture was stirred at room temperature for 5 minutes. Then, to the reaction mixture were added dimethyl sulfoxide (5 mL) and sodium cyanide (109 mg), and the reaction mixture was stirred at 60° C. for 30 minutes. The reaction mixture was quenched with water, and extracted with chloroform. The organic layer was dried over anhydrous sodium sulfate, filtered, and the filtrate was concentrated under reduced pressure. The obtained residue was purified by silica gel column chromatography to give the titled compound (110 mg) as a white solid.
$^1$H-NMR (400 MHz, CDCl$_3$) δ: 7.79 (1H, d, J=7.6 Hz), 7.49 (1H, s), 7.43 (1H, s), 7.27 (1H, t, J=7.1 Hz), 7.21-7.15 (3H, m), 5.29 (2H, s), 3.93 (2H, s), 2.29 (6H, s).

(3) Synthesis of 2-[1-(2,6-dimethylbenzyl)-1H-benzimidazole-6-yl]acetic acid To a solution of the compound [52-2] obtained in the process (2) (110 mg) in ethanol (3 mL) was added an aqueous solution of 3N-sodium hydroxide (3 mL) at room temperature, and then the reaction mixture was heated at reflux for 15 hours. To the reaction mixture was added 1N-hydrochloric acid for acidification, and the precipitated solid was filtered to give the titled compound (81 mg) as a white solid.

$^1$H-NMR (400 MHz, DMSO-$d_6$) δ: 7.63 (1H, s), 7.57 (1H, d, J=8.3 Hz), 7.43 (1H, s), 7.21 (1H, dd, J=8.2, 6.7 Hz), 7.13-7.09 (3H, m), 5.38 (2H, s), 3.64 (2H, s), 2.24 (6H, s).

Example 53

Synthesis of 1-(2,6-dimethylbenzyl)-1H-indazole-6-carboxylic acid [53] (Hereinafter Referred to as a Compound [53])

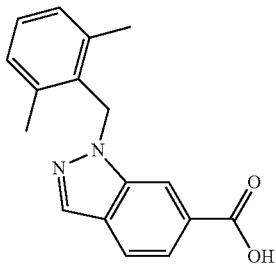 [SMILES: Cc1cccc(C)c1Cn1ncc2ccc(C(=O)O)cc21]

(1) Synthesis of 2,6-dimethylbenzyl 1-(2,6-dimethylbenzyl)-1H-indazole-6-carboxylate [53-1](Hereinafter Referred to as a Compound [53-1])

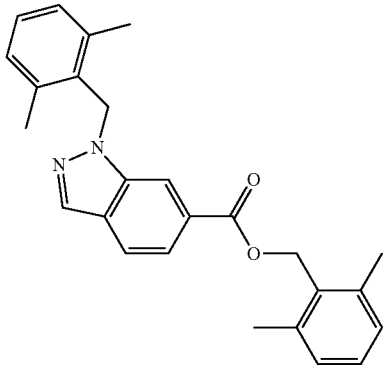 [SMILES: Cc1cccc(C)c1COC(=O)c1ccc2cnn(Cc3c(C)cccc3C)c2c1]

The titled compound (575 mg) as a yellow solid was prepared from 1H-indazole-6-carboxylic acid (498 mg) and 2,6-dimethylbenzyl chloride (1.10 g) according to the method of the process (1) of Example 51.

$^1$H-NMR (400 MHz, CDCl$_3$) δ: 8.02 (1H, d, J=1.0 Hz), 7.87-7.86 (1H, m), 7.77 (1H, dd, J=8.4, 1.3 Hz), 7.71 (1H, dd, J=8.5, 0.7 Hz), 7.24 (1H, dd, J=8.2, 6.7 Hz), 7.14 (2H, d, J=7.6 Hz), 7.08 (1H, dd, J=8.1, 7.1 Hz), 6.96 (2H, d, J=7.6 Hz), 5.59 (2H, s), 5.42 (2H, s), 2.44 (6H, s), 2.25 (6H, s).

(2) Synthesis of 1-(2,6-dimethylbenzyl)-1H-indazole-6-carboxylic acid [53]

The titled compound (51 mg) as a white solid was prepared from the compound [53-1] obtained in the process (1) (110 mg) according to the method of the process (2) of Example 51.

$^1$H-NMR (400 MHz, DMSO-$d_6$) δ: 8.33 (1H, d, J=1.2 Hz), 8.06 (1H, d, J=1.0 Hz), 7.77 (1H, dd, J=8.4, 0.6 Hz), 7.70 (1H, dd, J=8.3, 1.2 Hz), 7.14-7.12 (1H, m), 7.04 (2H, d, J=7.6 Hz), 5.62 (2H, s), 2.28 (6H, s).

Example 54

Synthesis of 2-[1-(2,6-dimethylbenzyl)-1H-indazole-6-yl]acetic acid [54](Hereinafter Referred to as a Compound [54])

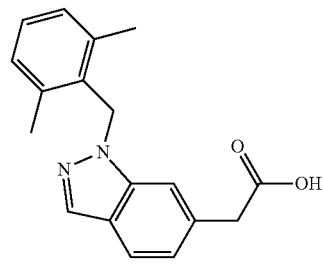 [SMILES: Cc1cccc(C)c1Cn1ncc2ccc(CC(=O)O)cc21]

(1) Synthesis of [1-(2,6-dimethylbenzyl)-1H-indazole-6-yl]methanol [54-1] (Hereinafter Referred to as a Compound [54-1])

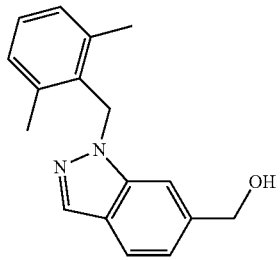

The titled compound (279 mg) as a white solid was prepared from the compound [53-1] obtained in the process (1) of Example 53 (465 mg) and lithium aluminum hydride according to the method of the process (2) of Example 4.

$^1$H-NMR (400 MHz, CDCl$_3$) δ: 7.96 (1H, s), 7.69 (1H, d, J=8.1 Hz), 7.27-7.26 (1H, m), 7.19-7.17 (1H, m), 7.11-7.09 (3H, m), 5.54 (2H, s), 4.79 (2H, d, J=5.9 Hz), 2.32 (6H, s), 1.82 (1H, t, J=5.6 Hz).

(2) Synthesis of 6-(bromomethyl)-1-(2,6-dimethylbenzyl)-1H-indazole [54-2] (Hereinafter Referred to as a Compound [54-2])

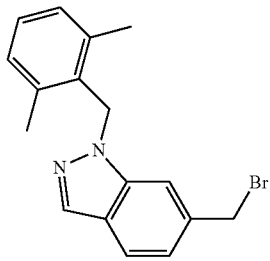 [SMILES: Cc1cccc(C)c1Cn1ncc2ccc(CBr)cc21]

To a solution of the compound [54-1] obtained in the process (1) (63 mg) in methylene chloride (3 mL) were added carbon tetrabromide (112 mg) and triphenylphosphine (97 mg) at room temperature, and then the reaction mixture was stirred at room temperature for 10 minutes. The reaction mixture was concentrated under reduced pressure, and the obtained residue was purified by silica gel column chromatography to give the titled compound (72 mg) as a white solid.
$^1$H-NMR (400 MHz, CDCl$_3$) δ: 7.97 (1H, d, J=1.0 Hz), 7.69 (1H, d, J=8.3 Hz), 7.26-7.25 (1H, m), 7.22-7.16 (2H, m), 7.11 (2H, d, J=7.3 Hz), 5.54 (2H, s), 4.60 (2H, s), 2.33 (6H, s).

(3) Synthesis of 2-[1-(2,6-dimethylbenzyl)-1H-indazole-6-yl]acetonitrile [54-3] (Hereinafter Referred to as a Compound [54-3])

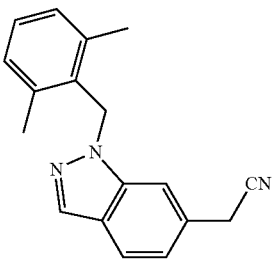 [SMILES: Cc1cccc(C)c1Cn1ncc2ccc(CC#N)cc21]

To a solution of the compound [54-2] obtained in the process (2) (250 mg) in dimethyl sulfoxide (5 mL) was added sodium cyanide (62 mg) at room temperature, and then the reaction mixture was stirred at 60° C. for 1 hour. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (152 mg) as a white solid.
$^1$H-NMR (400 MHz, CDCl$_3$) δ: 7.98 (1H, d, J=1.0 Hz), 7.71 (1H, dd, J=8.3, 0.7 Hz), 7.22-7.18 (2H, m), 7.11 (2H, d, J=7.6 Hz), 7.02 (1H, dd, J=8.5, 1.7 Hz), 5.57 (2H, s), 3.84 (2H, s), 2.32 (6H, s).

(4) Synthesis of 2-[1-(2,6-dimethylbenzyl)-1H-indazole-6-yl]acetic acid [54]

The titled compound (154 mg) as a white solid was prepared from the compound [54-3] obtained in the process (3) (148 mg) according to the method of the process (3) of Example 52.

$^1$H-NMR (400 MHz, DMSO-d$_6$) δ: 7.94 (1H, s), 7.65 (1H, d, J=8.3 Hz), 7.60 (1H, s), 7.11 (1H, dd, J=8.3, 6.6 Hz), 7.04-7.03 (3H, m), 5.49 (2H, s), 3.65 (2H, s), 2.27 (6H, s).

Example 55

Synthesis of (E)-3-[1-(2,6-dimethylbenzyl)-1H-indole-6-yl]acrylic acid [55] (Hereinafter Referred to as a Compound [55])

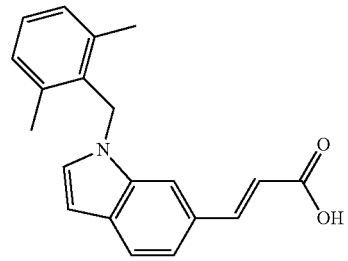 [SMILES: Cc1cccc(C)c1Cn1ccc2ccc(/C=C/C(=O)O)cc21]

(1) Synthesis of methyl (E)-3-(1H-indole-6-yl)acrylate [55-1] (Hereinafter Referred to as a Compound [55-1])

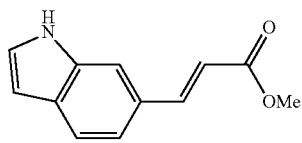

To a solution of indole-6-carboxaldehyde (499 mg) in tetrahydrofuran (20 mL), methyl (triphenylphosphoranylidene)acetate (2.5 g) was added at room temperature, and then the reaction mixture was subjected to microwave irradiation at 200° C. for 20 minutes. The reaction mixture was concentrated under reduced pressure, and the obtained residue was purified by silica gel column chromatography to give the titled compound (501 mg) as a yellow solid.
$^1$H-NMR (400 MHz, CDCl$_3$) δ: 8.33 (1H, s), 7.83 (1H, d, J=15.6 Hz), 7.64 (1H, d, J=6.3 Hz), 7.55 (1H, s), 7.36 (1H, d, J=8.3 Hz), 7.31-7.29 (1H, m), 6.58 (1H, t, J=3.9 Hz), 6.46 (1H, dd, J=15.9, 1.5 Hz), 3.82 (3H, s).

(2) Synthesis of methyl (E)-3-[1-(2,6-dimethylbenzyl)-1H-indole-6-yl]acrylate [55-2] (Hereinafter Referred to as a Compound [55-2])

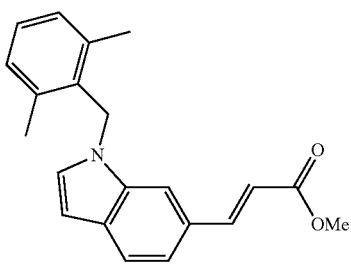 [SMILES: COC(=O)/C=C/c1ccc2ccn(Cc3c(C)cccc3C)c2c1]

To a solution of the compound [55-1] obtained in the process (1) (61 mg) in N,N-dimethylformamide (2 mL), potassium carbonate (89 mg) and 2,6-dimethylbenzyl chloride (81 mg) were added at room temperature, and then the reaction mixture was subjected to microwave irradiation at 160° C. for 30 minutes. The reaction mixture was added with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (96 mg) as a yellow solid.

$^1$H-NMR (400 MHz, CDCl$_3$) δ: 7.88 (1H, d, J=15.9 Hz), 7.61-7.59 (2H, m), 7.36 (1H, dd, J=8.7, 1.3 Hz), 7.21 (1H, dd, J=8.7, 6.2 Hz) 7.12-7.09 (2H, m), 6.68 (1H, d, J=3.4 Hz), 6.49 (1H, d, J=15.9 Hz), 6.40 (1H, d, J=3.2 Hz), 5.23 (2H, s), 3.81 (3H, s), 2.24 (6H, s).

(3) Synthesis of (E)-3-[1-(2,6-dimethylbenzyl)-1H-indole-6-yl]acrylic acid

To a solution of the compound [55-2] obtained in the process (2) (96 mg) in methanol (3 mL), an aqueous solution of 1 N-sodium hydroxide (3 mL) was added at room temperature, and then the reaction mixture was stirred at 60° C. for 18 hours. After cooling to room temperature, and added with 1 N-hydrochloric acid for acidification, and the precipitated solid was taken by filtration, whereby to give the titled compound (81 mg) as a yellow solid.

$^1$H-NMR (400 MHz, CDCl$_3$) δ: 7.99 (1H, d, J=15.4 Hz), 7.65-7.64 (2H, m), 7.41 (1H, dd, J=8.3, 1.7 Hz), 7.26-7.22 (1H, m), 7.14 (2H, d, J=7.8 Hz), 6.71 (1H, d, J=3.2 Hz), 6.52 (1H, d, J=15.6 Hz), 6.43 (1H, d, J=3.2 Hz), 5.28 (2H, s), 2.27 (6H, s).

Example 56

Synthesis of 3-[1-(2,6-dimethylbenzyl)-1H-indole-6-yl]propionic acid [56](Hereinafter Referred to as a Compound [56])

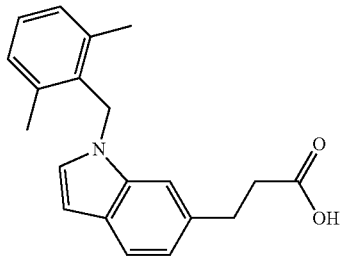 [SMILES: Cc1cccc(C)c1Cn1ccc2ccc(CCC(=O)O)cc21]

(1) Synthesis of methyl 3-(1H-indole-6-yl)propionate [56-1] (Hereinafter Referred to as a Compound [56-1])

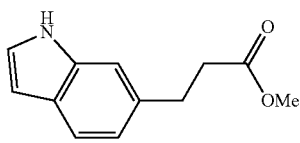 [SMILES: COC(=O)CCc1ccc2cc[nH]c2c1]

To a solution of the compound [55-1] obtained in the process (1) of Example 55 (98 mg) in methanol (3 mL), 5% palladium on carbon (103 mg) was added, and then the reaction mixture was stirred at room temperature for 4 hours under hydrogen atmosphere. The palladium on carbon was separated by filtration, and then the filtrate was concentrated under reduced pressure, whereby to give the titled compound (89 mg) as a colorless liquid.

$^1$H-NMR (400 MHz, CDCl$_3$) δ: 8.14 (1H, s), 7.57 (1H, d, J=8.3 Hz), 7.23 (1H, s), 7.17-7.16 (1H, m), 6.98 (1H, dd, J=8.1, 1.5 Hz), 6.53-6.51 (1H, m), 3.68 (3H, s), 3.07 (2H, t, J=7.8 Hz), 2.70 (2H, t, J=7.8 Hz)

(2) Synthesis of methyl 3-[1-(2,6-dimethylbenzyl)-1H-indole-6-yl]propionate [56-2] (Hereinafter Referred to as a Compound [56-2])

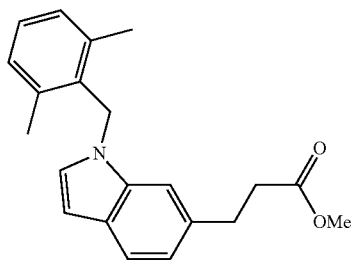 [SMILES: COC(=O)CCc1ccc2ccn(Cc3c(C)cccc3C)c2c1]

To a solution of the compound [56-1] obtained in the process (1) (89 mg) in N,N-dimethylformamide (2 mL), potassium carbonate (116 mg) and 2,6-dimethylbenzyl chloride (93 mg) were added at room temperature, and then the reaction mixture was subjected to microwave irradiation at 160° C. for 30 minutes. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (75 mg) as a yellow liquid.

$^1$H-NMR (400 MHz, CDCl$_3$) δ: 7.57 (1H, d, J=8.1 Hz), 7.34 (1H, s), 7.23 (1H, dd, J=8.2, 6.7 Hz), 7.14 (2H, d, J=7.6 Hz), 7.02 (1H, dd, J=8.1, 1.5 Hz), 6.57 (1H, d, J=3.2 Hz), 6.38 (1H, dd, J=3.2, 0.7 Hz), 5.23 (2H, s), 3.72 (3H, s), 3.15 (2H, t, J=7.9 Hz), 2.76 (2H, t, J=7.9 Hz), 2.28 (6H, s).

(3) Synthesis of 3-[1-(2,6-dimethylbenzyl)-1H-indole-6-yl]propionic acid [56]

To a solution of the compound [56-2] obtained in the process (2) (75 mg) in methanol (3 mL) was added an aqueous solution of 1 N-sodium hydroxide (3 mL) at room temperature, and then the reaction mixture was stirred at 60° C. for 18 hours. After cooling to room temperature, to the reaction mixture was added 1N-hydrochloric acid for acidification, and the precipitated solid was filtered to give the titled compound (61 mg) as a red solid.

$^1$H-NMR (400 MHz, CDCl$_3$) δ: 7.56 (1H, d, J=8.3 Hz), 7.33 (1H, s), 7.22 (1H, dd, J=8.1, 6.8 Hz), 7.12 (2H, d, J=7.6 Hz), 7.02 (1H, dd, J=8.1, 1.5 Hz), 6.57 (1H, d, J=3.2 Hz), 6.37

(1H, dd, J=3.2, 0.7 Hz), 5.22 (2H, s), 3.15 (2H, t, J=7.9 Hz), 2.80 (2H, t, J=7.8 Hz), 2.26 (6H, s).

Example 57

Synthesis of 3-[1-(2,6-dimethylbenzyl)-1H-indole-6-yl]-3-hydroxypropionic acid [57] (Hereinafter Referred to as a Compound [57])

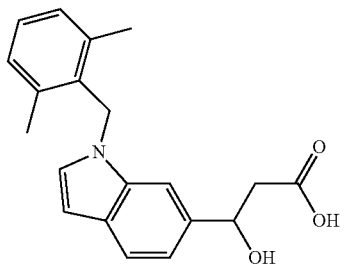 [SMILES: Cc1cccc(C)c1Cn1ccc2ccc(C(O)CC(=O)O)cc21]

(1) Synthesis of 1-(2,6-dimethylbenzyl)-1H-indole-6-carbaldehyde [57-1](Hereinafter Referred to as a Compound [57-1])

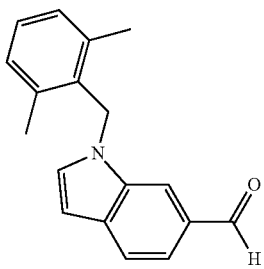 [SMILES: Cc1cccc(C)c1Cn1ccc2ccc(C=O)cc21]

To a solution of indole-6-carboxaldehyde (457 mg) in N,N-dimethylformamide (5 mL) were added potassium carbonate (936 mg) and 2,6-dimethylbenzyl chloride (752 mg) at room temperature, and then the reaction mixture was subjected to microwave irradiation at 160° C. for 30 minutes. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (740 mg) as a yellow solid.
$^1$H-NMR (400 MHz, CDCl$_3$) δ: 10.11 (1H, s), 8.08 (1H, s), 7.73 (1H, d, J=8.1 Hz), 7.68 (1H, dd, J=8.2, 1.3 Hz), 7.24 (1H, dd, J=7.4, 6.5 Hz), 7.14 (2H, d, J=7.6 Hz), 6.83 (1H, d, J=3.2 Hz), 6.48 (1H, d, J=2.9 Hz), 5.34 (2H, s), 2.27 (6H, s).

(2) Synthesis of ethyl 3-[1-(2,6-dimethylbenzyl)-1H-indole-6-yl]-3-hydroxypropionate [57-2] (Hereinafter Referred to as a Compound [57-2])

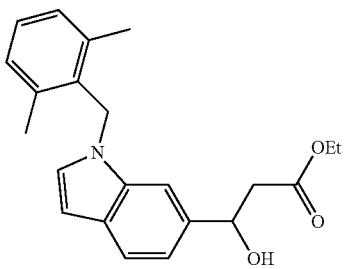 [SMILES: CCOC(=O)CC(O)c1ccc2ccn(Cc3c(C)cccc3C)c2c1]

To a solution of the compound [57-1] obtained in the process (1) (369 mg) in benzene (10 mL) were added ethyl bromoacetate (0.25 mL) and zinc (193 mg) at room temperature, and then the reaction mixture was heated at reflux for 1 hour. After cooling to room temperature, the insoluble materials were filtered, and the filtrate was concentrated under reduced pressure. The obtained residue was purified by silica gel column chromatography to give the titled compound (475 mg) as a yellow liquid.
$^1$H-NMR (400 MHz, CDCl$_3$) δ: 7.62-7.59 (2H, m), 7.22 (1H, dd, J=8.1, 6.8 Hz) 7.13-7.11 (3H, m), 6.59 (1H, d, J=3.2 Hz), 6.38 (1H, dd, J=3.2, 0.7 Hz), 5.35-5.31 (1H, m), 5.24 (2H, s), 4.22 (2H, q, J=7.1 Hz), 3.30 (1H, s), 2.92-2.80 (2H, m), 2.26 (6H, s), 1.29 (3H, t, J=7.2 Hz).

(3) Synthesis of 3-[1-(2,6-dimethylbenzyl)-1H-indole-6-yl]-3-hydroxypropionic acid [57]

To a solution of the compound [57-2] obtained in the process (2) (84 mg) in methanol (1 mL) was added an aqueous solution of 1N-sodium hydroxide (1 mL) at room temperature, and then the reaction mixture was stirred at 60° C. for 18 hours. After cooling to room temperature, to the reaction mixture was added 1N-hydrochloric acid for acidification, and the precipitated solid was filtered to give the titled compound (70 mg) as a white solid.
$^1$H-NMR (400 MHz, CDCl$_3$) δ: 7.62 (1H, d, J=8.1 Hz), 7.57 (1H, s), 7.22 (1H, dd, J=8.1, 7.1 Hz), 7.15-7.11 (3H, m), 6.61 (1H, d, J=3.2 Hz), 6.39 (1H, d, J=3.4 Hz), 5.36 (1H, dd, J=8.7, 3.5 Hz), 5.25 (2H, s), 2.98 (1H, dd, J=16.3, 9.3 Hz), 2.89 (1H, dd, J=16.5, 3.3 Hz), 2.26 (6H, s).

Example 58

Synthesis of 6-[1-(2,6-dimethylbenzyl)-1H-indole-6-yl]hexanoic acid [58] (Hereinafter Referred to as a Compound [58])

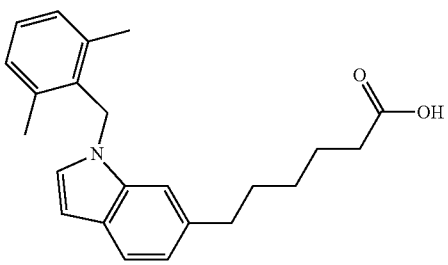 [SMILES: Cc1cccc(C)c1Cn1ccc2ccc(CCCCCC(=O)O)cc21]

(1) Synthesis of methyl 6-(1H-indole-6-yl)hexanoate [58-1] (Hereinafter Referred to as a Compound [58-1])

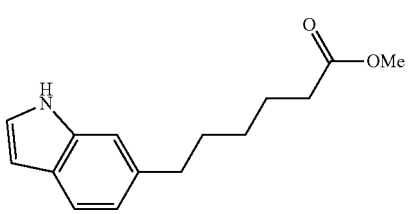 [SMILES: COC(=O)CCCCCc1ccc2cc[nH]c2c1]

To a solution of 4-(carboxylbutyl)triphenylphosphonium bromide (1.1 g) in dimethyl sulfoxide (10 mL) was added sodium hydride (205 mg) at room temperature, and then the reaction mixture was stirred at room temperature for 10 minutes. Indole-6-carboxaldehyde (292 mg) was added at room temperature, and then the reaction mixture was heated to 100° C. for 20 hours. After cooling to room temperature, to the reaction mixture was added 1N-hydrochloric acid for acidification, and extracted with chloroform. The obtained organic layer was dried over anhydrous sodium sulfate, filtered, and the filtrate was concentrated under reduced pressure. To a solution of the obtained residue in N,N-dimethylformamide (10 mL) were added potassium carbonate (421 mg) and methyl iodide (0.5 mL) at room temperature, and then the reaction mixture was stirred at room temperature for 10 minutes. The reaction mixture was quenched with water, and extracted with ethyl acetate. The obtained organic layer was dried over anhydrous sodium sulfate, filtered, and the filtrate was concentrated under reduced pressure. To a solution of the obtained residue in methanol (3 mL) was added 5% palladium on carbon (184 mg), and the reaction mixture was stirred at room temperature for 1 hour under hydrogen atmosphere. The palladium on carbon was separated by filtration, and then the filtrate was concentrated under reduced pressure to give the titled compound (182 mg) as a colorless oil.

$^1$H-NMR (400 MHz, CDCl$_3$) δ: 8.07 (1H, s), 7.55 (1H, d, J=8.1 Hz), 7.19 (1H, s), 7.16-7.15 (1H, m), 6.96 (1H, d, J=8.1 Hz), 6.51 (1H, s), 3.66 (3H, s), 2.72 (2H, t, J=7.6 Hz), 2.31 (2H, t, J=7.6 Hz), 1.72-1.63 (4H, m), 1.42-1.35 (2H, m).

(2) Synthesis of methyl 6-[1-(2,6-dimethylbenzyl)-1H-indole-6-yl]hexanoate [58-2](Hereinafter Referred to as a Compound [58-2])

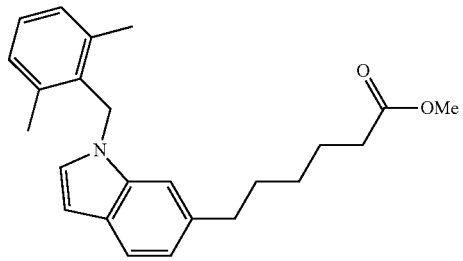 [SMILES: COC(=O)CCCCCc1ccc2ccn(Cc3c(C)cccc3C)c2c1]

To a solution of the compound [58-2] obtained in the process (1) (177 mg) in N,N-dimethylformamide (3 mL) were added potassium carbonate (258 mg) and 2,6-dimethylbenzyl chloride (258 mg) at room temperature, and then the reaction mixture was stirred at 130° C. for 5 hours. After cooling to room temperature, the reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (171 mg) as a white solid.

$^1$H-NMR (400 MHz, CDCl$_3$) δ: 7.53 (1H, d, J=8.1 Hz), 7.27 (1H, s), 7.22-7.20 (1H, m), 7.11 (2H, d, J=7.3 Hz), 6.98 (1H, d, J=8.8 Hz), 6.53 (1H, d, J=3.7 Hz), 6.35 (1H, d, J=3.4 Hz), 5.21 (2H, s), 3.67 (3H, s), 2.78 (2H, t, J=7.7 Hz), 2.33 (2H, t, J=7.7 Hz), 2.26 (6H, s), 1.77-1.66 (4H, m), 1.46-1.39 (2H, m).

(3) Synthesis of 6-[1-(2,6-dimethylbenzyl)-1H-indole-6-yl]hexanoic acid [58]

To a solution of the compound [58-2] obtained in the process (2) (169 mg) in methanol (3 mL) was added an aqueous solution of 1N-sodium hydroxide (3 mL) at room temperature, and then the reaction mixture was stirred at 60° C. for 2 hours. After cooling to room temperature, the reaction mixture was quenched with 1N-hydrochloric acid for acidification, and the precipitated solid was filtered to give the titled compound (120 mg) as a red solid.

$^1$H-NMR (400 MHz, CDCl$_3$) δ: 7.55 (1H, d, J=8.1 Hz), 7.28 (1H, s), 7.24-7.20 (1H, m), 7.12 (2H, d, J=7.6 Hz), 6.99 (1H, dd, J=8.2, 1.3 Hz), 6.55 (1H, d, J=3.2 Hz), 6.36 (1H, d, J=3.2 Hz), 5.22 (2H, s), 2.80 (2H, t, J=7.7 Hz), 2.38 (2H, t, J=7.4 Hz), 2.26 (6H, s), 1.79-1.68 (4H, m), 1.50-1.42 (2H, m).

Example 59

Synthesis of 4-[1-(2,6-dimethylbenzyl)-1H-indole-6-yl]-4-oxobutanoic acid [59] (Hereinafter Referred to as a Compound [59])

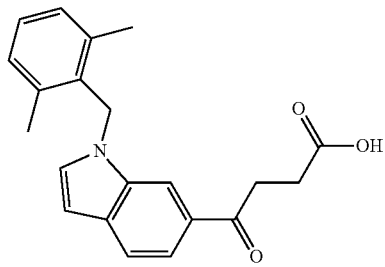 [SMILES: Cc1cccc(C)c1Cn1ccc2ccc(C(=O)CCC(=O)O)cc21]

(1) Synthesis of 1-[1-(2,6-dimethylbenzyl)-1H-indole-6-yl]ethanone [59-1] (Hereinafter Referred to as a Compound [59-1])

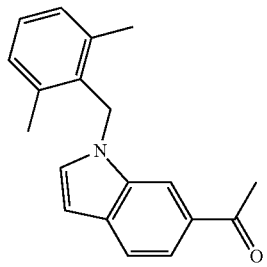 [SMILES: CC(=O)c1ccc2ccn(Cc3c(C)cccc3C)c2c1]

To a solution of the compound [57-1] obtained in the process (1) of Example 57 (1.4 g) in tetrahydrofuran (10 mL) was added a 1M solution of methylmagnesium bromide in tetrahydrofuran (7 mL) at room temperature, and then the reaction mixture was stirred at room temperature for 10 minutes. To the reaction mixture was added a saturated aqueous solution of ammonium chloride, and extracted with chloroform. The obtained organic layer was dried over anhydrous sodium sulfate, filtered, and the filtrate was concentrated under reduced pressure. To a solution of the obtained residue in acetone (20 mL) was added manganese dioxide (5.1 g), and the reaction mixture was stirred at room temperature for 2 days. The manganese dioxide was filtered through a pad of celite, and then the filtrate was concentrated under reduced pressure. The obtained residue was purified by silica gel column chromatography to give the titled compound (680 mg) as a yellow solid.

$^1$H-NMR (400 MHz, CDCl$_3$) δ: 8.20 (1H, d, J=3.7 Hz), 7.76 (1H, dd, J=8.3, 1.5 Hz), 7.66 (1H, dd, J=8.3, 0.7 Hz), 7.25-7.21 (1H, m), 7.13 (2H, d, J=7.6 Hz), 6.78 (1H, d, J=2.9 Hz), 6.44 (1H, dd, J=3.2, 0.7 Hz), 5.32 (2H, s), 2.70 (3H, s), 2.26 (6H, s).

(2) Synthesis of ethyl 4-[1-(2,6-dimethylbenzyl)-1H-indole-6-yl]-4-oxobutanoate [59-2] (Hereinafter Referred to as a Compound [59-2])

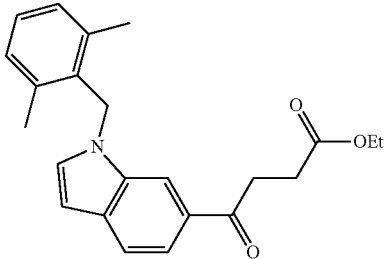 [SMILES: CCOC(=O)CCC(=O)c1ccc2ccn(Cc3c(C)cccc3C)c2c1]

The solution of the compound [59-1] obtained in the process (1) (103 mg) in tetrahydrofuran (3 mL) was cooled to 0° C. TO the solution was added 1M solution of lithium bis(trimethylsilyl)amide in tetrahydrofuran (0.5 mL) at 0° C. Then, the reaction mixture was stirred at 0° C. for 5 minutes, and to the reaction mixture was added ethyl bromoacetate (0.1 mL) at 0° C. and stirred for 30 minutes. The reaction mixture was allowed to warm to room temperature, and stirred for 2 hours. To the reaction mixture was added a saturated aqueous solution of ammonium chloride, and extracted with ethyl acetate. The obtained organic layer was dried over anhydrous sodium sulfate, filtered, and the filtrate was concentrated under reduced pressure. The obtained residue was purified by silica gel column chromatography to give the titled compound (55 mg) as a yellow solid.

$^1$H-NMR (400 MHz, CDCl$_3$) δ: 8.23 (1H, s), 7.80 (1H, dd, J=8.4, 1.6 Hz), 7.66 (1H, dd, J=8.3, 0.7 Hz), 7.26-7.21 (1H, m), 7.13 (2H, d, J=7.3 Hz), 6.77 (1H, d, J=3.4 Hz), 6.44 (1H, dd, J=3.2, 0.7 Hz), 5.32 (2H, s), 4.19 (2H, q, J=7.1 Hz), 3.45 (2H, t, J=6.8 Hz), 2.81 (2H, t, J=6.8 Hz), 2.26 (6H, s), 1.29 (3H, t, J=7.2 Hz).

(3) Synthesis of 4-[1-(2,6-dimethylbenzyl)-1H-indole-6-yl]-4-oxobutanoic acid [59]

To a solution of the compound [59-2] obtained in the process (2) (496 mg) in methanol (10 mL) was added an aqueous solution of 1N-sodium hydroxide (10 mL), and the reaction mixture was stirred at 60° C. for 2 hours. After cooling to room temperature, to the reaction mixture was added 1N-hydrochloric acid for acidification, and the precipitated solid was filtered to give the titled compound (425 mg) as a white solid.

$^1$H-NMR (400 MHz, CD$_3$OD) δ: 8.25 (1H, s), 7.76 (1H, dd, J=8.3, 1.5 Hz), 7.63 (1H, d, J=8.3 Hz), 7.23-7.19 (1H, m), 7.13 (2H, d, J=7.6 Hz), 6.87 (1H, d, J=3.2 Hz), 6.46 (1H, d, J=3.2 Hz), 5.44 (2H, d, J=2.0 Hz), 3.41 (2H, t, J=6.3 Hz), 2.73 (2H, t, J=6.5 Hz), 2.26 (6H, s).

Example 60

Synthesis of 4-[1-(2,6-dimethylbenzyl)-1H-indole-6-yl]butanoic acid [60] (Hereinafter Referred to as a Compound [60])

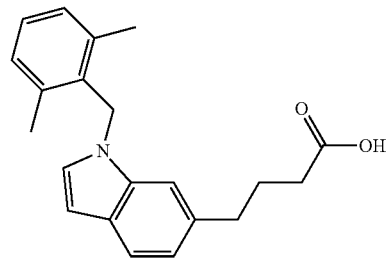 [SMILES: Cc1cccc(C)c1Cn1ccc2ccc(CCCC(=O)O)cc21]

To an aqueous solution (2 mL) of zinc powder (1.2 g) was added mercury chloride (124 mg) at room temperature, and then the reaction mixture was stirred at room temperature for 30 minutes. To the reaction mixture were added the compound [59] obtained in Example 59 (73 mg), toluene (1 mL), water (1 mL) and concentrated hydrochloric acid (1 mL) at room temperature, and then the reaction mixture was heated at reflux for 4 hours. After cooling to room temperature, the reaction mixture was quenched with water, and extracted with chloroform. The obtained organic layer was dried over anhydrous sodium sulfate, filtered, and the filtrate was concentrated under reduced pressure. The obtained residue was purified by silica gel column chromatography to give the titled compound (35 mg) as a yellow solid.

$^1$H-NMR (400 MHz, CDCl$_3$) δ: 7.55 (1H, d, J=8.8 Hz), 7.28 (1H, s), 7.23-7.19 (1H, m), 7.11 (2H, d, J=7.8 Hz), 6.99 (1H, d, J=7.8 Hz), 6.54 (1H, d, J=3.2 Hz), 6.35 (1H, d, J=3.2 Hz), 5.21 (2H, s), 2.85 (2H, t, J=7.3 Hz), 2.44 (2H, t, J=7.3 Hz), 2.26 (6H, s), 2.11-2.03 (2H, m).

Example 61

Synthesis of 1-(2,6-dimethylbenzyl)-3-methyl-1H-indole-6-carboxylic acid[61] (Hereinafter Referred to as a Compound [61])

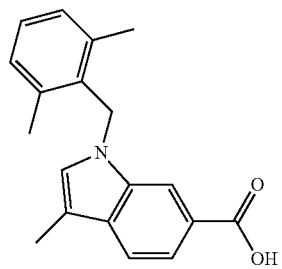 [SMILES: Cc1cccc(C)c1Cn1cc(C)c2ccc(C(=O)O)cc21]

(1) Synthesis of methyl 1-(2,6-dimethylbenzyl)-3-methyl-1H-indole-6-carboxylate [61-1] (Hereinafter Referred to as a Compound [61-1])

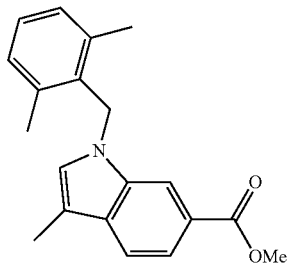

To a solution of methyl 3-methyl-1H-indole-6-carboxylate (2.2 g) obtained by the method described in the document (WO 1998/15530 A) in N,N-dimethylformamide (20 mL) were added potassium carbonate (3.1 g) and 2,6-dimethylbenzyl chloride (2.7 g) at room temperature, and then the reaction mixture was stirred at 130° C. for 5 hours. After cooling to room temperature, the reaction mixture was quenched with water, and extracted with ethyl acetate. The obtained organic layer was dried over anhydrous sodium sulfate, filtered, and the filtrate was concentrated under reduced pressure. The obtained residue was purified by recrystallization to give the titled compound (2.6 g) as a yellow solid.

$^1$H-NMR (400 MHz, CDCl$_3$) δ: 8.24 (1H, dd, J=1.3, 0.6 Hz), 7.83 (1H, dd, J=8.3, 1.5 Hz), 7.58 (1H, dd, J=8.4, 0.6 Hz), 7.23 (1H, dd, J=8.3, 6.8 Hz), 7.13 (2H, d, J=7.6 Hz), 6.51 (1H, s), 5.26 (2H, s), 3.97 (3H, s), 2.26 (6H, s), 2.23 (3H, s).

(2) Synthesis of 1-(2,6-dimethylbenzyl)-3-methyl-1H-indole-6-carboxylic acid

To a solution of the compound [61-1] obtained in the process (1) (77 mg) in methanol (1 mL) was added an aqueous solution of 1N-sodium hydroxide (1 mL) at room temperature, and then the reaction mixture was stirred at 60° C. for 10 hours. After cooling to room temperature, to the reaction mixture was added 1N-hydrochloric acid for acidification, and the precipitated solid was filtered to give the titled compound (73 mg) as a yellow solid.

$^1$H-NMR (400 MHz, CDCl$_3$) δ: 8.32 (1H, s), 7.91 (1H, dd, J=8.3, 1.5 Hz), 7.62 (1H, d, J=8.5 Hz), 7.24-7.22 (1H, m), 7.14 (2H, d, J=7.6 Hz), 6.55 (1H, d, J=1.0 Hz), 5.29 (2H, s), 5.28 (6H, s), 2.24 (3H, s).
ESI-MS found: 294 [M+H]$^+$ Example 62

Synthesis of potassium 1-(2,6-dimethylbenzyl)-3-methyl-1H-indole-6-carboxylate [62] (Hereinafter Referred to as a Compound [62])

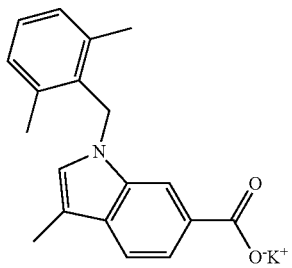

To a solution of the compound [61] (2.1 g) in ethanol (20 mL) was added an aqueous solution of 1N-potassium hydroxide (7.1 mL) at room temperature, and the solution was concentrated under reduced pressure to give the titled compound (2.4 g) as a yellow solid.

$^1$H-NMR (400 MHz, CD$_3$OD) δ: 8.19 (1H, s), 7.75 (1H, d, J=8.3, 1.5 Hz), 7.45 (1H, dd, J=8.3, 0.7 Hz), 7.19-7.17 (1H, m), 7.10 (2H, d, J=7.6 Hz), 6.40 (1H, s), 5.30 (2H, s), 2.24 (6H, s), 2.19 (3H, s).
ESI-MS found: 294 [M−K+2H]$^+$ Example 63

Synthesis of [1-(2,6-dimethylbenzyl)-3-methyl-1H-indole-6-yl]methanol [63] (Hereinafter Referred to as a Compound [63])

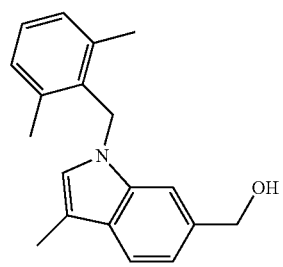 [SMILES: Cc1cccc(C)c1Cn1cc(C)c2ccc(CO)cc21]

To a solution of the compound [61-1] obtained in the process (1) of Example 61 (265 mg) in tetrahydrofuran (10 mL) was added lithium aluminum hydride (126 mg) at 0° C., and then the reaction mixture was stirred at room temperature for 10 minutes. The reaction mixture was quenched with water and 1N-hydrochloric acid, and then extracted with chloroform. The obtained organic layer was dried over anhydrous sodium sulfate, filtered, and the filtrate was concentrated under reduced pressure. The obtained residue was purified by silica gel column chromatography to give the titled compound (179 mg) as a white solid.

$^1$H-NMR (400 MHz, CDCl$_3$) δ: 7.56 (1H, d, J=7.8 Hz), 7.48 (1H, s), 7.24-7.20 (1H, m), 7.15-7.11 (3H, m), 6.37 (1H, s), 5.19 (2H, s), 4.86 (2H, d, J=5.6 Hz), 2.27 (6H, s), 2.22 (3H, s), 1.66 (1H, t, J=6.0 Hz).

Example 64

Synthesis of 2-[1-(2,6-dimethylbenzyl)-3-methyl-1H-indole-6-yl]acetic acid [64] (Hereinafter Referred to as a Compound [64])

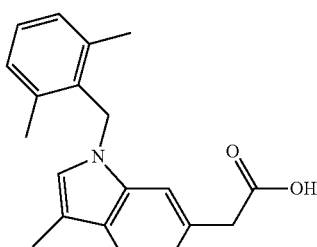

(1) Synthesis of (3-methyl-1-tosyl-1H-indole-6-yl)methanol [64-1] (Hereinafter Referred to as a Compound [64-1])

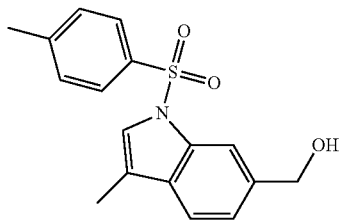 [SMILES: Cc1ccc(S(=O)(=O)n2cc(C)c3ccc(CC#N)cc32)cc1]

To a solution of methyl 3-methyl-1H-indole-6-carboxylate (1.3 g) obtained with the method described in the document (WO 1998/15530 A) in 2-pentanone (40 mL) were added 4-methylbenzenesulfonyl chloride (2.0 g) and potassium carbonate (2.9 g) at room temperature, and then the reaction mixture was heated at reflux for 8 hours. After cooling to room temperature, the reaction mixture was quenched with water, and extracted with ethyl acetate. The obtained organic layer was dried over anhydrous sodium sulfate, filtered, and the filtrate was concentrated under reduced pressure. To a solution of the obtained residue in tetrahydrofuran (20 mL) was added a solution of lithium aluminum hydride (518 mg) in tetrahydrofuran (20 mL) at 0° C., and then the reaction mixture was stirred for 10 minutes. The reaction mixture was quenched with water and 1N-hydrochloric acid, and then extracted with chloroform. The obtained organic layer was dried over anhydrous sodium sulfate, filtered, and the filtrate was concentrated under reduced pressure. The obtained residue was purified by silica gel column chromatography to give the titled compound (1.6 g) as a white solid.

$^1$H-NMR (400 MHz, CDCl$_3$) δ: 7.98 (1H, s), 7.75 (2H, d, J=8.3 Hz), 7.44 (1H, d, J=8.1 Hz), 7.31-7.26 (2H, m), 7.21 (2H, d, J=8.1 Hz), 4.81 (2H, d, J=5.1 Hz), 2.34 (3H, s), 2.24 (3H, s), 1.77 (1H, t, J=5.4 Hz).

(2) Synthesis of 2-(3-methyl-1-tosyl-1H-indole-6-yl)acetonitrile [64-2] (Hereinafter Referred to as a Compound [64-2])

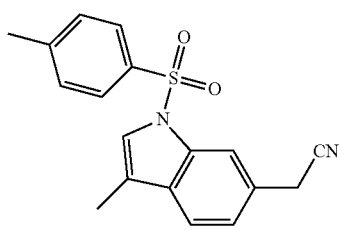

The solution of the compound [64-1] obtained in the process (1) (1.6 g) in chloroform (12 mL) was cooled to 0° C., and to the solution were added triethylamine (0.97 mL) and methanesulfonyl chloride (0.54 mL) at 0° C., and then the reaction mixture was stirred at 0° C. for 30 minutes, and subsequently stirred at room temperature for 16 hours. The reaction mixture was quenched with a saturated aqueous solution of ammonium chloride, and extracted with chloroform. The obtained organic layer was dried over anhydrous sodium sulfate, filtered, and the filtrate was concentrated under reduced pressure. To a solution of the obtained residue in dimethyl sulfoxide (20 mL) was added sodium cyanide (516 mg) at room temperature, and then the reaction mixture was stirred at room temperature for 20 hours. The reaction mixture was quenched with water, and extracted with chloroform. The obtained organic layer was dried over anhydrous sodium sulfate, filtered, and the filtrate was concentrated under reduced pressure. The obtained residue was purified by silica gel column chromatography to give the titled compound (1.3 g) as a white solid.

$^1$H-NMR (400 MHz, CDCl$_3$) δ: 7.93 (1H, s), 7.74 (2H, d, J=8.5 Hz), 7.45 (1H, d, J=8.1 Hz), 7.32 (1H, s), 7.23-7.21 (3H, m), 3.86 (2H, s), 2.34 (3H, s), 2.24 (3H, s).

(3) Synthesis of methyl 2-(3-methyl-1H-indole-6-yl)acetate [64-3] (Hereinafter Referred to as a Compound [64-3])

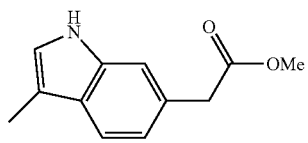

To a solution of the compound [64-2] obtained in the process (2) (1.3 g) in ethanol (10 mL) was added an aqueous solution of 3N-sodium hydroxide (10 mL) at room temperature, and then the reaction mixture was heated at reflux for 20 hours. After cooling to room temperature, to the reaction mixture was added 1N-hydrochloric acid for acidification, and extracted with chloroform. The obtained organic layer was dried over anhydrous sodium sulfate, filtered, and the filtrate was concentrated under reduced pressure. To a solution of the obtained residue in N,N-dimethylformamide (15 mL) were added potassium carbonate (846 mg) and methyl iodide (0.5 mL) at 0° C., and then the reaction mixture was stirred at room temperature for 10 minutes. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (677 mg) as a yellow solid.

$^1$H-NMR (400 MHz, CDCl$_3$) δ: 7.89 (1H, s), 7.53 (1H, d, J=7.8 Hz), 7.28 (1H, s), 7.05 (1H, d, J=8.1 Hz), 6.96 (1H, s), 3.74 (2H, s), 3.69 (3H, s), 2.33 (3H, s).

(4) Synthesis of methyl 2-[1-(2,6-dimethylbenzyl)-3-methyl-1H-indole-6-yl]acetate [64-4] (Hereinafter Referred to as a Compound [64-4])

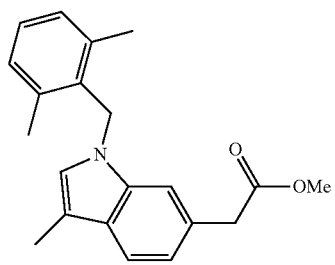

To a solution of the compound [64-3] obtained in the process (3) (677 mg) in N,N-dimethylformamide (5 mL) were added potassium carbonate (936 mg) and 2,6-dimethylbenzyl chloride (794 mg) at room temperature, and then the reaction mixture was stirred at 130° C. for 8 hours. After cooling to room temperature, the reaction mixture was quenched with water, and extracted with chloroform. The obtained organic layer was dried over anhydrous sodium sulfate, filtered, and the filtrate was concentrated under reduced pressure. The obtained residue was purified by silica gel column chromatography to give the titled compound (278 mg) as a yellow solid.

$^1$H-NMR (400 MHz, CDCl$_3$) δ: 7.53 (1H, d, J=7.6 Hz), 7.38 (1H, s), 7.24-7.21 (1H, m), 7.13 (2H, d, J=7.3 Hz), 7.07 (1H, d, J=7.6 Hz), 6.34 (1H, s), 5.18 (2H, s), 3.81 (2H, s), 3.72 (3H, s), 2.27 (6H, s), 2.21 (3H, s).

(5) Synthesis of 2-[1-(2,6-dimethylbenzyl)-3-methyl-1H-indole-6-yl]acetic acid [64]

To a solution of the compound [64-4] obtained in the process (4) (268 mg) in methanol (5 mL) was added an aqueous solution of 1N-sodium hydroxide (5 mL) at room temperature, and then the reaction mixture was stirred at 60° C. for 2 hours. After cooling to room temperature, to the reaction mixture was added 1N-hydrochloric acid for acidification, and the precipitated solid was filtered to give the titled compound (226 mg) as a yellow solid.

$^1$H-NMR (400 MHz, CDCl$_3$) δ: 7.53 (1H, d, J=8.1 Hz), 7.37 (1H, s), 7.24-7.20 (1H, m), 7.12 (2H, d, J=8.1 Hz), 7.07 (1H, d, J=8.1 Hz), 6.34 (1H, s), 5.17 (2H, s), 3.82 (2H, s), 2.26 (6H, s), 2.20 (3H, s). ESI-MS found: 308 [M+H]$^+$ Example 65

Synthesis of potassium 2-[1-(2,6-dimethylbenzyl)-3-methyl-1H-indole-6-yl]acetate [65] (Hereinafter Referred to as a Compound [65])

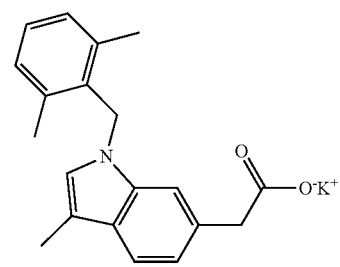

To a solution of the compound [64] (226 mg) in ethanol (5 mL) was added an aqueous solution of 1N-potassium hydroxide (0.74 mL) at room temperature, and the solution was concentrated under reduced pressure to give the titled compound (254 mg) as a yellow solid.

$^1$H-NMR (400 MHz, CD$_3$OD) δ: 7.46 (1H, s), 7.37 (1H, d, J=8.1 Hz) 7.19-7.15 (1H, m), 7.09 (2H, d, J=7.6 Hz), 7.06 (1H, dd, J=8.1, 1.5 Hz), 6.23-6.22 (1H, m), 5.22 (2H, s), 3.61 (2H, s), 2.23 (6H, s), 2.15 (3H, s).

ESI-MS found: 308 [M−K+2H]$^+$

Example 66

Synthesis of 2-[1-(2,6-dimethylbenzyl)-3-methyl-1H-indazole-6-yl]acetic acid [66] (Hereinafter Referred to as a Compound [66])

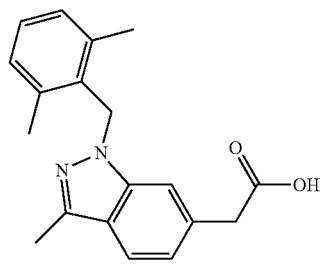 [SMILES: Cc1cccc(C)c1Cn1nc(C)c2ccc(CC(=O)O)cc21]

(1) Synthesis of 6-bromo-1-(2,6-dimethylbenzyl)-3-methyl-1H-indazole [66-1] (Hereinafter Referred to as a Compound [66-1])

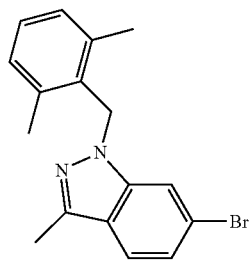 [SMILES: Cc1cccc(C)c1Cn1nc(C)c2ccc(Br)cc21]

To a solution of 6-bromo-3-methyl-1H-indazole (467 mg) obtained with the method described in the document (JP 2009-528363 W) in N,N-dimethylformamide (10 mL) were added potassium carbonate (618 mg) and 2,6-dimethylbenzyl chloride (518 mg) at room temperature, and then the reaction mixture was stirred at room temperature for 20 hours. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (555 mg) as a white solid.

$^1$H-NMR (400 MHz, CDCl$_3$) δ: 7.47 (1H, d, J=8.8 Hz), 7.22-7.14 (2H, m), 7.11-7.09 (3H, m), 5.45 (2H, s), 2.51 (3H, s), 2.33 (6H, s).

(2) Synthesis of 6-allyl-1-(2,6-dimethylbenzyl)-3-methyl-1H-indazole [66-2] (Hereinafter Referred to as a Compound [66-2])

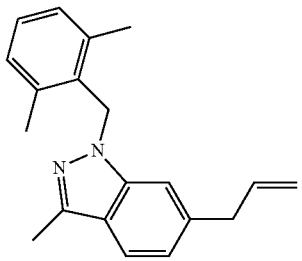 [SMILES: C=CCc1ccc2c(C)nn(Cc3c(C)cccc3C)c2c1]

To a solution of the compound [66-1] obtained in the process (1) (98 mg) in N,N-dimethylformamide (3 mL) were added allyltributyl tin (0.3 mL), lithium chloride (41 mg) and bis(triphenylphosphine)palladium(II) dichloride (21 mg) at room temperature, and then the reaction mixture was stirred at 120° C. for 2 hours. After cooling to room temperature, the reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (86 mg) as a white solid.

$^1$H-NMR (400 MHz, CDCl$_3$) δ: 7.52 (1H, d, J=7.8 Hz), 7.18-7.15 (1H, m), 7.07 (2H, d, J=7.3 Hz), 6.91 (1H, dd, J=8.3, 1.2 Hz), 6.75 (1H, s), 5.96-5.85 (1H, m), 5.47 (2H, s), 5.07-5.02 (2H, m), 3.40 (2H, d, J=6.6 Hz), 2.52 (3H, s), 2.33 (6H, s).

(3) Synthesis of 2-[1-(2,6-dimethylbenzyl)-3-methyl-1H-indazole-6-yl]acetaldehyde [66-3] (Hereinafter Referred to as a Compound [66-3])

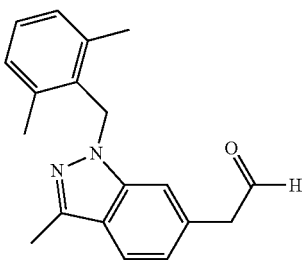 [SMILES: Cc1cccc(C)c1Cn1nc(C)c2ccc(CC=O)cc21]

The solution of the compound [66-2] obtained in the process (2) (432 mg) in tert-butanol (10 mL) and water (5 mL) was cooled to 0° C. To the solution were added sodium periodate (1.3 g) and an aqueous solution of 4% osmium tetraoxide (0.3 mL) at 0° C. The reaction mixture was stirred at 0° C. for 30 minutes, and then stirred at room temperature for 4 hours. The reaction mixture was quenched with water, and extracted with chloroform. The obtained organic layer was dried over anhydrous sodium sulfate, filtered, and the filtrate was concentrated under reduced pressure. The obtained residue was purified by silica gel column chromatography to give the titled compound (152 mg) as a yellow solid.

$^1$H-NMR (400 MHz, CDCl$_3$) δ: 9.68 (1H, t, J=2.4 Hz), 7.60 (1H, d, J=7.8 Hz) 7.20-7.16 (1H, m), 7.08 (2H, d, J=7.8 Hz), 6.90 (1H, d, J=8.3 Hz), 6.74 (1H, s), 5.49 (2H, s), 3.68 (2H, d, J=2.0 Hz), 2.53 (3H, s), 2.32 (6H, s).

(4) Synthesis of 2-[1-(2,6-dimethylbenzyl)-3-methyl-1H-indazole-6-yl]acetic acid [66]

To a solution of the compound [66-3] obtained in the process (3) (149 mg) in tert-butanol (10 mL) and water (5 mL) were added 2-methyl-2-butene (0.25 mL), sodium dihydrogen phosphate 2 hydrate (86 mg) and sodium chlorite (175 mg) at room temperature, and the reaction mixture was stirred at room temperature for 1 hour. To the reaction mixture was added hydrochloric acid, and extracted with chloroform. The obtained organic layer was dried over anhydrous sodium sulfate, filtered, and the filtrate was concentrated under reduced pressure. The obtained residue was purified by silica gel column chromatography to give the titled compound (126 mg) as a white solid.

$^1$H-NMR (400 MHz, CDCl$_3$) δ: 7.58 (1H, d, J=8.3 Hz), 7.18-7.15 (1H, m), 7.07 (2H, d, J=7.3 Hz), 7.00 (1H, dd, J=8.3, 1.5 Hz), 6.88 (1H, s), 5.49 (2H, s), 3.68 (2H, s), 2.53 (3H, s), 2.33 (6H, s).

ESI-MS found: 309 [M+H]$^+$

Example 67

Synthesis of 2-(1-benzyl-3-chloro-1H-indole-6-yl)acetic acid [67] (Hereinafter Referred to as a Compound [67])

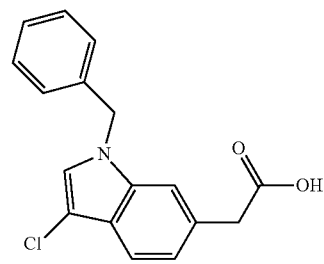 [SMILES: O=C(O)Cc1ccc2c(Cl)cn(Cc3ccccc3)c2c1]

To a solution of the compound [4] obtained in Example 4 (82 mg) in tetrahydrofuran (1 mL) was added N-chlorosuccinimide (26 mg) at room temperature, and then the reaction mixture was stirred at room temperature for 1 hour. To the reaction mixture was added 4N-hydrochloric acid for acidification, and then extracted with ethyl acetate. The obtained organic layer was dried over anhydrous sodium sulfate, filtered, and the filtrate was concentrated under reduced pressure. The obtained residue was purified by silica gel column chromatography to give the titled compound (19 mg) as a red solid.

$^1$H-NMR (400 MHz, CD$_3$OD) δ: 7.47 (1H, d, J=8.3 Hz), 7.31-7.22 (5H, m), 7.18-7.12 (2H, m), 7.07 (1H, dd, J=8.2, 1.1 Hz), 5.33 (2H, s), 3.66 (2H, s).

ESI-MS found: 300 [M+H]$^+$

Example 68

Synthesis of 2-[3-chloro-1-(2,6-dimethylbenzyl)-1H-indole-6-yl]acetic acid [68] (Hereinafter Referred to as a Compound [68])

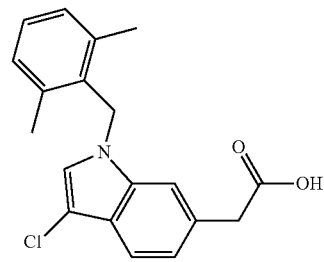 [SMILES: Cc1cccc(C)c1Cn1cc(Cl)c2ccc(CC(=O)O)cc21]

The titled compound (43 mg) as a white solid was prepared from the compound [5] obtained in Example 5 (80.8 mg) and N-chlorosuccinimide (42.9 mg) according to the method of Example 67.

$^1$H-NMR (400 MHz, CD$_3$OD) δ: 7.51 (1H, s), 7.46 (1H, d, J=8.1 Hz), 7.21 (1H, t, J=7.7 Hz), 7.17-7.08 (3H, m), 6.51 (1H, s), 5.30 (2H, s), 3.74 (2H, s), 2.25 (6H, s).
ESI-MS found: 328 [M+H]$^+$ Example 69

Synthesis of 1-(2,6-dimethylbenzyl)-2-methyl-1H-indole-6-carboxylic acid[69] (Hereinafter Referred to as a Compound [69])

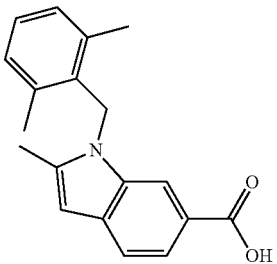 [SMILES: Cc1cccc(C)c1Cn1c(C)cc2ccc(C(=O)O)cc21]

(1) Synthesis of methyl 4-methyl-3-nitrobenzoate [69-1](Hereinafter Referred to as a Compound [69-1])

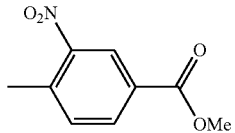

To a solution of 4-Methyl-3-nitrobenzoic acid (25.4 g) in methanol (300 mL) was slowly added concentrated sulfuric acid (2 mL), and then the reaction mixture was heated at reflux for 16 hours. The reaction mixture was concentrated under reduced pressure, and then the reaction mixture was neutralized with a saturated aqueous solution of sodium hydrogen carbonate, and extracted with ethyl acetate. The obtained organic layer was dried over anhydrous sodium sulfate, filtered, and the filtrate was concentrated under reduced pressure to give the titled compound (26.9 g) as a pale yellow solid.
$^1$H-NMR (400 MHz, CDCl$_3$) δ: 8.62 (1H, s), 8.15 (1H, dd, J=7.8, 1.2 Hz), 7.45 (1H, d, J=7.8 Hz), 3.96 (3H, s), 2.67 (3H, s).

(2) Synthesis of methyl 3-nitro-4-(2-oxopropyl)benzoate [69-2] (Hereinafter Referred to as a Compound [69-2])

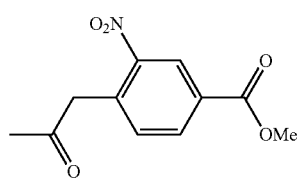 [SMILES: COC(=O)c1ccc(CC(C)=O)c([N+](=O)[O-])c1]

To a solution of the compound [69-1] obtained in the process (1) (693 mg) in N,N-dimethylformamide (3.5 mL) was added N,N-dimethylformamide dimethyl acetal (1.5 mL) at room temperature, and then the reaction mixture was subjected to microwave irradiation at 160° C. for 20 minutes. The reaction mixture was concentrated under reduced pressure to give a reddish brown solid. To a solution of the obtained solid in chloroform (6 mL) were added pyridine (0.46 mL) and acetyl chloride (0.36 mL) at room temperature, and then the reaction mixture was stirred at room temperature for 3 days. The reaction mixture was quenched with water, and concentrated under reduced pressure. To the obtained residue were added 1,4-dioxane (3 mL) and water (1.5 mL), and then the reaction mixture was stirred at 100° C. for 18 hours. The reaction mixture was concentrated under reduced pressure, and then quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (589 mg) as a brown oil.
$^1$H-NMR (400 MHz, CDCl$_3$) δ: 8.75 (1H, d, J=1.2 Hz), 8.24 (1H, dd, J=7.8, 2.0 Hz), 7.38 (1H, d, J=7.8 Hz), 4.20 (2H, s), 3.97 (3H, s), 2.35 (3H, s).

(3) Synthesis of methyl 2-methyl-1H-indole-6-carboxylate [69-3] (Hereinafter Referred to as a Compound [69-3])

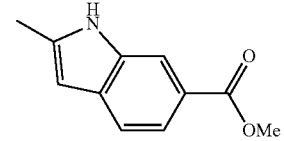

To a solution of the compound [69-2] obtained in the process (2) (589 mg) in acetic acid (5 mL) were added iron powder (691 mg), and then the reaction mixture was stirred at 100° C. for 8 hours. After cooling to room temperature, the insoluble materials were filtered, and the filtrate was concentrated under reduced pressure. The residue was added water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (303 mg) as a brown solid.
$^1$H-NMR (400 MHz, CDCl$_3$) δ: 8.21-8.20 (1H, br), 8.04 (1H, s), 7.77 (1H, dd, J=8.5, 1.5 Hz), 7.51 (1H, d, J=8.3 Hz), 6.28-6.27 (1H, m), 3.92 (3H, s), 2.49 (3H, s).

(4) Synthesis of 1-(2,6-dimethylbenzyl)-2-methyl-1H-indole-6-carboxylic acid

The titled compound (19 mg) as a brown solid was prepared from the compound [69-3] obtained in the process (3) (70 mg) and 2,6-dimethylbenzyl chloride (69 mg) according to the method of the process (7) of Example 4.
$^1$H-NMR (400 MHz, DMSO-d$_6$) δ: 7.74 (1H, s), 7.54 (1H, d, J=8.3 Hz), 7.46 (1H, d, J=8.3 Hz), 7.15-7.10 (1H, m), 7.04 (2H, d, J=7.8 Hz), 6.33 (1H, s), 5.45 (2H, s), 2.28 (3H, s), 2.08 (6H, s).
ESI-MS found: 294 [M+H]$^+$

Example 70

Synthesis of 1-benzyl-2-methyl-1H-indole-6-carboxylic acid [70] (Hereinafter Referred to as a Compound [70])

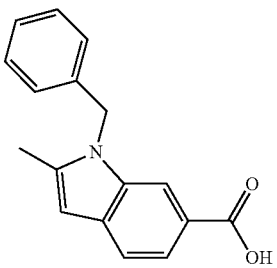 [SMILES: Cc1cc2ccc(C(=O)O)cc2n1Cc1ccccc1]

The titled compound (68 mg) as a white solid was prepared from the compound [69-3] obtained in the process (3) of Example 69 (70 mg) and benzyl chloride (63 µL) according to the method of the process (7) of Example 4.

$^1$H-NMR (400 MHz, CD$_3$OD) δ: 7.98 (1H, s), 7.70 (1H, dd, J=8.3, 1.2 Hz), 7.51 (1H, d, J=8.3 Hz), 7.29-7.19 (3H, m), 6.96 (2H, d, J=7.3 Hz), 6.38 (1H, s), 5.47 (2H, s), 2.38 (3H, s).

ESI-MS found: 266 [M+H]$^+$

Example 71

Synthesis of 2-methyl-1-(2-methylbenzyl)-1H-indole-6-carboxylic acid [71] (Hereinafter Referred to as a Compound [71])

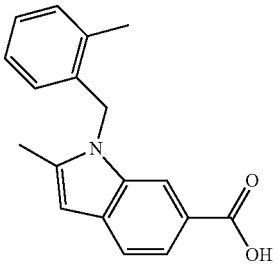 [SMILES: Cc1ccccc1Cn1c(C)cc2ccc(C(=O)O)cc21]

The titled compound (63 mg) as a white solid was prepared from the compound [69-3] obtained in the process (3) of Example 69 (72 mg) and 2-methylbenzyl chloride (73 µL) according to the method of the process (7) of Example 4.

$^1$H-NMR (400 MHz, CD$_3$OD) δ: 7.86 (1H, s), 7.71 (1H, dd, J=8.5, 1.2 Hz), 7.53 (1H, d, J=7.6 Hz), 7.22 (1H, d, J=7.3 Hz), 7.11 (1H, t, J=7.6 Hz), 6.93 (1H, t, J=7.6 Hz), 6.42 (1H, s), 6.05 (1H, d, J=7.3 Hz), 5.39 (2H, s), 2.45 (3H, s), 2.35 (3H, s).

ESI-MS found: 280 [M+H]$^+$

Example 72

Synthesis of 1-(2-chlorobenzyl)-2-methyl-1H-indole-6-carboxylic acid [72] (Hereinafter Referred to as a Compound [72])

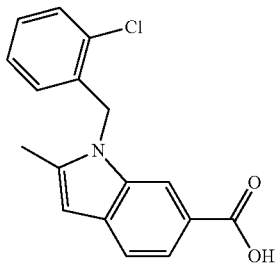 [SMILES: Cc1cc2ccc(C(=O)O)cc2n1Cc1ccccc1Cl]

The titled compound (71 mg) as a white solid was prepared from the compound [69-3] obtained in the process (3) of Example 69 (72 mg) and 2-chlorobenzyl chloride (72 µL) according to the method of the process (7) of Example 4.

$^1$H-NMR (400 MHz, CD$_3$OD) δ: 7.87 (1H, s), 7.72 (1H, d, J=7.8 Hz), 7.54 (1H, d, J=7.8 Hz), 7.47 (1H, d, J=7.1 Hz), 7.24 (1H, t, J=7.6 Hz), 7.08 (1H, t, J=6.8 Hz), 6.44 (1H, s), 6.18 (1H, d, J=6.8 Hz), 5.51 (2H, s), 2.38 (3H, s).

ESI-MS found: 300 [M+H]$^+$

Example 73

Synthesis of 1-(2,6-dimethylbenzyl)-2-(trifluoromethyl)-1H-benzimidazole-6-carboxylic acid [73] (Hereinafter Referred to as a Compound [73])

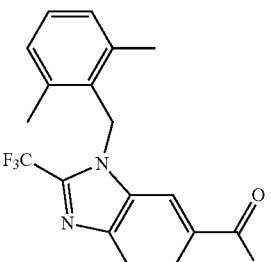

(1) Synthesis of methyl 3-nitro-4-(2,2,2-trifluoroacetamido)benzoate [73-1] (Hereinafter Referred to as a Compound [73-1])

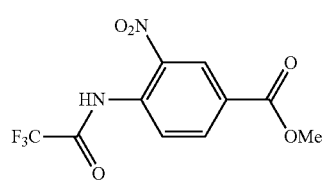 [SMILES: COC(=O)c1ccc(NC(=O)C(F)(F)F)c([N+](=O)[O-])c1]

Methyl 4-aminobenzoate (1.0 g) was dissolved in trifluoroacetic acid anhydride (13 mL). Potassium nitrate (736 mg) was added at 0° C., and then the reaction mixture was stirred at room temperature for 15 hours. The reaction mixture was quenched with water, and extracted with ethyl acetate. The obtained organic layer was washed with brine, dried over anhydrous sodium sulfate, filtered, and the filtrate was concentrated under reduced pressure to give the titled compound (1.9 g) as a pale brown solid.

$^1$H-NMR (400 MHz, CDCl$_3$) δ: 11.58 (1H, s), 8.99 (1H, d, J=2.0 Hz), 8.87 (1H, d, J=8.8 Hz), 8.40 (1H, dd, J=8.8, 2.0 Hz), 4.00 (3H, s).

ESI-MS found: 291 [M−H]$^+$ (2) Synthesis of methyl 1-(2,6-dimethylbenzyl)-2-(trifluoromethyl)-3H-benzimidazole-6-carboxylate [73-2A] (Hereinafter Referred to as a Compound [73-2A]) and methyl 1-(2,6-dimethylbenzyl)-2-(trifluoromethyl)-1H-benzimidazole-5-carboxylate [73-2B] (Hereinafter Referred to as a Compound [73-2B])

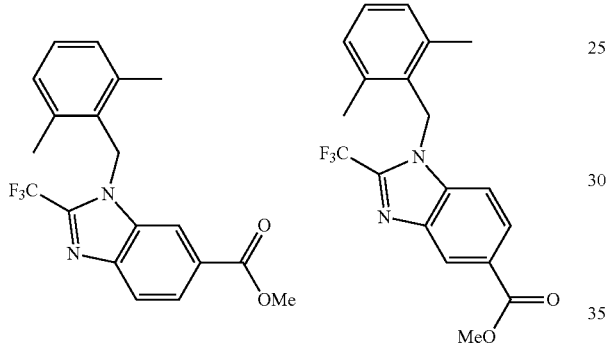

To a solution of the compound [73-1] obtained in the process (1) (616 mg) in ethanol (14 mL) were added water (7 mL), iron powder (453 mg) and ammonium chloride (857 mg), and then the reaction mixture was heated at reflux for 4 hours. The insoluble materials were filtered through a pad of celite, and the pad was washed with water and ethyl acetate. The organic layer was separated from the filtrate and washed with brine, dried over anhydrous sodium sulfate, filtered, and the filtrate was concentrated under reduced pressure. The obtained residue was purified by silica gel column chromatography to give a benzoimidazole (225 mg) as a yellow solid. The obtained benzoimidazole (105 mg) was dissolved in N-methyl-2-pyrrolidone (2.3 mL). Potassium carbonate (227 mg) and 2,6-dimethylbenzyl chloride (139 mg) were added, and then the reaction mixture was subjected to microwave irradiation at 160° C. for 30 minutes. The reaction mixture was quenched with water, and extracted with ethyl acetate. The obtained organic layer was washed with brine, dried over anhydrous sodium sulfate, filtered, and the filtrate was concentrated under reduced pressure. The obtained residue was purified by silica gel column chromatography to give a mixture of the titled compounds [73-2A] and [73-2B] in 118 mg (79%) as a yellow solid.

ESI-MS found: 363 [M+H]$^+$ (3) Synthesis of 1-(2,6-dimethylbenzyl)-2-(trifluoromethyl)-1H-benzimidazole-6-carboxylic acid [73]

To a solution of the mixture of the compounds [73-2A] and [73-2B] obtained in the process (2) (118 mg) in tetrahydrofuran (3.3 mL) was added 1N-sodium hydroxide (1.7 mL), and then the reaction mixture was subjected to microwave irradiation at 120° C. for 20 minutes. The reaction mixture was added 1N-hydrochloric acid, and extracted with ethyl acetate. The obtained organic layer was washed with brine, dried over anhydrous sodium sulfate, filtered, and the filtrate was concentrated under reduced pressure. The obtained residue was purified by COOH column chromatography to give the titled compound (13 mg) as a pale yellow solid.

$^1$H-NMR (400 MHz, CDCl$_3$) δ: 7.97 (1H, dd, J=8.5, 1.5 Hz), 7.85 (1H, d, J=8.5 Hz), 7.29-7.23 (2H, m), 7.15 (2H, d, J=7.6 Hz), 5.64 (2H, s), 2.25 (6H, s).

ESI-MS found: 349 [M+H]$^+$

Example 74

Synthesis of potassium 2-(1-benzyl-2,3-dihydro-1H-indole-6-yl)acetate [74](Hereinafter Referred to as a Compound [74])

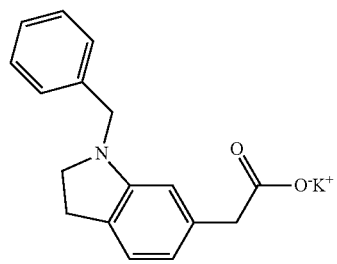

(1) Synthesis of tert-butyl 6-allyl-2,3-dihydro-1H-indole-1-carboxylate [74-1](Hereinafter Referred to as a Compound [74-1])

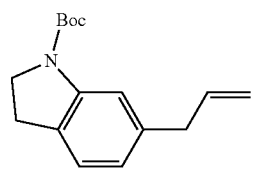 [SMILES: C=CCc1ccc2c(c1)N(C(=O)OC(C)(C)C)CC2]

The titled compound (5.7 g) as a colorless oil was prepared from tert-butyl 6-bromo-2,3-dihydro-1H-indole-1-carboxylate (7.5 g) obtained with the method described in the document (WO 1998/43956 A) according to the method of the process (2) of Example 66.

$^1$H-NMR (400 MHz, CDCl$_3$) δ: 7.72 (1H, brs), 7.05 (1H, d, J=7.4 Hz), 6.76 (1H, d, J=7.4 Hz), 6.02-5.89 (1H, m), 5.16-4.98 (2H, m), 4.03-3.91 (2H, m), 3.36 (2H, d, J=6.6 Hz), 3.04 (2H, t, J=8.5 Hz), 1.56 (9H, brs).

ESI-MS found: 204 [M−tBu+H]$^+$

(2) Synthesis of tert-butyl 2,3-dihydro-6-(2-oxoethyl)-1H-indole-1-carboxylate [74-2](Hereinafter Referred to as a Compound [74-2])

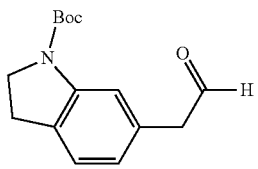 [SMILES: CC(C)(C)OC(=O)N1CCc2ccc(CC=O)cc21]

The titled compound (3.8 g) as a colorless oil was prepared from the compound [74-1] obtained in the process (1) (5.9 g) according to the method of the process (3) of Example 66.

$^1$H-NMR (400 MHz, CDCl$_3$) δ: 9.73 (1H, t, J=2.0 Hz), 7.78 (1H, brs), 7.13 (1H, d, J=7.4 Hz), 6.76 (1H, d, J=7.4 Hz), 3.99 (2H, t, J=8.7 Hz), 3.64 (2H, d, J=2.0 Hz), 3.08 (2H, t, J=8.7 Hz), 1.56 (9H, brs).

ESI-MS found: 206 [M−tBu+H]$^+$

(3) Synthesis of methyl 2-(2,3-dihydro-1H-indole-6-yl)acetate [74-3A] (Hereinafter Referred to as a Compound [74-3A]) and methyl 2-(5-chloro-2,3-dihydro-1H-indole-6-yl)acetate [74-3B] (Hereinafter Referred to as a Compound [74-3B])

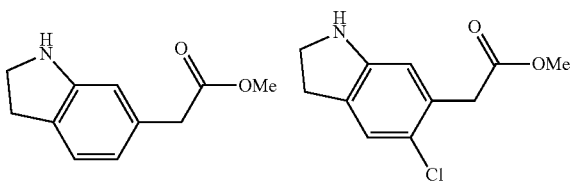

To a solution of the compound [74-2] obtained in the process (2) (3.8 g) in tert-butanol (144 mL) were added water (36 mL), sodium dihydrogen phosphate 2 hydrate (2.3 g), 2-methyl-2-butene (4.6 g) and sodium chlorite (3.7 g), and the reaction mixture was stirred for 2 hours on an ice bath. The reaction mixture was quenched with water and 1 N-hydrochloric acid, and extracted with ethyl acetate. The obtained organic layer was washed with brine, dried over anhydrous sodium sulfate, filtered, and the filtrate was concentrated under reduced pressure to give a crude carboxylate (3.8 g) as a colorless foamy substance.

The obtained crude carboxylate (3.8 g) was dissolved in N,N-dimethylformamide (70 mL). Sodium hydrogen carbonate (2.3 g) and methyl iodide (4.2 mL) were added, and then the reaction mixture was stirred at 60° C. for 2 hours. The reaction mixture was quenched with water, and extracted with ethyl acetate. The obtained organic layer was washed with brine, dried over anhydrous sodium sulfate, filtered, and the filtrate was concentrated under reduced pressure to give a crude ester as a pale brown oil.

The obtained crude ester was dissolved in chloroform (80 mL). Trifluoroacetic acid (80 mL) was added at room temperature, and then the reaction mixture was stirred at room temperature for 2 hours. The mixture was concentrated under reduced pressure, and then the reaction mixture was added an aqueous solution of sodium hydrogen carbonate, and extracted with ethyl acetate. The obtained organic layer was washed with brine, dried over anhydrous sodium sulfate, filtered, and the filtrate was concentrated under reduced pressure. The obtained residue was purified by silica gel column chromatography to give the titled compound [74-3A](0.8 g) as a brown solid. The titled compound [74-3B](0.8 g) as a brown solid was also obtained.

[74-3A]
$^1$H-NMR (400 MHz, CDCl$_3$) δ: 7.05 (1H, d, J=7.4 Hz), 6.59 (1H, d, J=7.4 Hz), 6.57 (1H, s), 3.68 (3H, s), 3.56 (2H, t, J=8.4 Hz), 3.52 (2H, s), 3.00 (2H, t, J=8.4 Hz).
ESI-MS found: 192 [M−Boc+H]$^+$

[74-3B]
$^1$H-NMR (400 MHz, CDCl$_3$) δ: 7.09 (1H, s), 6.54 (1H, s), 3.71 (3H, s), 3.67 (2H, s), 3.57 (2H, t, J=8.4 Hz), 3.00 (2H, t, J=8.4 Hz).
ESI-MS found: 226 [M−Boc+H]$^+$

(4) Synthesis of methyl 2-(1-benzyl-2,3-dihydro-1H-indole-6-yl)acetate [74-4](Hereinafter Referred to as a Compound [74-4])

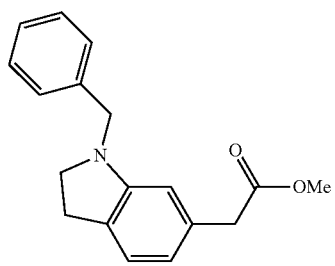

To a solution of the compound [74-3A] obtained in the process (3) (30 mg) in N,N-dimethylformamide (1.6 mL) were added cesium carbonate (163 mg) and benzyl bromide (37 mL) at room temperature, and then the reaction mixture was subjected to microwave irradiation at 90° C. for 30 minutes. The reaction mixture was quenched with water, and extracted with ethyl acetate. The obtained organic layer was washed with brine, dried over anhydrous sodium sulfate, filtered, and the filtrate was concentrated under reduced pressure. The obtained residue was purified by silica gel column chromatography to give the titled compound (30 mg) as a white solid.

$^1$H-NMR (400 MHz, CDCl$_3$) δ: 7.37-7.27 (5H, m), 7.03 (1H, d, J=7.3 Hz), 6.57 (1H, dd, J=7.3, 1.0 Hz), 6.44 (1H, d, J=1.0 Hz), 4.26 (2H, s), 3.67 (3H, s), 3.53 (2H, s), 3.31 (2H, t, J=8.4 Hz), 2.94 (2H, t, J=8.4 Hz).
ESI-MS found: 282 [M+H]$^+$

(5) Synthesis of potassium 2-(1-benzyl-2,3-dihydro-1H-indole-6-yl)acetate [74]

To a solution of the compound [74-4] obtained in the process (4) (30 mg) in tetrahydrofuran (1 mL) was added 1N-sodium hydroxide (0.5 mL), and then the reaction mixture was stirred at room temperature for 24 hours. The reaction mixture was added 1N-hydrochloric acid, and extracted with ethyl acetate. The obtained organic layer was washed with brine, dried over anhydrous sodium sulfate, filtered, and the filtrate was concentrated under reduced pressure. The obtained residue was dissolved in methanol and 1 M potassium hydroxide-methanol solution (92.4 μL) was added, and the solvent was concentrated under reduced pressure. The obtained residue was suspended in ethyl acetate, and the solid was filtered to give the titled compound (23 mg) as a white solid.

$^1$H-NMR (400 MHz, DMSO-$d_6$) δ: 7.37-7.22 (5H, m), 6.85 (1H, d, J=7.3 Hz), 6.47 (1H, d, J=1.2 Hz), 6.42 (1H, dd, J=7.3, 1.2 Hz), 4.19 (2H, s), 3.15 (2H, t, J=8.3 Hz), 3.00 (2H, s), 2.79 (2H, t, J=8.3 Hz).

ESI-MS found: 268 [M−K+2H]$^+$

Example 75

Synthesis of 2-[1-(2,6-dimethylbenzyl)-2,3-dihydro-1H-indole-6-yl]acetic acid [75] (Hereinafter Referred to as a Compound [75])

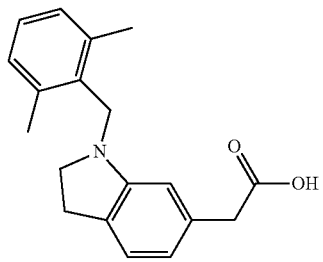 [SMILES: Cc1cccc(C)c1CN1CCc2ccc(CC(=O)O)cc21]

(1) Synthesis of methyl 2-[1-(2,6-dimethylbenzyl)-2,3-dihydro-1H-indole-6-yl]acetate [75-1] (Hereinafter Referred to as a Compound [75-1])

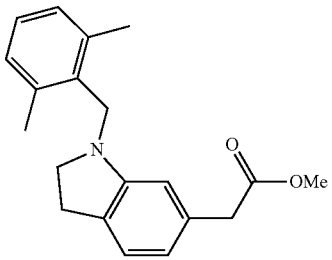 [SMILES: COC(=O)Cc1ccc2c(c1)N(Cc1c(C)cccc1C)CC2]

To a solution of the compound [74-3A] obtained in the process (3) of Example 74 (0.7 g) in N,N-dimethylformamide (18 mL) were added potassium carbonate (1.5 g) and 2,6-dimethylbenzyl chloride (1.2 g) at room temperature. Then, the reaction mixture was subjected to microwave irradiation at 90° C. for 30 minutes, and subsequently at 100° C. for 15 minutes. The reaction mixture was quenched with water, and extracted with ethyl acetate. The obtained organic layer was washed with brine, dried over anhydrous sodium sulfate, filtered, and the filtrate was concentrated under reduced pressure. The obtained residue was purified by silica gel column chromatography to give the titled compound (1.0 g) as a white solid.

$^1$H-NMR (400 MHz, CDCl$_3$) δ: 7.12 (1H, dd, J=8.4, 6.5 Hz), 7.06-7.00 (3H, m), 6.57 (1H, dd, J=7.4, 1.1 Hz), 6.53 (1H, d, J=1.1 Hz), 4.21 (2H, s), 3.71 (3H, s), 3.59 (2H, s), 3.11 (2H, t, J=8.3 Hz), 2.82 (2H, t, J=8.3 Hz), 2.38 (6H, s).

ESI-MS found: 310 [M+H]$^+$ (2) Synthesis of 2-[1-(2,6-dimethylbenzyl)-2,3-dihydro-1H-indole-6-yl]acetic acid [75]

To a solution of the compound [75-1] obtained in the process (1) (35 mg) in tetrahydrofuran (1 mL) was added 1N-sodium hydroxide (0.6 mL), and then the reaction mixture was stirred at room temperature for 24 hours. Then, the reaction mixture was added 1N-hydrochloric acid, and extracted with ethyl acetate. The obtained organic layer was washed with brine, dried over anhydrous sodium sulfate, filtered, and the filtrate was concentrated under reduced pressure to give the titled compound (33 mg) as a white solid.

$^1$H-NMR (400 MHz, CDCl$_3$) δ: 7.11 (1H, dd, J=8.5, 6.7 Hz), 7.07-7.01 (3H, m), 6.58 (1H, dd, J=6.7, 1.2 Hz), 6.52 (1H, d, J=1.2 Hz), 4.21 (2H, s), 3.62 (2H, s), 3.11 (2H, t, J=8.2 Hz), 2.82 (2H, t, J=8.2 Hz), 2.38 (6H, s).

ESI-MS found: 296 [M+H]$^+$

Example 76

Synthesis of potassium 2-[1-(2,6-dimethylbenzyl)-2,3-dihydro-1H-indole-6-yl]acetate [76] (Hereinafter Referred to as a Compound [76])

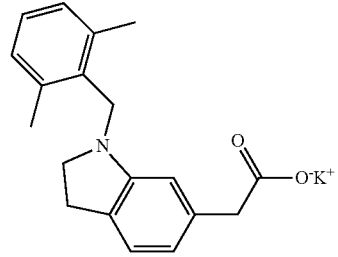

To a solution of the compound [75-1] obtained in the process (1) of Example 75 (1.1 g) in tetrahydrofuran (35 mL) was added 1N-sodium hydroxide (19 mL), and then the reaction mixture was stirred at room temperature for 24 hours. The reaction mixture was added 1N-hydrochloric acid, and extracted with ethyl acetate. The obtained organic layer was washed with brine, dried over anhydrous sodium sulfate, filtered, and the filtrate was concentrated under reduced pressure. The obtained residue was dissolved in methanol and 1 M potassium hydroxide-methanol solution (3.48 mL) was added, and the solvent was concentrated under reduced pressure. The obtained residue was suspended in ethyl acetate, and the solid was filtered to give the titled compound (1.0 g) as a white solid.

$^1$H-NMR (400 MHz, DMSO-$d_6$) δ: 7.12-7.01 (3H, m), 6.89 (1H, d, J=7.2 Hz), 6.60 (1H, s), 6.46 (1H, d, J=7.2 Hz), 4.14 (2H, s), 3.25 (2H, s), 2.98 (2H, t, J=8.2 Hz), 2.71 (2H, t, J=8.2 Hz), 2.34 (6H, s).

ESI-MS found: 296 [M−K+2H]$^+$

Example 77

Synthesis of 2-[5-chloro-1-(2,6-dimethylbenzyl)-2,3-dihydro-1H-indole-6-yl]acetic acid [77] (Hereinafter Referred to as a Compound [77])

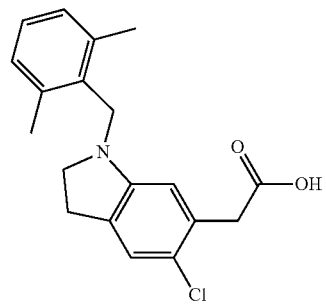 [SMILES: Cc1cccc(C)c1CN1CCc2cc(Cl)c(CC(=O)O)cc21]

(1) Synthesis of methyl 2-[5-chloro-1-(2,6-dimethyl-benzyl)-2,3-dihydro-1H-indol-6-yl]acetate [77-1] (Hereinafter Referred to as a Compound [77-1])

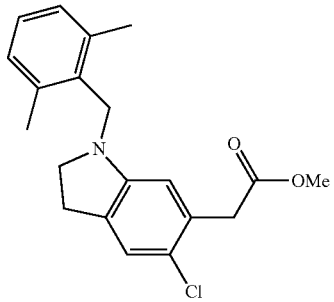 [SMILES: COC(=O)Cc1cc2c(cc1Cl)CCN2Cc1c(C)cccc1C]

The titled compound (57 mg) as a white solid was prepared from the compound [74-3B] obtained in the process (3) of Example 74 (43 mg) in N,N-dimethylformamide (1.8 mL), potassium carbonate (123 mg) and 2,6-dimethylbenzyl chloride (65 mg) according to the method of the process (1) of Example 75.

$^1$H-NMR (400 MHz, CDCl$_3$) δ: 7.12 (1H, dd, J=8.3, 6.6 Hz), 7.05-7.04 (3H, m), 6.46 (1H, s), 4.18 (2H, s), 3.73 (3H, s), 3.72 (2H, s), 3.11 (2H, t, J=8.1 Hz), 2.82 (2H, t, J=8.1 Hz), 2.37 (6H, s).

ESI-MS found: 344 [M+H]$^+$ (2) Synthesis of 2-[5-chloro-1-(2,6-dimethylbenzyl)-2,3-dihydro-1H-indol-6-yl]acetic acid [77]

To a solution of the compound [77-1] obtained in the process (1) (57 mg) in tetrahydrofuran (1.6 mL) was added 1N-sodium hydroxide (0.9 mL), and then the reaction mixture was stirred at room temperature for 20 hours. The reaction mixture was added 1N-hydrochloric acid, and extracted with ethyl acetate. The obtained organic layer was washed with brine, dried over anhydrous sodium sulfate, filtered, and the filtrate was concentrated under reduced pressure to give the titled compound (35 mg) as a white solid.

$^1$H-NMR (400 MHz, DMSO-d$_6$) δ: 7.12 (1H, dd, J=8.3, 6.6 Hz), 7.07-7.02 (3H, m), 6.45 (1H, s), 4.18 (2H, s), 3.77 (2H, s), 3.12 (2H, t, J=8.3 Hz), 2.82 (2H, t, J=8.3 Hz), 2.37 (6H, s).

ESI-MS found: 330 [M+H]$^+$

Example 78

Synthesis of (3-RS)-2-[1-(2,6-dimethylbenzyl)-2,3-dihydro-3-methyl-1H-indol-6-yl]acetic acid [78] (Hereinafter Referred to as a Compound [78])

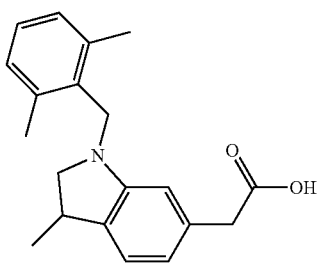 [SMILES: Cc1cccc(C)c1CN1CC(C)c2ccc(CC(=O)O)cc21]

(1) Synthesis of (3-RS)-6-bromo-2,3-dihydro-3-methyl-1H-indol-2-one [78-1](Hereinafter Referred to as a Compound [78-1])

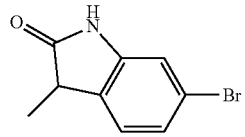

Sodium hydride (3.9 g) was suspended in dimethyl sulfoxide (24 mL), and diethyl methyl malonate (16 mL) was added at 0° C., and then the reaction mixture was stirred at room temperature for 1.5 hours. The reaction mixture was heated to 100° C., and a solution of 2,5-dibromonitrobenzene (15.3 g) in dimethyl sulfoxide (17 mL) was added at 100° C., and then the reaction mixture was stirred at 100° C. for 5 hours. The reaction mixture was quenched with water, and extracted with ethyl acetate. The obtained organic layer was washed with brine, dried over anhydrous sodium sulfate, filtered, and the filtrate was concentrated under reduced pressure. The residue was dissolved in ethanol (75 mL), and tin (11.5 g) was added at room temperature. Concentrated hydrochloric acid (45 mL) was added at 0° C., and then the reaction mixture was heated at reflux for 2 hours. After cooling to room temperature, the reaction mixture was quenched with water, and extracted with ethyl acetate. The obtained organic layer was washed with a saturated aqueous solution of sodium hydrogen carbonate and brine, dried over anhydrous sodium sulfate, filtered, and the filtrate was concentrated under reduced pressure. The obtained residue was purified by silica gel column chromatography to give the titled compound (4.9 g) as a brown solid.

$^1$H-NMR (400 MHz, CDCl$_3$) δ: 8.48 (1H, brs), 7.17 (1H, dd, J=7.9, 1.3 Hz), 7.08 (1H, d, J=7.9 Hz), 7.07 (1H, s), 3.41 (1H, q, J=7.8 Hz), 1.48 (3H, d, J=7.8 Hz).

ESI-MS found: 226 [M+H]$^+$ (2) Synthesis of tert-butyl (3-RS)-6-bromo-2,3-dihydro-3-methyl-1H-indole-1-carboxylate [78-2] (Hereinafter Referred to as a Compound [78-2])

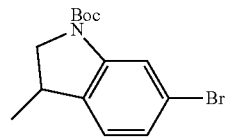 [SMILES: CC1CN(C(=O)OC(C)(C)C)c2cc(Br)ccc21]

The compound [78-1] obtained in the process (1) (4.9 g) was suspended in toluene (22 mL), and borane dimethyl sulfide complex (4.4 mL) was added at 0° C., and then the reaction mixture was heated at reflux for 2 hours. The reaction mixture was cooled with ice-water bath, and an aqueous solution of 5N-sodium hydroxide (8 mL), an aqueous solution of 8N-sodium hydroxide (8 mL) and ethyl acetate (8 mL) were added, successively, and then the reaction mixture was stirred at room temperature for 2.5 hours. The reaction mixture was quenched with water, and extracted with ethyl acetate. The obtained organic layer was washed with brine, dried over anhydrous sodium sulfate, filtered, and the filtrate was concentrated under reduced pressure. The residue was dissolved in tetrahydrofuran (100 mL), and triethylamine (4.55 mL) and a solution of di-tert-butyl dicarbonate (6.2 g) in tetrahydrofuran (10 mL) were added successively at room temperature, and then a grain of dimethylaminopyridine was added, and the reaction mixture was stirred at room temperature for 22 hours. The reaction mixture was quenched with water, and extracted with ethyl acetate. The obtained organic layer was washed with brine, dried over anhydrous sodium sulfate, filtered, and the filtrate was concentrated under reduced pressure. The obtained residue was purified by silica gel column chromatography to give the titled compound (4.6 g) as a colorless oil.

$^1$H-NMR (400 MHz, CDCl$_3$) δ: 8.03 (1H, s), 7.07 (1H, dd, J=7.9, 1.6 Hz), 6.96 (1H, d, J=8.3 Hz), 4.19-4.08 (1H, m), 3.57-3.43 (1H, m), 3.39-3.27 (1H, m), 1.53 (9H, brs), 1.30 (3H, d, J=6.8 Hz).

ESI-MS found: 256 [M−tBu+H]$^+$ (3) Synthesis of methyl (3-RS)-2-(2,3-dihydro-3-methyl-1H-indol-6-yl)acetate [78-3] (Hereinafter Referred to as a Compound [78-3])

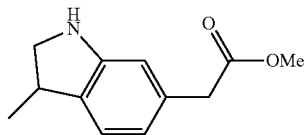

The titled compound (134 mg) as a colorless oil was prepared from the compound [78-2] obtained in the process (2) (4.6 g) according to the methods of the processes (1) to (3) of Example 74.

$^1$H-NMR (400 MHz, CDCl$_3$) δ: 7.01 (1H, d, J=7.3 Hz), 6.62 (1H, d, J=7.3 Hz), 6.57 (1H, s), 3.73-3.64 (2H, m), 3.68 (3H, s), 3.53 (2H, s), 3.39-3.27 (1H, m), 3.11 (1H, t, J=8.7 Hz), 1.30 (3H, d, J=6.8 Hz).

ESI-MS found: 206 [M+H]$^+$ (4) Synthesis of methyl (3-RS)-2-[1-(2,6-dimethylbenzyl)-2,3-dihydro-3-methyl-1H-indol-6-yl]acetate [78-4] (hereinafter referred to as a compound [78-4])

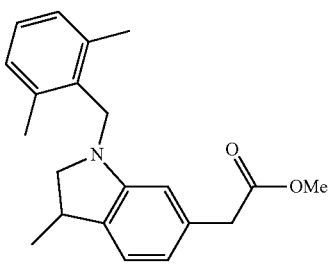 [SMILES: COC(=O)Cc1ccc2c(c1)N(Cc1c(C)cccc1C)CC2C]

The titled compound (46 mg) as a colorless oil was prepared from the compound [78-3] obtained in the process (3) (40 mg) and 2,6-dimethylbenzyl chloride according to the method of the process (1) of Example 75.

$^1$H-NMR (400 MHz, CDCl$_3$) δ: 7.12 (1H, dd, J=8.3, 6.6 Hz), 7.07-7.02 (2H, m), 6.99 (1H, d, J=7.3 Hz), 6.60 (1H, d, J=7.3 Hz), 6.52 (1H, s), 4.30 (1H, d, J=12.9 Hz), 4.10 (1H, d, J=12.9 Hz), 3.71 (3H, s), 3.59 (2H, s), 3.24 (1H, t, J=8.4 Hz), 3.13 (1H, tq, J=8.3, 6.6 Hz), 2.67 (1H, t, J=8.2 Hz), 2.38 (6H, s), 1.21 (3H, d, J=6.6 Hz).

ESI-MS found: 324 [M+H]$^+$ (5) Synthesis of (3-RS)-2-[1-(2,6-dimethylbenzyl)-2,3-dihydro-3-methyl-1H-indol-6-yl]acetic acid [78]

The titled compound (26 mg) as a white solid was prepared from the compound [78-4] obtained in the process (4) (46 mg) according to the method of the process (2) of Example 77.

$^1$H-NMR (400 MHz, CDCl$_3$) δ: 7.12 (1H, dd, J=8.2, 6.5 Hz), 7.07-7.02 (2H, m), 7.00 (1H, d, J=7.3 Hz), 6.61 (1H, d, J=7.3 Hz), 6.51 (1H, s), 4.30 (1H, d, J=12.9 Hz), 4.10 (1H, d, J=12.9 Hz), 3.62 (2H, s), 3.25 (1H, t, J=8.4 Hz), 3.14 (1H, td, J=14.8, 7.3 Hz), 2.67 (1H, t, J=8.3 Hz), 2.37 (6H, s), 1.21 (3H, d, J=6.6 Hz).

ESI-MS found: 310 [M+H]$^+$

Example 79

Synthesis of (3R*)-2-[1-(2,6-dimethylbenzyl)-2,3-dihydro-3-methyl-1H-indol-6-yl]acetic acid [79A] (Hereinafter Referred to as a Compound [79A]) and (3S*)-2-[1-(2,6-dimethylbenzyl)-2,3-dihydro-3-methyl-1H-indol-6-yl]acetic acid [79B] (Hereinafter Referred to as a Compound [79B])

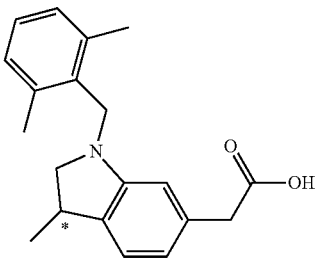 [SMILES: Cc1cccc(C)c1CN1CC(C)c2ccc(CC(=O)O)cc21]

The compound [78] obtained in Example 78 (26 mg) was optically resolved by chiral column chromatography (CHIRALCEL (registered trademark) OD CHIRALCEL OD) manufactured by Daicel Corporation, 2 cm ×25 cm; 0.1% trifluoroacetic acid, hexane/isopropyl alcohol=85/15; flow rate 20 mL/min). (3R*)-2-[1-(2,6-dimethylbenzyl)-2,3-dihydro-3-methyl-1H-indol-6-yl]acetic acid [79A] (15 mg) as a pale brown solid was obtained from the preceding fraction (retention time: 5.3 minutes), and (3S*)-2-[1-(2,6-dimethylbenzyl)-2,3-dihydro-3-methyl-1H-indol-6-yl]acetic acid [79B] of the same (16 mg) as a pale brown solid was obtained from the posterior fraction (retention time: 10.8 minutes). (Both of them were un-identified, and thus one of them was referred to as 3R*, and the other one as 3S* for convenience.)

Compound [79A]

1H-NMR and ESI-MS are the same as a compound [78].

Compound [79B]

1H-NMR and ESI-MS are the same as a compound [78].

Example 80

Synthesis of 2-[1-(2,6-dimethylbenzyl)-2,3-dihydro-3,3-dimethyl-1H-indol-6-yl]acetic acid [80] (Hereinafter Referred to as a Compound [80])

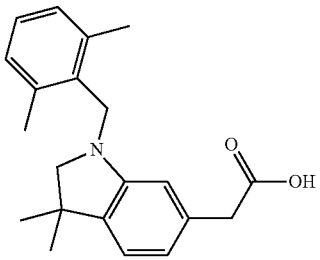 [SMILES: Cc1cccc(C)c1CN1CC(C)(C)c2ccc(CC(=O)O)cc21]

(1) Synthesis of 6-bromo-2,3-dihydro-3,3-dimethyl-1H-indole-2-one [80-1](Hereinafter Referred to as a Compound [80-1])

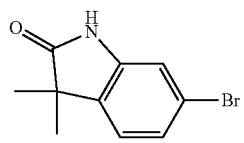

Potassium tert-butoxide (6.2 g) was suspended in tetrahydrofuran (55 mL), and a suspension of 6-bromo-1,3-dihydroindole-2-one (2.3 g) in tetrahydrofuran (39 mL) and copper(I) bromide dimethyl sulfide complex (252 mg) were added. To the reaction mixture, methyl iodide (1.9 mL) was added at 0° C., and then the reaction mixture was stirred at 0° C. for 5 minutes, and subsequently stirred at room temperature for 30 minutes. To the reaction mixture, an aqueous solution of ammonium chloride was added, and the reaction mixture was extracted with ethyl acetate. The obtained organic layer was washed with brine, dried over anhydrous sodium sulfate, filtered, and the filtrate was concentrated under reduced pressure. The obtained residue was purified by silica gel column chromatography to give the titled compound (1.4 g) as a white solid.
$^1$H-NMR (400 MHz, CDCl$_3$) δ: 7.65 (1H, brs), 7.18 (1H, dd, J=7.8, 2.0 Hz), 7.06 (1H, d, J=2.0 Hz), 7.05 (1H, d, J=7.8 Hz), 1.38 (6H, s).
ESI-MS found: 240 [M+H]$^+$ (2) Synthesis of tert-butyl 6-bromo-2,3-dihydro-3,3-dimethyl-1H-indole-1-carboxylate [80-2] (Hereinafter Referred to as a Compound [80-2])

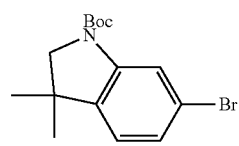 [SMILES: CC(C)(C)OC(=O)N1CC(C)(C)c2ccc(Br)cc21]

The titled compound (992 mg) as a colorless oil was prepared from the compound [80-1] obtained in the process (1) (1.4 g) according to the method of the process (2) of Example 78.
$^1$H-NMR (400 MHz, CDCl$_3$) δ: 8.05 (1H, s), 7.08 (1H, dd, J=1.7, 7.8 Hz), 6.94 (1H, d, J=7.8 Hz), 3.70 (2H, s), 1.57 (9H, s), 1.30 (6H, s).
ESI-MS found: 270 [M−tBu+H]$^+$ (3) Synthesis of methyl 2-(2,3-dihydro-3,3-dimethyl-1H-indol-6-yl)acetate [80-3](Hereinafter Referred to as a Compound [80-3])

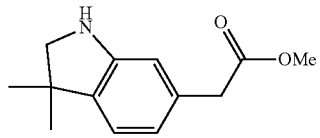 [SMILES: COC(=O)Cc1ccc2c(c1)NCC2(C)C]

The titled compound (20 mg) as a colorless oil was prepared from the compound [80-2] obtained in the process (2) (992 mg) according to the methods of the processes (1) to (3) of Example 74.
$^1$H-NMR (400 MHz, CDCl$_3$) δ: 6.97 (1H, d, J=7.3 Hz), 6.63 (1H, d, J=7.6 Hz), 6.57 (1H, s), 3.68 (3H, s), 3.53 (2H, s), 3.31 (2H, s), 1.29 (6H, s).
ESI-MS found: 220 [M+H]$^+$ (4) Synthesis of methyl 2-[1-(2,6-dimethylbenzyl)-2,3-dihydro-3,3-dimethyl-1H-indol-6-yl]acetate [80-4] (Hereinafter Referred to as a Compound [80-4])

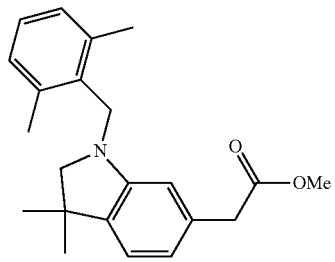 [SMILES: COC(=O)Cc1ccc2c(c1)N(Cc1c(C)cccc1C)CC2(C)C]

The titled compound (14 mg) as a colorless oil was prepared from the compound [80-3] obtained in the process (3) (20 mg) and 2,6-dimethylbenzyl chloride according to the method of the process (1) of Example 75.
$^1$H-NMR (400 MHz, CDCl$_3$) δ: 7.12 (1H, dd, J=8.2, 6.6 Hz), 7.08-7.02 (2H, m), 6.95 (1H, d, J=7.6 Hz), 6.60 (1H, d, J=7.3 Hz), 6.52 (1H, s), 4.22 (2H, s), 3.71 (3H, s), 3.59 (2H, s), 2.84 (2H, s), 2.39 (6H, s), 1.19 (6H, s).
ESI-MS found: 338 [M+H]$^+$ (5) Synthesis of 2-[1-(2,6-dimethylbenzyl)-2,3-dihydro-3,3-dimethyl-1H-indol-6-yl]acetic acid [80]

The titled compound (6 mg) as a white solid was prepared from the compound [80-4] obtained in the process (4) (14 mg) according to the method of the process (2) of Example 77.
$^1$H-NMR (400 MHz, CDCl$_3$) δ: 7.12 (1H, dd, J=8.2, 6.7 Hz), 7.07-7.02 (2H, m), 6.96 (1H, d, J=7.6 Hz), 6.62 (1H, d, J=7.3 Hz), 6.51 (1H, s), 4.22 (2H, s), 3.62 (2H, s), 2.84 (2H, s), 2.37 (6H, s), 1.19 (6H, s).
ESI-MS found: 324 [M+H]$^+$

Example 81

Synthesis of 2,3-dihydro-1-(2,6-dimethylbenzyl)-1H-indole-6-carboxylic acid [81] (Hereinafter Referred to as a Compound [81])

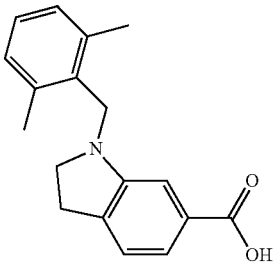

(1) Synthesis of tert-butyl 2,3-dihydro-6-vinyl-1H-indole-1-carboxylate [81-1] (Hereinafter Referred to as a Compound [81-1])

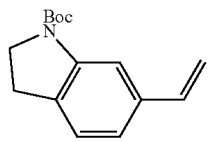 [SMILES: C=Cc1ccc2c(c1)N(C(=O)OC(C)(C)C)CC2]

The titled compound (207 mg) as a white solid was prepared from tert-butyl 6-bromo-2,3-dihydro-1H-indole-1-carboxylate obtained by the method described in the document (WO 1998/43956 A) and tributyl(vinyl)tin according to the method of the process (2) of Example 66.

$^1$H-NMR (400 MHz, CDCl$_3$) δ: 7.96 (1H, brs), 7.09 (1H, d, J=7.6 Hz) 7.01-6.92 (1H, brm), 6.69 (1H, dd, J=17.6-10.8 Hz), 5.80-5.66 (1H, brm), 5.19 (1H, d, J=10.8 Hz), 4.06-3.91 (2H, brm), 3.07 (2H, t, J=8.7 Hz), 1.57 (9H, s).

ESI-MS found: 190 [M−tBu+H]$^+$

(2) Synthesis of methyl 2,3-dihydro-1H-indole-6-carboxylate [81-2] (Hereinafter Referred to as a Compound [81-2])

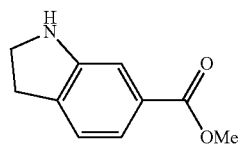 [SMILES: COC(=O)c1ccc2c(c1)NCC2]

The titled compound (41 mg) as a pale brown solid was prepared from the compound [81-1] obtained in the process (1) (207 mg) according to the methods of the processes (2) and (3) of Example 74.

$^1$H-NMR (400 MHz, CDCl$_3$) δ: 7.41 (1H, dd, J=7.6, 1.5 Hz), 7.26 (1H, d, J=1.5 Hz), 7.14 (1H, d, J=7.6 Hz), 3.87 (3H, s), 3.61 (2H, t, J=8.5 Hz), 3.07 (2H, t, J=8.5 Hz).

ESI-MS found: 178 [M+H]$^+$

(3) Synthesis of methyl 2,3-dihydro-1-(2,6-dimethylbenzyl)-1H-indole-6-carboxylate [81-3] (Hereinafter Referred to as a Compound [81-3])

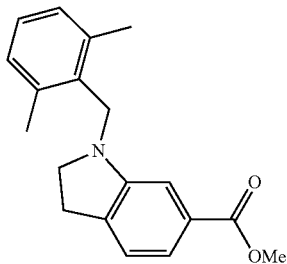 [SMILES: COC(=O)c1ccc2c(c1)N(Cc1c(C)cccc1C)CC2]

The titled compound (55 mg) as a white solid was prepared from the compound [81-2] obtained in the process (2) (41 mg) and 2,6-dimethylbenzyl chloride according to the method as described in the process (1) of Example 75.

$^1$H-NMR (400 MHz, CDCl$_3$) δ: 7.40 (1H, dd, J=7.6, 1.5 Hz), 7.23 (1H, d, J=1.5 Hz), 7.15-7.03 (4H, m), 4.27 (2H, s), 3.91 (3H, s), 3.15 (2H, t, J=8.3 Hz), 2.89 (2H, t, J=8.3 Hz), 2.39 (6H, s).

ESI-MS found: 296 [M+H]$^+$

(4) Synthesis of 2,3-dihydro-1-(2,6-dimethylbenzyl)-1H-indole-6-carboxylic acid [81]

To a solution of the compound [81-3] obtained in the process (3) (55 mg) in tetrahydrofuran (1.8 mL) was added 1N-sodium hydroxide (1.0 mL), and then the reaction mixture was subjected to microwave irradiation at 120° C. for 20 minutes. Then, the reaction mixture was added 1N-hydrochloric acid, and extracted with ethyl acetate. The obtained organic layer was washed with brine, dried over anhydrous sodium sulfate, filtered, and the filtrate was concentrated under reduced pressure. The obtained residue was purified by silica gel column chromatography to give the titled compound (42 mg) as a white solid.

$^1$H-NMR (400 MHz, CDCl$_3$) δ: 7.49 (1H, d, J=7.6 Hz), 7.28 (1H, s), 7.17-7.10 (2H, m), 7.08-7.03 (2H, m), 4.28 (2H, s), 3.17 (2H, t, J=8.2 Hz), 2.91 (2H, t, J=8.2 Hz), 2.40 (6H, s).

ESI-MS found: 282 [M+H]$^+$

Example 82

Synthesis of 2-[1-(2,6-dichlorobenzyl)-3-methyl-1H-indole-6-yl]acetic acid [82] (Hereinafter Referred to as a Compound [82])

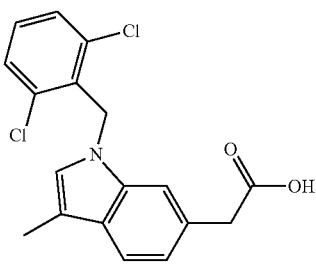 [SMILES: Cc1cn(Cc2c(Cl)cccc2Cl)c2cc(CC(=O)O)ccc12]

To a solution of the compound obtained in the process (3) of Example 64 [64-3](272 mg) in N-methyl-2-pyrrolidone (4 mL) were added potassium carbonate (555 mg) and 2,6-dichlorobenzyl chloride (516 mg) at room temperature, and then the reaction mixture was subjected to microwave irradiation at 130° C. for 40 minutes. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give a brown oil. The obtained oil was dissolved in tetrahydrofuran (2 mL) and methanol (2 mL). 3N-sodium hydroxide (1 mL) was added at room temperature, and then the reaction mixture was subjected to microwave irradiation at 160° C. for 10 minutes. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (194 mg) as a white solid.

$^1$H-NMR (400 MHz, CD$_3$OD) δ: 7.48-7.32 (5H, m), 6.99 (1H, dd, J=8.1, 1.5 Hz), 6.61 (1H, d, J=1.0 Hz), 5.50 (2H, s), 3.70 (2H, s), 2.20 (3H, s).

ESI-MS found: 348 [M+H]$^+$

Example 83

Synthesis of potassium 2-[1-(2,6-dichlorobenzyl)-3-methyl-1H-indol-6-yl]acetate [83] (Hereinafter Referred to as a Compound [83])

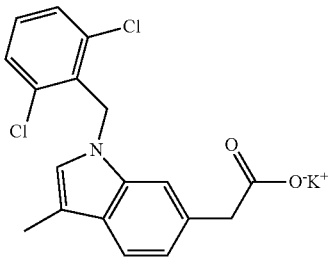

To a solution of the compound [82](126 mg) in ethanol (2 mL) was added an aqueous solution of 1N-potassium hydroxide (0.36 mL) at room temperature, and the solution was concentrated under reduced pressure to give the titled compound (110 mg) as a white solid.

$^1$H-NMR (400 MHz, CD$_3$OD) δ: 7.52-7.30 (5H, m), 7.05 (1H, d, J=8.1 Hz), 6.51 (1H, s), 5.48 (2H, s), 3.61 (2H, s), 2.18 (3H, s).

ESI-MS found: 348 [M−K+2H]$^+$

Example 84

Synthesis of 2-[1-(2,3-dichlorobenzyl)-3-methyl-1H-indol-6-yl]acetic acid [84] (Hereinafter Referred to as a Compound [84])

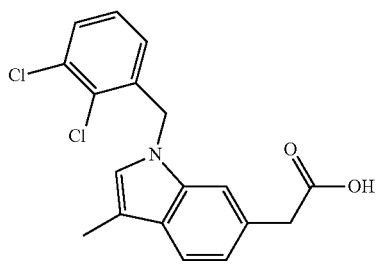 [SMILES: Cc1cn(Cc2cccc(Cl)c2Cl)c2cc(CC(=O)O)ccc12]

The titled compound (33 mg) as a white solid was prepared from the compound [64-3] obtained in the process (3) of Example 64 (55 mg) and 2,3-dichlorobenzyl chloride (72 µL) according to the method of Example 82.

$^1$H-NMR (400 MHz, CD$_3$OD) δ: 7.44 (1H, d, J=8.1 Hz), 7.40 (1H, d, J=7.8 Hz), 7.17 (1H, s), 7.13-7.03 (2H, m), 6.93 (1H, s), 6.39 (1H, d, J=7.6 Hz), 5.42 (2H, s), 3.52 (2H, s), 2.30 (3H, s).

ESI-MS found: 348 [M+H]$^+$

Example 85

Synthesis of 2-[1-(2,5-dimethylbenzyl)-3-methyl-1H-indol-6-yl]acetic acid [85] (Hereinafter Referred to as a Compound [85])

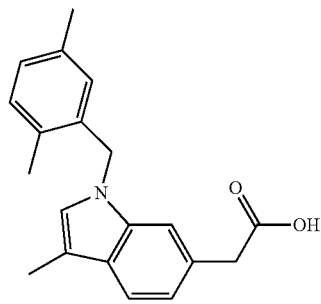 [SMILES: Cc1ccc(C)c(Cn2cc(C)c3ccc(CC(=O)O)cc32)c1]

The titled compound (35 mg) as a white solid was prepared from the compound [64-3] obtained in the process (3) of Example 64 (58 mg) and 2,5-dimethylbenzyl chloride (81 µL) according to the method of Example 82.

$^1$H-NMR (400 MHz, CD$_3$OD) δ: 7.41 (1H, d, J=8.1 Hz), 7.24 (1H, s), 7.07-7.02 (2H, m), 6.95 (1H, d, J=7.1 Hz), 6.73 (1H, d, J=1.0 Hz), 6.54 (1H, s), 5.21 (2H, s), 3.54 (2H, s), 2.27 (3H, s), 2.23 (3H, s), 2.14 (3H, s).

ESI-MS found: 308 [M+H]$^+$

Example 86

Synthesis of 2-[1-(2-chloro-6-fluorobenzyl)-3-methyl-1H-indol-6-yl]acetic acid [86] (Hereinafter Referred to as a Compound [86])

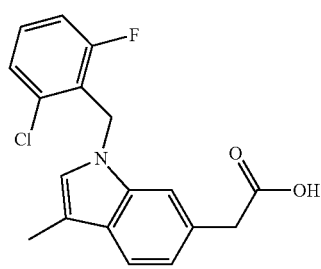 [SMILES: Cc1cn(Cc2c(F)cccc2Cl)c2cc(CC(=O)O)ccc12]

The titled compound (38 mg) as a white solid was prepared from the compound [64-3] obtained in the process (3) of Example 64 (50 mg) and 2-chloro-6-fluorobenzyl chloride (72 µL) according to the method of Example 82.

$^1$H-NMR (400 MHz, CD$_3$OD) δ: 7.46-7.26 (4H, m), 7.15 (1H, t, J=8.8 Hz), 6.97 (1H, d, J=8.1 Hz), 6.85 (1H, s), 5.41 (2H, s), 3.68 (2H, s), 2.22 (3H, s).

ESI-MS found: 332 [M+H]$^+$

Example 87

Synthesis of 2-[1-(2-chlorobenzyl)-3-methyl-1H-indol-6-yl]acetic acid [87] (Hereinafter Referred to as a Compound [87])

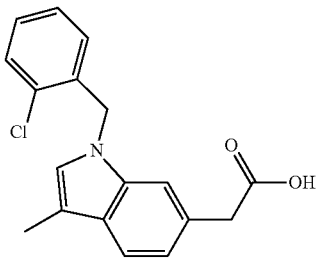 [SMILES: Cc1cn(Cc2ccccc2Cl)c2cc(CC(=O)O)ccc12]

The titled compound (21 mg) as a white solid was prepared from the compound [64-3] obtained in the process (3) of Example 64 (52 mg) and 2-chlorobenzyl chloride (72 μL) according to the method of Example 82.

$^1$H-NMR (400 MHz, CD$_3$OD) δ: 7.48 (1H, d, J=8.1 Hz), 7.42 (1H, d, J=8.1 Hz), 7.22 (1H, t, J=7.2 Hz), 7.14 (1H, s), 7.10 (1H, t, J=7.3 Hz), 7.02-6.95 (2H, m), 6.60 (1H, d, J=7.6 Hz), 5.39 (2H, s), 3.63 (2H, s), 2.30 (3H, s).

ESI-MS found: 314 [M+H]$^+$

Example 88

Synthesis of 2-{1-[(6-chlorobenzo[d][1,3]dioxol-5-yl)methyl]-3-methyl-1H-indol-6-yl}acetic acid [88] (Hereinafter, Referred to as a Compound [88])

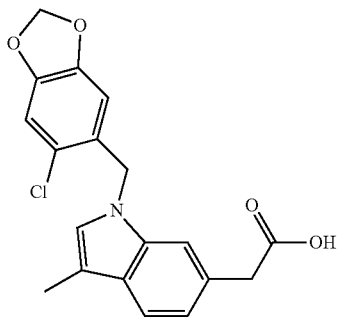 [SMILES: Cc1cn(Cc2cc3c(cc2Cl)OCO3)c2cc(CC(=O)O)ccc12]

The titled compound (30 mg) as a white solid was prepared from the compound [64-3] obtained in the process (3) of Example 64 (55 mg) and 6-chloropiperonyl chloride (127 mg) according to the method of Example 82.

$^1$H-NMR (400 MHz, CD$_3$OD) δ: 7.47 (1H, d, J=8.1 Hz), 7.17 (1H, s), 7.00 (1H, d, J=8.1 Hz), 6.96 (1H, s), 6.92 (1H, s), 6.05 (1H, s), 5.89 (2H, s), 5.28 (2H, s), 3.65 (2H, s), 2.30 (3H, s).

ESI-MS found: 358 [M+H]$^+$

Example 89

Synthesis of 3-[1-(2,6-dichlorobenzyl)-3-methyl-1H-indol-6-yl]propionic acid [89] (Hereinafter Referred to as a Compound [89])

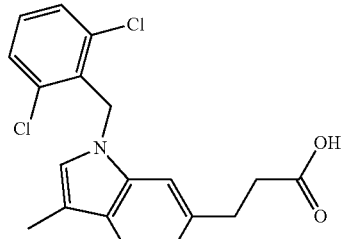

(1) Synthesis of 3-methyl-1-tosyl-1H-indole-6-carbaldehyde [89-1] (Hereinafter Referred to as a Compound [89-1])

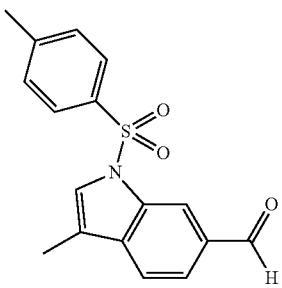 [SMILES: Cc1ccc(S(=O)(=O)n2cc(C)c3ccc(C=O)cc32)cc1]

To a solution of the compound [64-1] obtained in the process (1) of Example 64 (1.01 g) in dichloromethane (30 mL), and Dess-Martin periodinane (2.44 g) at 0° C., and then the reaction mixture was stirred at room temperature for 3 hours. To the reaction mixture, 10% aqueous solution of sodium thiosulfate was added, and the reaction mixture was extracted with chloroform. The obtained organic layer was dried over anhydrous sodium sulfate, filtered, and the filtrate was concentrated under reduced pressure. The obtained residue was purified by silica gel column chromatography to give the titled compound (1.00 g) as a brown solid.

$^1$H-NMR (400 MHz, CDCl$_3$) δ: 10.09 (1H, s), 8.47 (1H, s), 7.81-7.76 (3H, m), 7.57 (1H, d, J=8.1 Hz), 7.52 (1H, s), 7.26-7.23 (2H, m), 2.35 (3H, s), 2.28 (3H, s).

(2) Synthesis of methyl (E)-3-(3-methyl-1-tosyl-1H-indol-6-yl)acrylate [89-2] (Hereinafter Referred to as a Compound [89-2])

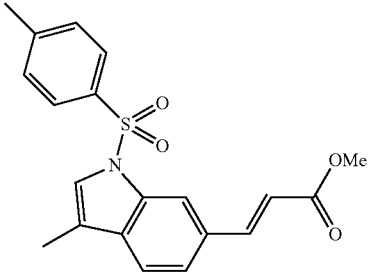 [SMILES: COC(=O)/C=C/c1ccc2c(C)cn(S(=O)(=O)c3ccc(C)cc3)c2c1]

To a solution of the compound [89-1] obtained in the process (1) (1.0 g) in tetrahydrofuran (20 mL) was added methyl (triphenylphosphoranylidene) acetate (2.39 g) at room temperature, and then the reaction mixture was heated at reflux for 24 hours. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (1.03 g) as a white solid.

$^1$H-NMR (400 MHz, CDCl$_3$) δ: 8.12 (1H, s), 7.81 (1H, d, J=16.1 Hz), 7.74 (2H, d, J=8.3 Hz), 7.44 (2H, s), 7.37 (1H, s), 7.22 (2H, d, J=8.3 Hz), 6.50 (1H, d, J=16.1 Hz), 3.83 (3H, s), 2.34 (3H, s), 2.24 (3H, s).

(3) Synthesis of methyl 3-(3-methyl-1-tosyl-1H-indole-6-yl)propionate [89-3] (Hereinafter Referred to as a Compound [89-3])

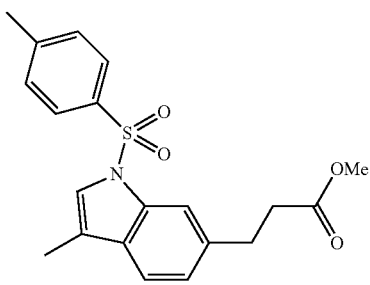 [SMILES: COC(=O)CCc1ccc2c(C)cn(S(=O)(=O)c3ccc(C)cc3)c2c1]

The compound [89-2] (99 mg) obtained in the process (2) was suspended in methanol (2 mL) and ethyl acetate (2 mL). To the mixture was added 5% palladium on carbon (38 mg) at room temperature, and then the reaction mixture was stirred at room temperature for 3 hours under hydrogen atmosphere. The palladium on carbon was filtered, and then the filtrate was concentrated under reduced pressure. The obtained residue was purified by silica gel column chromatography to give the titled compound (101 mg) as a colorless oil.

$^1$H-NMR (400 MHz, CDCl$_3$) δ: 7.82 (1H, s), 7.73 (2H, d, J=8.3 Hz), 7.35 (1H, d, J=8.1 Hz), 7.26-7.18 (3H, m), 7.08 (1H, d, J=7.8 Hz), 3.68 (3H, s), 3.07 (2H, t, J=7.7 Hz), 2.67 (2H, t, J=7.8 Hz), 2.33 (3H, s), 2.21 (3H, s).

(4) Synthesis of methyl 3-(3-methyl-1H-indole-6-yl)propionate [89-4] (Hereinafter Referred to as a Compound [89-4])

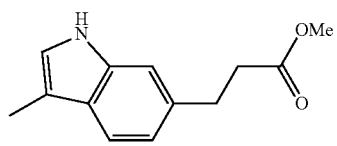 [SMILES: COC(=O)CCc1ccc2c(C)c[nH]c2c1]

To a solution of the compound [89-3] obtained in the process (3) (94.5 mg) in methanol (2 mL) was added an aqueous solution of 1N-sodium hydroxide (1 mL), and then the reaction mixture was subjected to microwave irradiation at 160° C. for 10 minutes. The reaction mixture was added 2N-hydrochloric acid, and extracted with ethyl acetate. The obtained organic layer was dried over anhydrous sodium sulfate, filtered, and the filtrate was concentrated under reduced pressure. The obtained residue was dissolved in N,N-dimethylformamide (1 mL). To the solution were added potassium carbonate (48 mg) and methyl iodide (18 μL) at room temperature, and then the reaction mixture was stirred at room temperature for 2 days. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (41.6 mg).

$^1$H-NMR (400 MHz, CDCl$_3$) δ: 7.88-7.73 (1H, br), 7.49 (1H, d, J=8.1 Hz), 7.17 (1H, s), 6.97 (1H, d, J=7.3 z), 6.92 (1H, s), 3.67 (3H, s), 3.06 (2H, t, J=7.8 Hz), 2.68 (2H, t, J=7.8 z), 2.31 (3H, s).

(5) Synthesis of 3-[1-(2,6-dichlorobenzyl)-3-methyl-1H-indole-6-yl]propionic acid [89]

The titled compound (8.9 mg) as a pale brown solid was prepared from the compound [89-4] obtained in the process (4) (41 mg) and 2,6-dichlorobenzyl chloride (60 mg) according to the method of Example 82.

$^1$H-NMR (400 MHz, CD$_3$OD) δ: 7.47 (2H, d, J=8.1 Hz), 7.41-7.33 (3H, m), 6.93 (1H, d, J=8.1 Hz), 6.59 (1H, s), 5.47 (2H, s), 3.03 (2H, t, J=7.7 Hz), 2.65 (2H, t, J=7.7 Hz), 2.19 (3H, s).

ESI-MS found: 362 [M+H]$^+$

Example 90

Synthesis of 3-acetyl-1-(2,6-dimethylbenzyl)-1H-indole-6-carboxylic acid [90] (Hereinafter Referred to as a Compound [90])

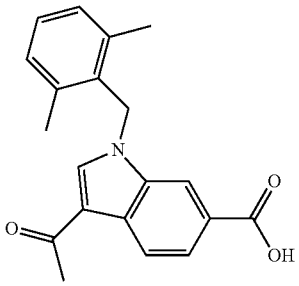 [SMILES: CC(=O)c1cn(Cc2c(C)cccc2C)c2cc(C(=O)O)ccc12]

(1) Synthesis of methyl 3-acetyl-1H-indole-6-carboxylate [90-1] (Hereinafter Referred to as a Compound [90-1])

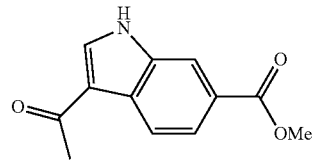 [SMILES: COC(=O)c1ccc2c(C(C)=O)c[nH]c2c1]

To a solution of methyl indole-6-carboxylate (1.01 g) in dichloromethane (30 mL) were added aluminum chloride (1.53 g) and acetyl chloride (0.5 mL) at room temperature, and then the reaction mixture was stirred at room temperature for 1 hour. To the reaction mixture was added a saturated aqueous solution of sodium hydrogen carbonate, and extracted with ethyl acetate. The obtained organic layer was dried over anhydrous sodium sulfate, filtered, and the filtrate was concentrated under reduced pressure. The obtained residue was purified by silica gel column chromatography to give the titled compound (625 mg) as a white solid.

¹H-NMR (400 MHz, CD₃OD) δ: 8.34 (1H, s), 8.29 (1H, dd, J=8.5, 0.7 Hz), 8.15 (1H, dd, J=1.5, 0.7 Hz), 7.87 (1H, dd, J=8.5, 1.5 Hz), 3.92 (3H, s), 2.54 (3H, s).

(2) Synthesis of methyl 3-acetyl-1-(2,6-dimethylbenzyl)-1H-indole-6-carboxylate [90-2] (Hereinafter Referred to as a Compound [90-2])

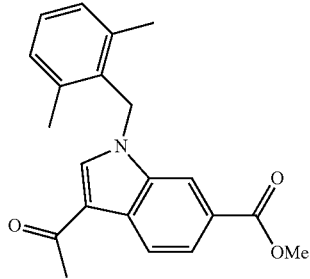 [SMILES: COC(=O)c1ccc2c(C(C)=O)cn(Cc3c(C)cccc3C)c2c1]

To a solution of the compound [90-1] obtained in the process (1) (155 mg) in N,N-dimethylformamide (2 mL) were added potassium carbonate (200 mg) and 2,6-dimethylbenzyl chloride (170 mg) at room temperature. The reaction mixture was subjected to microwave irradiation at 160° C. for 20 minutes. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (135 mg) as a yellow solid.

¹H-NMR (400 MHz, CDCl₃) δ: 8.41 (1H, d, J=8.1 Hz), 8.32 (1H, s), 8.03 (1H, dd, J=8.4, 1.3 Hz), 7.31-7.29 (1H, m), 7.26 (1H, s), 7.19 (2H, d, J=7.6 Hz), 5.34 (2H, s), 3.99 (3H, s), 2.39 (3H, s), 2.28 (6H, s).

(3) Synthesis of 3-acetyl-1-(2,6-dimethylbenzyl)-1H-indole-6-carboxylic acid

To a solution of the compound [90-2] obtained in the process (2) (132 mg) in methanol (3 mL) was added an aqueous solution of 1 N-sodium hydroxide (3 mL) at room temperature, and then the reaction mixture was stirred at 50° C. for 20 hours. The reaction mixture was added 1 N-hydrochloric acid for acidification, and the precipitated solid was filtered to give the titled compound (160 mg) as a white solid.

¹H-NMR (400 MHz, CDCl₃) δ: 8.46 (1H, d, J=8.3 Hz), 8.39 (1H, s), 8.10 (1H, dd, J=8.5, 1.2 Hz), 7.32-7.30 (2H, m), 7.20 (2H, d, J=7.3 Hz), 5.37 (2H, s), 2.40 (3H, s), 2.29 (6H, s).

Example 91

Synthesis of 1-(2,6-dimethylbenzyl)-3-ethyl-1H-indole-6-carboxylic acid [91] (Hereinafter Referred to as a Compound [91])

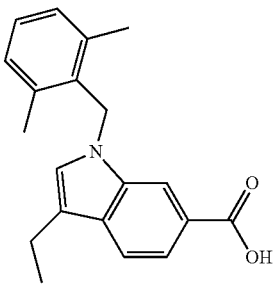 [SMILES: CCc1cn(Cc2c(C)cccc2C)c2cc(C(=O)O)ccc12]

(1) Synthesis of methyl 3-ethyl-1H-indole-6-carboxylate [91-1] (Hereinafter Referred to as a Compound [91-1])

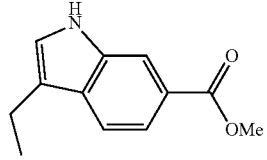

To a solution of the compound [90-1] obtained in the process (1) of Example 90 (455 mg) in tetrahydrofuran (15 mL), 1.2M tetrahydrofuran solution (6.0 mL) of a borane-tetrahydrofuran complex at room temperature, and then the reaction mixture was stirred at 50° C. for 1 hour. To the reaction mixture was added a saturated aqueous solution of ammonium chloride, and the reaction mixture was extracted with ethyl acetate. The obtained organic layer was dried over anhydrous sodium sulfate, filtered, and the filtrate was concentrated under reduced pressure. The obtained residue was purified by silica gel column chromatography to give the titled compound (354 mg) as a yellow solid.

¹H-NMR (400 MHz, CDCl₃) δ: 8.12 (1H, d, J=0.7 Hz), 7.81 (1H, dd, J=8.3, 1.5 Hz), 7.63 (1H, d, J=8.3 Hz), 7.15 (1H, t, J=1.2 Hz), 3.94 (3H, s), 2.80 (2H, q, J=7.5 Hz), 1.34 (3H, t, J=7.6 Hz).

(2) Synthesis of methyl 1-(2,6-dimethylbenzyl)-3-ethyl-1H-indole-6-carboxylate [91-2] (Hereinafter Referred to as a Compound [91-2])

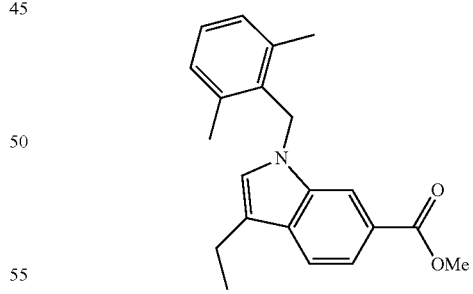

The titled compound (187 mg) as a yellow solid was prepared from the compound [91-1] obtained in the process (1) (145 mg) and 2,6-dimethylbenzyl chloride (171 mg) according to the method of the process (2) of Example 90.

¹H-NMR (400 MHz, CDCl₃) δ: 8.24 (1H, s), 7.82 (1H, dd, J=8.4, 1.3 Hz), 7.62 (1H, d, J=8.3 Hz), 7.24-7.22 (1H, m), 7.14 (2H, d, J=7.6 Hz), 6.52 (1H, s), 5.26 (2H, s), 3.97 (3H, s), 2.68 (2H, q, J=7.6 Hz), 2.26 (6H, s), 1.21 (3H, t, J=7.6 Hz).

(3) Synthesis of 1-(2,6-dimethylbenzyl)-3-ethyl-1H-indole-6-carboxylic acid

The titled compound (160 mg) as a white solid was prepared from the compound [91-2] obtained in the process (2) (184 mg) according to the method of the process (3) of Example 90.

¹H-NMR (400 MHz, CDCl₃) δ: 8.32 (1H, s), 7.90 (1H, dd, J=8.4, 1.3 Hz), 7.65 (1H, d, J=8.3 Hz), 7.28-7.22 (1H, m), 7.14 (2H, d, J=7.6 Hz), 6.56 (1H, s), 5.29 (2H, s), 2.70 (2H, q, J=7.6 Hz), 2.28 (6H, s), 1.22 (3H, t, J=7.6 Hz).

ESI-MS found: 308 [M+H]⁺

Example 92

Synthesis of 1-(2,6-dimethylbenzyl)-3-isopropyl-1H-indole-6-carboxylic acid [92] (Hereinafter Referred to as a Compound [92])

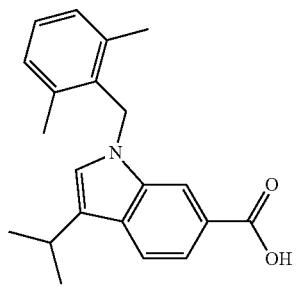 [SMILES: Cc1cccc(C)c1Cn1cc(C(C)C)c2ccc(C(=O)O)cc21]

(1) Synthesis of methyl 3-isopropyl-1H-indole-6-carboxylate [92-1] (Hereinafter Referred to as a Compound [92-1])

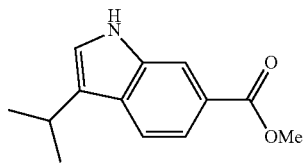 [SMILES: COC(=O)c1ccc2c(C(C)C)c[nH]c2c1]

To a solution of methyl indole-6-carboxylate (497 mg) in dichloromethane (15 mL) were added aluminum chloride (831 mg) and 2-bromopropane (0.27 mL) at room temperature, and then the reaction mixture was stirred at room temperature for 1 hour. To the reaction mixture was added a saturated aqueous solution of sodium hydrogen carbonate, and extracted with ethyl acetate. The obtained organic layer was dried over anhydrous sodium sulfate, filtered, and the filtrate was concentrated under reduced pressure. The obtained residue was purified by silica gel column chromatography to give the titled compound (65 mg) as a white solid.

¹H-NMR (400 MHz, CDCl₃) δ: 8.34 (1H, s), 8.13 (1H, d, J=0.7 Hz), 7.82-7.80 (1H, m), 7.68 (1H, d, J=8.3 Hz), 7.13 (1H, dd, J=2.4, 0.7 Hz), 3.94 (3H, s), 3.28-3.18 (1H, m), 1.36 (6H, d, J=8.1 Hz).

(2) Synthesis of methyl 1-(2,6-dimethylbenzyl)-3-isopropyl-1H-indole-6-carboxylate [92-2] (Hereinafter Referred to as a Compound [92-2])

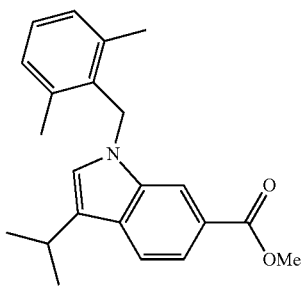 [SMILES: COC(=O)c1ccc2c(C(C)C)cn(Cc3c(C)cccc3C)c2c1]

The titled compound (68 mg) as a yellow solid was prepared from the compound [92-1] obtained in the process (1) (65 mg) and 2,6-dimethylbenzyl chloride (79 mg) according to the method of the process (2) of Example 90.

¹H-NMR (400 MHz, CDCl₃) δ: 8.24 (1H, s), 7.82 (1H, d, J=8.3 Hz), 7.67 (1H, d, J=8.3 Hz), 7.25-7.23 (1H, m), 7.14 (2H, d, J=7.6 Hz), 6.50 (1H, s), 5.26 (2H, s), 3.97 (3H, s), 3.16-3.09 (1H, m), 2.27 (6H, s), 1.25 (6H, d, J=6.8 Hz).

(3) Synthesis of 1-(2,6-dimethylbenzyl)-3-isopropyl-1H-indole-6-carboxylic acid [92]

The titled compound (30 mg) as a white solid was prepared from the compound [92-2] obtained in the process (2) (68 mg) according to the method of the process (3) of Example 90.

¹H-NMR (400-MHz, CDCl₃) δ: 8.34 (1H, s), 7.92-7.90 (1H, m), 7.71 (1H, d, J=8.3 Hz), 7.27-7.23 (1H, m), 7.15 (2H, d, J=7.6 Hz), 6.56 (1H, s), 5.29 (2H, d, J=3.4 Hz), 3.19-3.12 (1H, m), 2.29 (6H, s), 1.27 (6H, d, J=7.1 Hz).

ESI-MS found: 322 [M+H]⁺

Example 93

Synthesis of 2-{1-[(5-chlorothiophene-2-yl)methyl]-1H-indole-6-yl}acetic acid [93] (Hereinafter Referred to as a Compound [93])

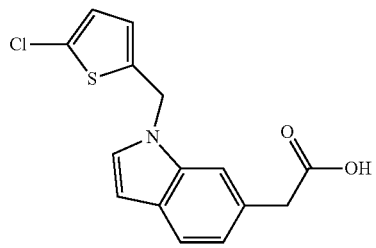 [SMILES: O=C(O)Cc1ccc2ccn(Cc3ccc(Cl)s3)c2c1]

The titled compound (15 mg) as a reddish brown solid was prepared from the compound [4-6] obtained in the process (6) of Example 4 (100 mg) and 2-chloro-5-chloromethylthiophene (63 μL) according to the method of the process (7) of Example 4.

ESI-MS found: 306 [M+H]⁺

Example 94

Synthesis of 3-chloro-1-(2,6-dimethylbenzyl)-6-(1H-tetrazole-5-yl)-1H-indole [94] (Hereinafter Referred to as a Compound [94])

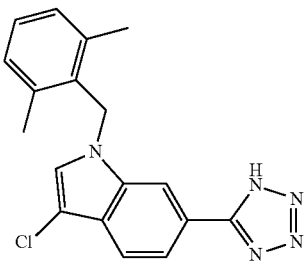 [SMILES: Cc1cccc(C)c1Cn1cc(Cl)c2ccc(-c3nnn[nH]3)cc21]

(1) Synthesis of 3-chloro-1H-indole-6-carbonitrile [94-1] (Hereinafter Referred to as a Compound [94-1])

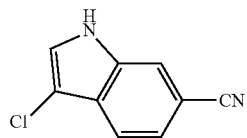 [SMILES: N#Cc1ccc2c(Cl)c[nH]c2c1]

To a solution of 6-indole carbonitrile (1.0 g) in methanol (10 mL) was added N-chlorosuccinimide (1.2 g) at room temperature, and then the reaction mixture was stirred at room temperature for 16 hours. To the reaction mixture was added a saturated aqueous solution of sodium hydrogen carbonate, and extracted with ethyl acetate. The obtained organic layer was dried over anhydrous sodium sulfate, filtered, and the filtrate was concentrated under reduced pressure. The obtained residue was purified by silica gel column chromatography to give the titled compound (1.3 g) as a white solid.

$^1$H-NMR (400 MHz, CDCl$_3$) δ: 8.55-8.45 (1H, br), 7.75-7.70 (2H, m), 7.44 (1H, dd, J=8.3, 1.2 Hz), 7.40 (1H, d, J=2.7 Hz).

(2) Synthesis of 3-chloro-1-(2,6-dimethylbenzyl)-1H-indole-6-carbonitrile [94-2] (Hereinafter Referred to as a Compound [94-2])

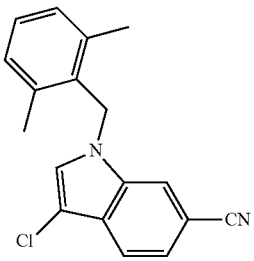 [SMILES: Cc1cccc(C)c1Cn1cc(Cl)c2ccc(C#N)cc21]

To a solution of the compound [94-1] obtained in the process (1) (112 mg) in N-methyl-2-pyrrolidone (3 mL) were added potassium carbonate (148 mg) and 2,6-dimethylbenzyl chloride (122 mg) at room temperature, and then the reaction mixture was subjected to microwave irradiation at 160° C. for 20 minutes. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (166 mg) as a yellow solid.

$^1$H-NMR (400 MHz, CDCl$_3$) δ: 7.82 (1H, d, J=0.5 Hz), 7.69 (1H, d, J=8.3 Hz), 7.44 (1H, dd, J=8.3, 1.2 Hz), 7.30-7.15 (1H, m), 7.15 (2H, d, J=7.6 Hz), 6.75 (1H, s), 5.25 (2H, s), 2.26 (6H, s).

(3) Synthesis of 3-chloro-1-(2,6-dimethylbenzyl)-6-(1H-tetrazole-5-yl)-1H-indole [94]

To a solution of the compound [94-2] obtained in the process (2) (164 mg) in N,N-dimethylformamide (2 mL) were added ammonium chloride (47 mg) and sodium azide (45 mg) at room temperature, and then the reaction mixture was stirred at 100° C. for 17 hours. Furthermore, ammonium chloride (55 mg) and sodium azide (45 mg) were added, and the reaction mixture was stirred at 100° C. for 24 hours. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (10 mg) as a brown solid.

$^1$H-NMR (400 MHz, CD$_3$OD) δ: 8.35 (1H, s), 7.82 (1H, dd, J=8.3, 1.5 Hz), 7.71 (1H, d, J=8.3 Hz), 7.24 (1H, dd, J=8.4, 6.7 Hz), 7.16 (2H, d, J=7.8 Hz), 6.71 (1H, s), 5.43 (2H, s), 2.28 (6H, s).

ESI-MS found: 338 [M+H]$^+$

Example 95

Synthesis of 1-(2,6-dimethylbenzyl)-1H-pyrrolo[3,2-b]pyridine-6-carboxylic acid [95] (Hereinafter Referred to as a Compound [95])

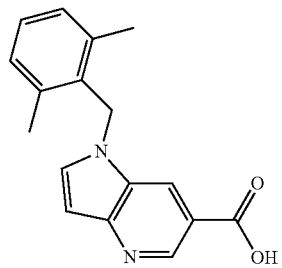 [SMILES: Cc1cccc(C)c1Cn1ccc2ncc(C(=O)O)cc21]

(1) Synthesis of methyl 1-(2,6-dimethylbenzyl)-1H-pyrrolo[3,2-b]pyridine-6-carboxylate [95-1] (Hereinafter Referred to as a Compound [95-1])

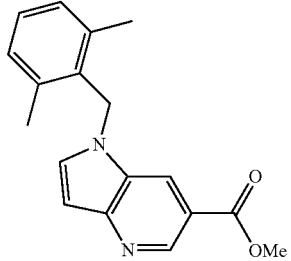 [SMILES: COC(=O)c1cnc2ccn(Cc3c(C)cccc3C)c2c1]

To a solution of methyl 1H-pyrrolo[3,2-b]pyridin-6-carboxylate (50 mg) in N-methyl-2-pyrrolidone (1 mL) were added potassium carbonate (158 mg) and 2,6-dimethylbenzyl chloride (91 mg), and then the reaction mixture was subjected to microwave irradiation at 160° C. for 30 minutes. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (21 mg) as a white solid.
$^1$H-NMR (400 MHz, CDCl$_3$) δ: 9.14 (1H, s), 8.45 (1H, s), 7.25 (1H, t, J=7.3 Hz), 7.15 (2H, d, J=7.3 Hz), 7.02 (1H, d, J=3.0 Hz), 6.67 (1H, d, J=3.0 Hz), 5.33 (2H, s), 4.00 (3H, s), 2.26 (6H, s).
ESI-MS found: 295 [M+H]$^+$ (2) Synthesis of 1-(2,6-dimethylbenzyl)-1H-pyrrolo[3,2-b]pyridine-6-carboxylic acid [95]

To a solution of the compound [95-1] obtained in the process (1) (21 mg) in tetrahydrofuran (1 mL) and methanol (1 mL) were added an aqueous solution of 1N-sodium hydroxide (0.5 mL), and then the reaction mixture was subjected to microwave irradiation at 140° C. for 30 minutes. The reaction mixture was added with 1N-hydrochloric acid, and extracted with ethyl acetate. The obtained organic layer was dried over anhydrous sodium sulfate, filtered, and the filtrate was concentrated under reduced pressure to give the titled compound (13 mg) as a pale brown solid.
$^1$H-NMR (400 MHz, DMSO-d$_6$) δ: 13.01 (1H, brs), 8.91 (1H, d, J=1.7 Hz) 8.53-8.51 (1H, m), 7.28 (1H, d, J=3.4 Hz), 7.23-7.17 (1H, m), 7.14-7.10 (2H, m), 6.62 (1H, dd, J=3.4, 1.7 Hz), 5.48 (2H, s), 2.20 (6H, s).
ESI-MS found: 281 [M+H]$^+$ Example 96

Synthesis of 1-(2,6-dimethylbenzyl)-1H-pyrrolo[2,3-b]pyridine-6-carboxylic acid [96] (Hereinafter Referred to as a Compound [96])

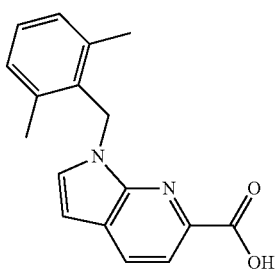 [SMILES: Cc1cccc(C)c1Cn1ccc2ccc(C(=O)O)nc21]

(1) Synthesis of 1H-pyrrolo[2,3-b]pyridine-7-oxide [96-1] (Hereinafter Referred to as a Compound [96-1])

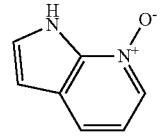

To a solution of 1H-pyrrolo[2,3-b]pyridine (495 mg) in 1,2-dimethoxyethane (20 mL) was added 3-chloroperbenzoic acid (1.48 g) at room temperature, and then the reaction mixture was stirred at room temperature for 2 hours. The reaction mixture was quenched with water, and extracted with chloroform. The obtained organic layer was dried over anhydrous sodium sulfate, filtered, and the filtrate was concentrated under reduced pressure. The obtained residue was purified by silica gel column chromatography to give the titled compound (360 mg) as a white solid.
$^1$H-NMR (400 MHz, CDCl$_3$) δ: 13.1 (1H, s), 8.23 (1H, d, J=6.1 Hz), 7.70 (1H, d, J=7.8 Hz), 7.42 (1H, d, J=3.2 Hz), 7.06 (1H, dd, J=7.8, 6.3 Hz), 6.56 (1H, d, J=3.2 Hz).

(2) Synthesis of 1H-pyrrolo[2,3-b]pyridine-6-carbonitrile [96-2] (Hereinafter Referred to as a Compound [96-2])

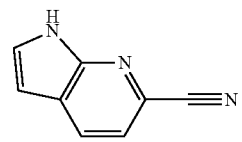 [SMILES: N#Cc1ccc2cc[nH]c2n1]

To a solution of the compound [96-1] obtained in the process (1) (360 mg) in acetonitrile (5 mL) were added triethylamine (0.75 mL) and trimethylsilyl cyanide (0.33 mL) at room temperature, and then the reaction mixture was stirred at 85° C. for 2 hours. To the reaction mixture was added aqueous solution of 1N-sodium hydroxide, and extracted with chloroform. The obtained organic layer was dried over anhydrous sodium sulfate, filtered, and the filtrate was concentrated under reduced pressure. The obtained residue was purified by silica gel column chromatography to give the titled compound (41 mg) as a white solid.
$^1$H-NMR (400 MHz, CDCl$_3$) δ: 8.08 (1H, d, J=8.1 Hz), 7.71 (1H, dd, J=3.5, 2.6 Hz), 7.52 (1H, d, J=8.1 Hz), 6.65 (1H, dd, J=3.7, 2.0 Hz).

(3) Synthesis of 1-(2,6-dimethylbenzyl)-1H-pyrrolo[2,3-b]pyridine-6-carbonitrile [96-3] (Hereinafter Referred to as a Compound [96-3])

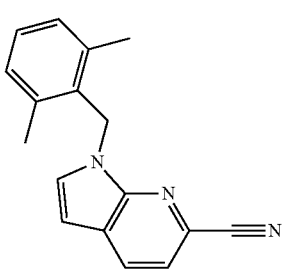 [SMILES: Cc1cccc(C)c1Cn1ccc2ccc(C#N)nc21]

To a solution of the compound [96-2] obtained in the process (2) (40 mg) in N,N-dimethylformamide (2 mL) were added potassium carbonate (82 mg) and 2,6-dimethylbenzyl chloride (69 mg) at room temperature, and then the reaction mixture was stirred at room temperature for 3 hours. The reaction mixture was quenched with water, and extracted with chloroform. The obtained organic layer was dried over anhydrous sodium sulfate, filtered, and the filtrate was concentrated under reduced pressure. The obtained residue was purified by silica gel column chromatography to give the titled compound (67 mg) as a white solid.

$^1$H-NMR (400 MHz, CDCl$_3$) δ: 7.98 (1H, d, J=7.8 Hz), 7.49 (1H, d, J=8.1 Hz), 7.22 (1H, dd, J=8.2, 7.0 Hz), 7.12 (2H, d, J=7.6 Hz), 6.96 (1H, d, J=3.4 Hz), 6.46 (1H, d, J=3.7 Hz), 5.49 (2H, s), 2.27 (6H, s).

(4) Synthesis of 1-(2,6-dimethylbenzyl)-1H-pyrrolo[2,3-b]pyridine-6-carboxylic acid [96]

To a solution of the compound [96-3] obtained in the process (3) (66 mg) in ethanol (2 mL) was added an aqueous solution of 3N-sodium hydroxide (2 mL) at room temperature, and then the reaction mixture was heated at reflux for 1 hour. To the reaction mixture was added 1N-hydrochloric acid, and the precipitated solid was filtered to give the titled compound (15 mg) as a white solid.

$^1$H-NMR (400 MHz, CD$_3$OD) δ: 8.08 (1H, d, J=8.1 Hz), 7.96 (1H, d, J=8.1 Hz), 7.20-7.18 (1H, m), 7.11 (2H, d, J=7.6 Hz), 6.97 (1H, d, J=3.7 Hz), 6.51 (1H, d, J=3.7 Hz), 5.62 (2H, s), 2.25 (6H, s).

Example 97

Synthesis of 2-[1-(2,6-dichlorobenzyl)-3-methyl-1H-indazole-6-yl]acetic acid [97] (Hereinafter Referred to as a Compound [97])

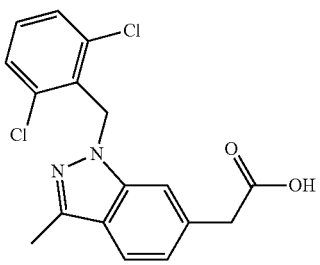 [SMILES: Cc1nn(Cc2c(Cl)cccc2Cl)c2cc(CC(=O)O)ccc12]

(1) Synthesis of 6-bromo-1-(2,6-dichlorobenzyl)-3-methyl-1H-indazole [97-1] (Hereinafter Referred to as a Compound [97-1])

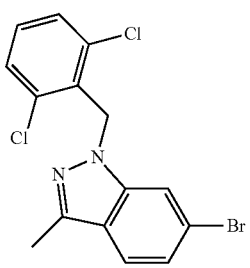 [SMILES: Cc1nn(Cc2c(Cl)cccc2Cl)c2cc(Br)ccc12]

The titled compound (10.4 g) as a white solid was prepared from the 6-bromo-3-methyl-1H-indazole (9.57 g) obtained with the method described in the document (JP 2009-528363 W) and 2,6-dichlorobenzyl chloride (9.79 g) according to the method of the process (1) of Example 66.

$^1$H-NMR (400 MHz, CDCl$_3$) δ: 7.55 (1H, s), 7.47 (1H, d, J=8.5 Hz), 7.38 (2H, d, J=8.1 Hz), 7.25 (1H, d, J=5.9 Hz), 7.22-7.20 (1H, m), 5.66 (2H, s), 2.50 (3H, s).

(2) Synthesis of 6-allyl-1-(2,6-dichlorobenzyl)-3-methyl-1H-indazole [97-2](Hereinafter Referred to as a Compound [97-2])

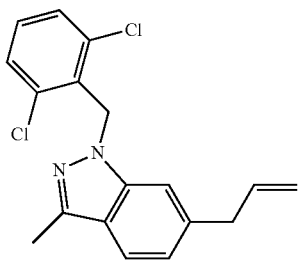 [SMILES: C=CCc1ccc2c(C)nn(Cc3c(Cl)cccc3Cl)c2c1]

The titled compound (3.25 g) as a white solid was prepared from the compound [97-1] obtained in the process (1) (5.02 g) and allyltributyl tin (4.6 mL) according to the method of the process (2) of Example 66.

$^1$H-NMR (400 MHz, CDCl$_3$) δ: 7.53-7.52 (1H, m), 7.37-7.36 (2H, m), 7.25-7.18 (2H, m), 6.95 (1H, d, J=8.1 Hz), 6.03-5.94 (1H, m), 5.69 (2H, s), 5.12-5.10 (2H, m), 3.51-3.49 (2H, m), 2.51 (3H, s).

(3) Synthesis of 2-[1-(2,6-dichlorobenzyl)-3-methyl-1H-indazole-6-yl]acetaldehyde [97-3] (Hereinafter Referred to as a Compound [97-3])

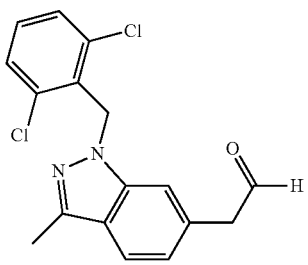 [SMILES: Cc1nn(Cc2c(Cl)cccc2Cl)c2cc(CC=O)ccc12]

The titled compound (1.03 g) as a white solid was prepared from the compound [97-2] obtained in the process (2) (3.25 g) according to the method of the process (3) of Example 66.

$^1$H-NMR (400 MHz, CDCl$_3$) δ: 9.77 (1H, t, J=2.3 Hz), 7.62 (1H, d, J=8.3 Hz), 7.37 (2H, d, J=8.1 Hz), 7.25-7.23 (2H, m), 6.95 (1H, d, J=8.3 Hz), 5.70 (2H, s), 3.80 (2H, d, J=2.2 Hz), 2.52 (3H, s).

(4) Synthesis of 2-[1-(2,6-dichlorobenzyl)-3-methyl-1H-indazol-6-yl]acetic acid [97]

The titled compound (1.06 g) as a white solid was prepared from the compound [97-3] obtained in the process (3) (1.03 g) according to the method of the process (4) of Example 66.

$^1$H-NMR (400 MHz, CD$_3$OD) δ: 7.62 (1H, d, J=8.3 Hz), 7.46-7.44 (3H, m), 7.35-7.33 (1H, m), 7.09 (1H, d, J=8.3 Hz), 5.72 (2H, s), 3.73 (2H, s), 2.46 (3H, s).

ESI-MS found: 349 [M+H]$^+$

Example 98

Synthesis of potassium 2-[1-(2,6-dichlorobenzyl)-3-methyl-1H-indazol-6-yl]acetate [98] (Hereinafter Referred to as a Compound [98])

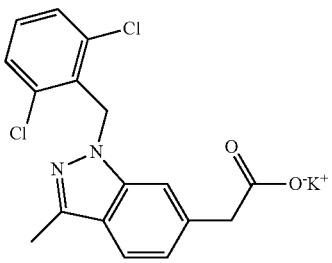

To a solution of the compound [97] (118 mg) in ethanol (5 mL) was added an aqueous solution of 1N-potassium hydroxide (0.34 mL) at room temperature, and then the reaction mixture was stirred at room temperature for 10 minutes. The reaction mixture was concentrated under reduced pressure to give the titled compound (128 mg) as a white solid.

$^1$H-NMR (400 MHz, CD$_3$OD) δ: 7.56 (1H, d, J=8.3 Hz), 7.47-7.43 (3H, m), 7.35-7.31 (1H, m), 7.15 (1H, d, J=8.1 Hz), 5.70 (2H, s), 3.61 (2H, s), 2.44 (3H, s).

ESI-MS found: 349 [M−K+2H]$^+$

Example 99

Synthesis of 2-[1-(2,3-dichlorobenzyl)-3-methyl-1H-indazol-6-yl]acetic acid [99] (Hereinafter Referred to as a Compound [99])

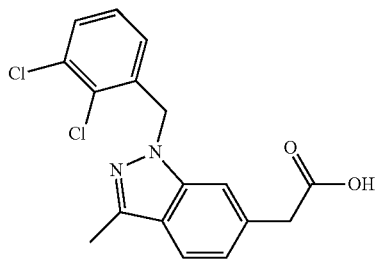 [SMILES: Cc1nn(Cc2cccc(Cl)c2Cl)c2cc(CC(=O)O)ccc12]

(1) Synthesis of 6-bromo-1-(2,3-dichlorobenzyl)-3-methyl-1H-indazole [99-1] (Hereinafter Referred to as a Compound [99-1])

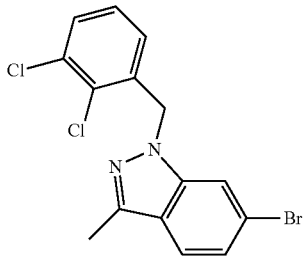 [SMILES: Cc1nn(Cc2cccc(Cl)c2Cl)c2cc(Br)ccc12]

The titled compound (228 mg) as a white solid was prepared from the 6-bromo-3-methyl-1H-indazole (152 mg) obtained with the method described in the document (JP 2009-528363 W) and 2,3-dichlorobenzyl chloride (215 mg) according to the method of the process (1) of Example 66.

$^1$H-NMR (400 MHz, CDCl$_3$) δ: 7.84-7.82 (2H, m), 7.70 (1H, d, J=8.4 Hz), 7.40 (1H, d, J=8.1 Hz), 7.08-7.04 (1H, m), 6.57-6.54 (1H, m), 5.73 (2H, s), 2.65 (3H, s).

(2) Synthesis of 2-[1-(2,3-dichlorobenzyl)-3-methyl-1H-indazol-6-yl]acetic acid [99]

The titled compound (50 mg) as a white solid was prepared from the compound [99-1] obtained in the process (1) according to the method of the processes (2) to (4) of Example 66.

$^1$H-NMR (400 MHz, CDCl$_3$) δ: 7.65 (1H, d, J=8.3 Hz), 7.34 (1H, d, J=7.3 Hz), 7.17 (1H, s), 7.09 (1H, d, J=8.3 Hz), 7.02-7.00 (1H, m), 6.50 (1H, d, J=7.8 Hz), 5.62 (2H, s), 3.74 (2H, s), 2.59 (3H, s).

ESI-MS found: 349 [M+H]$^+$

Example 100

Synthesis of potassium 2-[1-(2,3-dichlorobenzyl)-3-methyl-1H-indazol-6-yl]acetate [100] (Hereinafter Referred to as a Compound [100])

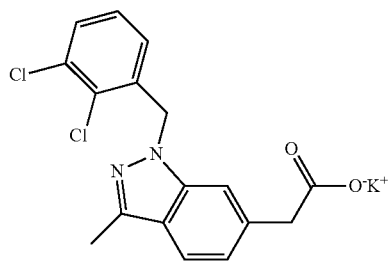

To a solution of the compound [99] (37 mg) in ethanol (2 mL) was added an aqueous solution of 1N-potassium hydroxide (106 μL) at room temperature, and then the reaction mixture was stirred at room temperature for 10 minutes. The reaction mixture was concentrated under reduced pressure to give the titled compound (38 mg) as a white solid.

$^1$H-NMR (400 MHz, CD$_3$OD) δ: 7.63 (1H, d, J=8.3 Hz), 7.43 (1H, d, J=7.6 Hz), 7.34 (1H, s), 7.18 (1H, d, J=8.3 Hz), 7.11-7.10 (1H, m), 6.45 (1H, d, J=7.8 Hz), 5.66 (2H, s), 3.57 (2H, s), 2.54 (3H, s).

ESI-MS found: 349 [M−K+2H]$^+$

Example 101

Synthesis of 2-[1-(2,5-dimethylbenzyl)-3-methyl-1H-indazole-6-yl]acetic acid [101] (Hereinafter Referred to as a Compound [101])

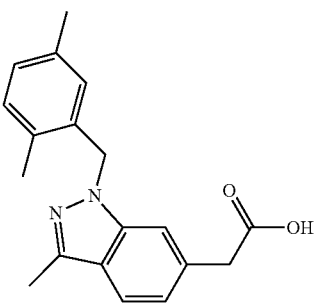 [SMILES: Cc1ccc(C)c(Cn2nc(C)c3ccc(CC(=O)O)cc32)c1]

(1) Synthesis of 6-bromo-1-(2,5-dimethylbenzyl)-3-methyl-1H-indazole [101-1] (Hereinafter Referred to as a Compound [101-1])

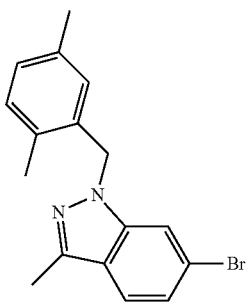 [SMILES: Cc1ccc(C)c(Cn2nc(C)c3ccc(Br)cc32)c1]

The titled compound (158 mg) as a white solid was prepared from 6-bromo-3-methyl-1H-indazole (148 mg) obtained with the method described in the document (JP 2009-528363 W) and 2,5-dimethylbenzyl chloride (164 mg) according to the method of the process (1) of Example 66.

$^1$H-NMR (400 MHz, CDCl$_3$) δ: 7.59 (1H, d, J=4.1 Hz), 7.06-7.04 (2H, m), 6.98-6.96 (2H, m), 6.61 (1H, s), 5.44 (2H, s), 2.58 (3H, s), 2.31 (3H, s), 2.19 (3H, s).

(2) Synthesis of 2-[1-(2,5-dimethylbenzyl)-3-methyl-1H-indazole-6-yl]acetic acid [101]

The titled compound (59 mg) as a white solid was prepared from the compound [101-1] obtained in the process (1) according to the methods of the processes (2) to (4) of Example 66.

$^1$H-NMR (400 MHz, CDCl$_3$) δ: 7.64 (1H, d, J=8.3 Hz), 7.13 (1H, s), 7.06-7.04 (2H, m), 6.98-6.96 (1H, m), 6.60 (1H, s), 5.46 (2H, s), 3.72 (2H, s), 2.59 (3H, s), 2.29 (3H, s), 2.17 (3H, s).

ESI-MS found: 309 [M+H]$^+$

Example 102

Synthesis of 2-[1-(2-chloro-6-methylbenzyl)-3-methyl-1H-indazole-6-yl]acetic acid [102] (Hereinafter Referred to as a Compound [102])

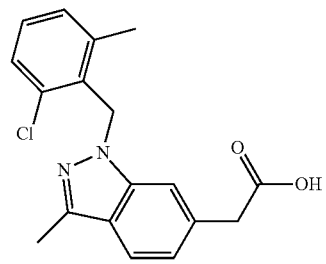 [SMILES: Cc1cccc(Cl)c1Cn1nc(C)c2ccc(CC(=O)O)cc21]

(1) Synthesis of 6-bromo-3-methyl-1-[2-(trimethylsilyl)ethoxymethyl]-1H-indazole [102-1] (Hereinafter Referred to as a Compound [102-1])

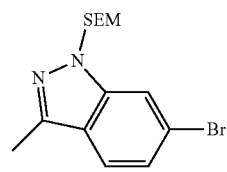 [SMILES: Cc1nn(COCC[Si](C)(C)C)c2cc(Br)ccc12]

To a solution of 6-bromo-3-methyl-1H-indazole (4.4 g) obtained with the method described in the document (JP-A No. 2009-528363) in chloroform (50 mL) were added diisopropylethylamine (5.3 mL) and 2-(trimethylsilyl)ethoxymethyl chloride (4.4 mL) at room temperature, and then the reaction mixture was stirred at room temperature for 22 hours. To the reaction mixture was added 5% aqueous solution of potassium hydrogen sulfate, and the reaction mixture was extracted with ethyl acetate. The obtained organic layer was dried over anhydrous sodium sulfate, filtered, and the filtrate was concentrated under reduced pressure. The obtained residue was purified by silica gel column chromatography to give the titled compound (1.8 g) as a white solid.

$^1$H-NMR (400 MHz, CDCl$_3$) δ: 7.69 (1H, s), 7.51 (1H, d, J=8.5 Hz), 7.27 (1H, d, J=6.8 Hz), 5.61 (2H, s), 3.54 (2H, t, J=8.2 Hz), 2.55 (3H, s), 0.89 (2H, t, J=8.2 Hz), 0.00 (9H, s).

(2) Synthesis of tert-butyl 2-[3-methyl-1-[2-(trimethylsilyl)ethoxymethyl]-1H-indazole-6-yl]acetate [102-2] (Hereinafter Referred to as a Compound [102-2])

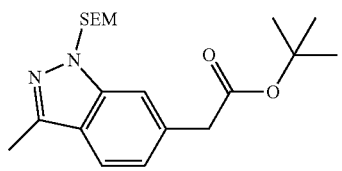 [SMILES: Cc1nn(COCC[Si](C)(C)C)c2cc(CC(=O)OC(C)(C)C)ccc12]

To a solution of dicyclohexylamine (1.8 mL) in toluene (26 mL) was added 1.63M hexane solution of n-butyl lithium (5.5 mL) at 0° C., and then the reaction mixture was stirred at 0° C. for 30 minutes. To the reaction mixture was added tert-butyl acetate (1.1 mL) at 0° C., and then the reaction mixture was stirred at 0° C. for 30 minutes. The obtained solution was added to the mixture of the compound [102-1] obtained in the process (1) (1.8 g), bis(dibenzylideneacetone)palladium(0) (303 mg) and 2-(dicyclohexylphosphino)-2'-(dimethylamino)biphenyl (207 mg) at room temperature, and the reaction mixture was stirred for 48 hours. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (422 mg) as a yellow oil.

$^1$H-NMR (400 MHz, CDCl$_3$) δ: 7.59 (1H, d, J=8.1 Hz), 7.40 (1H, s), 7.10 (1H, d, J=8.1 Hz), 5.64 (2H, s), 3.66 (2H, s), 3.55 (2H, t, J=8.2 Hz), 2.55 (3H, s), 1.44 (9H, s), 0.89 (2H, t, J=8.3 Hz), 0.00 (9H, s).

(3) Synthesis of 2-(3-methyl-1H-indazole-6-yl)acetic acid [102-3] (Hereinafter Referred to as a Compound [102-3])

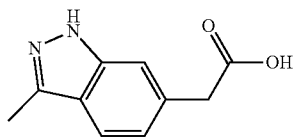

To the compound [102-2] obtained in the process (2) (193 mg) were added water (0.5 mL) and trifluoroacetic acid (4.7 mL) at room temperature, and then the reaction mixture was stirred at room temperature for 1.5 hours. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (61 mg) as a yellow oil.

$^1$H-NMR (400 MHz, CDCl$_3$) δ: 7.76 (1H, s), 7.68 (1H, d, J=8.5 Hz), 7.18 (1H, d, J=8.3 Hz), 3.82 (2H, s), 2.66 (3H, s).

(4) Synthesis of methyl 2-(3-methyl-1H-indazole-6-yl)acetate [102-4] (Hereinafter Referred to as a Compound [102-4])

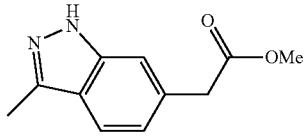

To a solution of the compound [102-3] obtained in the process (3) (340.5 mg) in tetrahydrofuran (3.6 mL) were added methanol (3.6 mL) and 0.6M hexane solution of trimethylsilyldiazomethane (3.6 mL) at room temperature, and then the reaction mixture was stirred at room temperature for 24 hours. The reaction solution was concentrated under reduced pressure, and then The obtained residue was purified by silica gel column chromatography to give the titled compound (236 mg) as a white solid.

$^1$H-NMR (400 MHz, CDCl$_3$) δ: 7.63 (1H, d, J=8.3 Hz), 7.34 (1H, s), 7.07 (1H, d, J=8.3 Hz), 3.76 (2H, s), 3.70 (3H, s), 2.57 (3H, s).

(5) Synthesis of 2-[1-(2-chloro-6-methylbenzyl)-3-methyl-1H-indazole-6-yl]acetic acid [102]

To a solution of the compound [102-4] obtained in the process (4) (19.4 mg) in N,N-dimethylformamide (0.5 mL) were added potassium carbonate (20.7 mg) and 2-chloro-6-methylbenzyl chloride (25.0 mg) at room temperature, and then the reaction mixture was stirred at room temperature for 20 hours. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give a colorless oil. To the obtained colorless oil was added methanol (0.2 mL) and tetrahydrofuran (0.2 mL). To the solution was added an aqueous solution of 1N-sodium hydroxide (0.2 mL) at room temperature, and then the reaction mixture was stirred at room temperature for 40 minutes. The reaction mixture was added 1N-hydrochloric acid for acidification, and extracted with chloroform. The obtained organic layer was dried over anhydrous sodium sulfate, filtered, and the filtrate was concentrated under reduced pressure. The obtained residue was purified by reverse phase preparative liquid chromatography to give the titled compound (6.0 mg) as a white solid.

$^1$H-NMR (400 MHz, CD$_3$OD) δ: 7.60 (1H, d, J=8.3 Hz), 7.35 (1H, s), 7.30 (1H, d, J=7.6 Hz), 7.21 (1H, t, J=7.7 Hz), 7.15 (1H, d, J=7.3 Hz), 7.05 (1H, d, J=8.3 Hz), 5.61 (2H, s), 3.70 (2H, s), 2.46 (3H, s), 2.29 (3H, s).

ESI-MS found: 329 [M+H]$^+$

Example 103

Synthesis of potassium 2-[1-(2-chloro-6-methylbenzyl)-3-methyl-1H-indazole-6-yl]acetate [103] (Hereinafter Referred to as a Compound [103])

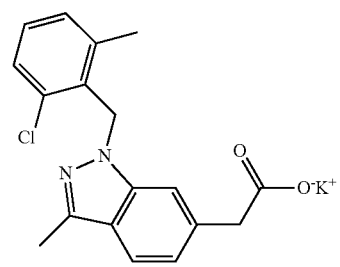

To a solution of the compound [102](33.1 mg) in ethanol (3.0 mL) was added an aqueous solution of 1N-potassium hydroxide (0.1 mL) at room temperature, and the solution was concentrated under reduced pressure to give the titled compound (35.5 mg) as a white solid.

$^1$H-NMR (400 MHz, CD$_3$OD) δ: 7.56 (1H, d, J=8.3 Hz), 7.39 (1H, s), 7.29 (1H, d, J=7.8 Hz), 7.20 (1H, t, J=7.8 Hz), 7.15-7.13 (2H, m), 5.60 (2H, s), 3.60 (2H, s), 2.45 (3H, s), 2.28 (3H, s).

ESI-MS found: 329 [M−K+2H]$^+$

Example 104

Synthesis of 2-[1-(2-chloro-6-fluorobenzyl)-3-methyl-1H-indazole-6-yl]acetic acid [104] (Hereinafter Referred to as a Compound [104])

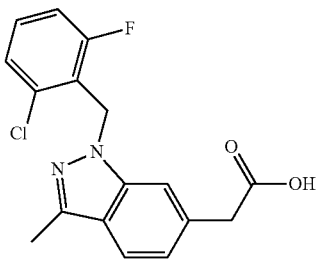 [SMILES: Cc1nn(Cc2c(F)cccc2Cl)c2cc(CC(=O)O)ccc12]

To a solution of the compound [102-4] obtained in the process (4) of Example 102 (60.9 mg) in N,N-dimethylformamide (1.6 mL) were added potassium carbonate (221.2 mg) and 2-chloro-6-fluorobenzyl chloride (0.16 mL) at room temperature, and then the reaction mixture was stirred at 80° C. for 18 hours. The reaction mixture was quenched with water, and extracted with diethyl ether. The obtained organic layer was dried over anhydrous sodium sulfate, filtered, and the filtrate was concentrated under reduced pressure. The obtained residue was purified by silica gel column chromatography. To a solution of the purified compound in methanol (1 mL) were added 1N-sodium hydroxide (1 mL) and tetrahydrofuran (1 mL), and then the reaction mixture was stirred at 65° C. for 16 hours. The reaction mixture was added 1 N-hydrochloric acid for acidification, and extracted with chloroform. The obtained organic layer was dried over anhydrous sodium sulfate, filtered, and the filtrate was concentrated under reduced pressure. The obtained residue was purified by reverse phase preparative liquid chromatography to give the titled compound (4.5 mg) as a white solid.

$^1$H-NMR (400 MHz, CDCl$_3$) δ: 7.59 (1H, d, J=8.3 Hz), 7.39 (1H, s), 7.23-7.19 (2H, m), 7.07-6.98 (2H, m), 5.64 (2H, s), 3.79 (2H, s), 2.53 (3H, s).

ESI-MS found: 333 [M+H]+

Example 105

Synthesis of 2-[1-(3,5-dimethylisoxazole-4-ylmethyl)-3-methyl-1H-indazole-6-yl]acetic acid [105] (Hereinafter Referred to as a Compound [105])

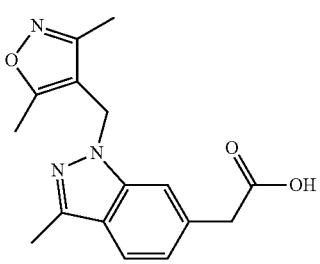 [SMILES: Cc1noc(C)c1Cn1nc(C)c2ccc(CC(=O)O)cc21]

The titled compound (16.5 mg) as a white solid was prepared from the compound [102-4] obtained in the process (4) of Example 102 (21.0 mg) and 4-(chloromethyl)-3,5-dimethylisoxazole according to the method of the process (5) of Example 102.

$^1$H-NMR (400 MHz, CDCl$_3$) δ: 7.59 (1H, d, J=8.3 Hz), 7.19 (1H, s), 7.05 (1H, d, J=8.1 Hz), 5.21 (2H, s), 3.75 (2H, s), 2.52 (3H, s), 2.34 (3H, s), 2.12 (3H, s).

ESI-MS found: 300 [M+H]+

Example 106

Synthesis of 2-{1-[(5-chlorobenzo[b]thiophene-3-yl)methyl]-3-methyl-1H-indazole-6-yl}acetic acid [106] (Hereinafter Referred to as a Compound [106])

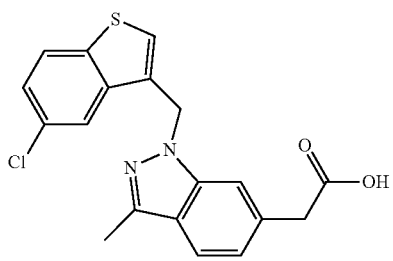 [SMILES: Cc1nn(Cc2csc3ccc(Cl)cc23)c2cc(CC(=O)O)ccc12]

The titled compound (4.3 mg) as a brown solid was prepared from the compound [102-4] obtained in the process (4) of Example 102 (24.7 mg) and 3-bromomethyl-5-chlorobenzo[b]thiophene according to the method of the process (5) of Example 102.

$^1$H-NMR (400 MHz, CDCl$_3$) δ: 7.84 (1H, s), 7.72 (1H, d, J=8.5 Hz), 7.63 (1H, d, J=8.3 Hz), 7.31-7.23 (2H, m), 7.13 (1H, s), 7.06 (1H, d, J=8.3 Hz), 5.68 (2H, s), 3.74 (2H, s), 2.59 (3H, s).

ESI-MS found: 371 [M+H]+

Example 107

Synthesis of 2-[3-methyl-1-(naphthalene-1-ylmethyl)-1H-indazole-6-yl]acetic acid [107] (Hereinafter Referred to as a Compound [107])

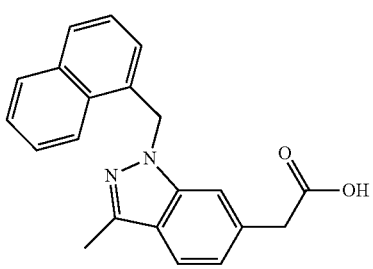 [SMILES: Cc1nn(Cc2cccc3ccccc23)c2cc(CC(=O)O)ccc12]

The titled compound (19.5 mg) as a white solid was prepared from the compound [102-4] obtained in the process (4) of Example 102 (26.3 mg) and 1-(chloromethyl)naphthalene according to the method of the process (5) of Example 102.

$^1$H-NMR (400 MHz, CDCl$_3$) δ: 8.13 (1H, d, J=8.1 Hz), 7.88 (1H, d, J=7.3 Hz), 7.78 (1H, d, J=8.1 Hz), 7.66 (1H, d, J=8.3 Hz), 7.55 (1H, t, J=8.4 Hz), 7.51 (1H, t, J=8.4 Hz), 7.33 (1H, t, J=7.7 Hz), 7.16 (1H, s), 7.07 (1H, d, J=7.8 Hz), 6.92 (1H, d, J=6.8 Hz), 6.02 (2H, s), 3.70 (2H, s), 2.62 (3H, s).

ESI-MS found: 331 [M+H]+

Example 108

Synthesis of 2-[3-methyl-1-(2,4,6-trimethyl benzyl)-1H-indazole-6-yl]acetic acid [108] (Hereinafter Referred to as a Compound [108])

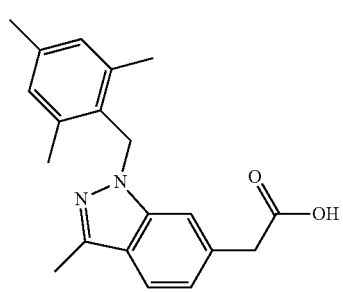 [SMILES: Cc1cc(C)c(Cn2nc(C)c3ccc(CC(=O)O)cc32)c(C)c1]

The titled compound (10.3 mg) as a white solid was prepared from the compound [102-4] obtained in the process (4) of Example 102 (21.2 mg) and 2,4,6-trimethylbenzyl chloride according to the method of the process (5) of Example 102.

$^1$H-NMR (400 MHz, CDCl$_3$) δ: 7.56 (1H, d, J=8.3 Hz), 6.99 (1H, d, J=8.3 Hz), 6.91 (1H, s), 6.88 (2H, s), 5.43 (2H, s), 3.67 (2H, s), 2.51 (3H, s), 2.27 (9H, s).

ESI-MS found: 323 [M+H]$^+$

Example 109

Synthesis of 2-[1-(2-chloro-6-cyanobenzyl)-3-methyl-1H-indazole-6-yl]acetic acid [109] (Hereinafter Referred to as a Compound [109])

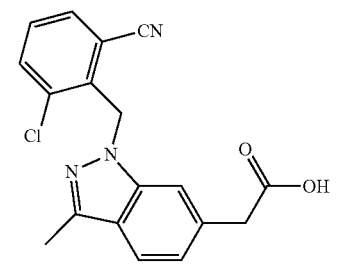 [SMILES: Cc1nn(Cc2c(Cl)cccc2C#N)c2cc(CC(=O)O)ccc12]

To a solution of the compound [97](30.1 mg) in N,N-dimethylformamide (0.9 mL) were added zinc cyanide (20.2 mg), tris(dibenzylideneacetone)dipalladium(0) (7.9 mg) and 2-dicyclohexylphosphino-2,4,6-triisopropylbiphenyl (5.1 mg) at room temperature, and then the reaction mixture was subjected to microwave irradiation at 150° C. for 2 hours. The reaction mixture was extracted with ethyl acetate, and then the obtained organic layer was dried over anhydrous sodium sulfate, filtered, and the filtrate was concentrated under reduced pressure. The obtained residue was purified by reverse phase preparative liquid chromatography to give the titled compound (5.0 mg) as a yellow solid.

$^1$H-NMR (400 MHz, CD$_3$OD) δ: 7.78 (1H, d, J=7.6 Hz), 7.74 (1H, d, J=8.1 Hz), 7.63 (1H, d, J=8.1 Hz), 7.54-7.52 (2H, m), 7.11 (1H, d, J=8.3 Hz), 5.73 (2H, s), 3.77 (2H, s), 2.46 (3H, s).

ESI-MS found: 340 [M+H]$^+$

Example 110

Synthesis of potassium 2-[1-(2-chloro-6-cyanobenzyl)-3-methyl-1H-indazole-6-yl]acetate [110] (Hereinafter Referred to as a Compound [110])

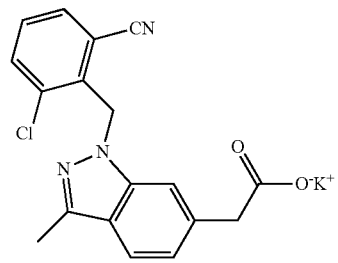

To a solution of compound [109](11.2 mg) in ethanol (1.1 mL) was added an aqueous solution of 1 N-potassium hydroxide (33 μL) at room temperature, and the solution was concentrated under reduced pressure to give the titled compound (12.5 mg) as a yellow solid.

$^1$H-NMR (400 MHz, CD$_3$OD) δ: 7.78 (1H, d, J=7.8 Hz), 7.74 (1H, d, J=8.1 Hz), 7.57 (1H, d, J=8.3 Hz), 7.54-7.50 (2H, m), 7.17 (1H, d, J=8.3 Hz), 5.72 (2H, s), 3.63 (2H, s), 2.45 (3H, s).

ESI-MS found: 340 [M−K+2H]$^+$

Example 111

Synthesis of 2-[1-(2,6-dichlorobenzyl)-3-methyl-1H-indazole-6-yl]propionic acid [111] (Hereinafter Referred to as a Compound [111])

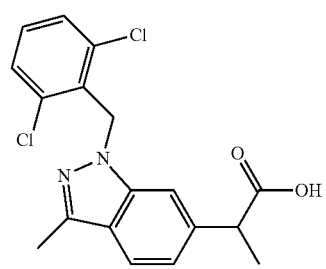 [SMILES: Cc1nn(Cc2c(Cl)cccc2Cl)c2cc(C(C)C(=O)O)ccc12]

(1) Synthesis of tert-butyl [1-(2,6-dichlorobenzyl)-3-methyl-1H-indazole-6-yl]acetate [111-1] (Hereinafter Referred to as a Compound [111-1])

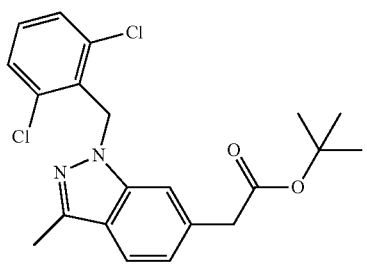 [SMILES: Cc1nn(Cc2c(Cl)cccc2Cl)c2cc(CC(=O)OC(C)(C)C)ccc12]

To a solution of dicyclohexylamine (0.4 mL) in toluene (5.7 mL) was added 1.63 M hexane solution of n-butyl lithium (1.2 mL) at 0° C., and the reaction mixture was stirred at 0° C. for 30 minutes. Subsequently, tert-butyl acetate was added at 0° C., and the reaction mixture was stirred at 0° C. for 30 minutes. The obtained solution was added to the mixture of the compound [97-1] obtained in the process (1) of Example 97 (421 mg), bis(dibenzylideneacetone)palladium(0) (196 mg) and tri-tert-butylphosphonium tetrafluoroborate (99 mg), and the reaction mixture was stirred at room temperature for 18 hours. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (422 mg) as a yellow oil.

$^1$H-NMR (400 MHz, CDCl$_3$) δ: 7.55 (1H, d, J=8.3 Hz), 7.36 (2H, d, J=8.1 Hz), 7.29 (1H, s), 7.22 (1H, t, J=8.1 Hz), 7.03 (1H, d, J=8.3 Hz), 5.69 (2H, s), 3.63 (2H, s), 2.50 (3H, s), 1.43 (9H, s).

(2) Synthesis of 2-[1-(2,6-dichlorobenzyl)-3-methyl-1H-indazol-6-yl]propionic acid [111]

The compound [111-1] obtained in the process (1) (45.3 mg) and methyl iodide (9.1 μL) were dissolved in tetrahydrofuran (0.6 mL). To the solution was added 0.5M toluene solution of potassium bis(trimethylsilyl)amide (0.3 mL) at 0° C., and then the reaction mixture was stirred at room temperature for 9 hours. The reaction mixture was quenched with a saturated aqueous solution of ammonium chloride, and extracted with ethyl acetate. The obtained organic layer was dried over anhydrous sodium sulfate, filtered, and the filtrate was concentrated under reduced pressure. The obtained residue was purified by silica gel column chromatography. To the purified compound was added water (50 μL) and trifluoroacetic acid (500 μL) at room temperature, and then the reaction mixture was stirred at room temperature for 1.5 hours. The reaction mixture was quenched with water, and extracted with ethyl acetate. The obtained organic layer was dried over anhydrous sodium sulfate, filtered, and the filtrate was concentrated under reduced pressure. The obtained residue was purified by reverse phase preparative liquid chromatography to give the titled compound (13.7 mg) as a white solid.

$^1$H-NMR (400 MHz, CD$_3$OD) δ: 7.61 (1H, d, J=8.3 Hz), 7.44 (2H, d, J=4.9 Hz), 7.42 (1H, s), 7.33 (1H, t, J=8.1 Hz), 7.11 (1H, d, J=8.3 Hz), 5.72 (2H, s), 3.84 (1H, q, J=7.1 Hz), 2.46 (3H, s), 1.50 (3H, d, J=7.1 Hz).

ESI-MS found: 364 [M+H]$^+$

Example 112

Synthesis of 2-[1-(2,6-dichlorobenzyl)-3-methyl-1H-indazol-6-yl]-2-methylpropionic acid [112] (Hereinafter Referred to as a Compound [112])

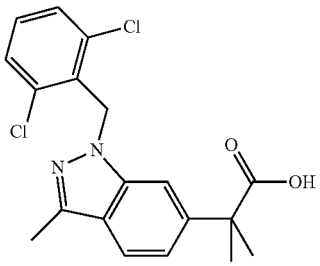 [SMILES: Cc1nn(Cc2c(Cl)cccc2Cl)c2cc(C(C)(C)C(=O)O)ccc12]

The titled compound (3.8 mg) as a white solid was prepared from the compound [111-1] obtained in the process (1) of Example 111 (30.0 mg) and methyl iodide (13.8 μL) according to the method of the process (2) of Example 111.

$^1$H-NMR (400 MHz, CDCl$_3$) δ: 7.58 (1H, d, J=8.5 Hz), 7.34 (2H, d, J=8.1 Hz), 7.31 (1H, s), 7.20 (1H, t, J=8.0 Hz), 7.15 (1H, d, J=8.4 Hz), 5.77 (2H, s), 2.53 (3H, s), 1.61 (6H, s).

ESI-MS found: 378 [M+H]$^+$

Example 113

Synthesis of 2-[1-(2,6-dichlorobenzyl)-3-methyl-1H-indazol-6-yl]butyric acid [113] (Hereinafter Referred to as a Compound [113])

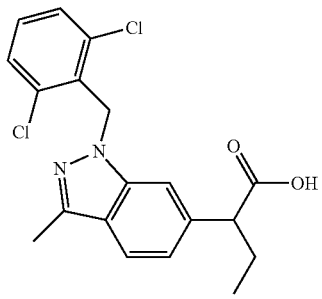 [SMILES: CCC(C(=O)O)c1ccc2c(C)nn(Cc3c(Cl)cccc3Cl)c2c1]

The titled compound (21.6 mg) as a white solid was prepared from the compound [111-1] obtained in the process (1) of Example 111 (54.5 mg) and ethyl iodide (32 μL) according to the method of the process (2) of Example 111.

$^1$H-NMR (400 MHz, CDCl$_3$) δ: 7.62 (1H, d, J=8.3 Hz), 7.32 (2H, d, J=8.1 Hz), 7.26 (1H, s), 7.18 (1H, t, J=8.1 Hz), 7.12 (1H, d, J=8.3 Hz), 5.80 (2H, s), 3.56 (1H, t, J=7.6 Hz), 2.56 (3H, s), 2.16-2.05 (1H, m), 1.87-1.76 (1H, m), 0.89 (3H, t, J=7.3 Hz).

ESI-MS found: 378 [M+H]$^+$

Example 114

Synthesis of 2-(3-methyl-1-phenethyl-1H-indazol-6-yl)acetic acid [114] (Hereinafter Referred to as a Compound [114])

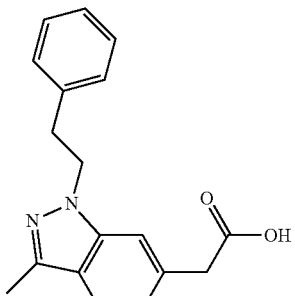

The titled compound (1.9 mg) as a white solid was prepared from the compound [102-4] obtained in the process (4) of Example 102 (42.6 mg) and (2-chloroethyl)benzene according to the method of the process (5) of Example 102.

$^1$H-NMR (400 MHz, CDCl$_3$) δ: 7.59 (1H, d, J=8.3 Hz), 7.26-7.18 (3H, m), 7.12 (2H, d, J=6.8 Hz), 7.03-7.00 (2H, m), 4.51 (2H, t, J=7.4 Hz), 3.72 (2H, s), 3.15 (2H, t, J=7.4 Hz), 2.58 (3H, s).

ESI-MS found: 295 [M+H]$^+$

Example 115

Synthesis of 2-[3-methyl-1-(quinoline-8-ylmethyl)-1H-indazole-6-yl]acetic acid [115] (Hereinafter Referred to as a Compound [115])

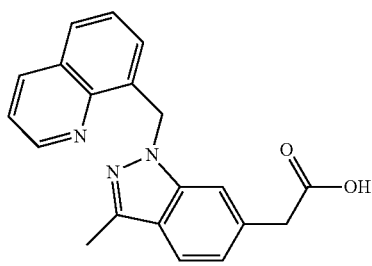 [SMILES: Cc1nn(Cc2cccc3cccnc23)c2cc(CC(=O)O)ccc12]

The titled compound (73.8 mg) as a yellow solid was prepared from the compound [102-4] obtained in the process (4) of Example 102 (102 mg) and 8-(bromomethyl)quinoline according to the method of the process (5) of Example 102.

$^1$H-NMR (400 MHz, CD$_3$OD) δ: 8.98 (1H, d, J=2.7 Hz), 8.32 (1H, d, J=6.8 Hz), 7.82 (1H, d, J=8.1 Hz), 7.68 (1H, d, J=8.3 Hz), 7.56 (1H, dd, J=8.3 Hz, 4.1 Hz), 7.45 (1H, s), 7.40 (1H, t, J=7.7 Hz), 7.10 (1H, t, J=8.3 Hz), 6.98 (1H, d, J=6.8 Hz), 6.23 (2H, s), 3.67 (2H, s), 2.57 (3H, s).

ESI-MS found: 332 [M+H]$^+$

Example 116

Synthesis of potassium 2-[3-methyl-1-(quinoline-8-ylmethyl)-1H-indazole-6-yl]acetate [116] (Hereinafter Referred to as a Compound [116])

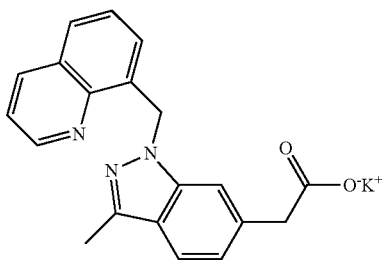

To a solution of the compound [115](73.8 mg) in ethanol (7.4 mL), was added an aqueous solution of 1N-potassium hydroxide (223 μL) at room temperature, and the solution was concentrated under reduced pressure to give the titled compound (82.3 mg) as a yellow solid.

$^1$H-NMR (400 MHz, CD$_3$OD) δ: 8.99 (1H, d, J=2.8), 8.32 (1H, d, J=7.2 Hz), 7.81 (1H, d, J=8.3 Hz), 7.64 (1H, d, J=8.3 Hz), 7.56 (1H, dd, J=8.3 Hz, 4.4 Hz), 7.41 (1H, s), 7.37 (1H, t, J=7.7 Hz), 7.17 (1H, d, J=8.3 Hz), 6.85 (1H, d, J=7.1 Hz), 6.23 (2H, s), 3.54 (2H, s), 2.57 (3H, s).

ESI-MS found: 332 [M−K+2H]$^+$

Example 117

Synthesis of 1-(2,6-dimethylbenzyl)-3-methyl-1H-indazole-6-carboxylic acid [117] (Hereinafter Referred to as a Compound [117])

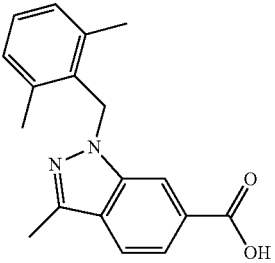 [SMILES: Cc1cccc(C)c1Cn1nc(C)c2ccc(C(=O)O)cc21]

(1) Synthesis of ethyl 1-(2,6-dimethylbenzyl)-3-methyl-1H-indazole-6-carboxylate [117-1] (Hereinafter Referred to as a Compound [117-1])

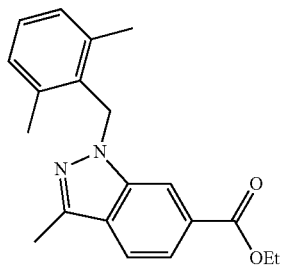 [SMILES: CCOC(=O)c1ccc2c(C)nn(Cc3c(C)cccc3C)c2c1]

To a solution of the compound [66-1] obtained in the process (1) of Example 66 (1.74 g) in ethanol (20 mL) were added triethylamine (2.2 mL) and [1,1'-bis(diphenylphosphino)ferrocene]dichloropalladium(II) (52 mg) at room temperature, and then the reaction mixture was flushed with carbon monoxide and heated at reflux for 18 hours. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (639 mg) as a yellow solid.

$^1$H-NMR (400 MHz, CDCl$_3$) δ: 7.77 (1H, s), 7.73 (1H, d, J=8.3 Hz), 7.63 (1H, d, J=8.3 Hz), 7.20-7.18 (1H, m), 7.10 (2H, d, J=7.6 Hz), 5.55 (2H, s), 4.36 (2H, q, J=7.1 Hz), 2.55 (3H, s), 2.35 (6H, s), 1.40 (3H, t, J=7.2 Hz).

(2) Synthesis of 1-(2,6-dimethylbenzyl)-3-methyl-1H-indazole-6-carboxylic acid [117]

To a solution of the compound [117-1] obtained in the process (1) (636 mg) in ethanol (10 mL) was added an aqueous solution of 1N-sodium hydroxide (10 mL) at room temperature, and then the reaction mixture was stirred at 70° C. for 2 hours. To the reaction mixture was added 1N-hydrochloric acid, and the precipitated solid was filtered to give the titled compound (568 mg) as a white solid.

¹H-NMR (400 MHz, CD₃OD) δ: 8.04 (1H, s), 7.73 (2H, s), 7.15-7.13 (1H, m), 7.07 (2H, d, J=7.6 Hz), 5.59 (2H, s), 2.52 (3H, s), 2.29 (6H, s).
ESI-MS found: 295 [M+H]⁺

Example 118

Synthesis of potassium 1-(2,6-dimethylbenzyl)-3-methyl-1H-indazole-6-carboxylate [118] (Hereinafter Referred to as a Compound [118])

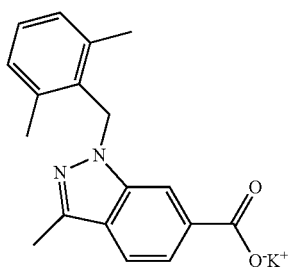

To a solution of the compound [117](568 mg) in ethanol (20 mL) was added an aqueous solution of 1N-potassium hydroxide (1.93 mL) at room temperature, and then the reaction mixture was stirred at room temperature for 10 minutes. The reaction mixture was concentrated under reduced pressure to give the titled compound (636 mg) as a white solid.

¹H-NMR (400 MHz, CD₃OD) δ: 8.06 (1H, s), 7.73 (1H, d, J=8.3 Hz), 7.62 (1H, d, J=8.5 Hz), 7.12-7.11 (1H, m), 7.05 (2H, d, J=7.3 Hz), 5.53 (2H, s), 2.48 (3H, s), 2.29 (6H, s).
ESI-MS found: 295 [M+K−2H]⁺

Example 119

Synthesis of 1-(2,6-dichlorobenzyl)-3-methyl-1H-indazole-6-carboxylic acid [119] (Hereinafter Referred to as a Compound [119])

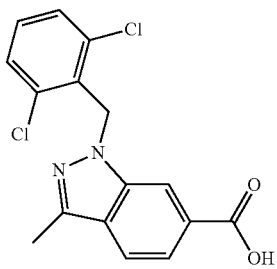

The titled compound (28 mg) as a white solid was prepared from the compound [97-1] obtained in the process (1) of Example 1097 (60 mg) according to the method described in Example 117.

¹H-NMR (400 MHz, CD₃OD) δ: 8.28 (1H, s), 7.78-7.75 (2H, m), 7.45 (2H, d, J=7.8 Hz), 7.36-7.34 (1H, m), 5.81 (2H, s), 2.50 (3H, s).
ESI-MS found: 335 [M+H]⁺

Example 120

Synthesis of 1-(2,3-dichlorobenzyl)-3-methyl-1H-indazole-6-carboxylic acid [120] (Hereinafter Referred to as a Compound [120])

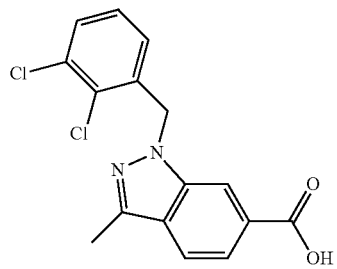 [SMILES: Cc1nn(Cc2cccc(Cl)c2Cl)c2cc(C(=O)O)ccc12]

The titled compound (40 mg) as a white solid was prepared from the compound [99-1] obtained in the process (1) of Example 99 (87 mg) according to the method described in Example 117.

¹H-NMR (400 MHz, CD₃OD) δ: 8.17 (1H, s), 7.82 (2H, s), 7.47 (1H, d, J=7.1 Hz), 7.18-7.16 (1H, m), 6.66 (1H, d, J=7.6 Hz), 5.75 (2H, s), 2.59 (3H, s).

Example 121

Synthesis of 3-[1-(2,6-dimethylbenzyl)-3-methyl-1H-indazole-6-yl]propionic acid [121] (Hereinafter Referred to as a Compound [121])

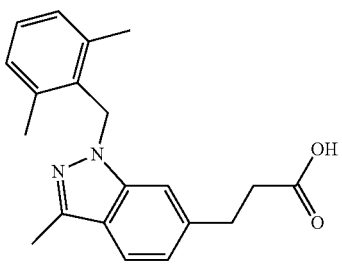 [SMILES: Cc1cccc(C)c1Cn1nc(C)c2ccc(CCC(=O)O)cc21]

(1) Synthesis of methyl (E)-3-[1-(2,6-dimethylbenzyl)-3-methyl-1H-indazole-6-yl]acrylate [112-1] (Hereinafter Referred to as a Compound [112-1])

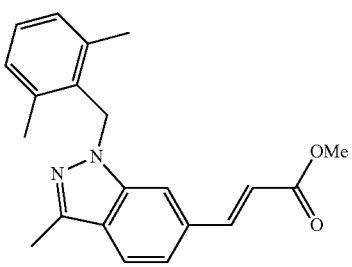 [SMILES: COC(=O)/C=C/c1ccc2c(C)nn(Cc3c(C)cccc3C)c2c1]

To a solution of the compound [66-1] obtained in the process (1) of Example 66 (33 mg) in N,N-dimethylformamide (270 μL) were added methyl acrylate (18 μL), [1,1'-bis(diphenylphosphino)ferrocene]palladium(II)dichloride dichloromethane adduct (9.9 mg), tetrabutylammonium bromide (34 mg) and triethylamine (28 μL) at room temperature, and then the reaction mixture was subjected to microwave irradiation at 115° C. for 15 minutes. After cooling to room temperature, to the reaction mixture was added 10% aqueous solution of citric acid, and the reaction mixture was extracted with ethyl acetate. The obtained organic layer was washed with brine, dried over anhydrous sodium sulfate, filtered, and the filtrate was concentrated under reduced pressure. The obtained residue was purified by silica gel column chromatography to give the titled compound (27 mg) as a yellowish white solid.

¹H-NMR (400 MHz, CDCl₃) δ: 7.64 (1H, d, J=15.9 Hz), 7.60 (1H, d, J=8.3 Hz) 7.27-7.26 (1H, m), 7.21 (1H, t, J=7.3 Hz), 7.10 (2H, d, J=7.6 Hz), 6.96 (1H, s), 6.37 (1H, d, J=15.9 Hz), 5.52 (2H, s), 3.81 (3H, s), 2.54 (3H, s), 2.33 (6H, s).

ESI-MS found: 335 [M+H]⁺

(2) Synthesis of methyl 3-[1-(2,6-dimethylbenzyl)-3-methyl-1H-indazole-6-yl]propionate [112-2] (Hereinafter Referred to as a Compound [112-2])

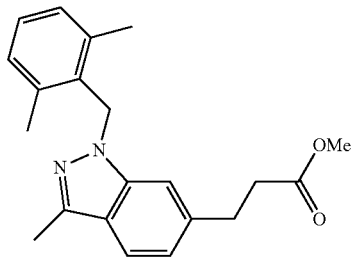 [SMILES: COC(=O)CCc1ccc2c(C)nn(Cc3c(C)cccc3C)c2c1]

To a solution of the compound [112-1] obtained in the process (1) (21 mg) in ethanol (3.0 mL) was added 5% palladium-activated carbon (21 mg) at room temperature, and then the reaction mixture was stirred at room temperature for 2 hours under hydrogen atmosphere. The palladium on carbon was filtered, and the filtrate was concentrated under reduced pressure. The obtained residue was purified by silica gel column chromatography to give the titled compound (13 mg) as a colorless oil.

¹H-NMR (400 MHz, CDCl₃) δ: 7.52 (1H, d, J=8.3 Hz), 7.19-7.15 (1H, m), 7.08 (2H, d, J=7.6 Hz), 6.91 (1H, d, J=8.1 Hz), 6.75 (1H, s), 5.47 (2H, s), 3.65 (3H, s), 2.96 (2H, t, J=7.8 Hz), 2.58 (2H, t, J=7.8 Hz), 2.51 (3H, s) 2.33 (6H, s).

ESI-MS found: 337 [M+H]⁺

(3) Synthesis of 3-[1-(2,6-dimethylbenzyl)-3-methyl-1H-indazole-6-yl]propionic acid [121]

The titled compound (13 mg) as a white solid was prepared from the compound [112-2] obtained in the process (2) (13 mg) according to the method of the process (2) of Example 117.

¹H-NMR (400 MHz, CDCl₃) δ: 7.52 (1H, d, J=8.3 Hz), 7.19-7.15 (1H, m), 7.07 (2H, d, J=7.6 Hz), 6.91 (1H, d, J=8.1 Hz), 6.72 (1H, s), 5.48 (2H, s), 2.97 (2H, t, J=7.7 Hz), 2.62 (2H, t, J=7.7 Hz), 2.51 (3H, s), 2.31 (6H, s).

ESI-MS found: 323 [M+H]⁺

Example 122

Synthesis of 3-[1-(2,6-dichlorobenzyl)-3-methyl-1H-indazole-6-yl]propionic acid [122] (Hereinafter Referred to as a Compound [122])

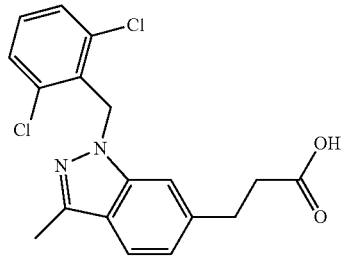 [SMILES: Cc1nn(Cc2c(Cl)cccc2Cl)c2cc(CCC(=O)O)ccc12]

(1) Synthesis of methyl (E)-3-(3-methyl-1H-indazole-6-yl)acrylate [122-1] (Hereinafter Referred to as a Compound [122-1])

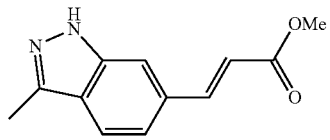 [SMILES: COC(=O)/C=C/c1ccc2c(C)n[nH]c2c1]

To a solution of 6-Bromo-3-methyl-1H-indazole (2.1 g) obtained with the method described in the document (JP 2009-528363 W) in N,N-dimethylformamide (10 mL) were added methyl acrylate (1.8 mL), palladium acetate (II) (225 mg), tris(2-methylphenyl)phosphine (609 mg) and triethylamine (2.8 mL) at room temperature, and then the reaction mixture was subjected to microwave irradiation at 150° C. for 10 minutes. After cooling to room temperature, the reaction mixture was quenched with water, and extracted with chloroform. The obtained organic layer was washed with brine, dried over anhydrous sodium sulfate, filtered, and the filtrate was concentrated under reduced pressure. The obtained residue was purified by silica gel column chromatography to give the titled compound (1.8 g) as a yellowish white solid.

¹H-NMR (400 MHz, CDCl₃) δ: 9.91 (1H, br), 7.81 (1H, d, J=15.9 Hz), 7.67 (1H, d, J=8.3 Hz), 7.54 (1H, s), 7.36 (1H, d, J=8.3 Hz), 6.52 (1H, d, J=15.9 Hz), 3.83 (3H, s), 2.57 (3H, s)

ESI-MS found: 217 [M+H]⁺

(2) Synthesis of methyl 3-(3-methyl-1H-indazole-6-yl)propionate [122-2] (Hereinafter Referred to as a Compound [122-2])

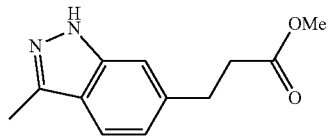 [SMILES: COC(=O)CCc1ccc2c(C)n[nH]c2c1]

The titled compound (1.5 g) as a white solid was prepared from the compound [122-1] obtained in the process (1) (1.8 g) according to the method of the process (2) of Example 121.

$^1$H-NMR (400 MHz, CDCl$_3$) δ: 9.72 (1H, br), 7.59 (1H, d, J=8.3 Hz), 7.24 (1H, s), 7.00 (1H, d, J=8.1 Hz), 3.67 (3H, s), 3.08 (2H, t, J=7.7 Hz), 2.69 (2H, t, J=7.8 Hz), 2.56 (3H, s).

ESI-MS found: 219 [M+H]$^+$ (3) Synthesis of methyl 3-[1-(2,6-dichlorobenzyl)-3-methyl-1H-indazole-6-yl]propionate [122-3] (Hereinafter Referred to as a Compound [122-3])

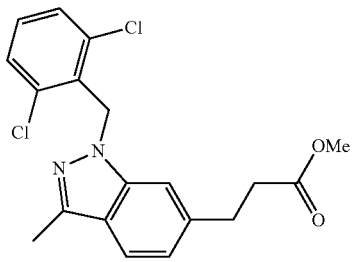 [SMILES: COC(=O)CCc1ccc2c(C)nn(Cc3c(Cl)cccc3Cl)c2c1]

The titled compound (1.27 g) as a yellowish white solid was prepared from the compound [122-2] obtained in the process (2) (871 mg) and 2,6-dichlorobenzyl chloride according to the method of the process (1) of Example 66.

$^1$H-NMR (400 MHz, CDCl$_3$) δ: 7.53 (1H, d, J=8.3 Hz), 7.37 (2H, d, J=8.1 Hz) 7.24-7.20 (1H, m), 7.18 (1H, s), 6.95 (1H, d, J=8.3 Hz), 5.69 (2H, s), 3.67 (3H, s), 3.07 (2H, t, J=7.7 Hz), 2.68 (2H, t, J=7.8 Hz), 2.50 (3H, s).

ESI-MS found: 337 [M+H]$^+$ (4) Synthesis of 3-[1-(2,6-dichlorobenzyl)-3-methyl-1H-indazole-6-yl]propionic acid [122]

The titled compound (680 mg) as a yellowish white solid was prepared from the compound [122-3] obtained in the process (3) (871 mg) according to the method of the process (2) of Example 117.

$^1$H-NMR (400 MHz, CD$_3$OD) δ: 7.57 (1H, d, J=8.1 Hz), 7.44 (2H, d, J=8.1 Hz), 7.34 (1H, s), 7.33 (1H, t, J=7.2 Hz), 7.02 (1H, d, J=8.3 Hz), 5.70 (2H, s), 3.04 (2H, t, J=7.7 Hz), 2.65 (2H, t, J=7.7 Hz), 2.44 (3H, s).

ESI-MS found: 363 [M+H]$^+$

Example 123

Synthesis of potassium 3-[1-(2,6-dichlorobenzyl)-3-methyl-1H-indazole-6-yl]propionate [123] (Hereinafter Referred to as a Compound [123])

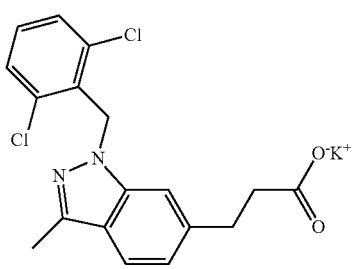

To a solution of the compound [122] (24 mg) in ethanol (2.0 mL) was added an aqueous solution of 1N-potassium hydroxide (65 μL) at room temperature, and the solution was concentrated under reduced pressure to give the titled compound (27 mg) as a yellow solid.

$^1$H-NMR (400 MHz, CD$_3$OD) δ: 7.55 (1H, d, J=8.3 Hz), 7.44 (2H, d, J=8.1 Hz), 7.36 (1H, s), 7.36-7.32 (1H, m), 7.05 (1H, d, J=8.3 Hz), 5.71 (2H, s), 3.04 (2H, t, J=8.1 Hz), 2.50 (2H, t, J=8.2 Hz), 2.44 (3H, s).

ESI-MS found: 363 [M−K+2H]$^+$

Example 124

Synthesis of 3-{1-[(5-chlorobenzo[b]thiophene-3-yl)methyl]-3-methyl-1H-indazole-6-yl}propionic acid [124] (Hereinafter Referred to as a Compound [124])

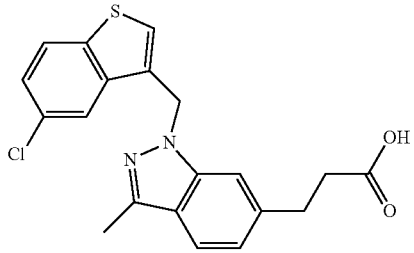 [SMILES: Cc1nn(Cc2csc3ccc(Cl)cc23)c2cc(CCC(=O)O)ccc12]

The titled compound (7.0 mg) was prepared from the compound [122-2] obtained in the process (2) of Example 122 (93 mg) and 3-(bromomethyl)-5-chlorobenzo[b]thiophene according to the method of the process (5) of Example 102.

$^1$H-NMR (400 MHz, CDCl$_3$) δ: 7.85 (1H, s), 7.71 (1H, d, J=8.5 Hz), 7.58 (1H, d, J=7.8 Hz), 7.29 (1H, dd, J=8.7, 1.6 Hz), 7.14 (1H, s), 7.13 (1H, s), 6.99 (1H, d, J=8.3 Hz), 5.66 (2H, s), 3.05 (2H, t, J=7.7 Hz), 2.70 (2H, t, J=7.7 Hz), 2.58 (3H, s).

ESI-MS found: 385 [M+H]$^+$

Example 125

Synthesis of 3-[1-(2-chloro-6-cyanobenzyl)-3-methyl-1H-indazole-6-yl]propionic acid [125] (Hereinafter Referred to as a Compound [125])

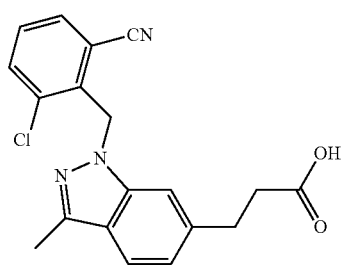 [SMILES: Cc1nn(Cc2c(Cl)cccc2C#N)c2cc(CCC(=O)O)ccc12]

To a solution of the compound [122](29.7 mg) in N,N-dimethylformamide (0.8 mL) were added zinc cyanide (4.8 mg), tris(dibenzylideneacetone)dipalladium(0) (3.7 mg) and 2-dicyclohexylphosphino-2,4,6-triisopropylbiphenyl (7.8 mg) at room temperature, and then the reaction mixture was subjected to microwave irradiation at 160° C. for 30 minutes. The reaction mixture was quenched with water, and extracted with ethyl acetate, and then the obtained organic layer was dried over anhydrous sodium sulfate, filtered, and the filtrate was concentrated under reduced pressure. The obtained residue was purified by reverse phase preparative liquid chromatography to give the titled compound (13.3 mg) as a white solid.

$^1$H-NMR (400 MHz, CD$_3$OD) δ: 7.78 (1H, d, J=7.6 Hz), 7.74 (1H, d, J=8.1 Hz), 7.59 (1H, d, J=8.3 Hz), 7.54-7.50 (1H, m), 7.45 (1H, s), 7.06 (1H, d, J=8.3 Hz), 5.72 (2H, s), 3.08 (2H, t, J=7.7 Hz), 2.68 (2H, t, J=7.6 Hz), 2.44 (3H, s).

ESI-MS found: 354 [M+H]$^+$

Example 126

Synthesis of potassium 3-[1-(2-chloro-6-cyanobenzyl)-3-methyl-1H-indazole-6-yl]propionate [126] (Hereinafter Referred to as a Compound [126])

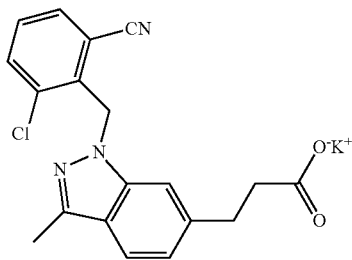

To a solution of the compound [125](13.3 mg) in ethanol (1.3 mL) was added 1M-potassium hydroxide solution (38 μL) at room temperature, and the solution was concentrated under reduced pressure to give the titled compound (10.1 mg) as a white solid.

$^1$H-NMR (400 MHz, CD$_3$OD) δ: 7.78 (1H, d, J=7.8 Hz), 7.74 (1H, d, J=8.3 Hz), 7.57 (1H, d, J=8.3 Hz), 7.54-7.50 (1H, m), 7.45 (1H, s), 7.08 (1H, d, J=8.3 Hz), 5.72 (2H, s), 3.06 (2H, t, J=8.1 Hz), 2.52 (2H, t, J=8.1 Hz), 2.44 (3H, s).

ESI-MS found: 354 [M−K+2H]$^+$

Example 127

Synthesis of 3-[1-(2,6-dichlorobenzyl)-3-methyl-1H-indazole-6-yl]-3-hydr oxypropionic acid [127] (Hereinafter Referred to as a Compound [127])

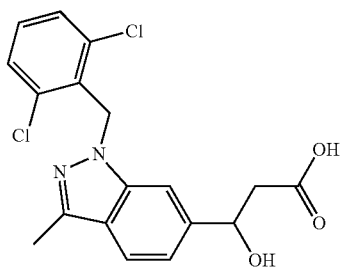 [SMILES: Cc1nn(Cc2c(Cl)cccc2Cl)c2cc(C(O)CC(=O)O)ccc12]

(1) Synthesis of 1-(2,6-dichlorobenzyl)-3-methyl-6-vinyl-1H-indazole [127-1](Hereinafter Referred to as a Compound [127-1])

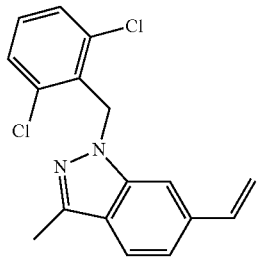 [SMILES: C=Cc1ccc2c(C)nn(Cc3c(Cl)cccc3Cl)c2c1]

To a solution of the compound [97-1] obtained in the process (1) of Example 97 (537 mg) in dimethyl formamide (10 mL) were added tributylvinyltin (0.5 mL), lithium chloride (204 mg) and bis(triphenylphosphine)palladium(II)dichloride (54 mg) at room temperature, and then the reaction mixture was stirred at 120° C. for 2 hours. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (326 mg) as a white solid.

$^1$H-NMR (400 MHz, CDCl$_3$) δ: 7.55 (1H, d, J=8.3 Hz), 7.46-7.21 (5H, m), 6.81 (1H, dd, J=17.4-10.9 Hz), 5.79 (1H, d, J=17.6 Hz), 5.71 (2H, s), 5.29 (1H, d, J=11.0 Hz), 2.51 (3H, s).

(2) Synthesis of 1-(2,6-dichlorobenzyl)-3-methyl-1H-indazole-6-carbaldehyde [127-2] (Hereinafter Referred to as a Compound [127-2])

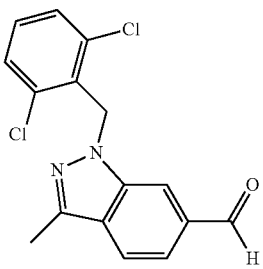 [SMILES: Cc1nn(Cc2c(Cl)cccc2Cl)c2cc(C=O)ccc12]

The titled compound (140 mg) as a yellow solid was prepared from the compound [127-1] obtained in the process (1) (323 mg) according to the method of the process (3) of Example 66.

$^1$H-NMR (400 MHz, CDCl$_3$) δ: 10.1 (1H, s), 7.92 (1H, s), 7.75 (1H, d, J=8.3 Hz), 7.64 (1H, d, J=8.3 Hz), 7.39 (2H, d, J=8.1 Hz), 7.29-7.25 (1H, m), 5.81 (2H, s), 2.56 (3H, s)

(3) Synthesis of 3-[1-(2,6-dichlorobenzyl)-3-methyl-1H-indazole-6-yl]-3-hydroxypropionic acid [127]

To a solution of the compound [127-2] obtained in the process (2) (105 mg) in benzene (5 mL) were added zinc powder (40 mg) and ethyl bromoacetate (0.1 mL) at room temperature, and then the reaction mixture was heated at reflux for 2 hours. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give a yellow solid. The obtained yellow solid was dissolved in ethanol (3 mL), and an aqueous solution of 1N-sodium hydroxide (3 mL) was added at room temperature. The reaction mixture was stirred at 60° C. for 2 hours. To the reaction mixture was added 1N hydrochloric acid, and the precipitated solid was filtered to give the titled compound (108 mg) as a white solid.

$^1$H-NMR (400 MHz, CD$_3$OD) δ: 7.65 (1H, dd, J=8.3 Hz), 7.57 (1H, s), 7.44 (2H, d, J=8.1 Hz), 7.35-7.33 (1H, m), 7.18 (1H, d, J=8.3 Hz), 5.73 (2H, s), 5.24-5.22 (1H, m), 2.74-2.73 (2H, m), 2.46 (3H, s).

Example 128

Synthesis of [1-(2,6-dichlorobenzyl)-3-methyl-1H-indazole-6-yl]hydroxyacetic acid [128] (Hereinafter Referred to as a Compound [128])

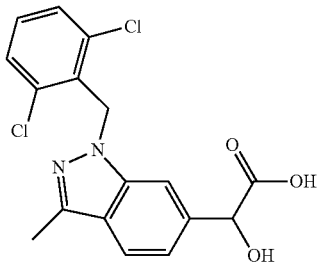 [SMILES: Cc1nn(Cc2c(Cl)cccc2Cl)c2cc(C(O)C(=O)O)ccc12]

(1) Synthesis of [1-(2,6-dichlorobenzyl)-3-methyl-11H-indazole-6-yl]hydroxyacetonitrile [128-1] (Hereinafter Referred to as a Compound [128-1])

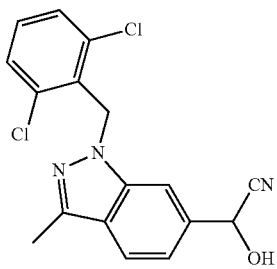 [SMILES: Cc1nn(Cc2c(Cl)cccc2Cl)c2cc(C(O)C#N)ccc12]

To a solution of the compound [127-2] obtained in the process (2) of Example 127 (225 mg) in tetrahydrofuran (1 mL) were added trimethylsilyl cyanide (875 mL) and zinc iodide (14 mg) at room temperature, and the reaction mixture was stirred at room temperature for 5 days. The reaction mixture was quenched with water, and extracted with ethyl acetate. The obtained organic layer was dried over anhydrous sodium sulfate, filtered, and the filtrate was concentrated under reduced pressure to give a brown oil. The obtained oil was dissolved in methanol (2 mL), and p-toluene sulfonic acid (12 mg) was added at room temperature, and the reaction mixture was stirred at room temperature for 3 hours. To the reaction mixture was added a saturated aqueous solution of sodium hydrogen carbonate, and the reaction mixture was extracted with ethyl acetate. The obtained organic layer was dried over anhydrous sodium sulfate, filtered, and the filtrate was concentrated under reduced pressure. The obtained residue was purified by silica gel column chromatography to give the titled compound (218 mg) as a white solid.

$^1$H-NMR (400 MHz, CDCl$_3$) δ: 7.70 (1H, d, J=8.3 Hz), 7.56 (1H, s), 7.38 (2H, d, J=8.1 Hz), 7.30-7.20 (2H, m), 5.75 (2H, s), 5.66 (1H, d, J=6.6 Hz), 2.54 (3H, s), 1.60-1.50 (1H, br).

(2) Synthesis of [1-(2,6-dichlorobenzyl)-3-methyl-1H-indazole-6-yl]hydroxyacetic acid [128] (Hereinafter Referred to as a Compound [128])

To a solution of the compound [128-1] obtained in the process (1) (24 mg) in acetic acid (1 mL) was added concentrated hydrochloric acid (1 mL) at room temperature, and the reaction mixture was stirred at 60° C. for 5 hours. The reaction mixture was quenched with water, and extracted with ethyl acetate. The obtained organic layer was dried over anhydrous sodium sulfate, filtered, and the filtrate was concentrated under reduced pressure. The obtained residue was purified by reverse phase preparative liquid chromatography to give the titled compound (19 mg) as a white solid.

$^1$H-NMR (400 MHz, CD$_3$OD) δ: 7.65 (2H, d, J=9.8 Hz), 7.42 (2H, d, J=8.1 Hz), 7.34-7.26 (2H, m), 5.73 (2H, s), 5.29 (1H, s), 2.46 (3H, s).

ESI-MS found: 365 [M+H]$^+$

Example 129

Synthesis of potassium [1-(2,6-dichlorobenzyl)-3-methyl-1H-indazole-6-yl]hydroxyacetate [129] (Hereinafter Referred to as a Compound [129])

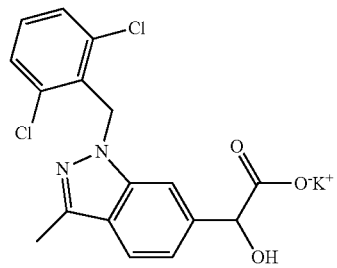

To a solution of the compound [128] (19 mg) in ethanol (1 mL) was added an aqueous solution of 1N-potassium hydroxide (58 mL) at room temperature, and the solution was concentrated under reduced pressure to give the titled compound (20 mg) as a white solid.

$^1$H-NMR (400 MHz, CD$_3$OD) δ: 7.67 (1H, s), 7.59 (1H, d, J=8.3 Hz), 7.43 (2H, d, J=7.8 Hz), 7.36-7.28 (2H, m), 5.71 (2H, s), 4.99 (1H, s), 2.44 (3H, s).

ESI-MS found: 365 [M−K+2H]$^+$

Example 130

Synthesis of 4-[1-(2,6-dichlorobenzyl)-3-methyl-1H-indazole-6-yl]-4-oxobutyric acid [130] (Hereinafter Referred to as a Compound [130])

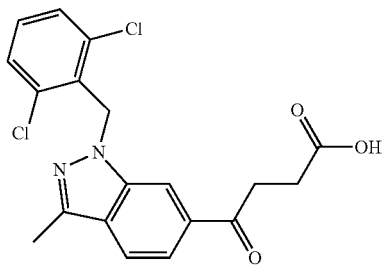 [SMILES: Cc1nn(Cc2c(Cl)cccc2Cl)c2cc(C(=O)CCC(=O)O)ccc12]

(1) Synthesis of 1-(2,6-dichlorobenzyl)-3-methyl 6-tributylstannyl-1H-indazole-[130-1] (hereinafter referred to as a compound [130-1])

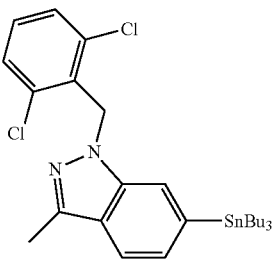

To a solution of the compound [97-1] obtained in the process (1) of Example 97 (1.12 g) in toluene (30 mL) were added bis(tributyltin) (1.8 mL) and tetrakis(triphenylphosphine) palladium(0) (177 mg) at room temperature, and then the reaction mixture was heated at reflux for 2 hours. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (774 mg) as a colorless oil.

$^1$H-NMR (400-MHz, CDCl$_3$) δ: 7.59 (1H, d, J=7.8 Hz), 7.37-7.36 (3H, m), 7.23-7.21 (1H, m), 7.16 (1H, d, J=7.8 Hz), 5.77 (2H, s), 2.53 (3H, s), 1.54-1.48 (6H, m), 1.39-1.28 (12H, m), 0.95-0.87 (9H, m).

(2) Synthesis of ethyl 4-[1-(2,6-dichlorobenzyl)-3-methyl-1H-indazole-6-yl]-4-oxobutyrate [130-2] (Hereinafter Referred to as a Compound [130-2])

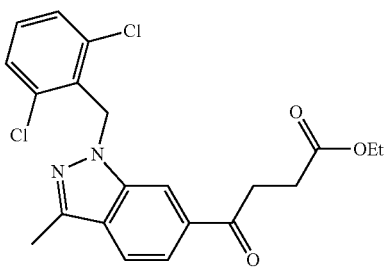 [SMILES: CCOC(=O)CCC(=O)c1ccc2c(C)nn(Cc3c(Cl)cccc3Cl)c2c1]

To a solution of the compound [130-1] obtained in the process (1) (568 mg) in toluene (10 mL) were added ethyl succinyl chloride (0.2 mL) and tetrakis(triphenylphosphine) palladium (0) (62 mg) at room temperature, and then reaction mixture was heated at reflux for 30 minutes. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (103 mg) as a colorless oil.

$^1$H-NMR (400 MHz, CDCl$_3$) δ: 8.06 (1H, s), 7.73-7.68 (2H, m), 7.39 (2H, d, J=8.1 Hz), 7.28-7.25 (1H, m), 5.79 (2H, s), 4.19 (2H, q, J=7.2 Hz), 3.37 (2H, t, J=6.6 Hz), 2.79 (2H, t, J=6.7 Hz), 2.55 (3H, s), 1.29 (3H, t, J=7.2 Hz).

(3) Synthesis of 4-[1-(2,6-dichlorobenzyl)-3-methyl-1H-indazole-6-yl]-4-oxobutyric acid [130]

To a solution of the compound [130-2] obtained in the process (2) (136 mg) in methanol (3 mL) was added an aqueous solution of 1N-sodium hydroxide (3 mL) at room temperature, and then the reaction mixture was stirred at 60° C. for 2 hours. To the reaction mixture was added 1N-hydrochloric acid, and the precipitated solid was filtered to give the titled compound (119 mg) as a white solid.

$^1$H-NMR (400 MHz, CD$_3$OD) δ: 8.25 (1H, s), 7.76 (2H, s), 7.46 (2H, d, J=7.8 Hz), 7.38-7.34 (1H, m), 5.85 (2H, s), 3.39 (2H, t, J=6.5 Hz), 2.72 (2H, t, J=6.3 Hz), 2.50 (3H, s)

ESI-MS found: 391 [M+H]$^+$

Example 131

Synthesis of 2-[1-(2,6-dichlorobenzyl)-3-methyl-1H-indazole-6-yl]acetamide [131] (Hereinafter Referred to as a Compound [131])

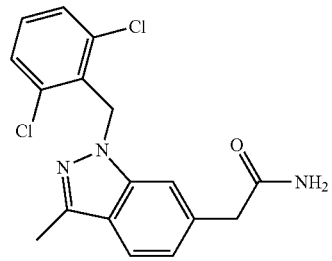 [SMILES: Cc1nn(Cc2c(Cl)cccc2Cl)c2cc(CC(N)=O)ccc12]

To a solution of the compound [97](299 mg) in tetrahydrofuran (5 mL) was added thionyl chloride (0.5 mL) at room temperature, and then the reaction mixture was stirred at 50° C. for 1 hour. The reaction mixture was concentrated under reduced pressure, and then the obtained residue was dissolved in tetrahydrofuran (5 mL). To the solution was added 30% ammonia water at 0° C., and the reaction mixture was stirred for 1 hour. To the reaction mixture was added 3N-hydrochloric acid, and extracted with chloroform. The obtained organic layer was washed with brine, dried over anhydrous sodium sulfate, filtered, and the filtrate was concentrated under reduced pressure. The obtained residue was purified by silica gel column chromatography to give the titled compound (196 mg) as a white solid.

$^1$H-NMR (400 MHz, CD$_3$OD) δ: 7.61 (1H, d, J=8.1 Hz), 7.47 (1H, s), 7.43 (2H, d, J=7.8 Hz), 7.33 (1H, dd, J=8.8, 7.3 Hz), 7.09 (1H, d, J=8.3 Hz), 5.72 (2H, s), 4.90-4.80 (2H, brs), 3.65 (2H, s), 2.45 (3H, s).

ESI-MS found: 348 [M+H]$^+$

Example 132

Synthesis of 3-[1-(2,6-dichlorobenzyl)-3-methyl-1H-indazole-6-yl]propionamide [132] (Hereinafter Referred to as a Compound [132])

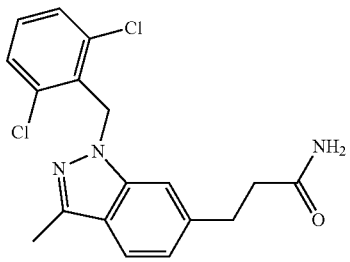 [SMILES: Cc1nn(Cc2c(Cl)cccc2Cl)c2cc(CCC(N)=O)ccc12]

The titled compound (141.3 mg) as a white solid was prepared from the compound [122](198.3 mg) according to the method of Example 131.

$^1$H-NMR (400 MHz, CDCl$_3$) δ: 7.54 (1H, d, J=8.3 Hz), 7.36 (2H, d, J=8.1 Hz) 7.26-7.20 (2H, m), 6.97 (1H, d, J=8.3 Hz), 5.69 (2H, s), 5.26 (2H, s), 3.09 (2H, t, J=7.6 Hz), 2.57 (2H, t, J=7.6 Hz), 2.50 (3H, s).

ESI-MS found: 362 [M+H]$^+$

Example 133

Synthesis of 4-[1-(2,6-dichlorobenzyl)-3-methyl-1H-indazole-6-yl]butyric acid [133] (Hereinafter Referred to as a Compound [133])

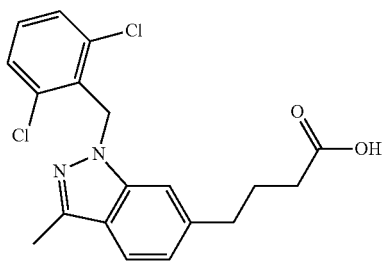 [SMILES: Cc1nn(Cc2c(Cl)cccc2Cl)c2cc(CCCC(=O)O)ccc12]

(1) Synthesis of methyl (E)-4-[3-methyl-1H-indazole-6-yl]-3-butenoate [133-1] (Hereinafter Referred to as a Compound [133-1])

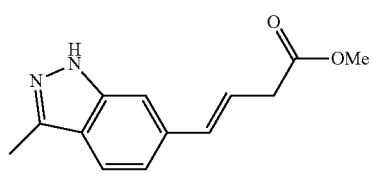 [SMILES: COC(=O)C/C=C/c1ccc2c(C)n[nH]c2c1]

To a solution of 6-bromo-3-methyl-1H-indazole obtained with the method described in the document (JP 2009-528363 W) (213 mg) in N,N-dimethylformamide (2 mL) were added triethylamine (0.28 mL), palladium acetate (II) (27 mg), tris(2-methylphenyl)phosphine (62 mg) and 3-butenoic acid (0.17 mL), and the reaction mixture was subjected to microwave irradiation at 150° C. for 10 minutes. The reaction mixture was quenched with water, and extracted with ethyl acetate. The obtained organic layer was dried over anhydrous sodium sulfate, filtered, and the filtrate was concentrated under reduced pressure. To a solution of the obtained residue in tetrahydrofuran (5 mL) was added 0.6M tetrahydrofuran solution of trimethylsilyl diazomethane (0.17 mL), and then the reaction mixture was concentrated under reduced pressure, and The obtained residue was purified by silica gel column chromatography to give the titled compound (90 mg) as a colorless oil.

$^1$H-NMR (400 MHz, CDCl$_3$) δ: 9.90-9.80 (1H, brs), 7.58 (1H, d, J=8.3 Hz), 7.33 (1H, s), 7.23 (1H, d, J=8.5 Hz), 6.58 (1H, d, J=15.9 Hz), 6.41-6.33 (1H, m), 3.73 (3H, s), 3.28 (2H, d, J=6.6 Hz), 2.57 (3H, s).

(2) Synthesis of methyl 4-[3-methyl-1H-indazole-6-yl]butanoate [133-2] (Hereinafter Referred to as a Compound [133-2])

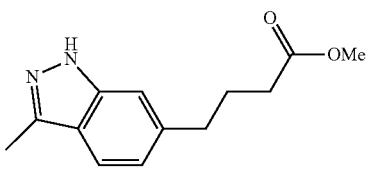 [SMILES: COC(=O)CCCc1ccc2c(C)n[nH]c2c1]

The titled compound (76 mg) as a colorless oil was prepared from the compound [133-1] obtained in the process (1) (90 mg) according to the method of the process (2) of Example 121.

$^1$H-NMR (400 MHz, CDCl$_3$) δ: 9.78 (1H, brs), 7.58 (1H, d, J=8.3 Hz), 7.21 (1H, s), 6.99 (1H, d, J=8.1 Hz), 3.66 (3H, s), 2.78 (2H, t, J=7.6 Hz), 2.57 (3H, s), 2.35 (2H, t, J=7.4 Hz), 2.05-1.97 (2H, m).

(3) Synthesis of 4-[1-(2,6-dichlorobenzyl)-3-methyl-1H-indazole-6-yl]butyric acid [133]

The titled compound (61 mg) as a white solid was prepared from the compound [133-2] obtained in the process (2) (76 mg) and 2,6-dichlorobenzyl chloride (98 mg) according to the method of the process (5) of Example 102.

$^1$H-NMR (400 MHz, CD$_3$OD) δ: 7.58 (1H, d, J=8.3 Hz), 7.44 (2H, d, J=8.1 Hz) 7.34-7.32 (1H, m), 7.28 (1H, s), 7.00 (1H, d, J=8.3 Hz), 5.71 (2H, s), 2.78 (2H, t, J=7.6 Hz), 2.45 (3H, s), 2.29 (2H, t, J=7.3 Hz), 1.99-1.92 (2H, m).

Example 134

Synthesis of 1-(2,6-dichlorobenzyl)-3-methyl-6-(1H-tetrazole-5-ylmethyl)-1H-indazole [134] (Hereinafter Referred to as a Compound [134])

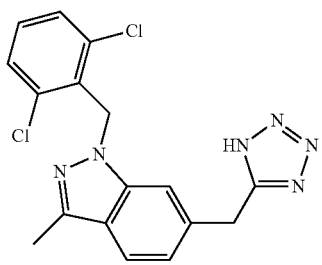 [SMILES: Cc1nn(Cc2c(Cl)cccc2Cl)c2cc(Cc3nnn[nH]3)ccc12]

(1) Synthesis of [1-(2,6-dichlorobenzyl)-3-methyl-1H-indazole-6-yl]acetonitrile [134-1] (Hereinafter Referred to as a Compound [134-1])

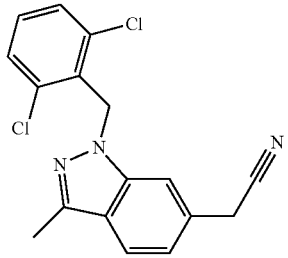 [SMILES: Cc1nn(Cc2c(Cl)cccc2Cl)c2cc(CC#N)ccc12]

To the compound [131](154 mg) was added thionyl chloride (6.0 mL) at room temperature, and the reaction mixture was stirred at room temperature for 5 minutes. The reaction mixture was cooled to 0° C., and then an aqueous solution of 3 N-sodium hydroxide was added, and the reaction mixture was extracted with chloroform. The obtained organic layer was washed with brine, dried over anhydrous sodium sulfate, filtered, and the filtrate was concentrated under reduced pressure. The obtained residue was purified by silica gel column chromatography to give the titled compound (112 mg) as a pale yellow solid.
$^1$H-NMR (400 MHz, CDCl$_3$) δ: 7.61 (1H, d, J=8.3 Hz), 7.38 (2H, d, J=8.1 Hz), 7.34 (1H, s), 7.26-7.23 (1H, m), 7.00 (1H, d, J=8.1 Hz), 5.73 (2H, s), 3.87 (2H, s), 2.52 (3H, s).
ESI-MS found: 330 [M+H]$^+$

(2) Synthesis of 1-(2,6-dichlorobenzyl)-3-methyl-6-(1H-tetrazole-5-ylmethyl)-1H-indazole [134]

To a solution of the compound [134-1] obtained in the process (1) (112 mg) in N,N-dimethylformamide (1.7 mL) were added ammonium chloride (73 mg) and sodium azide (66 mg) at room temperature, and then the reaction mixture was subjected to microwave irradiation at 160° C. for 2 hours. After cooling to room temperature, the reaction mixture was added 6N-hydrochloric acid, and extracted with ethyl acetate. The obtained organic layer was washed with brine, dried over anhydrous sodium sulfate, filtered, and the filtrate was concentrated under reduced pressure. The obtained residue was purified by silica gel column chromatography to give the titled compound (77 mg) as a white solid.
$^1$H-NMR (400 MHz, CD$_3$OD) δ: 7.64 (1H, d, J=8.3 Hz), 7.41 (2H, d, J=7.8 Hz), 7.33 (1H, t, J=8.1 Hz), 7.28 (1H, s), 7.05 (1H, d, J=8.3 Hz), 5.70 (2H, s), 4.44 (2H, s), 2.46 (3H, s).
ESI-MS found: 373 [M+H]$^+$

Example 135

Synthesis of 1-(2,6-dichlorobenzyl)-3-methyl-6-[2-(1H-tetrazole-5-yl)ethyl]-1H-indazole [135] (Hereinafter Referred to as a Compound [135])

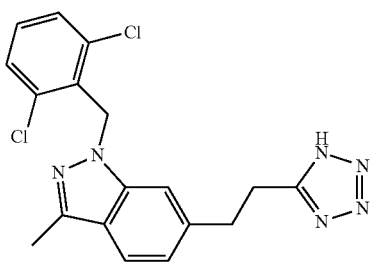 [SMILES: Cc1nn(Cc2c(Cl)cccc2Cl)c2cc(CCc3nnn[nH]3)ccc12]

(1) Synthesis of 3-[1-(2,6-dichlorobenzyl)-3-methyl-1H-indazole-6-yl]propionitrile [135-1] (Hereinafter Referred to as a Compound [135-1])

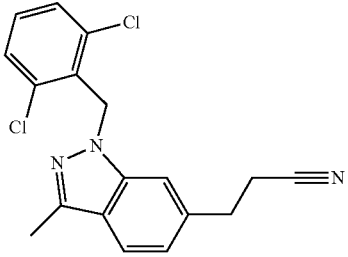 [SMILES: Cc1nn(Cc2c(Cl)cccc2Cl)c2cc(CCC#N)ccc12]

The titled compound (82.4 mg) as a white solid was prepared from the compound [132](125.8 mg) according to the method of the process (1) of Example 134.
$^1$H-NMR (400 MHz, CDCl$_3$) δ: 7.58 (1H, d, J=8.1 Hz), 7.37 (2H, d, J=8.1 Hz), 7.26-7.23 (2H, m), 6.96 (1H, d, J=8.1 Hz), 5.71 (2H, s), 3.07 (2H, t, J=7.3 Hz), 2.66 (2H, t, J=7.3 Hz), 2.51 (3H, s).

(2) Synthesis of 1-(2,6-dichlorobenzyl)-3-methyl-6-[2-(1H-tetrazole-5-yl)ethyl]-1H-indazole [135]

The titled compound (9.2 mg) as a white solid was prepared from the compound [135-1] obtained in the process (1) (40.7 mg) according to the method of the process (2) of Example 134.
$^1$H-NMR (400 MHz, CD$_3$OD) δ: 7.60 (1H, d, J=8.3 Hz), 7.43 (2H, d, J=7.8 Hz), 7.33-7.25 (2H, m), 7.00 (1H, d, J=8.1 Hz), 5.66 (2H, s), 3.31-3.22 (4H, m), 2.44 (3H, s).
ESI-MS found: 387 [M+H]$^+$

Example 136

Synthesis of 5-{[1-(2,6-dichlorobenzyl)-3-methyl-1H-indazole-6-yl]methyl}-1,3,4-oxadiazol-2(3H)-one [136] (Hereinafter Referred to as a Compound [136])

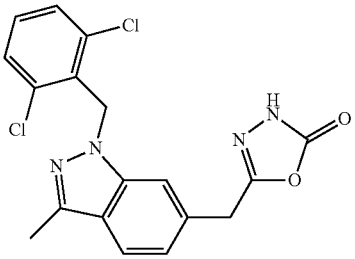 [SMILES: Cc1nn(Cc2c(Cl)cccc2Cl)c2cc(Cc3n[nH]c(=O)o3)ccc12]

(1) Synthesis of tert-butyl

N'-{2-[1-(2,6-dichlorobenzyl)-3-methyl-1H-indazole-6-yl]acetyl}hydrazinecarboxylate [136-1] (hereinafter referred to as a compound [136-1])

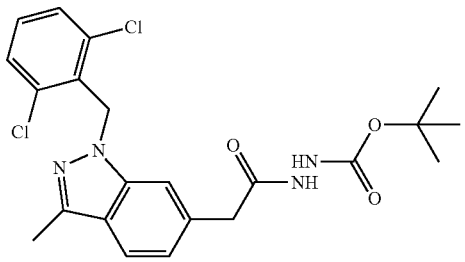

To a solution of the compound [97](73.2 mg) in chloroform (1.1 mL) were added tert-butylcarbazate (222.0 mg), 1-hydroxybenzotriazole monohydrate (113.5 mg) and 1-(3-dimethylaminopropyl)-3-ethylcarbodiimide hydrochloride (161.0 mg) at room temperature, and then the reaction mixture was stirred for 18 hours. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (84.0 mg) as a white solid.

$^1$H-NMR (400 MHz, CDCl$_3$) δ: 7.61 (1H, d, J=8.1 Hz), 7.37 (2H, d, J=8.0 Hz), 7.33 (1H, s), 7.23-7.08 (2H, m), 7.04 (1H, d, J=8.1 Hz), 6.39 (1H, s), 5.69 (2H, s), 3.76 (2H, s), 2.50 (3H, s), 1.45 (9H, s).)

(2) Synthesis of [1-(2,6-dichlorobenzyl)-3-methyl-1H-indazole-6-yl]acetic acid hydrazide [136-2] (Hereinafter Referred to as a Compound [136-2])

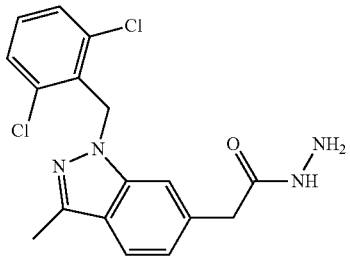 [SMILES: Cc1nn(Cc2c(Cl)cccc2Cl)c2cc(CC(=O)NN)ccc12]

To a solution of the compound [136-1] obtained in the process (1) (84.0 mg) in chloroform (0.9 mL) was added trifluoroacetic acid (0.6 mL) at room temperature, and then the reaction mixture was stirred for 1 hour. The reaction mixture was concentrated under reduced pressure, added saturated sodium hydrogen carbonate, and extracted with ethyl acetate. The obtained residue was purified by silica gel column chromatography to give the titled compound (62.7 mg) as a brown solid.

$^1$H-NMR (400 MHz, CDCl$_3$) δ: 7.60 (1H, d, J=8.1 Hz), 7.37 (2H, d, J=8.1 Hz), 7.24-7.20 (2H, m), 6.98 (1H, d, J=8.1 Hz), 6.59 (1H, s), 5.70 (2H, s), 3.84 (2H, s), 3.69 (2H, s), 2.51 (3H, s).

(3) Synthesis of 5-{[1-(2,6-dichlorobenzyl)-3-methyl-1H-indazole-6-yl]methyl}-1,3,4-oxadiazol-2(3H)-one [136]

To a solution of the compound [136-2] obtained in the process (2) (84.0 mg) in tetrahydrofuran (1.7 mL) were added N,N-diisopropylethylamine (0.15 mL) and 1,1'-carbonyldiimidazole (84.2 mg) at room temperature, and then the reaction mixture was stirred for 2.5 hours. The reaction mixture was concentrated under reduced pressure, and then the obtained residue was purified by reverse phase preparative liquid chromatography to give the titled compound (9.2 mg) as a white solid.

$^1$H-NMR (400 MHz, CD$_3$OD) δ: 7.65 (1H, d, J=8.3 Hz), 7.44 (2H, d, J=7.8 Hz), 7.36 (1H, s), 7.35-7.32 (1H, m), 7.07 (1H, d, J=8.3 Hz), 5.74 (2H, s), 4.03 (2H, s), 2.47 (3H, s).

ESI-MS found: 389 [M+H]$^+$

Example 137

Synthesis of 5-{[1-(2,6-dichlorobenzyl)-3-methyl-1H-indazole-6-yl]methyl}-1,3,4-oxadiazol-2(3H)-thione [137] (Hereinafter Referred to as a Compound [137])

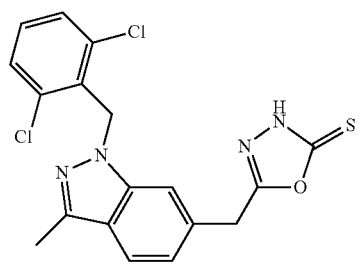 [SMILES: Cc1nn(Cc2c(Cl)cccc2Cl)c2cc(Cc3n[nH]c(=S)o3)ccc12]

To a solution of [136-2] obtained in the process (2) of Example 136 (9.1 mg) in ethanol (0.4 mL) were added carbon bisulfide (10.6 μL) and an aqueous solution of 1N-potassium hydroxide at room temperature, and then the reaction mixture was stirred at 80° C. for 16 hours. To the reaction mixture was added 2N-hydrochloric acid for acidification, and extracted with ethyl acetate. The obtained organic layer was dried over anhydrous sodium sulfate, filtered, and the filtrate was concentrated under reduced pressure. The obtained residue was purified by reverse phase preparative liquid chromatography to give the titled compound (5.8 mg) as a white solid.

$^1$H-NMR (400 MHz, CD$_3$OD) δ: 7.56 (1H, d, J=8.0 Hz), 7.35 (2H, d, J=7.6 Hz), 7.27 (1H, s), 7.26-7.23 (1H, m), 6.98 (1H, d, J=8.4 Hz), 5.64 (2H, s), 4.08 (2H, s), 2.37 (3H, s).

ESI-MS found: 405 [M+H]$^+$

Example 138

Synthesis of 2-[1-(2,6-dichlorobenzyl)-3-methyl-1H-indazole-6-yloxy]acetic acid [138] (Hereinafter Referred to as a Compound [138])

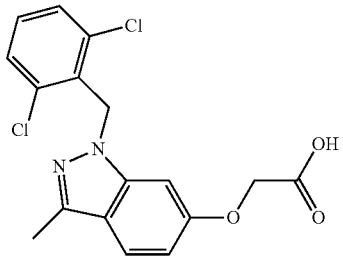 [SMILES: Cc1nn(Cc2c(Cl)cccc2Cl)c2cc(OCC(=O)O)ccc12]

(1) Synthesis of 6-methoxy-3-methyl-1H-indazole [138-1] (Hereinafter Referred to as a Compound [138-1])

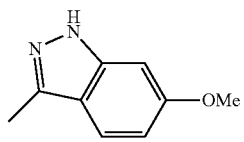

To 2'-fluoro-4'-methoxyacetophenone (5.24 g) was added hydrazine monohydrate (20 mL) at room temperature, and then the reaction mixture was stirred at 140° C. for 20 hours. The precipitated solid was filtered to give the titled compound (4.20 g) as a red solid.

$^1$H-NMR (400 MHz, CDCl$_3$) δ: 7.52 (1H, d, J=9.3 Hz), 6.80-6.78 (2H, m), 3.86 (3H, s), 2.54 (3H, s).

(2) Synthesis of 1-(2,6-dichlorobenzyl)-6-methoxy-3-methyl-1H-indazole [138-2] (Hereinafter Referred to as a Compound [138-2])

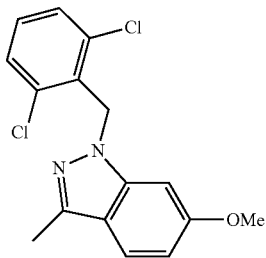 [SMILES: COc1ccc2c(C)nn(Cc3c(Cl)cccc3Cl)c2c1]

The titled compound (785 mg) as a yellow solid was prepared from the compound [138-1] obtained in the process (1) (585 mg) according to the method of the process (1) of Example 66.

$^1$H-NMR (400 MHz, CDCl$_3$) δ: 7.46 (1H, d, J=8.8 Hz), 7.37 (2H, d, J=8.1 Hz), 7.25-7.21 (1H, m), 6.74 (1H, dd, J=8.7, 1.8 Hz), 6.69 (1H, s), 5.67 (2H, s), 3.81 (3H, s), 2.49 (3H, s).

(3) Synthesis of 1-(2,6-dichlorobenzyl)-3-methyl-1H-indazole-6-ol [138-3] (Hereinafter Referred to as a Compound [138-3])

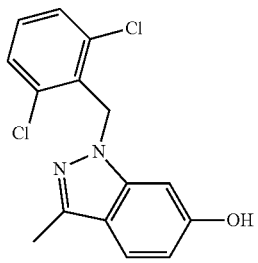 [SMILES: Cc1nn(Cc2c(Cl)cccc2Cl)c2cc(O)ccc12]

To a solution of the compound [138-2] obtained in the process (2) (785 mg) in dichloromethane (10 mL) was added 1M dichloromethane solution of boron tribromide (10 mL), and the reaction mixture was stirred at room temperature for 10 minutes. The reaction mixture was quenched with water, and extracted with chloroform. The obtained organic layer was dried over anhydrous sodium sulfate, filtered, and the filtrate was concentrated under reduced pressure. The obtained residue was purified by silica gel column chromatography to give the titled compound (84 mg) as a white solid.

$^1$H-NMR (400 MHz, CD$_3$OD) δ: 7.46-7.44 (3H, m), 7.35-7.31 (1H, m), 6.70 (1H, s), 6.68-6.65 (1H, m), 5.60 (2H, s), 2.40 (3H, s).

(4) Synthesis of ethyl [1-(2,6-dichlorobenzyl)-3-methyl-1H-indazole-6-yloxy]acetate [138-4] (Hereinafter Referred to as a Compound [138-4])

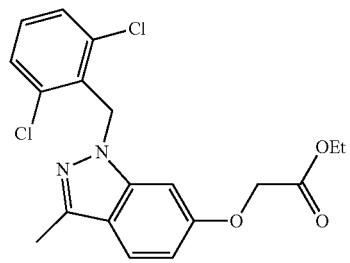 [SMILES: CCOC(=O)COc1ccc2c(C)nn(Cc3c(Cl)cccc3Cl)c2c1]

To a solution of the compound [138-3] obtained in the process (3) (81 mg) in dimethyl formamide (3 mL) were added potassium carbonate (78 mg) and ethyl bromoacetate (0.05 mL), and the reaction mixture was stirred at room temperature for 20 hours. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (89 mg) as a white solid.

$^1$H-NMR (400 MHz, CDCl$_3$) δ: 7.50 (1H, d, J=8.8 Hz), 7.37 (2H, d, J=8.1 Hz) 7.24-7.22 (1H, m), 6.81 (1H, dd, J=8.8, 2.0 Hz), 6.67 (1H, d, J=1.7 Hz), 5.65 (2H, s), 4.63 (2H, s), 4.28 (2H, q, J=7.2 Hz), 2.48 (3H, s), 1.30 (3H, t, J=7.2 Hz).

(5) Synthesis of 2-[1-(2,6-dichlorobenzyl)-3-methyl-1H-indazole-6-yloxy]acetic acid [138]

The titled compound (72 mg) as a white solid was prepared from the compound [138-4] obtained in the process (4) (89 mg) according to the method of the process (2) of Example 117.

$^1$H-NMR (400 MHz, CD$_3$OD) δ: 7.55 (1H, d, J=9.3 Hz), 7.44 (2H, d, J=8.1 Hz), 7.36-7.32 (1H, m), 6.83 (2H, d, J=7.1 Hz), 5.68 (2H, s), 4.68 (2H, s), 2.43 (3H, s)

Example 139

Synthesis of [1-(2,6-dichlorobenzyl)-3-methyl-1H-indazole-6-yl]methanesulfonic acid [139] (Hereinafter Referred to as a Compound [139])

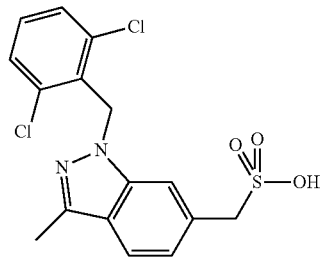 [SMILES: Cc1nn(Cc2c(Cl)cccc2Cl)c2cc(CS(=O)(=O)O)ccc12]

(1) Synthesis of 6-bromomethyl-1-(2,6-dichlorobenzyl)-3-methyl-1H-indazole [139-1] (Hereinafter Referred to as a Compound [139-1])

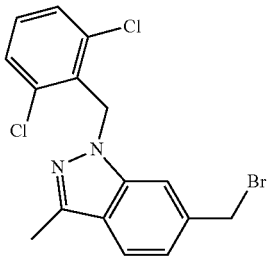 [SMILES: Cc1nn(Cc2c(Cl)cccc2Cl)c2cc(CBr)ccc12]

To a solution of the compound [127-2] obtained in the process (2) of Example 127 (197 mg) in ethanol (10 mL) was added sodium borohydride (32 mg), and the reaction mixture was stirred at room temperature for 1 hour. The reaction mixture was quenched with water, and extracted with ethyl acetate. The obtained organic layer was dried over anhydrous sodium sulfate, filtered, and the filtrate was concentrated under reduced pressure. To a solution of the obtained residue in dichloromethane (10 mL) were added carbon tetrabromide (304 mg) and triphenylphosphine (247 mg), and the reaction mixture was stirred at room temperature for 1 hour. The reaction mixture was concentrated under reduced pressure. The obtained residue was purified by silica gel column chromatography to give the titled compound (168 mg) as a white solid.

$^1$H-NMR (400 MHz, CDCl$_3$) δ: 7.59 (1H, d, J=8.3 Hz), 7.40-7.36 (3H, m), 7.23 (1H, d, J=8.1 Hz), 7.14 (1H, d, J=8.3 Hz), 5.70 (2H, s), 4.63 (2H, s), 2.50 (3H, s).

(2) Synthesis of [1-(2,6-dichlorobenzyl)-3-methyl-1H-indazole 6-yl]methanesulfonic acid [139]

To a solution of the compound [139-1] (119 mg) obtained in the process (1) in dimethyl sulfoxide (2 mL) and water (5 mL) was added sodium sulfite (49 mg), and the reaction mixture was stirred at 130° C. for 1 hour. The reaction mixture was quenched with water, and extracted with chloroform. The obtained organic layer was dried over anhydrous sodium sulfate, filtered, and the filtrate was concentrated under reduced pressure. The obtained residue was purified by silica gel column chromatography to give the titled compound (6 mg) as a white solid.

$^1$H-NMR (400 MHz, CD$_3$OD) δ: 7.65-7.63 (2H, brm), 7.45 (2H, d, J=7.8 Hz), 7.37-7.33 (1H, m), 7.29 (1H, s), 5.76 (2H, s), 4.22 (2H, s), 2.49 (3H, s).
ESI-MS found: 385 [M+H]$^+$ Example 140

Synthesis of 2-[1-(2,6-dichlorobenzyl)-3-ethyl-1H-indazole-6-yl]acetic acid [140] (Hereinafter Referred to as a Compound [140])

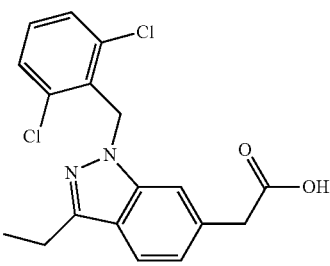 [SMILES: CCc1nn(Cc2c(Cl)cccc2Cl)c2cc(CC(=O)O)ccc12]

(1) Synthesis of 1-(4-bromo-2-fluorophenyl)propan-1-ol [140-1] (Hereinafter Referred to as a Compound [140-1])

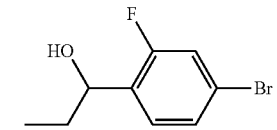

To a solution of 4-Bromo-2-fluorobenzaldehyde (5.1 g) in tetrahydrofuran (50 mL) was added 1M tetrahydrofuran solution of ethylmagnesium bromide (41 mL) at 0° C., and then the reaction mixture was stirred at room temperature for 1 hour. To the reaction mixture was added a saturated aqueous solution of ammonium chloride under ice-cooling, and the reaction mixture was extracted with ethyl acetate. The obtained organic layer was dried over anhydrous sodium sulfate, filtered, and the filtrate was concentrated under reduced pressure. The obtained residue was purified by silica gel column chromatography to give the titled compound (3.78 g) as a colorless liquid.

$^1$H-NMR (400 MHz, CDCl$_3$) δ: 7.39-7.16 (3H, m), 4.96-4.85 (1H, m), 1.88 (1H, d, J=2.9 Hz), 1.84-1.70 (2H, m), 0.94 (3H, t, J=7.4 Hz).

(2) Synthesis of 1-(4-bromo-2-fluorophenyl)propan-1-one [140-2] (Hereinafter Referred to as a Compound [140-2])

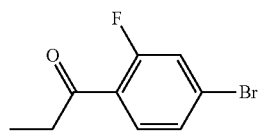

To a solution of the compound [140-1] obtained in the process (1) (3.78 g) in 1,4-dioxane (50 mL) was added manganese dioxide (10.6 g) at room temperature, and then the reaction mixture was stirred at 80° C. for 16 hours. The reaction mixture was filtered, and the filtrate was concentrated under reduced pressure. The obtained residue was purified by silica gel column chromatography to give the titled compound (1.84 g) as a white solid.

$^1$H-NMR (400 MHz, CDCl$_3$) δ: 7.77 (1H, t, J=8.2 Hz), 7.40-7.30 (2H, m), 3.02-2.94 (2H, m), 1.20 (3H, t, J=7.2 Hz).

(3) Synthesis of 6-bromo-3-ethyl-1H-indazole [140-3] (Hereinafter Referred to as a Compound [140-3])

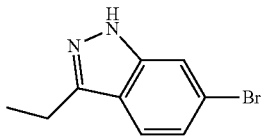

To a solution of the compound [140-2] obtained in the process (2) (1.84 g) in 1,4-dioxane (20 mL) was added hydrazine monohydrate (1.2 mL) at room temperature, and the reaction mixture was stirred at 110° C. for 17 hours. To the reaction mixture was added 0.1N-hydrochloric acid, and then extracted with ethyl acetate. The obtained organic layer was dried over anhydrous sodium sulfate, filtered, and the filtrate was concentrated under reduced pressure. The obtained residue was purified by silica gel column chromatography to give the titled compound (0.95 g) as a white solid.

$^1$H-NMR (400 MHz, CDCl$_3$) δ: 10.50-9.50 (1H, br), 7.61 (1H, s), 7.57 (1H, d, J=8.5 Hz), 7.28-7.21 (1H, m), 3.00 (2H, q, J=7.6 Hz), 1.41 (3H, t, J=7.6 Hz).

(4) Synthesis of 6-bromo-1-(2,6-dichlorobenzyl)-3-ethyl-1H-indazole [140-4] (Hereinafter Referred to as a Compound [140-4])

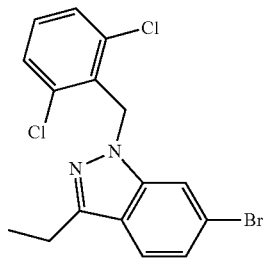 [SMILES: CCc1nn(Cc2c(Cl)cccc2Cl)c2cc(Br)ccc12]

The titled compound (295 mg) as a white solid was prepared from the compound [140-3](355 mg) obtained in the process (3) and 2,6-dichlorobenzyl chloride (610 mg) according to the method of the process (1) of Example 66.

$^1$H-NMR (400 MHz, CDCl$_3$) δ: 7.51 (2H, d, J=8.3 Hz), 7.37 (2H, d, J=8.1 Hz), 7.23 (1H, d, J=8.3 Hz), 7.18 (1H, d, J=9.8 Hz), 5.68 (2H, s), 2.92 (2H, q, J=7.6 Hz), 1.32 (3H, t, J=7.6 Hz).

(5) Synthesis of 6-allyl-1-(2,6-dichlorobenzyl)-3-ethyl-1H-indazole [140-5] (Hereinafter Referred to as a Compound [140-5])

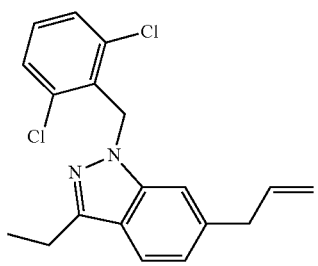 [SMILES: C=CCc1ccc2c(CC)nn(Cc3c(Cl)cccc3Cl)c2c1]

The titled compound (125 mg) as a white solid was prepared from the compound [140-4] obtained in the process (4) (159 mg) and allyltributyl tin (152 μL) according to the method of the process (2) of Example 66.

$^1$H-NMR (400 MHz, CDCl$_3$) δ: 7.57 (1H, d, J=8.3 Hz), 7.35 (2H, d, J=8.1 Hz) 7.26-7.18 (1H, m), 7.12 (1H, s), 6.93 (1H, d, J=8.1 Hz), 6.04-5.90 (1H, m), 5.70 (2H, s), 5.12-5.05 (2H, m), 3.48 (2H, d, J=6.6 Hz), 2.93 (2H, q, J=7.6 Hz), 1.33 (3H, t, J=7.6 Hz).

(6) Synthesis of [1-(2,6-dichlorobenzyl)-3-ethyl-1H-indazole-6-yl]acetaldehyde [140-6] (Hereinafter Referred to as a Compound [140-6])

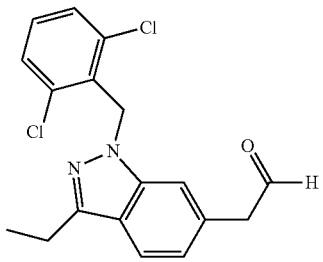 [SMILES: CCc1nn(Cc2c(Cl)cccc2Cl)c2cc(CC=O)ccc12]

The titled compound (71 mg) as a brown solid was prepared from the compound [140-5] obtained in the process (5) (125 mg) according to the method of the process (3) of Example 66.

1H-NMR (400 MHz, CDCl$_3$) δ: 9.76 (1H, t, J=2.2 Hz), 7.66 (1H, d, J=8.3 Hz), 7.37 (2H, d, J=8.1 Hz), 7.26-7.20 (1H, m), 7.18 (1H, s), 6.94 (1H, d, J=8.1 Hz), 5.72 (2H, s), 3.78 (2H, d, J=2.0 Hz), 2.94 (2H, q, J=7.6 Hz), 1.34 (3H, t, J=7.6 Hz).

(7) Synthesis of 2-[1-(2,6-dichlorobenzyl)-3-ethyl-1H-indazole-6-yl]acetic acid [140]

The titled compound (56 mg) as a brown solid was prepared from the compound [140-6] obtained in the process (6) (71 mg) according to the method of the process (4) of Example 66.

$^1$H-NMR (400 MHz, CD$_3$OD) δ: 7.65 (1H, d, J=8.3 Hz), 7.48-7.40 (3H, m), 7.34 (1H, dd, J=8.8, 7.3 Hz), 7.07 (1H, d, J=7.6 Hz), 5.73 (2H, s), 3.72 (2H, s), 2.90 (2H, q, J=7.6 Hz), 1.30 (3H, t, J=7.7 Hz).

ESI-MS found: 363 [M+H]$^+$

Example 141

Synthesis of potassium 2-[1-(2,6-dichlorobenzyl)-3-ethyl-1H-indazole-6-yl]acetate [141] (Hereinafter Referred to as a Compound [141])

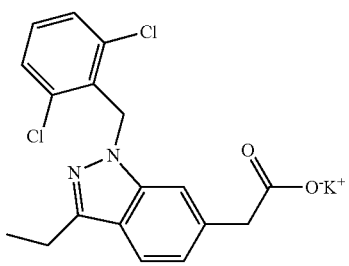

To a solution of the compound [140](42 mg) in ethanol (1 mL) was added an aqueous solution of 1N-potassium hydroxide (116 μL) at room temperature, and the solution was concentrated under reduced pressure to give the titled compound (110 mg) as a white solid.

¹H-NMR (400 MHz, CD₃OD) δ: 7.60 (1H, d, J=8.1 Hz), 7.46-7.38 (3H, m), 7.34-7.30 (1H, m), 7.13 (1H, d, J=8.1 Hz), 5.71 (2H, s), 3.61 (2H, s), 2.88 (2H, q, J=7.5 Hz), 1.28 (3H, t, J=7.6 Hz).
ESI-MS found: 363 [M−K+2H]⁺

Example 142

Synthesis of 2-[1-(2,6-dimethylbenzyl)-3-ethyl-1H-indazole-6-yl]acetic acid [142] (Hereinafter Referred to as a Compound [142])

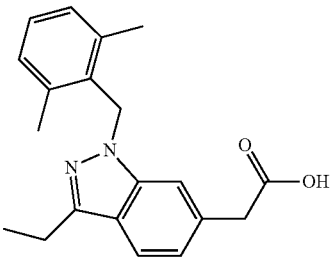 [SMILES: CCc1nn(Cc2c(C)cccc2C)c2cc(CC(=O)O)ccc12]

(1) Synthesis of 6-bromo-1-(2,6-dimethylbenzyl)-3-ethyl-1H-indazole [142-1](Hereinafter Referred to as a Compound [142-1])

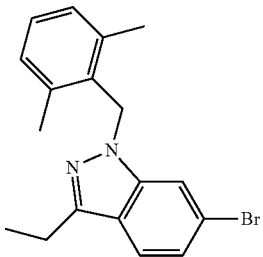 [SMILES: CCc1nn(Cc2c(C)cccc2C)c2cc(Br)ccc12]

The titled compound (0.80 g) as a white solid was prepared from the compound [140-3] obtained in the process (3) of Example 140 (1.03 g) and 2,6-dimethylbenzyl chloride (1.39 g) according to the method of the process (1) of Example 66.
¹H-NMR (400 MHz, CDCl₃) δ: 7.46 (1H, d, J=8.5 Hz), 7.21-7.08 (5H, m), 5.45 (2H, s), 2.93 (2H, q, J=7.6 Hz), 2.32 (6H, s), 1.35 (3H, t, J=7.6 Hz).

(2) Synthesis of 6-allyl-1-(2,6-dimethylbenzyl)-3-ethyl-1H-indazole [142-2](Hereinafter Referred to as a Compound [142-2])

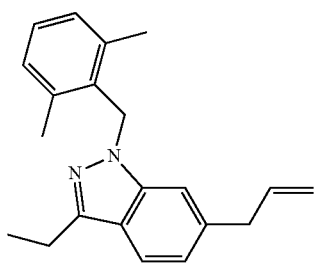 [SMILES: C=CCc1ccc2c(CC)nn(Cc3c(C)cccc3C)c2c1]

The titled compound (203 mg) as a colorless amorphous substance was prepared from the compound [142-1] obtained in the process (1) (225 mg) and allyltributyl tin (241 μL) according to the method of the process (2) of Example 66.
¹H-NMR (400 MHz, CDCl₃) δ: 7.55 (1H, d, J=8.3 Hz), 7.16 (1H, t, J=7.6 Hz), 7.06 (2H, d, J=7.6 Hz), 6.89 (1H, d, J=8.3 Hz), 6.71 (1H, s), 5.95-5.82 (1H, m), 5.49 (2H, s), 5.10-5.00 (2H, m), 3.37 (2H, d, J=6.8 Hz), 2.93 (2H, q, J=7.6 Hz), 2.33 (6H, s), 1.35 (3H, t, J=7.6 Hz).

(3) 1-(2,6-dimethylbenzyl)-3-ethyl-1H-indazole-6-carbaldehyde [142-3A] (Hereinafter Referred to as a Compound [142-3A]) and [1-(2,6-dimethylbenzyl)-3-ethyl-1H-indazole-6-yl]acetaldehyde [142-3B] (Hereinafter Referred to as a Compound [142-3B])

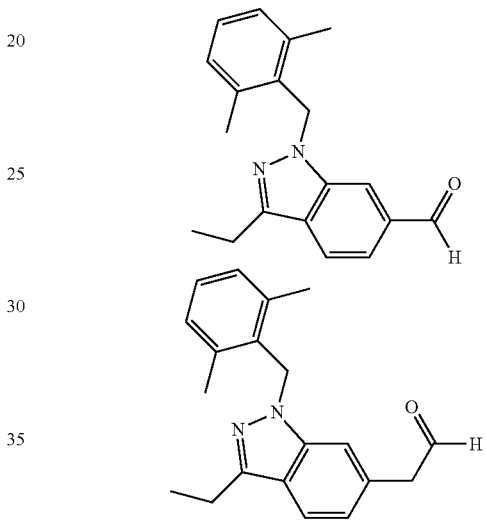

The titled compound [142-3A](37 mg) as a white solid was prepared from the compound [142-2](225 mg) obtained in the process (2) according to the method of the process (3) of Example 66. In addition, the titled compound [142-3B](51 mg) as a white solid was obtained.
[142-3A]
¹H-NMR (400 MHz, CDCl₃) δ: 9.91 (1H, s), 7.76 (1H, d, J=8.3 Hz), 7.58 (1H, d, J=8.3 Hz), 7.38 (1H, s), 7.23-7.19 (1H, m), 7.11 (2H, d, J=7.6 Hz), 5.61 (2H, s), 2.99 (2H, q, J=7.6 Hz), 2.34 (6H, s), 1.38 (3H, t, J=7.6 Hz).
[142-3B]
¹H-NMR (400 MHz, CDCl₃) δ: 9.67 (1H, s), 7.64 (1H, d, J=8.3 Hz) 7.20-7.16 (1H, m), 7.08 (2H, d, J=7.6 Hz), 6.88 (1H, d, J=7.8 Hz), 6.70 (1H, s), 5.51 (2H, s), 3.66 (2H, d, J=2.0 Hz), 2.96 (2H, q, J=7.6 Hz), 2.32 (6H, s), 1.36 (3H, t, J=7.6 Hz).

(4) Synthesis of 2-[1-(2,6-dimethylbenzyl)-3-ethyl-1H-indazole-6-yl]acetic acid [142]

The titled compound (35 mg) as a white solid was prepared from the compound [142-3B] obtained in the process (3) (51 mg) according to the method of the process (4) of Example 66.
¹H-NMR (400 MHz, CD₃OD) δ: 7.64 (1H, d, J=8.3 Hz), 7.17-7.00 (5H, m), 5.50 (2H, s), 3.64 (2H, s), 2.92 (2H, q, J=7.6 Hz), 2.27 (6H, s), 1.31 (3H, t, J=7.6 Hz).
ESI-MS found: 323 [M+H]⁺

Example 143

Synthesis of 1-(2,6-dimethylbenzyl)-3-ethyl-1H-indazole-6-carboxylic acid [143] (Hereinafter Referred to as a Compound [143])

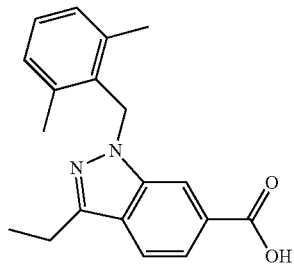 [SMILES: CCc1nn(Cc2c(C)cccc2C)c2cc(C(=O)O)ccc12]

The titled compound (25 mg) as a white solid was prepared from the compound [142-3A] obtained in the process (3) of Example 142 (37 mg) according to the method of the process (4) of Example 66.

$^1$H-NMR (400 MHz, DMSO-d$_6$) δ: 8.21 (1H, s), 7.80 (1H, d, J=8.3 Hz), 7.63 (1H, d, J=8.5 Hz), 7.14-7.03 (3H, m), 5.56 (2H, s), 2.87 (2H, q, J=7.5 Hz), 2.29 (6H, s), 1.24 (3H, t, J=7.6 Hz).

ESI-MS found: 309 [M+H]$^+$

Example 144

Synthesis of 1-(2,6-dichlorobenzyl)-3-ethyl-1H-indazole-6-carboxylic acid [144] (Hereinafter Referred to as a Compound [144])

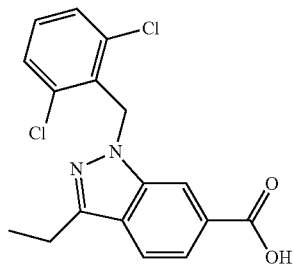 [SMILES: CCc1nn(Cc2c(Cl)cccc2Cl)c2cc(C(=O)O)ccc12]

To the compound [140-4] obtained in the process (4) of Example 140 (34 mg) were added water (2 mL), pyridine (32 μL), molybdenum hexacarbonyl (25 mg), 1,1'-bis(diphenylphosphino)ferrocene (9 mg) and palladium acetate (II) (2 mg) at room temperature, and then the reaction mixture was subjected to microwave irradiation at 160° C. for 20 minutes. The reaction mixture was quenched with water, and extracted with ethyl acetate. The obtained organic layer was dried over anhydrous sodium sulfate, filtered, and the filtrate was concentrated under reduced pressure. The obtained residue was purified by reverse phase preparative liquid chromatography to give the titled compound (5 mg) as a white solid.

$^1$H-NMR (400 MHz, CD$_3$OD) δ: 8.25 (1H, s), 7.79-7.75 (2H, m), 7.45 (2H, d, J=8.1 Hz), 7.35 (1H, t, J=8.1 Hz), 5.82 (2H, s), 2.94 (2H, q, J=7.6 Hz), 1.31 (3H, t, J=7.6 Hz).

ESI-MS found: 349 [M+H]$^+$

Example 145

Synthesis of 3-[1-(2,6-dichlorobenzyl)-3-ethyl-1H-indazole-6-yl]propionic acid [145] (Hereinafter Referred to as a Compound [145])

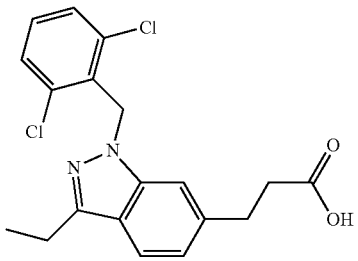 [SMILES: CCc1nn(Cc2c(Cl)cccc2Cl)c2cc(CCC(=O)O)ccc12]

(1) Synthesis of methyl (E)-3-[1-(2,6-dichlorobenzyl)-3-ethyl-1H-indazole-6-yl]acrylate [145-1] (Hereinafter Referred to as a Compound [145-1])

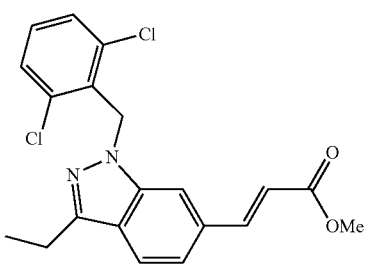 [SMILES: CCc1nn(Cc2c(Cl)cccc2Cl)c2cc(/C=C/C(=O)OC)ccc12]

The titled compound (132 mg) as a white solid was prepared from the compound [140-4] obtained in the process (4) of Example 140 (201 mg) and methyl acrylate (94 μL) according to the method of the process (1) of Example 121.

$^1$H-NMR (400 MHz, CDCl$_3$) δ: 7.77 (1H, d, J=16.1 Hz), 7.65 (1H, d, J=8.5 Hz) 7.44-7.34 (3H, m), 7.33-7.20 (2H, m), 6.47 (1H, d, J=16.1 Hz), 5.76 (2H, s), 3.83 (3H, s), 2.95 (2H, q, J=7.6 Hz), 1.34 (3H, t, J=7.6 Hz).

(2) Synthesis of methyl 3-[1-(2,6-dichlorobenzyl)-3-ethyl-1H-indazole-6-yl]propionate [145-2] (Hereinafter Referred to as a Compound [145-2])

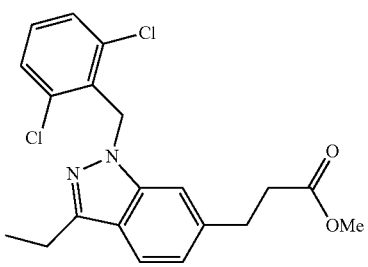 [SMILES: CCc1nn(Cc2c(Cl)cccc2Cl)c2cc(CCC(=O)OC)ccc12]

The compound [145-1] obtained in the process (1) (43 mg) was dissolved in a mixed solvent of ethyl acetate (2 mL) and tetrahydrofuran (2 mL). To the solution were added phenyl sulfide (2 μL) and 5% palladium on carbon (48 mg), and then the reaction mixture was stirred at room temperature for 24 hours under hydrogen atmosphere. The reaction mixture was filtered, and the filtrate was concentrated under reduced pressure. The obtained residue was purified by preparative thin layer chromatography to give the titled compound (5 mg) as a white solid.

$^{1}$H-NMR (400 MHz, CDCl$_{3}$) δ: 7.57 (1H, d, J=8.3 Hz), 7.36 (2H, d, J=7.8 Hz) 7.30-7.18 (1H, m), 7.14 (1H, s), 6.94 (1H, d, J=8.3 Hz), 5.70 (2H, s), 3.67 (3H, s), 3.05 (2H, t, J=7.8 Hz), 2.92 (2H, q, J=7.6 Hz), 2.66 (2H, t, J=7.7 Hz), 1.31 (3H, t, J=7.6 Hz).

(3) Synthesis of 3-[1-(2,6-dichlorobenzyl)-3-ethyl-1H-indazole-6-yl]propionic acid [145]

The titled compound (39 mg) as a white solid was prepared from the compound [145-2] obtained in the process (2) (40 mg) according to the method as described in the process (2) of Example 117.

$^{1}$H-NMR (400 MHz, CD$_{3}$OD) δ: 7.62 (1H, d, J=8.1 Hz), 7.44 (2H, d, J=8.1 Hz), 7.35 (1H, d, J=7.6 Hz), 7.31 (1H, s), 7.02 (1H, d, J=8.1 Hz), 5.72 (2H, s), 3.04 (2H, t, J=7.6 Hz), 2.89 (2H, q, J=7.6 Hz), 2.65 (2H, t, J=7, 7 Hz), 1.29 (3H, t, J=7.6 Hz).

ESI-MS found: 377 [M+H]$^{+}$

Example 146

Synthesis of (E)-3-[1-(2,6-dichlorobenzyl)-3-ethyl-1H-indazole-6-yl]acrylic acid [146] (Hereinafter Referred to as a Compound [146])

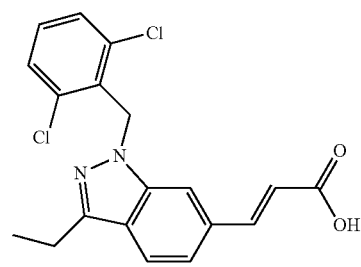 [SMILES: CCc1nn(Cc2c(Cl)cccc2Cl)c2cc(/C=C/C(=O)O)ccc12]

The titled compound (16 mg) as a white solid was prepared from the compound [145-1] obtained in the process (1) of Example 145 (21 mg) according to the method of the process (2) of Example 117.

$^{1}$H-NMR (400 MHz, CD$_{3}$OD) δ: 7.85-7.65 (3H, m), 7.50-7.30 (4H, m), 6.55 (1H, d, J=16.1 Hz), 5.80 (2H, s), 2.92 (2H, q, J=7.6 Hz), 1.31 (3H, t, J=7.7 Hz).

ESI-MS found: 375 [M+H]$^{+}$

Example 147

Synthesis of 2-[1-(2,6-dimethylbenzyl)-3-isopropyl-1H-indazole-6-yl]acetic acid [147] (Hereinafter Referred to as a Compound [147])

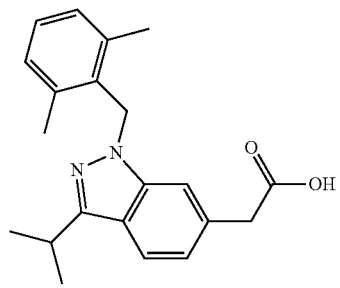 [SMILES: Cc1cccc(C)c1Cn1nc(C(C)C)c2ccc(CC(=O)O)cc21]

(1) Synthesis of 6-bromo-3-isopropyl-1H-indazole [147-1] (Hereinafter Referred to as a Compound [147-1])

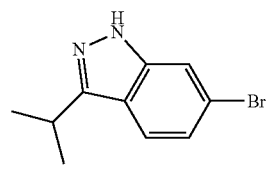

The titled compound (300 mg) as a white solid was prepared from 4-bromo-2-fluorobenzaldehyde (3.05 g) and 1 M tetrahydrofuran solution (25 mL) of isopropyl magnesium chloride according to the methods of the processes (1) to (3) of Example 140.

$^{1}$H-NMR (400 MHz, CDCl$_{3}$) δ: 7.64-7.61 (2H, m), 7.24 (1H, dd, J=8.5, 1.7 Hz), 3.45-3.35 (1H, m), 1.45 (6H, d, J=6.8 Hz).

(2) Synthesis of 6-bromo-1-(2,6-dimethylbenzyl)-3-isopropyl-1H-indazole [147-2] (Hereinafter Referred to as a Compound [147-2])

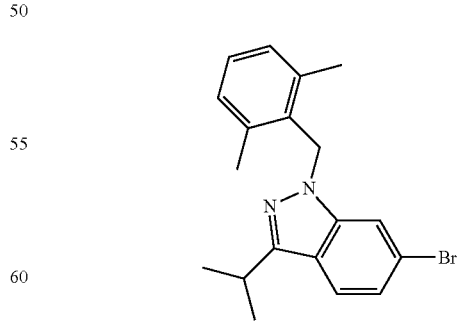

The titled compound (263 mg) as a white solid was prepared from the compound [147-1] obtained in the process (1) (300 mg) and 2,6-dimethylbenzyl chloride (292 mg) according to the method of the process (1) of Example 66.

¹H-NMR (400 MHz, CDCl₃) δ: 7.56 (1H, dd, J=8.5, 0.5 Hz), 7.21-7.17 (1H, m), 7.12-7.02 (4H, m), 5.48 (2H, s), 3.39-3.28 (1H, m), 2.33 (6H, s), 1.41 (6H, d, J=7.1 Hz).

(3) Synthesis of 2-[1-(2,6-dimethylbenzyl)-3-isopropyl-1H-indazole-6-yl]acetic acid [147]

The titled compound (41 mg) as a white solid was prepared from the compound [147-2] obtained in the process (2) (50 mg) according to the methods of the processes (2) to (4) of Example 66.

¹H-NMR (400 MHz, CD₃OD) δ: 7.69 (1H, dd, J=8.4, 0.6 Hz), 7.14-7.11 (1H, m), 7.06-7.04 (3H, m), 7.00 (1H, dd, J=8.3, 1.5 Hz), 5.50 (2H, s), 3.61 (2H, s), 3.38-3.29 (1H, m), 2.28 (6H, s), 1.39 (6H, d, J=6.8 Hz).

ESI-MS found: 337 [M+H]⁺

Example 148

Synthesis of 2-[3-cyclopropyl-1-(2,6-dichlorobenzyl)-1H-indazole-6-yl]acetic acid [148] (Hereinafter Referred to as a Compound [148])

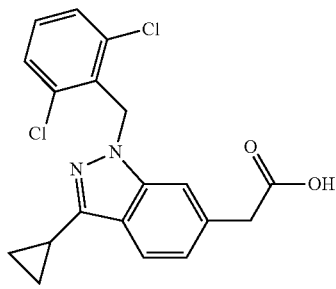 [SMILES: O=C(O)Cc1ccc2c(C3CC3)nn(Cc3c(Cl)cccc3Cl)c2c1]

(1) Synthesis of (4-bromo-2-fluorophenyl)cyclopropyl methanone [148-1] (Hereinafter Referred to as a Compound [148-1])

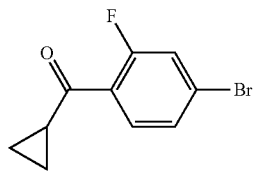 [SMILES: O=C(c1ccc(Br)cc1F)C1CC1]

To magnesium (265 mg), tetrahydrofuran (2 mL) was added, and cyclopropyl bromide (1.1 mL) was added slowly at room temperature, and then the reaction mixture was stirred at room temperature for 1 hour. To a solution of 4-bromo-2-fluorobenzaldehyde (2.0 g) in tetrahydrofuran (20 mL) was added the solution of the obtained Grignard reagent in tetrahydrofuran at 0° C., and then the reaction mixture was stirred at room temperature for 2 days. To the reaction mixture was added a saturated aqueous solution of ammonium chloride, and the reaction mixture was extracted with ethyl acetate. The obtained organic layer was dried over anhydrous sodium sulfate, filtered, and the filtrate was concentrated under reduced pressure. The obtained residue was purified by silica gel column chromatography to give the titled compound (2.19 g) as a brown oil.

¹H-NMR (400 MHz, CDCl₃) δ: 7.70-7.35 (1H, m), 7.40-7.20 (2H, m), 2.60-2.50 (1H, m), 1.43-1.25 (2H, m), 1.11-1.05 (2H, m).

(2) Synthesis of 6-bromo-3-cyclopropyl-1H-indazole [148-2] (Hereinafter Referred to as a Compound [148-2])

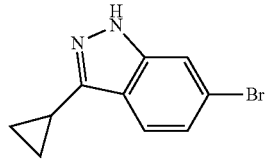 [SMILES: Brc1ccc2c(C3CC3)n[nH]c2c1]

The titled compound (483 mg) as a yellow solid was prepared from the compound [148-1] obtained in the process (1) (806 mg) according to the method of the process (3) of Example 140.

¹H-NMR (400 MHz, CDCl₃) δ: 10.0-9.50 (1H, br), 7.65-7.55 (2H, m), 7.23 (1H, d, J=8.5, 1.2 Hz), 2.24-2.16 (1H, m), 1.10-1.00 (4H, m).

(3) Synthesis of 6-bromo-3-cyclopropyl-1-(2,6-dichlorobenzyl)-1H-indazole [148-3] (Hereinafter Referred to as a Compound [148-3])

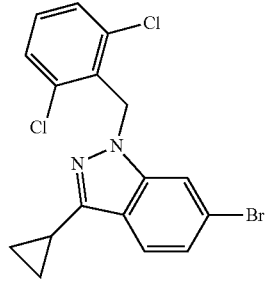 [SMILES: Clc1cccc(Cl)c1Cn1nc(C2CC2)c2ccc(Br)cc21]

The titled compound (299 mg) as a white solid was prepared from the compound [148-2] obtained in the process (2) (200 mg) and 2,6-dichlorobenzyl chloride (250 mg) according to the method of the process (1) of Example 66.

¹H-NMR (400 MHz, CDCl₃) δ: 7.51-7.49 (2H, m), 7.40-7.30 (2H, m), 7.27-7.10 (2H, m), 5.63 (2H, s), 2.16-2.08 (1H, m), 1.10-0.99 (4H, m).

(4) Synthesis of 2-[3-cyclopropyl-1-(2,6-dichlorobenzyl)-1H-indazole-6-yl]acetic acid [148]

The titled compound (28 mg) as a brown solid was prepared from the compound [148-3] obtained in the process (3) (286 mg) according to the methods of the processes (2) to (4) of Example 66.

¹H-NMR (400 MHz, CD₃OD) δ: 7.58 (1H, d, J=7.3 Hz), 7.45-7.36 (3H, m), 7.31 (1H, dd, J=8.8, 7.6 Hz), 7.10 (1H, d, J=7.3 Hz), 5.67 (2H, s), 3.59 (2H, s), 2.17-2.11 (1H, m), 0.94 (4H, d, J=5.4 Hz).

ESI-MS found: 375 [M+H]⁺

Example 149

Synthesis of 3-chloro-1-(2,6-dimethylbenzyl)-1H-indazole-6-carboxylic acid [149] (Hereinafter Referred to as a Compound [149])

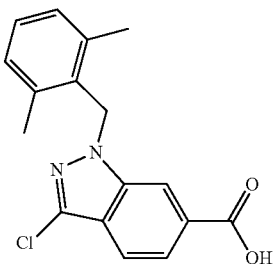

(1) Synthesis of 2,6-dimethyl benzyl 3-chloro-1-(2,6-dimethylbenzyl)-1H-indazole-6-carboxylate [149-1] (Hereinafter Referred to as a Compound [149-1])

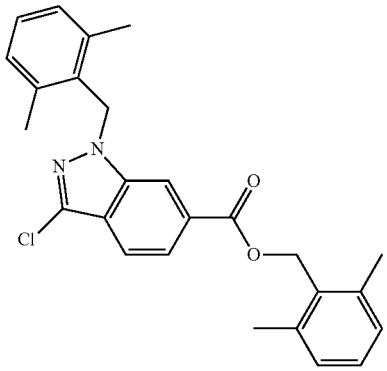 [SMILES: Cc1cccc(C)c1COC(=O)c1ccc2c(Cl)nn(Cc3c(C)cccc3C)c2c1]

To a solution of 1H-indazole-6-carboxylic acid (343 mg) in acetonitrile (10 mL) was added N-chlorosuccinimide (313 mg), and the reaction mixture was stirred at 60° C. for 2 hours. The reaction mixture was concentrated under reduced pressure, and then acetone (10 mL), potassium carbonate (883 mg) and 2,6-dimethylbenzyl chloride (724 mg) were added and the reaction mixture was stirred at room temperature for 2 days. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (195 mg) as a white solid.

$^1$H-NMR (400 MHz, CDCl$_3$) δ: 7.79 (1H, d, J=8.8 Hz), 7.65 (2H, d, J=8.1 Hz) 7.26-7.23 (1H, m), 7.14 (2H, d, J=7.6 Hz), 7.06-7.02 (1H, m), 6.92 (2H, d, J=7.6 Hz), 5.54 (2H, s), 5.40 (2H, s), 2.42 (6H, s), 2.25 (6H, s).

(2) Synthesis of 3-chloro-1-(2,6-dimethylbenzyl)-1H-indazole-6-carboxylic acid [149] (Hereinafter Referred to as a Compound [149])

The titled compound (15 mg) as a white solid was prepared from the compound [149-1] obtained in the process (1) (24 mg) according to the method of the process (2) of Example 117.

$^1$H-NMR (400 MHz, CD$_3$OD) δ: 8.19 (1H, s), 7.84 (1H, d, J=7.8 Hz), 7.71 (1H, d, J=8.5 Hz), 7.18-7.14 (1H, m), 7.08 (2H, d, J=7.3 Hz), 5.64 (2H, s), 2.31 (6H, s).

ESI-MS found: 315 [M+H]$^+$

Example 150

Synthesis of 3-cyano-1-(2,6-dichlorobenzyl)-1H-indazole-6-carboxylic acid [150] (Hereinafter Referred to as a Compound [150])

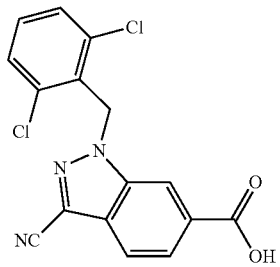 [SMILES: N#Cc1nn(Cc2c(Cl)cccc2Cl)c2cc(C(=O)O)ccc12]

(1) Synthesis of (2-amino-4-bromophenyl)acetonitrile [150-1] (Hereinafter Referred to as a Compound [150-1])

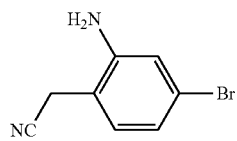 [SMILES: N#CCc1ccc(Br)cc1N]

To a solution of ethyl cyanoacetate (3.2 mL) in dimethyl sulfoxide (20 mL) was added sodium hydride (1.22 g) at room temperature, and then 1,4-dibromo-2-nitrobenzene (4.21 g) was added, and the reaction mixture was stirred at 90° C. for 3 hours. To the reaction mixture was added a saturated aqueous solution of ammonium chloride, and the reaction mixture was extracted with ethyl acetate. The obtained organic layer was dried over anhydrous sodium sulfate, filtered, and the filtrate was concentrated under reduced pressure. The obtained residue was suspended in an aqueous solution of 1M-sodium hydrogen carbonate (60 mL), and the reaction mixture was stirred at 80° C. for 24 hours. To the reaction mixture was added 2N-hydrochloric acid, and the reaction mixture was extracted with ethyl acetate. The obtained organic layer was dried over anhydrous sodium sulfate, filtered, and the filtrate was concentrated under reduced pressure. The obtained residue was dissolved in tetrahydrofuran (20 mL), ethanol (40 mL) and water (20 mL). To the solution were added ammonium chloride (4.03 g) and iron powder (4.22 g), and the reaction mixture was stirred at 100° C. for 5 hours. The reaction mixture was filtered through a cotton plug, and then the filtrate was extracted with ethyl acetate. The obtained organic layer was dried over anhydrous sodium sulfate, filtered, and the filtrate was concentrated under reduced pressure. The obtained residue was purified by silica gel column chromatography to give the titled compound (3.03 g) as a yellow solid.

$^1$H-NMR (400 MHz, CDCl$_3$) δ: 7.06 (1H, d, J=8.1 Hz), 6.94-6.91 (2H, m), 3.75 (2H, brs), 3.52 (2H, s).

(2) Synthesis of 6-bromo-1H-indazole-3-carbonitrile [150-2] (Hereinafter Referred to as a Compound [150-2])

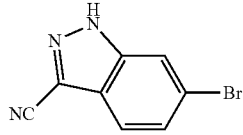 [SMILES: N#Cc1n[nH]c2cc(Br)ccc12]

To a solution of the compound [150-1] obtained in the process (1) (3.03 g) in 2N-hydrochloric acid (50 mL) was added sodium nitrite (1.61 g) at room temperature, and then the reaction mixture was stirred at room temperature for 20 hours. The precipitated solid was filtered, and the obtained solid was dissolved in acetic acid (15 mL). The reaction mixture was stirred at 100° C. for 2 hours. The reaction mixture was poured into ice water, an aqueous solution of 3N-sodium hydroxide was added. The reaction mixture was extracted with ethyl acetate. The obtained organic layer was dried over anhydrous sodium sulfate, filtered, and the filtrate was concentrated under reduced pressure. The obtained residue was purified by silica gel column chromatography to give the titled compound (1.55 g) as a yellow solid.

$^1$H-NMR (400 MHz, CD$_3$OD) δ: 7.91 (1H, s), 7.76 (1H, d, J=8.8 Hz), 7.49 (1H, d, J=8.8 Hz).

(3) Synthesis of 3-cyano-1-(2,6-dichlorobenzyl)-1H-indazole-6-carboxylic acid [150]

The titled compound (118 mg) as a white solid was prepared from the compound [150-2] obtained in the process (2) (570 mg) and 2,6-dichlorobenzyl chloride (747 mg) according to the method of Example 66.

$^1$H-NMR (400 MHz, DMSO-d$_6$) δ: 13.31 (1H, brs), 8.67 (1H, s), 7.97 (1H, d, J=8.5 Hz), 7.92 (1H, d, J=8.5 Hz), 7.55 (2H, d, J=7.8 Hz), 7.48-7.44 (1H, m), 6.04 (2H, s).

Example 151

Synthesis of 1-(2,6-dichlorobenzyl)-3-methyl-1H-pyrazolo[3,4-b]pyridine-6-carboxylic acid [151] (Hereinafter Referred to as a Compound [151])

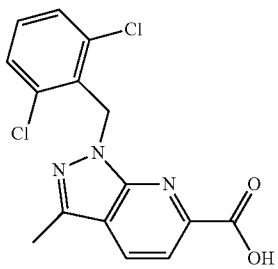 [SMILES: Cc1nn(Cc2c(Cl)cccc2Cl)c2nc(C(=O)O)ccc12]

(1) Synthesis of 2,6-dichloro-N-methoxy-N-methylnicotinamide [151-1] (Hereinafter Referred to as a Compound [151-1])

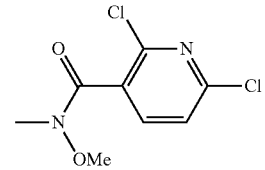

To a suspension of 2,6-dichloronicotinic acid (1.92 g), N,O-dimethylhydroxylamine hydrochloride (1.46 g) and triethylamine (2.1 mL) in N,N-dimethylformamide (30 mL) was added 1-ethyl-3-(3-dimethylaminopropyl)carbodiimide hydrochloride (2.30 g), and then the reaction mixture was stirred at room temperature for 4 days. The reaction mixture was diluted with ethyl acetate, washed with 5% aqueous solution of potassium hydrogen sulfate and a saturated aqueous solution of sodium hydrogen carbonate and brine. The obtained organic layer was dried over anhydrous sodium sulfate, filtered, and the filtrate was concentrated under reduced pressure. The obtained residue was purified by silica gel column chromatography to give the titled compound (1.61 g) as a white solid.

$^1$H-NMR (400 MHz, CDCl$_3$) δ: 7.65 (1H, d, J=8.0 Hz), 7.34 (1H, d, J=8.0 Hz), 3.51 (3H, s), 3.40 (3H, s).

ESI-MS found: 235 [M+H]$^+$ (2) Synthesis of 1-(2,6-dichloropyridine-3-yl)ethanone [151-2] (Hereinafter Referred to as a Compound [151-2])

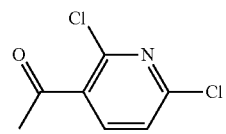

To a solution of the compound [151-1] obtained in the process (1) (487 mg) in tetrahydrofuran (10 mL) was added 2M diethyl ether solution of methylmagnesium iodide (1.24 mL) at 0° C., and then the reaction mixture was stirred at 70° C. for 72 hours. To the reaction mixture was added an aqueous solution of ammonium chloride, and the reaction mixture was extracted with ethyl acetate. The obtained organic layer was dried over anhydrous sodium sulfate, filtered, and the filtrate was concentrated under reduced pressure. The obtained residue was purified by silica gel column chromatography to give the titled compound (205 mg) as a colorless oil.

$^1$H-NMR (400 MHz, CDCl$_3$) δ: 7.93 (1H, d, J=8.1 Hz), 7.37 (1H, d, J=8.1 Hz), 2.71 (3H, s).

ESI-MS found: 190 [M+H]$^+$

(3) Synthesis of 6-chloro-3-methyl-1H-pyrazolo[3,4-b]pyridine [151-3](Hereinafter Referred to as a Compound [151-3])

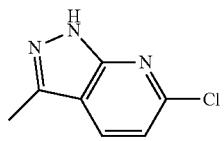

To a solution of the compound [151-2] obtained in the process (2) (205 mg) in dichloromethane (2.7 mL) was added titanium tetraisopropoxide (0.63 mL) at room temperature, and then the reaction mixture was stirred at room temperature for 15 minutes. Next, to the reaction mixture was added hydrazine monohydrate (0.11 mL), and stirred at room temperature for 3 hours. The reaction mixture was quenched with water, and stirred for 30 minutes, and then the insoluble materials were separated by filtration, and the insoluble materials were washed with chloroform. The filtrate was concentrated under reduced pressure to give a white solid. To the obtained solid, ethanol (1.5 mL) was added and the reaction mixture was subjected to microwave irradiation at 150° C. for 20 minutes. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (86 mg) as a white solid.

$^1$H-NMR (400-MHz, CD$_3$OD) δ: 10.15 (1H, brs), 7.97 (1H, d, J=8.3 Hz), 7.15 (1H, d, J=8.3 Hz), and 2.58 (3H, s).

ESI-MS found: 168 [M+H]$^+$

(4) Synthesis of 6-chloro-1-(2,6-dichlorobenzyl)-3-methyl-1H-pyrazolo[3,4-b]pyridine [151-4] (Hereinafter Referred to as a Compound [151-4])

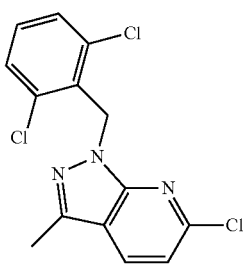 [SMILES: Cc1nn(Cc2c(Cl)cccc2Cl)c2nc(Cl)ccc12]

The titled compound (104 mg) as a white solid was prepared from the compound [151-3] obtained in the process (3) (86 mg) and 2,6-dichlorobenzyl chloride (208 mg) according to the method of the process (1) of Example 66.

H-NMR (400-MHz, CDCl$_3$) ?: 7.89 (1H, d, J=8.3 Hz), 7.39-7.31 (2H, m), 7.26-7.18 (1H, m), 7.09 (1H, d, J=8.3 Hz), 5.83 (2H, s), 2.47 (3H, s).

ESI-MS found: 326 [M+H]$^+$

(5) Synthesis of 1-(2,6 dichlorobenzyl)-3-methyl-1H-pyrazolo[3,4-b]pyridine-6-carbonitrile [151-5] (hereinafter referred to as a compound [151-5])

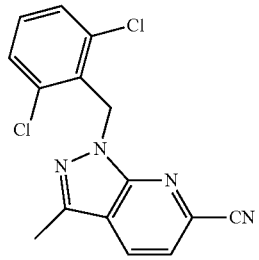 [SMILES: Cc1nn(Cc2c(Cl)cccc2Cl)c2nc(C#N)ccc12]

The compound [151-4] obtained in the process (4) (66 mg), zinc powder (4 mg), zinc cyanide (18 mg) and a solution of [1,1'-bis(diphenylphosphino)ferrocene]dichloropalladium (II) (18 mg) in N,N-dimethylformamide (2 mL) were subjected to microwave irradiation at 150° C. for 10 minutes under argon atmosphere. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (38 mg) as a white solid.

$^1$H-NMR (400-MHz, CDCl$_3$) ?: 8.09 (1H, d, J=8.1 Hz), 7.46 (1H, d, J=8.1 Hz), 7.37 (2H, d, J=8.1 Hz), 7.25 (1H, d, J=8.3 Hz), 5.90 (2H, s), 2.53 (3H, s).

ESI-MS found: 317 [M+H]$^+$

(6) Synthesis of 1-(2,6-dichlorobenzyl)-3-methyl-1H-pyrazolo[3,4-b]pyridine-6-carboxylic acid [151]

To a solution of the compound [151-5] obtained in the process (5) (38 mg) in tetrahydrofuran (0.5 mL) and methanol (0.5 mL) was added 3N-sodium hydroxide solution (0.6 mL), and then the reaction mixture was subjected to microwave irradiation at 150° C. for 5 minutes. To the reaction mixture, 1M hydrochloric acid (0.46 mL) was added, and the solvent was concentrated under reduced pressure. The obtained residue was purified by reverse phase preparative liquid chromatography to give the titled compound (34 mg) as a white solid.

$^1$H-NMR (400 MHz, DMSO-d$_6$) δ: 13.42 (1H, s), 8.37 (1H, d, J=8.3 Hz), 7.86 (1H, d, J=8.3 Hz), 7.52 (1H, d, J=8.7 Hz), 7.52 (1H, d, J=7.4 Hz), 7.42 (1H, dd, J=8.7, 7.4 Hz), 5.82 (2H, s), 2.44 (3H, s).

ESI-MS found: 336 [M+H]$^+$

Example 152

Synthesis of 1-(2,6-dichlorobenzyl)-3-methyl-6-(1H-tetrazole-5-ylmethyl)-1H-pyrazolo[3,4-b]pyridine [152] (Hereinafter Referred to as a Compound [152])

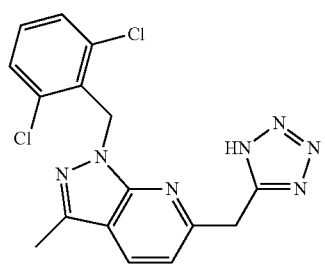 [SMILES: Cc1nn(Cc2c(Cl)cccc2Cl)c2nc(Cc3nnn[nH]3)ccc12]

(1) Synthesis of [1-(2,6-dichlorobenzyl)-3-methyl-1H-pyrazolo[3,4-b]pyridine-6-yl]acetonitrile [152-1] (Hereinafter Referred to as a Compound [152-1])

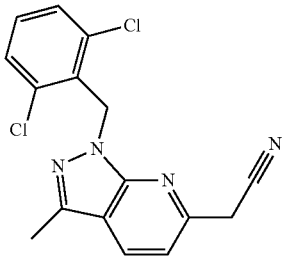 [SMILES: Cc1nn(Cc2c(Cl)cccc2Cl)c2nc(CC#N)ccc12]

To a solution of the compound [151-4] obtained in the process (4) of Example 151 (33 mg) in toluene (1.0 mL) was added acetonitrile (52 µL) under argon atmosphere, and then the reaction mixture was cooled to 0° C. Subsequently, 1.0M tetrahydrofuran solution (2.0 mL) of sodium hexamethyldisilazane was dropped, and the reaction mixture was stirred at 0° C. for 1 hour. To the reaction mixture was added a saturated aqueous solution of ammonium chloride, and the reaction mixture was extracted with ethyl acetate. The obtained organic layer was washed with brine, dried over anhydrous sodium sulfate, filtered, and the filtrate was concentrated under reduced pressure. The obtained residue was purified by silica gel column chromatography to give the titled compound (16 mg) as a yellow solid.
$^1$H-NMR (400 MHz, CDCl$_3$) δ: 7.98 (1H, d, J=8.1 Hz), 7.35 (2H, d, J=7.8 Hz), 7.24-7.20 (1H, m), 7.17 (1H, d, J=8.1 Hz), 5.86 (2H, s), 4.04 (2H, s), 2.50 (3H, s)
ESI-MS found: 331 [M+H]$^+$ (2) Synthesis of 1-(2,6-dichlorobenzyl)-3-methyl-6-(1H-tetrazole-5-ylmethyl)-1H-pyrazolo[3,4-b]pyridine [152]

The titled compound (4.4 mg) as a yellowish white solid was prepared from the compound [152-1] obtained in the process (1) (28 mg) according to the method of the process (2) of Example 134.
$^1$H-NMR (400 MHz, CD$_3$OD) δ: 8.11 (1H, d, J=8.0 Hz), 7.37 (2H, d, J=7.6 Hz), 7.29 (1H, dd, J=8.8, 7.1 Hz), 7.21 (1H, d, J=8.3 Hz), 5.79 (2H, s), 4.64 (2H, s), 2.45 (3H, s).
ESI-MS found: 374 [M+H]$^+$ Example 153

Synthesis of 1-(2,6-dichlorobenzyl)-3-methyl-1H-pyrazolo[4,3-b]pyridine-6-carboxylic acid [153] (Hereinafter Referred to as a Compound [153])

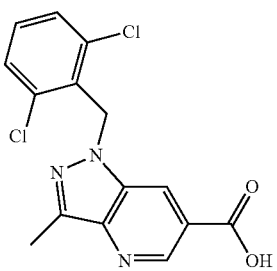 [SMILES: Cc1nn(Cc2c(Cl)cccc2Cl)c2cc(C(=O)O)cnc12]

(1) Synthesis of 1-(5-bromo-3-fluoropyridine-2-yl)ethanone [153-1] (Hereinafter Referred to as a Compound [153-1])

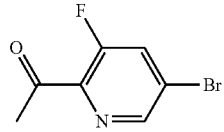

To a solution of 5-bromo-3-fluoropyridin-2-carbonitrile (2.2 g) obtained by the method described in the document (Journal of Organic Chemistry, 2009, Vol. 74, p. 4547) in toluene (22 mL) was added 3.0M tetrahydrofuran solution (5.4 mL) of methylmagnesium chloride at room temperature and the reaction mixture was stirred for 20 minutes. The reaction mixture was quenched with water, and extracted with chloroform. The obtained organic layer was washed with brine, dried over anhydrous sodium sulfate, filtered, and the filtrate was concentrated under reduced pressure. The obtained residue was purified by silica gel column chromatography to give the titled compound (793 mg) as a pale yellow oil.
$^1$H-NMR (400 MHz, CDCl$_3$) δ: 8.56 (1H, s), 7.74 (1H, d, J=9.6 Hz), 2.68 (3H, s)

(2) Synthesis of 6-bromo-3-methyl-1H-pyrazolo[4,3-b]pyridine [153-2] (Hereinafter Referred to as a Compound [153-2])

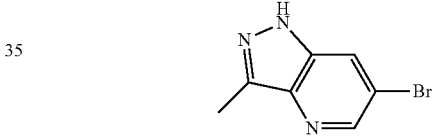

To a solution of the compound [153-1] obtained in the process (1) (1.2 g) in ethylene glycol (11 mL) was added hydrazine monohydrate (11 mL) at room temperature, and then the reaction mixture was stirred at 140° C. for 17 hours. After cooling to room temperature, to the reaction mixture was added water, and the precipitated solid was filtered to give the titled compound (788 mg) as a yellow crystal.
$^1$H-NMR (400 MHz, CD$_3$OD) δ: 8.51 (1H, d, J=1.7 Hz), 8.16 (1H, d, J=2.0 Hz), 2.59 (3H, s).
ESI-MS found: 212 [M+H]$^+$ (3) Synthesis of 6-bromo-1-(2,6-dichlorobenzyl)-3-methyl-1H-pyrazolo[4,3-b]pyridine [153-3] (Hereinafter Referred to as a Compound [153-3])

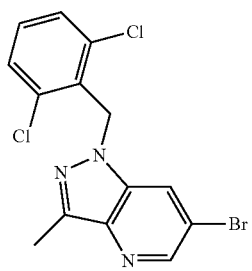 [SMILES: Cc1nn(Cc2c(Cl)cccc2Cl)c2cc(Br)cnc12]

The titled compound (274 mg) as a white solid was prepared from the compound [153-2] obtained in the process (2) (196 mg) and 2,6-dichlorobenzyl chloride according to the method of the process (1) of Example 66.

$^1$H-NMR (400 MHz, CDCl$_3$) δ: 8.51 (1H, d, J=1.7 Hz), 7.80 (1H, d, J=1.7 Hz), 7.39 (2H, d, J=7.8 Hz), 7.29-7.26 (1H, m), 5.69 (2H, s), 2.60 (3H, s).

ESI-MS found: 370 [M+H]$^+$ (4) Synthesis of 1-(2,6-dichlorobenzyl)-3-methyl-1H-pyrazolo[4,3-b]pyridine-6-carbonitrile [153-4] (Hereinafter Referred to as a Compound [153-4])

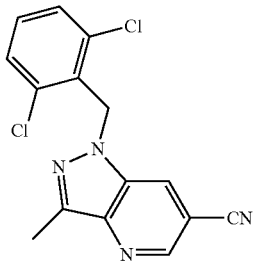 [SMILES: Cc1nn(Cc2c(Cl)cccc2Cl)c2cc(C#N)cnc12]

To a solution of the compound [153-3] obtained in the process (3) (100 mg) in N,N-dimethylformamide (1.3 mL) were added zinc cyanide (25 mg) and tetrakis(triphenylphosphine)palladium(0) (34 mg) at room temperature, and then the reaction mixture was subjected to microwave irradiation at 95° C. for 3 hours. After cooling to room temperature, to the reaction mixture was added a saturated aqueous solution of potassium carbonate, and extracted with ethyl acetate. The obtained organic layer was washed with brine, dried over anhydrous sodium sulfate, filtered, and the filtrate was concentrated under reduced pressure. The obtained residue was purified by silica gel column chromatography to give the titled compound (44 mg) as a white solid.

$^1$H-NMR (400 MHz, CDCl$_3$) δ: 8.69 (1H, d, J=1.5 Hz), 7.93 (1H, d, J=1.5 Hz), 7.41 (2H, d, J=8.1 Hz), 7.33-7.29 (1H, m), 5.80 (2H, s), 2.65 (3H, s).

(5) Synthesis of 1-(2,6-dichlorobenzyl)-3-methyl-1H-pyrazolo[4,3-b]pyridine-6-carboxylic acid [153] (Hereinafter Referred to as a Compound [153])

To a solution of the compound [153-4] obtained in the process (4) (44 mg) in ethanol (3.5 mL) was added an aqueous solution of 3N-sodium hydroxide (3.5 mL) at room temperature, and then the reaction mixture was stirred at 110° C. for 15 minutes. After cooling to room temperature, to the reaction mixture was added 3N-hydrochloric acid, and extracted with chloroform. The obtained organic layer was washed with brine, dried over anhydrous sodium sulfate, filtered, and the filtrate was concentrated under reduced pressure. The obtained residue was purified by reverse phase preparative liquid chromatography to give the titled compound (28 mg) as a white solid.

$^1$H-NMR (400 MHz, CD$_3$OD) δ: 9.05 (1H, s), 8.64 (1H, s), 7.46 (2H, d, J=7.8 Hz), 7.38-7.34 (1H, m), 5.87 (2H, s), 2.56 (3H, s)

ESI-MS found: 336 [M+H]$^+$

Example 154

Synthesis of potassium 1-(2,6-dichlorobenzyl)-3-methyl-1H-pyrazolo[4,3-b]pyridine-6-carboxylate [154] (Hereinafter Referred to as a Compound [154])

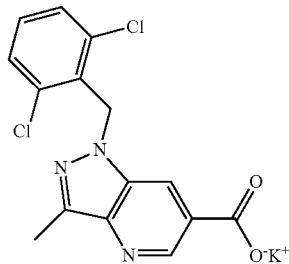

To a solution of the compound [153] (22 mg) in ethanol (2.0 mL) was added an aqueous solution of 1N-potassium hydroxide (66 μL) at room temperature, and the solution was concentrated under reduced pressure, whereby to give the titled compound (25 mg) as a white solid.

$^1$H-NMR (400 MHz, CD$_3$OD) δ: 9.06 (1H, s), 8.55 (1H, s), 7.44 (2H, d, J=7.8 Hz), 7.36-7.32 (1H, m), 5.83 (2H, s), 2.54 (3H, s).

ESI-MS found: 336 [M+H]$^+$

Example 155

Synthesis of (E)-3-[1-(2,6-dichlorobenzyl)-3-methyl-1H-pyrazolo[4,3-b]pyridine-6-yl]acrylic acid [155] (Hereinafter Referred to as a Compound [155])

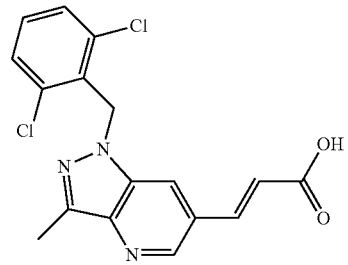 [SMILES: Cc1nn(Cc2c(Cl)cccc2Cl)c2cc(/C=C/C(=O)O)cnc12]

(1) Synthesis of methyl (E)-3-[1-(2,6-dichlorobenzyl)-3-methyl-1H-pyrazolo[4,3-b]pyridine-6-yl]acrylate [155-1] (Hereinafter Referred to as a Compound [155-1])

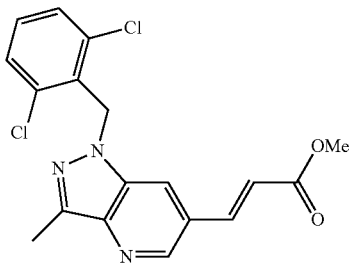 [SMILES: COC(=O)/C=C/c1cnc2c(C)nn(Cc3c(Cl)cccc3Cl)c2c1]

The titled compound (89 mg) as a white solid was prepared from the compound [153-3] obtained in the process (3) of Example 153 (100 mg) according to the method of the process (1) of Example 121.

$^1$H-NMR (400 MHz, CDCl$_3$) δ: 8.68 (1H, s), 7.79 (1H, d, J=16.1 Hz), 7.70 (1H, s), 7.41 (2H, d, J=8.1 Hz), 7.31-7.26 (1H, m), 6.55 (1H, d, J=16.1 Hz), 5.77 (2H, s), 3.84 (3H, s), 2.63 (3H, s).

ESI-MS found: 376 [M+H]$^+$ (2) Synthesis of (E)-3-[1-(2,6-dichlorobenzyl)-3-methyl-1H-pyrazolo[4,3-b]pyridine-6-yl]acrylic acid [155]

The titled compound (9.0 mg) as a white solid was prepared from the compound [155-1] obtained in the process (1) (25 mg) according to the method of the process (2) of Example 117.

$^1$H-NMR (400 MHz, CDCl$_3$) δ: 8.65 (1H, s), 7.76 (1H, d, J=16.3 Hz), 7.71 (1H, s), 7.39 (2H, d, J=8.1 Hz), 7.29-7.26 (1H, m), 6.52 (1H, d, J=15.9 Hz), 5.76 (2H, s), 2.61 (3H, s).

ESI-MS found: 362 [M+H]$^+$

Example 156

Synthesis of 1-(2,6-dichlorobenzyl)-3-methyl-6-(1H-tetrazole-5-yl)-1H-pyrazolo[4,3-b]pyridine [156] (Hereinafter Referred to as a Compound [156])

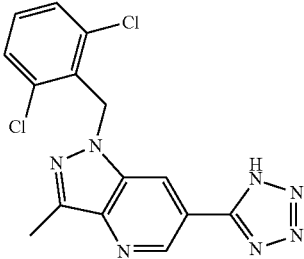 [SMILES: Cc1nn(Cc2c(Cl)cccc2Cl)c2cc(-c3nnn[nH]3)cnc12]

The titled compound (14 mg) as a white solid was prepared from the compound [153-4] obtained in the process (4) of Example 153 (71 mg) according to the method of the process (2) of Example 134.

$^1$H-NMR (400 MHz, CD$_3$OD) δ: 9.14 (1H, d, J=1.5 Hz), 8.74 (1H, d, J=1.5 Hz), 7.47 (2H, d, J=8.1 Hz), 7.37 (1H, dd, J=8.8, 7.3 Hz), 5.89 (2H, s), 2.58 (3H, s).

ESI-MS found: 360 [M+H]$^+$

Example 157

Synthesis of potassium 5-[1-(2,6-dichlorobenzyl)-3-methyl-1H-pyrazolo[4,3-b]pyridine-6-yl]-1H-tetrazole-1-ide [157] (Hereinafter Referred to as a Compound [157])

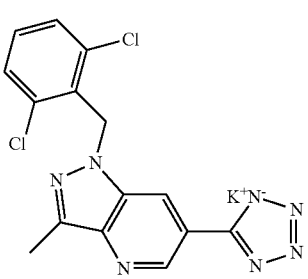

To a solution of the compound [156](30 mg) in ethanol (2.0 mL) was added an aqueous solution of 1N-potassium hydroxide (84 μL) at room temperature, and the solution was concentrated under reduced pressure to give the titled compound (32 mg) as a yellow solid.

$^1$H-NMR (400 MHz, CD$_3$OD) δ: 9.17 (1H, s), 8.69 (1H, s), 7.46 (2H, d, J=7.8 Hz), 7.38-7.34 (1H, m), 5.88 (2H, s), 2.57 (3H, s)

ESI-MS found: 360 [M−K+2H]$^+$

Example 158

Synthesis of 1-(2,3-dichlorobenzyl)-3-methyl-6-(1H-tetrazole-5-yl)-1H-pyrazolo[4,3-b]pyridine [158] (Hereinafter Referred to as a Compound [158])

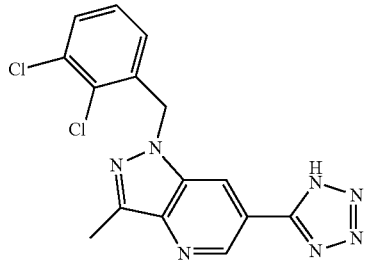 [SMILES: Cc1nn(Cc2cccc(Cl)c2Cl)c2cc(-c3nnn[nH]3)cnc12]

The titled compound (20 mg) as a white solid was prepared from the compound [153-2] obtained in the process (2) of Example 153 (103 mg) and 2,3-dichlorobenzyl chloride (100 μL) according to the methods of the processes (3) and (4) of Example 153 and the process (2) of Example 134.

$^1$H-NMR (400 MHz, CD$_3$OD) δ: 9.19 (1H, d, J=1.5 Hz), 8.64 (1H, d, J=1.5 Hz), 7.50 (1H, d, J=8.3 Hz), 7.25-7.21 (1H, m), 6.88 (1H, d, J=7.6 Hz), 6.82 (2H, s) 2.66 (3H, s).

ESI-MS found: 360 [M+H]$^+$

Example 159

Synthesis of potassium 5-[1-(2,3-dichlorobenzyl)-3-methyl-1H-pyrazolo[4,3-b]pyridine-6-yl]-1H-tetrazole-1-ide [159] (Hereinafter Referred to as a Compound [159])

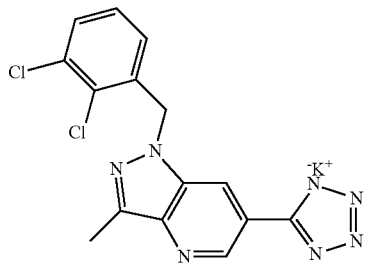

To a solution of the compound [158](20 mg) in ethanol (1.0 mL) was added an aqueous solution of 1N-potassium hydroxide (63 μL) at room temperature, and the solution was concentrated under reduced pressure to give the titled compound (24 mg) as a yellow solid.

$^1$H-NMR (400 MHz, CD$_3$OD) δ: 9.25 (1H, d, J=1.5 Hz), 8.55 (1H, d, J=1.5 Hz), 7.48 (1H, d, J=8.1 Hz), 7.23-7.19 (1H, m), 6.81 (1H, d, J=7.6 Hz), 5.80 (2H, s) 2.65 (3H, s).

ESI-MS found: 360 [M−K+2H]$^+$

Example 160

Synthesis of 1-(2-chloro-6-methylbenzyl)-3-methyl-6-(1H-tetrazole-5-yl)-1H-pyrazolo[4,3-b]pyridine [160] (Hereinafter Referred to as a Compound [160])

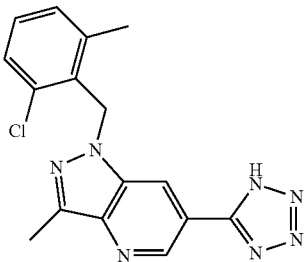 [SMILES: Cc1cccc(Cl)c1Cn1nc(C)c2ncc(-c3nnn[nH]3)cc21]

The titled compound (44.5 mg) as a white solid was prepared from the compound [153-2] obtained in the process (2) of Example 153 (111.4 mg) and 2-chloro-6-methylbenzyl chloride (138.0 mg) according to the methods of the process (1) of Example 66, the process (4) of Example 153 and the process (2) of Example 134.

$^1$H-NMR (400 MHz, CD$_3$OD) δ: 9.12 (1H, d, J=1.5 Hz), 8.69 (1H, d, J=1.5 Hz), 7.31 (1H, d, J=7.2 Hz), 7.28-7.25 (2H, m), 5.79 (2H, s), 2.59 (3H, s), 2.49 (3H, s).

ESI-MS found: 340 [M+H]$^+$

Example 161

Synthesis of potassium 5-[1-(2-chloro-6-methylbenzyl)-3-methyl-1H-pyrazolo[4,3-b]pyridine-6-yl]-1H-tetrazole-1-ide [161] (Hereinafter Referred to as a Compound [161])

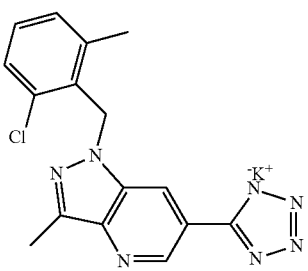

To a solution of the compound [160](44.5 mg) in ethanol (4.5 mL) was added an aqueous solution of 1N-potassium hydroxide (133 μL) at room temperature, and the solution was concentrated under reduced pressure to give the titled compound (46.0 mg) as a white solid.

$^1$H-NMR (400 MHz, CDCl$_3$) δ: 9.15 (1H, d, J=1.2 Hz), 8.64 (1H, s), 7.30 (1H, d, J=7.1 Hz), 7.27-7.22 (2H, m), 5.76 (2H, s), 2.58 (3H, s), 2.48 (3H, s).

ESI-MS found: 340 [M+K−2H]$^+$

Example 162

Synthesis of 3-methyl-1-(naphthalene-1-yl)methyl-6-(1H-tetrazole-5-yl)-1H-pyrazolo[4,3-b]pyridine [162] (Hereinafter Referred to as a Compound [162])

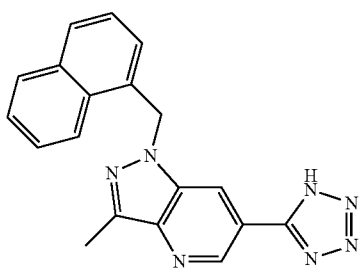 [SMILES: Cc1nn(Cc2cccc3ccccc23)c2cc(-c3nnn[nH]3)cnc12]

The titled compound (44 mg) as a white solid was prepared from the compound [153-2] obtained in the process (2) of Example 153 (80 mg) and 1-(chloromethyl)naphthalene (104 mg) according to the methods of the process (1) of Example 66, the process (4) of Example 153 and the process (2) of Example 134.

$^1$H-NMR (400 MHz, CD$_3$OD) δ: 9.20 (1H, d, J=1.2 Hz), 8.52 (1H, d, J=1.2 Hz), 8.25 (1H, d, J=8.3 Hz), 7.90 (1H, d, J=6.8 Hz), 7.84 (1H, d, J=8.3 Hz), 7.56-7.51 (2H, m), 7.43-7.39 (1H, m), 7.16 (1H, d, J=6.8 Hz), 6.16 (2H, s), 2.67 (3H, s).

Example 163

Synthesis of 1-(2,5-dimethylbenzyl)-3-methyl-6-(1H-tetrazole-5-yl)-1H-pyrazolo[4,3-b]pyridine [163] (Hereinafter Referred to as a Compound [163])

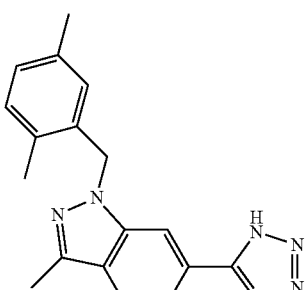

The titled compound (57 mg) as a white solid was prepared from the compound [153-2] obtained in the process (2) of Example 153 (102 mg) and 2,5-dimethylbenzyl chloride (112 mg) according to the methods of the process (1) of Example 66, the process (4) of Example 153 and the process (2) of Example 134.

¹H-NMR (400 MHz, CD₃OD) δ: 9.17 (1H, d, J=1.7 Hz), 8.48 (1H, d, J=1.5 Hz), 7.07 (1H, d, J=7.8 Hz), 7.00 (1H, d, J=7.3 Hz), 6.72 (1H, s), 5.62 (2H, s), 2.65 (3H, s), 2.31 (3H, s), 2.19 (3H, s).

Example 164

Synthesis of 1-(2-chloro-6-cyclopropylbenzyl)-3-methyl-6-(1H-tetrazole-5-yl)-1H-pyrazolo[4,3-b]pyridine [164] (Hereinafter Referred to as a Compound [164])

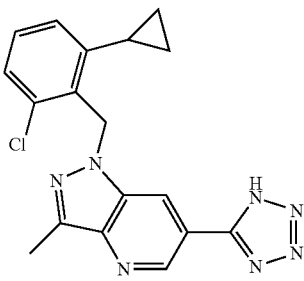 [SMILES: Cc1nn(Cc2c(Cl)cccc2C2CC2)c2cc(-c3nnn[nH]3)cnc12]

The compound [156] obtained in Example 156 (30 mg), cyclopropylboronic acid (15 mg), tetrakis(triphenylphosphine)palladium(0) (5 mg) and potassium carbonate (35 mg) were suspended in a mixed solvent (1.2 mL) of 1,4-dioxane/water (volume ratio 2/1), and the reaction mixture was subjected to microwave irradiation at 160° C. for 1 hour. After cooling to room temperature, to the reaction mixture was added 3N-hydrochloric acid, and extracted with ethyl acetate. The obtained organic layer was washed with water and brine successively, dried over anhydrous sodium sulfate, filtered, and the filtrate was concentrated under reduced pressure. The obtained residue was purified by reverse phase preparative liquid chromatography to give the titled compound (13 mg) as a white solid.

¹H-NMR (400 MHz, CD₃OD) δ: 9.12 (1H, d, J=1.5 Hz), 8.68 (1H, d, J=1.5 Hz), 7.27-7.26 (2H, m), 7.13 (1H, d, J=6.8 Hz), 6.00 (2H, s), 2.59 (3H, s), 2.24-2.17 (1H, m), 0.92-0.89 (2H, m), 0.70-0.68 (2H, m).

ESI-MS found: 366 [M+H]⁺

Example 165

Synthesis of potassium 5-[1-(2-chloro-6-cyclopropylbenzyl)-3-methyl-1H-pyrazolo[4,3-b]pyridine-6-yl]-1H-tetrazole-1-ide [165] (Hereinafter Referred to as a Compound [165])

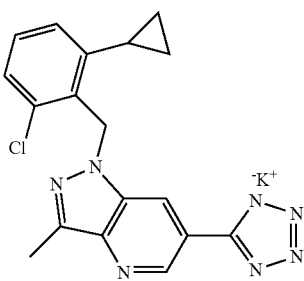

To a solution of the compound [164] (22 mg) in ethanol (2.0 mL) was added an aqueous solution of 1N-potassium hydroxide (60 μL) at room temperature, and the solution was concentrated under reduced pressure to give the titled compound (20 mg) as a pale yellow solid.

¹H-NMR (400 MHz, CD₃OD) δ: 9.19 (1H, d, J=1.5 Hz), 8.60 (1H, d, J=1.5 Hz), 7.32-7.25 (2H, m), 7.12 (1H, d, J=7.3 Hz), 5.96 (2H, s), 2.57 (3H, s), 2.18-2.16 (1H, m), 0.90-0.86 (2H, m), 0.68-0.66 (2H, m).

ESI-MS found: 366 [M−K+2H]⁺

Example 166

Synthesis of 1-(2,6-dicyclopropylbenzyl)-3-methyl-6-(1H-tetrazole-5-yl)-1H-pyrazolo[4,3-b]pyridine [166] (Hereinafter Referred to as a Compound [166])

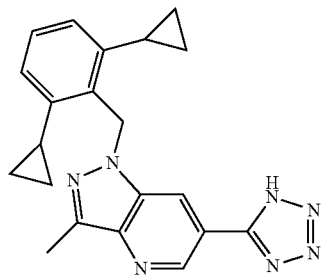 [SMILES: Cc1nn(Cc2c(C3CC3)cccc2C2CC2)c2cc(-c3nnn[nH]3)cnc12]

The compound [156] obtained in Example 156 (47 mg), cyclopropylboronic acid (33 mg), tetrakis(triphenylphosphine)palladium(0) (8 mg) and potassium carbonate (54 mg) were suspended in a mixed solvent (2.0 mL) of 1,4-dioxane/water (volume ratio 2/1), and the reaction mixture was subjected to microwave irradiation at 160° C. for 1 hour. After cooling to room temperature, to the reaction mixture was added 3N-hydrochloric acid, and extracted with ethyl acetate. The obtained organic layer was washed with water and brine successively, dried over anhydrous sodium sulfate, filtered, and the filtrate was concentrated under reduced pressure. The obtained residue was purified by reverse phase preparative liquid chromatography to give the titled compound (17 mg) as a white solid.

¹H-NMR (400 MHz, CDCl₃) δ: 9.55 (1H, s), 8.48 (1H, s), 7.05 (2H, d, J=7.3 Hz), 6.18 (2H, s), 2.78 (3H, s), 1.91-1.87 (2H, m), 0.90-0.86 (4H, m), 0.69-0.66 (4H, m).

ESI-MS found: 372 [M+H]⁺

Example 167

Synthesis of 1-(2,6-dichlorobenzyl)-3-ethyl-1H-pyrazolo[4,3-b]pyridine-6-carboxylic acid [167] (Hereinafter Referred to as a Compound [167])

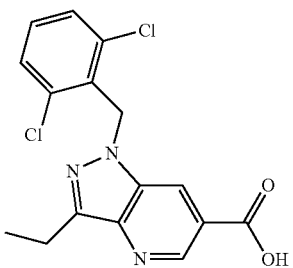 [SMILES: CCc1nn(Cc2c(Cl)cccc2Cl)c2cc(C(=O)O)cnc12]

(1) Synthesis of 6-bromo-3-ethyl-1H-pyrazolo[4,3-b]pyridine [167-1] (Hereinafter Referred to as a Compound [167-1])

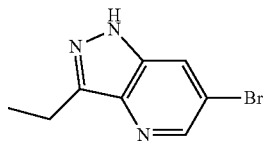

The titled compound (225 mg) as a white solid was prepared from 5-bromo-3-fluoropyridin-2-carbonitrile (201 mg) obtained by the method described in the document (Journal of Organic Chemistry, 2009, Vol. 74, p. 4547) and ethylmagnesium chloride according to the methods of the processes (1) and (2) of Example 153.

$^1$H-NMR (400 MHz, CDCl$_3$) δ: 9.87 (1H, s), 8.58 (1H, d, J=1.7 Hz), 7.95 (1H, d, J=1.7 Hz), 3.12 (2H, q, J=7.6 Hz), 1.45 (3H, t, J=7.6 Hz).

(2) Synthesis of 6-bromo-1-(2,6-dichlorobenzyl)-3-ethyl-1H-pyrazolo[4,3-b]pyridine [167-2] (Hereinafter Referred to as a Compound [167-2])

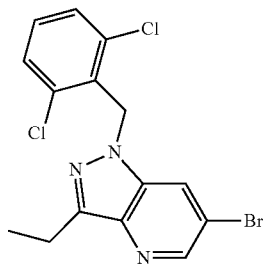 [SMILES: CCc1nn(Cc2c(Cl)cccc2Cl)c2cc(Br)cnc12]

The titled compound (325 mg) as a white solid was prepared from the compound [167-1] obtained in the process (1) (223 mg) and 2,6-dichlorobenzyl chloride (279 mg) according to the method of the process (1) of Example 66.

$^1$H-NMR (400 MHz, CDCl$_3$) δ: 8.51 (1H, d, J=1.7 Hz), 7.77 (1H, d, J=1.7 Hz), 7.40 (2H, d, J=8.1 Hz), 7.29-7.27 (1H, m), 5.71 (2H, s), 3.04 (2H, q, J=7.6 Hz), 1.39 (3H, t, J=7.6 Hz).

(3) Synthesis of ethyl 1-(2,6-dichlorobenzyl)-3-ethyl-1H-pyrazolo[4,3-b]pyridine-6-carboxylate [167-3] (Hereinafter Referred to as a Compound [167-3])

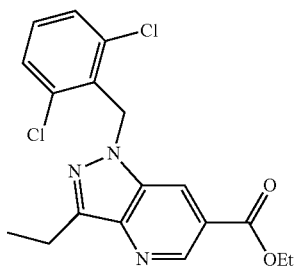 [SMILES: CCOC(=O)c1cnc2c(CC)nn(Cc3c(Cl)cccc3Cl)c2c1]

To a solution of the compound [167-2] obtained in the process (2) (101 mg) in ethanol (5 mL) were added triethylamine (0.2 mL) and [1,1'-bis(diphenylphosphino)ferrocene]dichloropalladium(II) (33 mg) at room temperature, and then the reaction mixture was flushed with carbon monoxide and heated at reflux for 18 hours. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (62 mg) as a yellow solid.

$^1$H-NMR (400 MHz, CDCl$_3$) δ: 9.11 (1H, s), 8.32 (1H, s), 7.40 (2H, d, J=8.1 Hz), 7.30-7.26 (1H, m), 5.81 (2H, s), 4.44 (2H, q, J=7.2 Hz), 3.10 (2H, q, J=7.6 Hz), 1.44-1.40 (6H, m).

(4) Synthesis of 1-(2,6-dichlorobenzyl)-3-ethyl-1H-pyrazolo[4,3-b]pyridine-6-carboxylic acid [167]

The titled compound (40 mg) as a white solid was prepared from the compound [167-3] obtained in the process (3) (62 mg) according to the method of the process (2) of Example 117.

$^1$H-NMR (400 MHz, CD$_3$OD) δ: 9.04 (1H, d, J=1.5 Hz), 8.64 (1H, d, J=1.5 Hz), 7.47 (2H, d, J=7.8 Hz), 7.38-7.36 (1H, m), 5.89 (2H, s), 3.03 (2H, q, J=7.5 Hz), 1.34 (3H, t, J=7.6 Hz).

Example 168

Synthesis of 1-(2,6-dimethylbenzyl)-3-ethyl-1H-pyrazolo[4,3-b]pyridine-6-carboxylic acid [168] (Hereinafter Referred to as a Compound [168])

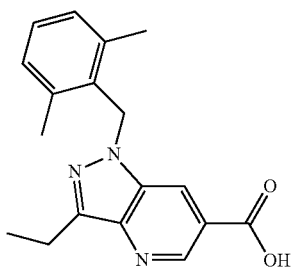

The titled compound (33 mg) as a white solid was prepared from the compound [167-1] obtained in the process (1) of Example 167 (81 mg) and 2,6-dimethylbenzyl chloride according to the methods of the process (1) of Example 66 and the processes (4) and (5) of Example 153.

$^1$H-NMR (400 MHz, CD$_3$OD) δ: 8.99 (1H, d, J=1.5 Hz), 8.20 (1H, d, J=1.5 Hz), 7.20-7.16 (1H, m), 7.09 (2H, d, J=7.3 Hz), 5.67 (2H, s), 3.05 (2H, q, J=7.6 Hz), 2.31 (6H, s), 1.37 (3H, t, J=7.6 Hz).

ESI-MS found: 310 [M+H]$^+$

Example 169

Synthesis of 1-(2,3-dichlorobenzyl)-3-ethyl-1H-pyrazolo[4,3-b]pyridine-6-carboxylic acid [169] (Hereinafter Referred to as a Compound [169])

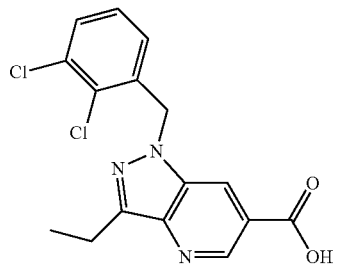 [SMILES: CCc1nn(Cc2cccc(Cl)c2Cl)c2cc(C(=O)O)cnc12]

The titled compound (74 mg) as a white solid was prepared from the compound [167-1] obtained in the process (1) of Example 167 (120 mg) and 2,3-dichlorobenzyl chloride according to the methods of the process (1) of Example 66, and the processes (4) and (5) of Example 153.

$^1$H-NMR (400 MHz, CD$_3$OD) δ: 9.06 (1H, d, J=1.5 Hz), 8.58 (1H, d, J=1.5 Hz), 7.48 (1H, d, J=7.8 Hz), 7.22-7.18 (1H, m), 6.84 (1H, d, J=7.3 Hz), 5.79 (2H, s), 3.09 (2H, q, J=7.6 Hz), 1.40 (3H, t, J=7.6 Hz).

ESI-MS found: 350 [M+H]$^+$

Example 170

Synthesis of 1-(2-chloro-6-methylbenzyl)-3-ethyl-1H-pyrazolo[4,3-b]pyridine-6-carboxylic acid [170] (Hereinafter Referred to as a Compound [170])

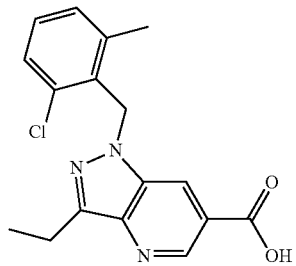 [SMILES: CCc1nn(Cc2c(C)cccc2Cl)c2cc(C(=O)O)cnc12]

The titled compound (1.1 mg) as a white solid was prepared from the compound [167-1] obtained in the process (1) of Example 167 (144.1 mg) and 2-chloro-6-methylbenzyl chloride (167.4 mg) according to the methods of the process (1) of Example 66, and the processes (4) and (5) of Example 153.

$^1$H-NMR (400 MHz, CDCl$_3$) δ: 9.02 (1H, d, J=1.2 Hz), 8.54 (1H, d, J=1.5 Hz), 7.32 (1H, d, J=7.3 Hz), 7.28-7.24 (1H, m), 7.22 (1H, d, J=6.8 Hz), 5.79 (2H, s), 3.04 (2H, q, J=7.6 Hz), 2.45 (3H, s), 1.36 (3H, t, J=7.6 Hz).

ESI-MS found: 330 [M+H]$^+$

Example 171

Synthesis of 1-(2,6-dichlorobenzyl)-3-ethyl-6-(1H-tetrazole-5-yl)-1H-pyrazolo[4,3-b]pyridine [171] (Hereinafter Referred to as a Compound [171])

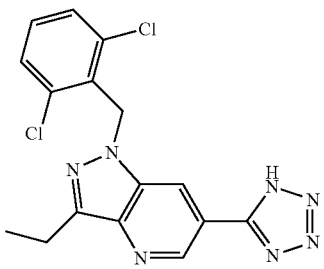 [SMILES: CCc1nn(Cc2c(Cl)cccc2Cl)c2cc(-c3nnn[nH]3)cnc12]

The titled compound (40 mg) as a white solid was prepared from the compound [167-1] obtained in the process (1) of Example 167 and 2,6-dichlorobenzyl chloride according to the methods of the process (1) of Example 66, the process (4) of Example 153 and the process (2) of Example 134.

$^1$H-NMR (400 MHz, CD$_3$OD) δ: 9.12 (1H, s), 8.72 (1H, d, J=1.5 Hz), 7.47 (2H, d, J=7.8 Hz), 7.39-7.35 (1H, m), 5.90 (2H, s), 3.04 (2H, q, J=7.6 Hz), 1.36 (3H, t, J=7.6 Hz).

ESI-MS found: 374 [M+H]$^+$

Example 172

Synthesis of 3-chloro-1-(2,6-dichlorobenzyl)-1H-pyrazolo[4,3-b]pyridine-6-carboxylic acid [172] (Hereinafter Referred to as a Compound [172])

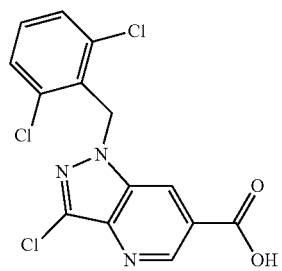

(1) Synthesis of 5-bromo-3-fluoropyridine-2-carbaldehyde [172-1] (Hereinafter Referred to as a Compound [172-1])

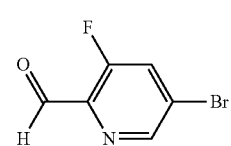

5-Bromo-3-fluoropyridin-2-carbonitrile obtained by the method described in the document (Journal of Organic Chemistry, 2009, Vol. 74, p. 4547) (4.5 g) was dissolved in dichloromethane (140 mL) and cooled to −78° C. 1.0M toluene solution (33 mL) of diisobutylaluminum hydride was added at −78° C., and then the reaction mixture was warmed to 0° C. and stirred for 5 minutes. The reaction mixture was cooled again to −78° C., and added 3N-hydrochloric acid, and extracted with chloroform. The obtained organic layer was washed with brine, dried over anhydrous sodium sulfate, filtered, and the filtrate was concentrated under reduced pressure. The obtained residue was purified by silica gel column chromatography to give the titled compound (848 mg) as a yellow solid.

$^1$H-NMR (400 MHz, CDCl$_3$) δ: 10.17 (1H, s), 8.69 (1H, s), 7.80 (1H, dd, J=9.1, 1.3 Hz).

(2) Synthesis of 6-bromo-1H-pyrazolo[4,3-b]pyridine [172-2] (Hereinafter Referred to as a Compound [172-2])

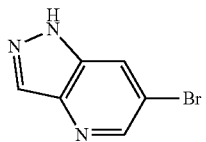

To a solution of the compound [172-1] obtained in the process (1) (426 mg) in ethylene glycol (2.1 mL) was added hydrazine monohydrate (197 μL) at room temperature, and then the reaction mixture was stirred at 140° C. for 23 hours. After cooling to room temperature, to the reaction mixture was added water, and extracted with a mixed solution of chloroform/isopropanol (volume ratio 10/1). The obtained organic layer was washed with brine, dried over anhydrous sodium sulfate, filtered, and the filtrate was concentrated under reduced pressure. The obtained residue was purified by silica gel column chromatography to give the titled compound (275 mg) as a yellow solid.

$^1$H-NMR (400 MHz, CDCl$_3$) δ: 10.17 (1H, br), 8.65 (1H, d, J=1.7 Hz), 8.31 (1H, s), 8.04 (1H, s).
ESI-MS found: 198 [M+H]$^+$ (3) Synthesis of 6-bromo-3-chloro-1H-pyrazolo[4,3-b]pyridine [172-3] (Hereinafter Referred to as a Compound [172-3])

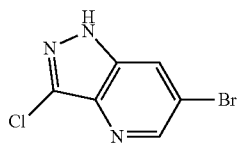 [SMILES: Clc1n[nH]c2cc(Br)cnc12]

The compound [172-2] obtained in the process (2) (123 mg) in acetonitrile (4.1 mL) was added N-chlorosuccinimide (91 mg) at room temperature, and then the reaction mixture was stirred at 60° C. for 3 hours. Furthermore, N-chlorosuccinimide (91 mg) was added at 60° C. and the reaction mixture was stirred for 2 hours. After cooling to room temperature, to the reaction mixture was added an aqueous solution of 1N-sodium hydroxide, and extracted with ethyl acetate. The obtained organic layer was washed with brine, dried over anhydrous sodium sulfate, filtered, and the filtrate was concentrated under reduced pressure to give the titled compound (140 mg) as a pale yellow solid.

$^1$H-NMR (400 MHz, CDCl$_3$) δ: 9.99 (1H, br), 8.69 (1H, d, J=2.0 Hz), 8.02 (1H, d, J=2.0 Hz).
ESI-MS found: 232 [M+H]$^+$ (4) Synthesis of 6-bromo-3-chloro-1-(2,6-dichlorobenzyl)-1H-pyrazolo[4,3-b]pyridine [172-4] (Hereinafter Referred to as a Compound [172-4])

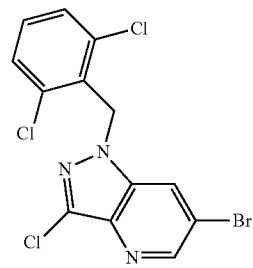 [SMILES: Clc1cccc(Cl)c1Cn1nc(Cl)c2ncc(Br)cc21]

The titled compound (171 mg) as a white solid was prepared from the compound [172-3] obtained in the process (3) (140 mg) and 2,6-dichlorobenzyl chloride according to the method of the process (1) of Example 66.

$^1$H-NMR (400 MHz, CDCl$_3$) δ: 8.62 (1H, d, J=1.5 Hz), 7.93 (1H, d, J=1.5 Hz), 7.41 (2H, d, J=8.1 Hz), 7.32-7.28 (1H, m), 5.72 (2H, s).
ESI-MS found: 390 [M+H]$^+$ (5) Synthesis of 3-chloro-1-(2,6-dichlorobenzyl)-1H-pyrazolo[4,3-b]pyridine-6-carbonitrile [172-5] (Hereinafter Referred to as a Compound [172-5])

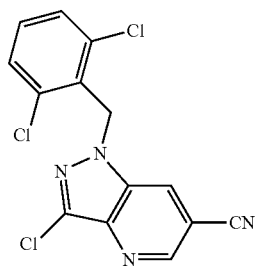 [SMILES: N#Cc1cnc2c(Cl)nn(Cc3c(Cl)cccc3Cl)c2c1]

The titled compound (64 mg) as a white solid was prepared from the compound [172-4] obtained in the process (4) (100 mg) according to the method of the process (4) of Example 153.

$^1$H-NMR (400 MHz, CDCl$_3$) δ: 8.79 (1H, d, J=1.5 Hz), 8.06 (1H, d, J=1.5 Hz), 7.43 (2H, d, J=7.8 Hz), 7.36-7.32 (1H, m), 5.84 (2H, s).
ESI-MS found: 337 [M+H]$^+$ (6) Synthesis of 3-chloro-1-(2,6-dichlorobenzyl)-1H-pyrazolo[4,3-b]pyridine-6-carboxylic acid [172]

The titled compound (33 mg) as a white solid was prepared from the compound [172-5] obtained in the process (5) (36 mg) according to the method of the process (5) of Example 153.

$^1$H-NMR (400 MHz, DMSO-d$_6$) δ: 9.08 (1H, s), 8.94 (1H, s), 7.57 (2H, d, J=8.1 Hz), 7.49-7.45 (1H, m), 5.95 (2H, s).
ESI-MS found: 356 [M+H]$^+$

Example 173

Synthesis of potassium 3-chloro-1-(2,6-dichlorobenzyl)-1H-pyrazolo[4,3-b]pyridine-6-carboxylate [173] (Hereinafter Referred to as a Compound [173])

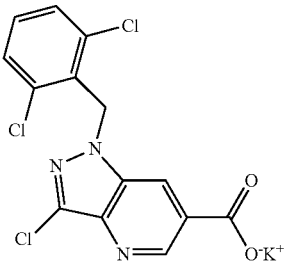

To a solution of the compound [172](27 mg) in ethanol (2.0 mL) was added an aqueous solution of 1N-potassium hydroxide (74 µL) at room temperature, and the solution was concentrated under reduced pressure to give the titled compound (28 mg) as a white solid.

$^1$H-NMR (400 MHz, DMSO-$d_6$) δ: 9.06 (1H, s), 8.56 (1H, s), 7.56 (2H, d, J=8.1 Hz), 7.47-7.43 (1H, m), 5.82 (2H, s).
ESI-MS found: 356 [M–K+2H]$^+$

Example 174

Synthesis of 3-chloro-1-(2-chloro-6-methylbenzyl)-1H-pyrazolo[4,3-b]pyridine-6-carboxylic acid [174] (Hereinafter Referred to as a Compound [174])

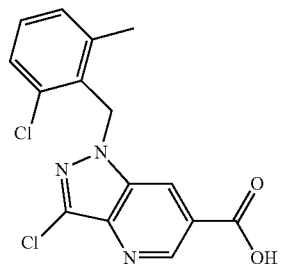 [SMILES: Cc1cccc(Cl)c1Cn1nc(Cl)c2ncc(C(=O)O)cc21]

(1) Synthesis of 6-bromo-3-chloro-1-(2-chloro-6-methylbenzyl)-1H-pyrazolo[4,3-b]pyridine [174-1] (Hereinafter Referred to as a Compound [174-1])

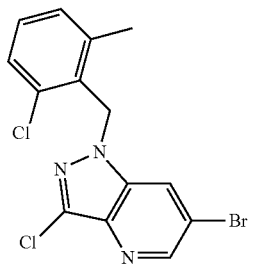 [SMILES: Cc1cccc(Cl)c1Cn1nc(Cl)c2ncc(Br)cc21]

The titled compound (143 mg) as a white solid was prepared from the compound [172-3] obtained in the process (3) of Example 172 (119 mg) and 2-chloro-6-methylbenzyl chloride (107 mg) according to the method of the process (1) of Example 66.

$^1$H-NMR (400 MHz, CDCl$_3$) δ: 8.59 (1H, d, J=1.5 Hz), 7.82 (1H, d, J=1.5 Hz), 7.32 (1H, d, J=8.1 Hz), 7.26-7.24 (1H, m), 7.18 (1H, d, J=7.3 Hz), 5.64 (2H, s), 2.45 (3H, s).
ESI-MS found: 370 [M+H]$^+$ (2) Synthesis of 3-chloro-1-(2-chloro-6-methylbenzyl)-1H-pyrazolo[4,3-b]pyridine-6-carbonitrile [174-2] (Hereinafter Referred to as a Compound [174-2])

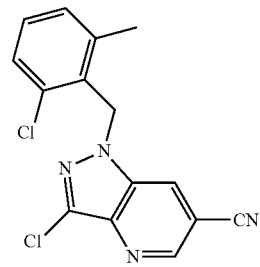 [SMILES: Cc1cccc(Cl)c1Cn1nc(Cl)c2ncc(C#N)cc21]

The titled compound (82 mg) as a white solid was prepared from the compound [174-1] obtained in the process (1) (114 mg) according to the method of the process (4) of Example 153.

$^1$H-NMR (400 MHz, CDCl$_3$) δ: 8.76 (1H, s), 7.95 (1H, s), 7.35-7.19 (3H, m), 5.74 (2H, s), 2.47 (3H, s).
ESI-MS found: 317 [M+H]$^+$ (3) Synthesis of 3-chloro-1-(2-chloro-6-methylbenzyl)-1H-pyrazolo[4,3-b]pyridine-6-carboxylic acid [174]

The titled compound (35 mg) as a white solid was prepared from the compound [174-2] obtained in the process (2) (38 mg) according to the method of the process (5) of Example 153.

$^1$H-NMR (400 MHz, DMSO-$d_6$) δ: 9.07 (1H, s), 8.93 (1H, s), 7.37-7.26 (3H, m), 5.84 (2H, s), 2.39 (3H, s).
ESI-MS found: 336 [M+H]$^+$

Example 175

Synthesis of 3-chloro-1-(2,6-dichlorobenzyl)-6-(1H-tetrazole-5-yl)-1H-pyrazolo[4,3-b]pyridine [175] (Hereinafter Referred to as a Compound [175])

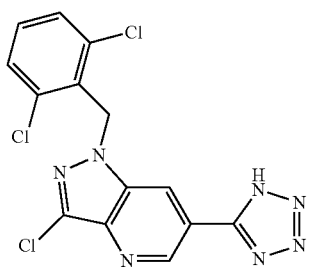 [SMILES: Clc1cccc(Cl)c1Cn1nc(Cl)c2ncc(-c3nnn[nH]3)cc21]

The titled compound (33 mg) as a white solid was prepared from the compound [172-5] obtained in the process (5) of Example 172 (30 mg) according to the method of the process (2) of Example 134.

$^1$H-NMR (400 MHz, DMSO-$d_6$) δ: 9.24 (1H, s), 9.05 (1H, s), 7.58 (2H, d, J=8.1 Hz), 7.50-7.46 (1H, m), 5.94 (2H, s).
ESI-MS found: 380 [M+H]$^+$

Example 176

Synthesis of potassium 5-[3-chloro-1-(2,6-dichlorobenzyl)-1H-pyrazolo[4,3-b]pyridine-6-yl]-1H-tetrazole-1-ide [176] (Hereinafter Referred to as a Compound [176])

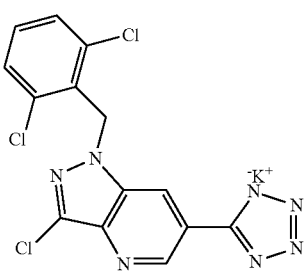

To a solution of the compound [175] (17 mg) in ethanol (2.0 mL) was added an aqueous solution of 1N-potassium hydroxide (43 µL) at room temperature, and the solution was concentrated under reduced pressure to give the titled compound (18 mg) as a white solid.

$^1$H-NMR (400 MHz, DMSO-$d_6$) δ: 9.27 (1H, s), 8.73 (1H, s), 7.57 (2H, d, J=8.1 Hz), 7.48-7.44 (1H, m), 5.88 (2H, s).
ESI-MS found: 380 [M+H]$^+$

Example 177

Synthesis of 3-chloro-1-(2-chloro-6-methylbenzyl)-6-(1H-tetrazole-5-yl)-1H-pyrazolo[4,3-b]pyridine [177] (Hereinafter Referred to as a Compound [177])

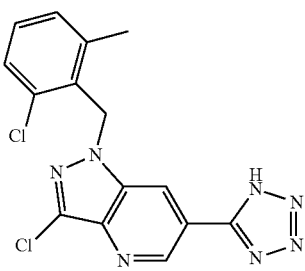 [SMILES: Cc1cccc(Cl)c1Cn1nc(Cl)c2ncc(-c3nnn[nH]3)cc21]

The titled compound (41 mg) as a pale yellow solid was prepared from the compound [174-2] obtained in the process (2) of Example 174 (42 mg) according to the method of the process (2) of Example 134.

$^1$H-NMR (400 MHz, DMSO-$d_6$) δ: 9.22 (1H, s), 9.06 (1H, s), 7.38-7.28 (3H, m), 5.84 (2H, s), 2.44 (3H, s).
ESI-MS found: 360 [M+H]$^+$

Example 178

Synthesis of potassium 5-[3-chloro-1-(2-chloro-6-methylbenzyl)-1H-pyrazolo[4,3-b]pyridine-6-yl]-1H-tetrazole-1-ide [178] (Hereinafter Referred to as a Compound [178])

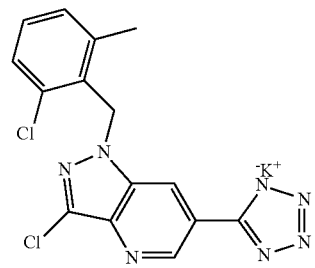

To a solution of the compound [177] (30 mg) in ethanol (2.0 mL) was added an aqueous solution of 1N-potassium hydroxide (82 µL) at room temperature, and the solution was concentrated under reduced pressure to give the titled compound (33 mg) as a white solid.

$^1$H-NMR (400 MHz, DMSO-$d_6$) δ: 9.26 (1H, s), 8.73 (1H, s), 7.38-7.26 (3H, m), 5.78 (2H, s), 2.41 (3H, s).
ESI-MS found: 360 [M−K+2H]$^+$

Example 179

Synthesis of 1-(2,6-dichlorobenzyl)-5-methoxy-3-methyl-1H-indazole-6-carboxylic acid [179] (Hereinafter Referred to as a Compound [179])

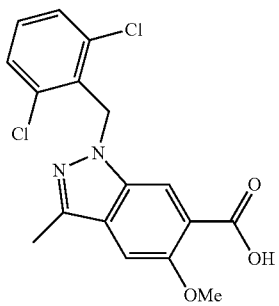 [SMILES: COc1cc2c(C)nn(Cc3c(Cl)cccc3Cl)c2cc1C(=O)O]

(1) Synthesis of 4-bromo-2-fluoro-5-methoxybenzaldehyde [179-1] (Hereinafter Referred to as a Compound [179-1])

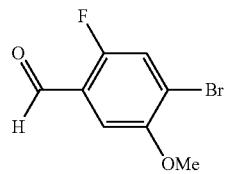

To a mixture of 2-bromo-4-fluoro-1-methoxybenzene (4.10 g) and titanium tetrachloride (4.4 mL), dichloromethyl methyl ether (3.5 mL) was added under ice cooling, and then the reaction mixture was stirred at 0° C. for 2.5 hours. To the reaction mixture was added chloroform, and the reaction mixture was poured into ice water, and then stirred at room temperature for 1 hour. The organic layer was separated and dried over anhydrous sodium sulfate, filtered, and the filtrate was concentrated under reduced pressure. The obtained residue was added hexane and the produced solid was filtered to give the titled compound (1.61 g) as a white solid.

$^1$H-NMR (400 MHz, CDCl$_3$) δ: 10.31 (1H, s), 7.46 (1H, d, J=9.0 Hz), 7.31 (1H, d, J=5.9 Hz), 3.93 (3H, s).

(2) Synthesis of 1-(4-bromo-2-fluoro-5-methoxyphenyl)ethanone [179-2] (Hereinafter Referred to as a Compound [179-2])

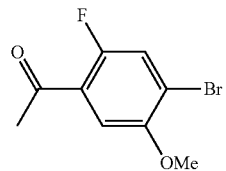 [SMILES: COc1cc(C=O)c(F)cc1Br]

The titled compound (382 mg) as a white solid was prepared from the compound [179-1] obtained in the process (1) (1.61 g) and methylmagnesium iodide according to the methods of the processes (1) and (2) of Example 140.

$^1$H-NMR (400 MHz, CDCl$_3$) δ: 7.40 (1H, d, J=9.8 Hz), 7.38 (1H, d, J=6.1 Hz), 3.92 (3H, s), 2.64 (3H, d, J=5.4 Hz).

(3) Synthesis of 6-bromo-1-(2,6-dichlorobenzyl)-5-methoxy-3-methyl-1H-indazole [179-3] (Hereinafter Referred to as a Compound [179-3])

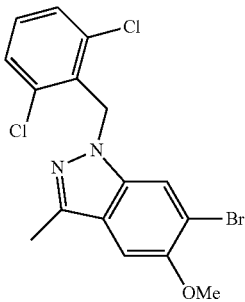 [SMILES: COc1cc2c(C)nn(Cc3c(Cl)cccc3Cl)c2cc1Br]

To a solution of the compound [179-2] obtained in the process (2) (101 mg) in dichloromethane (2 mL) was added titanium tetraisopropoxide (0.24 mL) at room temperature, and then the reaction mixture was stirred at room temperature for 15 minutes. Next, hydrazine monohydrate (0.04 mL) was added, and stirred at room temperature overnight. The reaction mixture was quenched with water and stirred for 3 hours, and then the insoluble materials were filtered, and washed with ethyl acetate. The filtrate was dried over anhydrous sodium sulfate, filtered, concentrated under reduced pressure to give a white solid. To the obtained solid was added 1,4-dioxane (2 mL) and water (1 mL). The reaction mixture was subjected to microwave irradiation at 200° C. for 60 minutes, and then the reaction mixture was concentrated under reduced pressure. To a solution of the obtained residue in N,N-dimethylformamide (2 mL) were added potassium carbonate (127 mg) and 2,6-dichlorobenzyl chloride (117 mg), and the reaction mixture was stirred at room temperature for 2 days. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (43 mg) as a white solid.

$^1$H-NMR (400 MHz, CDCl$_3$) δ: 7.61 (1H, s), 7.37 (2H, d, J=8.1 Hz), 7.26-7.22 (1H, m), 6.97 (1H, s), 5.64 (2H, s), 3.93 (3H, s), 2.49 (3H, s).

ESI-MS found: 399 [M+H]$^+$ (4) Synthesis of 1-(2,6-dichlorobenzyl)-5-methoxy-3-methyl-1H-indazole-6-carbonitrile [179-4] (Hereinafter Referred to as a Compound [179-4])

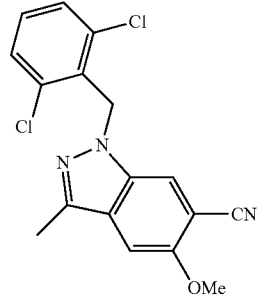 [SMILES: COc1cc2c(C)nn(Cc3c(Cl)cccc3Cl)c2cc1C#N]

To a solution of the compound [179-3] obtained in the process (3) (39 mg) in N,N-dimethylformamide (1.2 mL) were added zinc powder (7.2 mg), zinc cyanide (6.7 mg), tris(dibenzylideneacetone)palladium(0) (8.3 mg) and 1,1-bis(diphenylphosphino)ferrocene (5.8 mg). The reaction mixture was stirred at 120° C. for 3 hours under argon atmosphere. To the reaction mixture was added 5% aqueous solution of potassium hydrogen sulfate, and extracted with ethyl acetate. The obtained organic layer was dried over anhydrous sodium sulfate, filtered, and the filtrate was concentrated under reduced pressure. The obtained residue was purified by silica gel column chromatography to give the titled compound (23 mg) as a white solid.

$^1$H-NMR (400 MHz, CDCl$_3$) δ: 7.60 (1H, s), 7.39 (2H, d, J=8.1 Hz), 7.29-7.25 (1H, m), 7.01 (1H, s), 5.71 (2H, s), 3.96 (3H, s), 2.51 (3H, s).

ESI-MS found: 346 [M+H]$^+$ (5) Synthesis of 1-(2,6-dichlorobenzyl)-5-methoxy-3-methyl-1H-indazole-6-carboxylic acid [179]

To a solution of the compound [179-4](23 mg) obtained in the process (4) in tetrahydrofuran (0.5 mL) and methanol (0.5 mL) was added an aqueous solution of 3N-sodium hydroxide (0.6 mL), and then the reaction mixture was subjected to microwave irradiation at 150° C. for 30 minutes. To the reaction mixture was added 5% aqueous solution of potassium hydrogen sulfate, and extracted with ethyl acetate. The obtained organic layer was dried over anhydrous sodium sulfate, filtered, and the filtrate was concentrated under reduced pressure. The obtained residue was purified by silica gel column chromatography to give the titled compound (13 mg) as a white solid.

¹H-NMR (400 MHz, CDCL₃) δ: 11.25 (1H, brs), 8.41 (1H, s), 7.38 (2H, d, J=7.8 Hz), 7.27-7.23 (1H, m), 7.14 (1H, s), 5.74 (2H, s), 4.13 (3H, s), 2.52 (3H, s).
ESI-MS found: 365 [M+H]⁺

Example 180

Synthesis of 1-(2,6-dichlorobenzyl)-5-hydroxy-3-methyl-1H-indazole-6-carboxylic acid [180] (Hereinafter Referred to as a Compound [180])

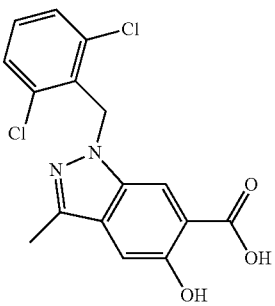 [SMILES: Cc1nn(Cc2c(Cl)cccc2Cl)c2cc(C(=O)O)c(O)cc12]

To a suspension of the compound [179](7.4 mg) in methylenechloride (0.2 mL) was added 1M methylenechloride solution of borane tribromide (0.2 mL) under ice-cooling, and then the reaction mixture was stirred at 0° C. for 3 hours. The reaction mixture was quenched with water, and extracted with ethyl acetate. The obtained organic layer was dried over anhydrous sodium sulfate, filtered, and the filtrate was concentrated under reduced pressure. The obtained residue was purified by reverse phase preparative liquid chromatography to give the titled compound (3.7 mg) as a pale brown solid.
¹H-NMR (400 MHz, CD₃OD) δ: 8.17 (1H, s), 7.45 (1H, d, J=7.7 Hz), 7.45 (1H, d, J=8.4 Hz), 7.34 (1H, dd, J=8.4, 7.7 Hz), 7.07 (1H, s), 5.73 (2H, s), 2.43 (3H, s).
ESI-MS found: 351 [M+H]⁺

Example 181

Synthesis of 3-[1-(2,6-dichlorobenzyl)-3-methyl-1H-indazole-6-yl]-2-hydroxypropionic acid [181] (Hereinafter Referred to as a Compound [181])

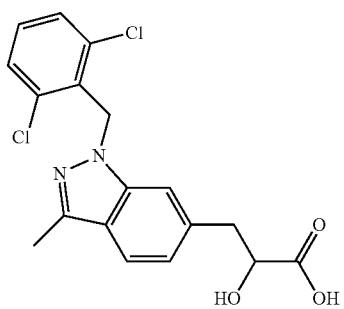 [SMILES: Cc1nn(Cc2c(Cl)cccc2Cl)c2cc(CC(O)C(=O)O)ccc12]

The titled compound (28 mg) as a white solid was prepared from the compound [97-3] obtained in the process (3) of Example 97 (221 mg) according to the method of Example 128.

¹H-NMR (400 MHz, CD₃OD) δ: 7.52 (1H, d, J=7.6 Hz), 7.41-7.39 (3H, m), 7.30 (1H, d, J=7.6 Hz), 7.09 (1H, d, J=8.1 Hz), 5.62 (2H, s), 4.32 (1H, s), 3.34-3.30 (1H, m), 3.01-2.98 (1H, m), 2.40 (3H, s).

Example 182

Synthesis of 1-(2,6-dichlorobenzyl)-3-ethyl-6-(1H-tetrazole-5-yl)-1H-indazole [182] (Hereinafter Referred to as a Compound [182])

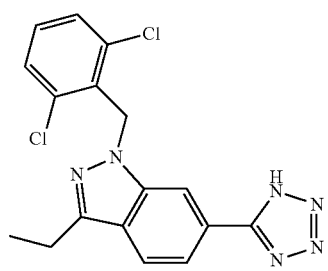 [SMILES: CCc1nn(Cc2c(Cl)cccc2Cl)c2cc(-c3nnn[nH]3)ccc12]

The titled compound (9 mg) as a white solid was prepared from the compound [140-4] obtained in the process (4) of Example 140 (76 mg) according to the methods of the process (4) of Example 153 and the process (2) of Example 134.
¹H-NMR (400 MHz, DMSO-d₆) δ: 8.44 (1H, s), 7.98 (1H, d, J=8.3 Hz), 7.76 (1H, d, J=8.3 Hz), 7.55 (2H, d, J=7.8 Hz), 7.46-7.42 (1H, m), 5.79 (2H, s) 2.88 (2H, q, J=7.6 Hz), 1.25 (3H, t, J=7.6 Hz).
ESI-MS found: 373 [M+H]⁺

Example 183

Synthesis of [1-(2,6-dichlorobenzyl)-3-methyl-1H-indazole-6-yl]difluoroacetic acid [183] (Hereinafter Referred to as a Compound [183])

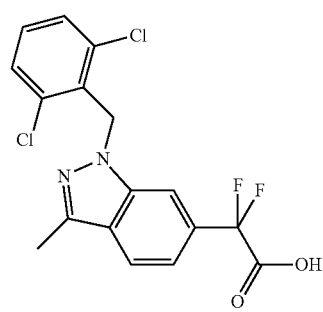 [SMILES: Cc1nn(Cc2c(Cl)cccc2Cl)c2cc(C(F)(F)C(=O)O)ccc12]

(1) Synthesis of ethyl [1-(2,6-dichlorobenzyl)-3-methyl-1H-indazole-6-yl] oxoacetate [183-1] (Hereinafter Referred to as a Compound [183-1])

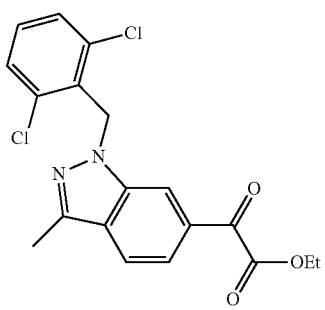 [SMILES: CCOC(=O)C(=O)c1ccc2c(C)nn(Cc3c(Cl)cccc3Cl)c2c1]

To a solution of the compound [130-1](1.47 g) obtained in the process (1) of Example 130 in tetrahydrofuran (15 mL) were added diisopropylethylamine (0.56 mL), tris(dibenzylideneacetone)dipalladium(0) (118 mg) and ethyl chloroglyoxylate (0.42 mL) at 0° C., and then the reaction mixture was stirred at room temperature for 24 hours. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (218 mg) as a yellow solid.

$^1$H-NMR (400 MHz, CDCl$_3$) δ: 8.10 (1H, s), 7.72 (2H, s), 7.38 (2H, d, J=8.1 Hz), 7.27-7.25 (1H, m), 5.81 (2H, s), 4.48 (2H, q, J=7.2 Hz), 2.56 (3H, s), 1.45 (3H, t, J=7.1 Hz).

(2) Synthesis of ethyl [1-(2,6-dichlorobenzyl)-3-methyl-1H-indazol-6-yl]difluoroacetate [183-2] (Hereinafter Referred to as a Compound [183-2])

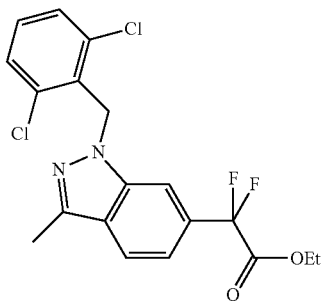 [SMILES: CCOC(=O)C(F)(F)c1ccc2c(C)nn(Cc3c(Cl)cccc3Cl)c2c1]

To a solution of the compound [183-1] obtained in the process (1) (102 mg) in dichloromethane (1 mL) was added N,N-diethylaminosulfur trifluoride (0.35 mL), and then the reaction mixture was stirred at room temperature for 24 hours. The reaction mixture was quenched with water and a saturated aqueous solution of sodium bicarbonate, and extracted with chloroform. The obtained organic layer was dried over anhydrous sodium sulfate, filtered, and the filtrate was concentrated under reduced pressure. The obtained residue was purified by silica gel column chromatography to give the titled compound (100 mg) as a white solid.

$^1$H-NMR (400 MHz, CDCl$_3$) δ: 7.70-7.68 (2H, m), 7.38 (2H, d, J=8.1 Hz), 7.32 (1H, d, J=9.0 Hz), 7.25-7.23 (1H, m), 5.75 (2H, s), 4.29 (2H, q, J=7.2 Hz), 2.53 (3H, s), 1.29 (3H, t, J=7.1 Hz).

(3) Synthesis of [1-(2,6-dichlorobenzyl)-3-methyl-1H-indazol-6-yl]difluoroacetic acid [183]

To a solution of the compound [183-2] obtained in the process (2) (96 mg) in ethanol (2 mL) was added an aqueous solution of 1N-sodium hydroxide (2 mL) at room temperature, and then the reaction mixture was stirred at 60° C. for 1 hour. The reaction mixture was added 1N-hydrochloric acid, and the precipitated solid was filtered to give the titled compound (89 mg) as a white solid.

$^1$H-NMR (400 MHz, CD$_3$OD) δ: 7.81-7.79 (2H, m), 7.45 (2H, d, J=8.1 Hz), 7.36-7.34 (2H, m), 5.81 (2H, s), 2.50 (3H, s).

ESI-MS found: 385 [M+H]$^+$

Example 184

Synthesis of potassium [1-(2,6-dichlorobenzyl)-3-methyl-1H-indazol-6-yl]difluoroacetate [184] (Hereinafter Referred to as a Compound [184])

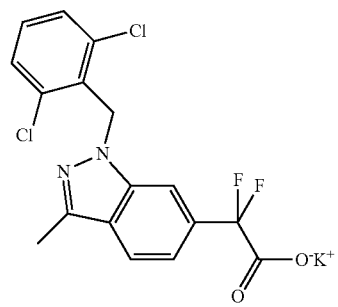

To a solution of the compound [183](89 mg) in ethanol (2 mL) was added an aqueous solution of 1N-potassium hydroxide (233 μL) at room temperature, and then the reaction mixture was stirred at room temperature for 10 minutes. The reaction mixture was concentrated under reduced pressure to give the titled compound (98 mg) as a white solid.

$^1$H-NMR (400 MHz, CD$_3$OD) δ: 7.88 (1H, s), 7.71 (1H, d, J=8.5 Hz), 7.44-7.42 (3H, m), 7.35-7.33 (1H, m), 5.77 (2H, s), 2.48 (3H, s).

ESI-MS found: 385 [M−K+2H]$^+$

Example 185

Synthesis of 3-[1-(2-chloro-6-cyclopropylbenzyl)-3-methyl-1H-indazol-6-yl]propionic acid [185] (Hereinafter Referred to as a Compound [185])

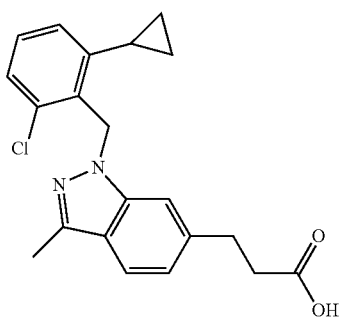 [SMILES: Cc1nn(Cc2c(Cl)cccc2C2CC2)c2cc(CCC(=O)O)ccc12]

The titled compound (5.6 mg) as a white solid was prepared from the compound [122-3] obtained in the process (3) of Example 122 (38 mg) according to the method of Example 164.

¹H-NMR (400 MHz, CDCl₃) δ: 7.53 (1H, d, J=8.3 Hz), 7.29 (1H, d, J=8.1 Hz) 7.21-7.17 (1H, m), 7.07 (1H, s), 6.97 (1H, d, J=7.6 Hz), 6.94 (1H, d, J=8.4 Hz), 5.83 (2H, s), 3.03 (2H, t, J=7.7 Hz), 2.68 (2H, t, J=7.6 Hz), 2.51 (3H, s), 2.10-2.03 (1H, m), 0.87-0.82 (2H, m), 0.61-0.58 (2H, m).

ESI-MS found: 369 [M+H]⁺

Example 186

Synthesis of 3-(2,6-dimethylbenzyl)-1-isopropyl-2-oxo-2,3-dihydro-1H-benzimidazole-5-carboxylic acid [186] (Hereinafter Referred to as a Compound [186])

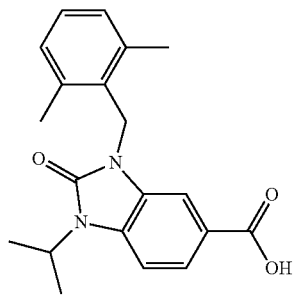 [SMILES: Cc1cccc(C)c1Cn1c(=O)n(C(C)C)c2ccc(C(=O)O)cc21]

(1) Synthesis of methyl 3-nitro-4-(2,2,2-trifluoro-acetylamino)benzoate [186-1] (Hereinafter Referred to as a Compound [186-1])

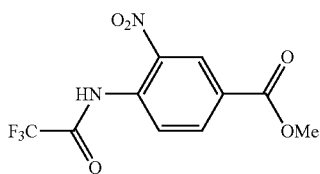

To a solution of methyl 4-aminobenzoate (1.00 g) in trifluoroacetic anhydride (13 mL) was added potassium nitrate (0.74 g) under ice cooling, and then the reaction mixture was stirred overnight. The reaction mixture was quenched with ice water, and extracted with ethyl acetate. The obtained organic layer was washed with a saturated aqueous solution of sodium hydrogen carbonate and a saturated aqueous solution of sodium chloride, and then dried over anhydrous sodium sulfate, filtered, and the filtrate was concentrated under reduced pressure. The obtained residue was purified by silica gel column chromatography to give the titled compound (1.9 g) as a pale brown solid.

¹H-NMR (400 MHz, CDCl₃) δ: 11.58 (1H, s), 8.99 (1H, d, J=2.0 Hz), 8.87 (1H, d, J=8.8 Hz), 8.40 (1H, dd, J=8.8, 2.0 Hz), 4.00 (3H, s).

ESI-MS found: 291 [M−H]⁺

(2) Synthesis of methyl 4,4-di-tert-butoxycarbonylamino-3-nitrobenzoate [186-2] (Hereinafter Referred to as a Compound [186-2])

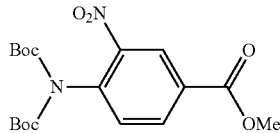

To a solution of the compound [186-1] obtained in the process (1) (0.55 g) in methanol (11 mL) was added 7% aqueous solution of potassium carbonate (5.5 mL), and then the reaction mixture was stirred at room temperature for 1.5 hours. The precipitated solid was filtered and washed with water, and then eluted using chloroform-methanol. The solution was concentrated under reduced pressure. To the obtained residue were added a solution of di-tert-butyl dicarbonate (930 mg) in tetrahydrofuran (15 mL), and triethylamine (0.31 mL), and then the reaction mixture was stirred at room temperature overnight. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give the titled compound (0.68 g) as a white solid.

¹H-NMR (400 MHz, CDCl₃) δ: 8.71 (1H, d, J=2.0 Hz), 8.29 (1H, dd, J=8.1, 2.0 Hz), 7.42 (1H, d, J=8.1 Hz), 3.99 (3H, s), 1.39 (18H, s).

ESI-MS found: 396 [M−H]⁻

(3) Synthesis of 1-tert-butyl-5-methyl-2-oxo-2,3-dihydro-1H-benzimidazole-1,5-dicarboxylate [186-3] (Hereinafter Referred to as a Compound [186-3])

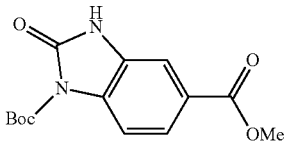 [SMILES: COC(=O)c1ccc2c(c1)[nH]c(=O)n2C(=O)OC(C)(C)C]

To a solution of the compound [186-2] (118 mg) obtained in the process (2) in tetrahydrofuran (3 mL) was added 20% palladium hydroxide (66 mg), and the reaction mixture was stirred at room temperature for 1.5 hours under hydrogen atmosphere. The palladium on carbon was filtered, and then the filtrate was concentrated under reduced pressure to give the titled compound (43 mg) as a white solid.

¹H-NMR (400 MHz, CDl₃) δ: 10.28 (1H, brs), 7.87 (1H, dd, J=8.8, 2.0 Hz), 7.84 (1H, d, J=2.0 Hz), 7.79 (1H, d, J=8.8 Hz), 3.93 (3H, s), 1.72 (9H, s).

ESI-MS found: 291 [M−H]⁻

(4) Synthesis of methyl 3-(2,6-dimethylbenzyl)-2-oxo-2,3-dihydro-1H-benzimidazole-5-carboxylate [186-4] (Hereinafter Referred to as a Compound [186-4])

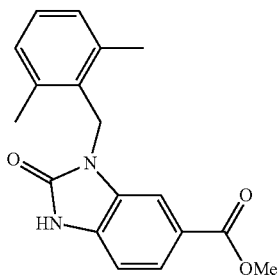 [SMILES: COC(=O)c1ccc2[nH]c(=O)n(Cc3c(C)cccc3C)c2c1]

To a solution of the compound [186-3] obtained in the process (3) (154 mg) and 2,6-dimethylbenzyl chloride (163 mg) in N,N-dimethylformamide (2.6 mL) was added sodium hydride (31 mg), and then the reaction mixture was stirred at room temperature for 4.5 hours. The reaction mixture was quenched with water, and extracted with ethyl acetate. The obtained organic layer was dried over anhydrous sodium sulfate, filtered, and the filtrate was concentrated under reduced pressure. The obtained residue was purified by silica gel column chromatography to give a benzyl adduct (220 mg). To a solution of the obtained benzyl adduct (311 mg) in chloroform (7.6 mL) was added trifluoroacetic acid (7.6 mL), and then the reaction mixture was stirred at room temperature for 1.5 hours. The reaction mixture was concentrated under reduced pressure, and then ethyl acetate and hexane were added to the residue. The obtained solid was filtered, and dried under reduced pressure to give the titled compound (207 mg) as a white solid.

$^1$H-NMR (400 MHz, DMSO-d6) δ: 11.40 (1H, brs), 7.60 (1H, d, J=8.5 Hz), 7.13 (1H, dd, J=8.1, 6.8 Hz), 7.10 (1H, s), 7.08-7.03 (3H, m), 5.05 (2H, s), 3.74 (3H, s), 2.29 (6H, s).

ESI-MS found: 309 [M–H]$^-$ (5) Synthesis of methyl 3-(2,6-dimethylbenzyl)-1-isopropyl-2-oxo-2,3-dihydro-1H-benzimidazole-5-carboxylate [186-5] (hereinafter referred to as a compound [186-5])

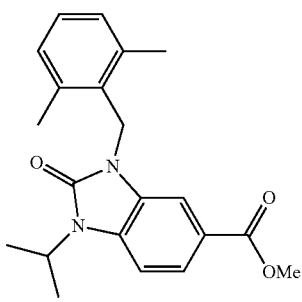 [SMILES: COC(=O)c1ccc2c(c1)n(Cc1c(C)cccc1C)c(=O)n2C(C)C]

To a solution of the compound [186-4] obtained in the process (4) (20 mg) and 2-iodopropane (0.013 mL) in N,N-dimethylformamide (0.6 mL) was added sodium hydride (4 mg), and then the reaction mixture was stirred at room temperature overnight. To the reaction mixture was added 10 mL water, and the reaction mixture was filled with InertSep K-solute (registered trademark). The reaction mixture was eluted with ethyl acetate and the eluted liquid was concentrated under reduced pressure. The obtained residue was purified by silica gel column chromatography to give the titled compound (10 mg) as a white solid.

$^1$H-NMR (400 MHz, CDCl$_3$) δ: 7.73 (1H, dd, J=8.3, 1.5 Hz), 7.18-7.04 (6H, m), 5.15 (2H, s), 4.77 (1H, septet, J=7.1 Hz), 3.82 (3H, s), 2.36 (6H, s), 1.56 (6H, d, J=7.1 Hz).

ESI-MS found: 353 [M+H]$^+$ (6) Synthesis of 3-(2,6-dimethylbenzyl)-1-isopropyl-2-oxo-2,3-dihydro-1H-benzimidazole-5-carboxylic acid [186]

To a solution of the compound [186-5] obtained in the process (5) (10 mg) in tetrahydrofuran (2 mL) was added an aqueous solution of 1N-sodium hydroxide (0.5 mL), and then the reaction mixture was subjected to microwave irradiation at 130° C. for 45 minutes. To the reaction mixture was added 1M-hydrochloric acid, and the reaction mixture was extracted with ethyl acetate. The obtained organic layer was concentrated under reduced pressure. The obtained residue was purified by reverse phase preparative liquid chromatography to give the titled compound (3 mg) as a white solid.

ESI-MS found: 339 [M+H]$^+$

Example 187

Test for Uric Acid Transport Inhibition Using Human URAT1 Expression Cell

In this Example, it was evaluated whether the Example compound has the URAT1 inhibitory activity.

Human URAT1 full-length cDNA was introduced to an expression vector pcDNA5/FRT/V5-His TOPO (registered trademark) (Invitrogen Corporation). The obtained expression plasmid was introduced to Chinese hamster ovary cell (hereinafter referred to as the CHO cell) by the liposome method using Lipofectamine LTX (Invitrogen), and cultured in a selection medium including hygromycin, whereby to prepare human URAT1 stable expression cell.

The human URAT1 expression CHO cell was cultured using D-MEM/F-12 (1:1) mixed medium including 10% bovine fetal serum and hygromycin at 37° C. in the presence of 5% CO$_2$. The cells were seeded onto a 96 well plate (Corning Incorporated) in 0.8×10$^5$ cells/well, and after 24 hours, the test for uric acid transport inhibition below was performed.

The medium was removed by aspiration, and then the cells were washed once with an assay buffer including 125 mM of sodium gluconate, 4.8 mM of potassium gluconate, 1.2 mM of potassium dihydrogen phosphate, 1.2 mM of magnesium sulfate, 1.3 mM of calcium gluconate and 5.6 mM of glucose. 50 μL assay buffer including the test compound in various concentrations was added, and further 50 μL assay buffer including a radioactive ligand (uric acid labeled with $^{14}$C; 38 μM final concentration) was added, and incorporation reaction was performed at room temperature for 5 minutes. Immediately after completion of the reaction, the reaction mixture was washed twice with 100 μL ice-cold assay buffer, and 100 μL of 0.1 N sodium hydroxide was added. The reaction mixture was stirred to lyse the cells, and 4 mL Hionic-Fluor (Packard BioScience CO) was added, and then the radioactivity was measured with a liquid scintillation counter (Beckman Coulter, Inc. and Packard BioScience CO).

The radioactivity when each concentration of the test compound was added (uric acid incorporation activity, %) was calculated in which the difference of the radioactivity when the test compound was not added (DMSO added), and the radioactivity when a positive control compound, benzbromarone (known URAT1 inhibitor) was added in 100 μM, was taken as 100%, and the concentration of the test compound when the uric acid incorporation activity was inhibited to 50% ($IC_{50}$) was obtained. The results thereof are shown in Table 1.

TABLE 1

| Test Compound | URAT1 Inhibitory Activity ($IC_{50}$, nM) |
| --- | --- |
| Compound of Example 61 | 46 |
| Compound of Example 64 | 22 |
| Compound of Example 66 | 67 |
| Compound of Example 68 | 30 |
| Compound of Example 75 | 77 |
| Compound of Example 78 | 24 |
| Compound of Example 80 | 18 |
| Compound of Example 82 | 15 |
| Compound of Example 84 | 53 |
| Compound of Example 85 | 63 |
| Compound of Example 86 | 28 |
| Compound of Example 87 | 88 |
| Compound of Example 88 | 98 |
| Compound of Example 89 | 23 |
| Compound of Example 91 | 43 |
| Compound of Example 92 | 71 |
| Compound of Example 97 | 18 |
| Compound of Example 99 | 41 |
| Compound of Example 102 | 52 |
| Compound of Example 104 | 101 |
| Compound of Example 106 | 55 |
| Compound of Example 107 | 77 |
| Compound of Example 108 | 94 |
| Compound of Example 109 | 335 |
| Compound of Example 111 | 75 |
| Compound of Example 112 | 98 |
| Compound of Example 115 | 394 |
| Compound of Example 117 | 91 |
| Compound of Example 119 | 65 |
| Compound of Example 120 | 91 |
| Compound of Example 121 | 41 |
| Compound of Example 122 | 10 |
| Compound of Example 124 | 31 |
| Compound of Example 125 | 72 |

TABLE 1-continued

| Test Compound | URAT1 Inhibitory Activity ($IC_{50}$, nM) |
| --- | --- |
| Compound of Example 128 | 576 |
| Compound of Example 130 | 68 |
| Compound of Example 132 | 186 |
| Compound of Example 133 | 16 |
| Compound of Example 134 | 13 |
| Compound of Example 135 | 23 |
| Compound of Example 136 | 34 |
| Compound of Example 137 | 10 |
| Compound of Example 138 | 916 |
| Compound of Example 139 | 653 |
| Compound of Example 140 | 24 |
| Compound of Example 142 | 50 |
| Compound of Example 143 | 35 |
| Compound of Example 144 | 42 |
| Compound of Example 145 | 26 |
| Compound of Example 146 | 53 |
| Compound of Example 147 | 76 |
| Compound of Example 148 | 49 |
| Compound of Example 149 | 53 |
| Compound of Example 150 | 295 |
| Compound of Example 152 | 184 |
| Compound of Example 153 | 361 |
| Compound of Example 156 | 438 |
| Compound of Example 158 | 292 |
| Compound of Example 160 | 124 |
| Compound of Example 163 | 113 |
| Compound of Example 164 | 55 |
| Compound of Example 167 | 80 |
| Compound of Example 170 | 80 |
| Compound of Example 171 | 52 |
| Compound of Example 172 | 162 |
| Compound of Example 174 | 148 |
| Compound of Example 175 | 163 |
| Compound of Example 177 | 104 |
| Compound of Example 182 | 52 |
| Compound of Example 183 | 15 |
| Compound of Example 185 | 17 |
| Compound of Example 186 | 165 |

From above, it was shown that the compound of the present invention accomplishes excellent URAT1 inhibitory action activity.

The correspondence relation of the compounds of Examples 1 to 186 with Formula (I) are shown below.

TABLE 2

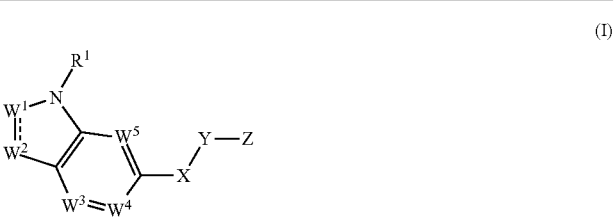

(I)

| | $R^1$ | ---- | $W^1$ | $W^2$ | $W^3$ | $W^4$ | $W^5$ | X | Y | Z |
| --- | --- | --- | --- | --- | --- | --- | --- | --- | --- | --- |
| Example 1 | —$Q^1$—$A^1$<br>$Q^1$: Methylene<br>$A^1$: Ph<br>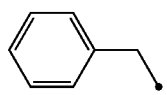 | Double Bond | =C($R^a$)—<br>$R^a$: Hydrogen Atom | =C($R^b$)—<br>$R^b$: Hydrogen Atom | Methine | Methine | Methine | Single Bond | Single Bond | COOH |

TABLE 2-continued

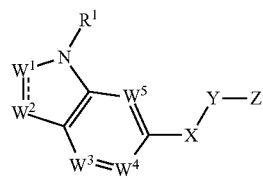

(I)

| | R¹ | ---- | W¹ | W² | W³ | W⁴ | W⁵ | X | Y | Z |
|---|---|---|---|---|---|---|---|---|---|---|
| Example 2 | —Q¹—A¹<br>Q¹: Methylene<br>A¹: 2,6-Me₂Ph<br>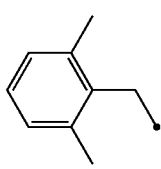 | Double Bond | =C(Rᵃ)—<br>Rᵃ: Hydrogen Atom | =C(Rᵇ)—<br>Rᵇ: Hydrogen Atom | Methine | Methine | Methine | Single Bond | Single Bond | COOH |

TABLE 3

| | R¹ | ---- | W¹ | W² | W³ | W⁴ | W⁵ | X | Y | Z |
|---|---|---|---|---|---|---|---|---|---|---|
| Example 3 | —Q¹—A¹<br>Q¹: Methylene<br>A¹: 2,4,6-Me₃Ph<br>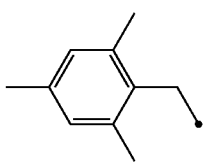 | Double Bond | =C(Rᵃ)—<br>Rᵃ: Hydrogen Atom | =C(Rᵇ)—<br>Rᵇ: Hydrogen Atom | Methine | Methine | Methine | Single Bond | Single Bond | COOH |
| Example 4 | —Q¹—A¹<br>Q¹: Methylene<br>A¹: Ph<br>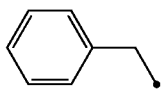 | Double Bond | =C(Rᵃ)—<br>Rᵃ: Hydrogen Atom | =C(Rᵇ)—<br>Rᵇ: Hydrogen Atom | Methine | Methine | Methine | Single Bond | $(CR^{\eta}R^{\eta})_n$<br>n = 1<br>—CH₂— | COOH |
| Example 5 | —Q¹—A¹<br>Q¹: Methylene<br>A¹: 2,6-Me₂Ph<br>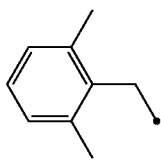 | Double Bond | =C(Rᵃ)—<br>Rᵃ: Hydrogen Atom | =C(Rᵇ)—<br>Rᵇ: Hydrogen Atom | Methine | Methine | Methine | Single Bond | $(CR^{\eta}R^{\eta})_n$<br>n = 1<br>—CH₂— | COOH |
| Example 6 | —Q¹—A¹<br>Q¹: Methylene<br>A¹: 2-Me—Ph<br>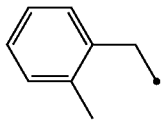 | Double Bond | =C(Rᵃ)—<br>Rᵃ: Hydrogen Atom | =C(Rᵇ)—<br>Rᵇ: Hydrogen Atom | Methine | Methine | Methine | Single Bond | $(CR^{\eta}R^{\eta})_n$<br>n = 1<br>—CH₂— | COOH |

TABLE 4

| | R¹ | ---- | W¹ | W² | W³ | W⁴ | W⁵ | X | Y | Z |
|---|---|---|---|---|---|---|---|---|---|---|
| Example 7 | —Q¹—A¹<br>Q¹: Methylene<br>A¹: 2-Cl—Ph | Double Bond | =C(Rᵃ)—<br>Rᵃ: Hydrogen Atom | =C(Rᵇ)—<br>Rᵇ: Hydrogen Atom | Methine | Methine | Methine | Single Bond | $(CR^{\eta}R^{\eta})_n$<br>n = 1<br>—CH₂— | COOH |
| Example 8 | —Q¹—A¹<br>Q¹: Methylene<br>A¹: 2-CF₃—Ph | Double Bond | =C(Rᵃ)—<br>Rᵃ: Hydrogen Atom | =C(Rᵇ)—<br>Rᵇ: Hydrogen Atom | Methine | Methine | Methine | Single Bond | $(CR^{\eta}R^{\eta})_n$<br>n = 1<br>—CH₂— | COOH |
| Example 9 | —Q¹—A¹<br>Q¹: Methylene<br>A¹: 2-F—Ph | Double Bond | =C(Rᵃ)—<br>Rᵃ: Hydrogen Atom | =C(Rᵇ)—<br>Rᵇ: Hydrogen Atom | Methine | Methine | Methine | Single Bond | $(CR^{\eta}R^{\eta})_n$<br>n = 1<br>—CH₂— | COOH |
| Example 10 | —Q¹—A¹<br>Q¹: Methylene<br>A¹: 3-F—Ph | Double Bond | =C(Rᵃ)—<br>Rᵃ: Hydrogen Atom | =C(Rᵇ)—<br>Rᵇ: Hydrogen Atom | Methine | Methine | Methine | Single Bond | $(CR^{\eta}R^{\eta})_n$<br>n = 1<br>—CH₂— | COOH |

TABLE 5

| | R¹ | ---- | W¹ | W² | W³ | W⁴ | W⁵ | X | Y | Z |
|---|---|---|---|---|---|---|---|---|---|---|
| Example 11 | —Q¹—A¹<br>Q¹: Methylene<br>A¹: 4-F—Ph | Double Bond | =C(Rᵃ)—<br>Rᵃ: Hydrogen Atom | =C(Rᵇ)—<br>Rᵇ: Hydrogen Atom | Methine | Methine | Methine | Single Bond | $(CR^{\eta}R^{\eta})_n$<br>n = 1<br>—CH₂— | COOH |
| Example 12 | —Q¹—A¹<br>Q¹: Methylene<br>A¹: 2-Cl-6-F—Ph | Double Bond | =C(Rᵃ)—<br>Rᵃ: Hydrogen Atom | =C(Rᵇ)—<br>Rᵇ: Hydrogen Atom | Methine | Methine | Methine | Single Bond | $(CR^{\eta}R^{\eta})_n$<br>n = 1<br>—CH₂— | COOH |

TABLE 5-continued

| | R¹ | ---- | W¹ | W² | W³ | W⁴ | W⁵ | X | Y | Z |
|---|---|---|---|---|---|---|---|---|---|---|
| Example 13 | —Q¹—A¹<br>Q¹: Methylene<br>A¹: 2-Cl-4-F—Ph | Double Bond | =C(Rᵃ)—<br>Rᵃ: Hydrogen Atom | =C(Rᵇ)—<br>Rᵇ: Hydrogen Atom | Methine | Methine | Methine | Single Bond | $(CR^{\eta}R^{\eta})_n$<br>n = 1<br>—CH₂— | COOH |
| Example 14 | —Q¹—A¹<br>Q¹: Methylene<br>A¹: 2-Cl-5-F—Ph | Double Bond | =C(Rᵃ)—<br>Rᵃ: Hydrogen Atom | =C(Rᵇ)—<br>Rᵇ: Hydrogen Atom | Methine | Methine | Methine | Single Bond | $(CR^{\eta}R^{\eta})_n$<br>n = 1<br>—CH₂— | COOH |

TABLE 6

| | R¹ | ---- | W¹ | W² | W³ | W⁴ | W⁵ | X | Y | Z |
|---|---|---|---|---|---|---|---|---|---|---|
| Example 15 | —Q¹—A¹<br>Q¹: Methylene<br>A¹: 3-Cl—Ph | Double Bond | =C(Rᵃ)—<br>Rᵃ: Hydrogen Atom | =C(Rᵇ)—<br>Rᵇ: Hydrogen Atom | Methine | Methine | Methine | Single Bond | $(CR^{\eta}R^{\eta})_n$<br>n = 1<br>—CH₂— | COOH |
| Example 16 | —Q¹—A¹<br>Q¹: Methylene<br>A¹: 4-Cl—Ph | Double Bond | =C(Rᵃ)—<br>Rᵃ: Hydrogen Atom | =C(Rᵇ)—<br>Rᵇ: Hydrogen Atom | Methine | Methine | Methine | Single Bond | $(CR^{\eta}R^{\eta})_n$<br>n = 1<br>—CH₂— | COOH |
| Example 17 | —Q¹—A¹<br>Q¹: Methylene<br>A¹: 2,6-Cl₂Ph | Double Bond | =C(Rᵃ)—<br>Rᵃ: Hydrogen Atom | =C(Rᵇ)—<br>Rᵇ: Hydrogen Atom | Methine | Methine | Methine | Single Bond | $(CR^{\eta}R^{\eta})_n$<br>n = 1<br>—CH₂— | COOH |
| Example 18 | —Q¹—A¹<br>Q¹: Methylene<br>A¹: 2,3-Cl₂Ph | Double Bond | =C(Rᵃ)—<br>Rᵃ: Hydrogen Atom | =C(Rᵇ)—<br>Rᵇ: Hydrogen Atom | Methine | Methine | Methine | Single Bond | $(CR^{\eta}R^{\eta})_n$<br>n = 1<br>—CH₂— | COOH |

TABLE 7

| | R$^1$ | ---- | W$^1$ | W$^2$ | W$^3$ | W$^4$ | W$^5$ | X | Y | Z |
|---|---|---|---|---|---|---|---|---|---|---|
| Example 19 | —Q$^1$—A$^1$<br>Q$^1$: Methylene<br>A$^1$: 6-Cl-benzodioxole-5-yl | Double Bond | =C(R$^a$)—<br>R$^a$: Hydrogen Atom | =C(R$^b$)—<br>R$^b$: Hydrogen Atom | Methine | Methine | Methine | Single Bond | (CR$^\eta$R$^\eta$)$_n$<br>n = 1<br>—CH$_2$— | COOH |
| Example 20 | —Q$^1$—A$^1$<br>Q$^1$: Methylene<br>A$^1$: 2,4-Cl$_2$Ph | Double Bond | =C(R$^a$)—<br>R$^a$: Hydrogen Atom | =C(R$^b$)—<br>R$^b$: Hydrogen Atom | Methine | Methine | Methine | Single Bond | (CR$^\eta$R$^\eta$)$_n$<br>n = 1<br>—CH$_2$— | COOH |
| Example 21 | —Q$^1$—A$^1$<br>Q$^1$: Methylene<br>A$^1$: 2,5-Cl$_2$Ph | Double Bond | =C(R$^a$)—<br>R$^a$: Hydrogen Atom | =C(R$^b$)—<br>R$^b$: Hydrogen Atom | Methine | Methine | Methine | Single Bond | (CR$^\eta$R$^\eta$)$_n$<br>n = 1<br>—CH$_2$— | COOH |

TABLE 8

| | R$^1$ | ---- | W$^1$ | W$^2$ | W$^3$ | W$^4$ | W$^5$ | X | Y | Z |
|---|---|---|---|---|---|---|---|---|---|---|
| Example 22 | —Q$^1$—A$^1$<br>Q$^1$: Methylene<br>A$^1$: 2-F-6-CF$_3$Ph | Double Bond | =C(R$^a$)—<br>R$^a$: Hydrogen Atom | =C(R$^b$)—<br>R$^b$: Hydrogen Atom | Methine | Methine | Methine | Single Bond | (CR$^\eta$R$^\eta$)$_n$<br>n = 1<br>—CH$_2$— | COOH |
| Example 23 | —Q$^1$—A$^1$<br>Q$^1$: Methylene<br>A$^1$: 4-F-2-CF$_3$Ph | Double Bond | =C(R$^a$)—<br>R$^a$: Hydrogen Atom | =C(R$^b$)—<br>R$^b$: Hydrogen Atom | Methine | Methine | Methine | Single Bond | (CR$^\eta$R$^\eta$)$_n$<br>n = 1<br>—CH$_2$— | COOH |
| Example 24 | —Q$^1$—A$^1$<br>Q$^1$: Methylene<br>A$^1$: 4-EtPh | Double Bond | =C(R$^a$)—<br>R$^a$: Hydrogen Atom | =C(R$^b$)—<br>R$^b$: Hydrogen Atom | Methine | Methine | Methine | Single Bond | (CR$^\eta$R$^\eta$)$_n$<br>n = 1<br>—CH$_2$— | COOH |

TABLE 8-continued

| | R¹ | ---- | W¹ | W² | W³ | W⁴ | W⁵ | X | Y | Z |
|---|---|---|---|---|---|---|---|---|---|---|
| Example 25 | —Q¹—A¹<br>Q¹: Methylene<br>A¹: 2,4-F₂Ph | Double Bond | =C(Rᵃ)—<br>Rᵃ: Hydrogen Atom | =C(Rᵇ)—<br>Rᵇ: Hydrogen Atom | Methine | Methine | Methine | Single Bond | $(CR^{y_1}R^{y_1})_n$<br>n = 1<br>—CH₂— | COOH |

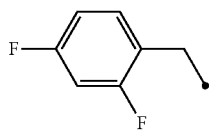

TABLE 9

| | R¹ | ---- | W¹ | W² | W³ | W⁴ | W⁵ | X | Y | Z |
|---|---|---|---|---|---|---|---|---|---|---|
| Example 26 | —Q¹—A¹<br>Q¹: Methylene<br>A¹: 2,6-F₂Ph | Double Bond | =C(Rᵃ)—<br>Rᵃ: Hydrogen Atom | =C(Rᵇ)—<br>Rᵇ: Hydrogen Atom | Methine | Methine | Methine | Single Bond | $(CR^{y_1}R^{y_1})_n$<br>n = 1<br>—CH₂— | COOH |

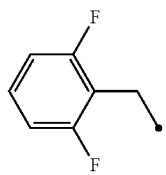

| Example 27 | —Q¹—A¹<br>Q¹: Methylene<br>A¹: 2,5-F₂Ph | Double Bond | =C(Rᵃ)—<br>Rᵃ: Hydrogen Atom | =C(Rᵇ)—<br>Rᵇ: Hydrogen Atom | Methine | Methine | Methine | Single Bond | $(CR^{y_1}R^{y_1})_n$<br>n = 1<br>—CH₂— | COOH |

| Example 28 | —Q¹—A¹<br>Q¹: Methylene<br>A¹: 2,3-F₂Ph | Double Bond | =C(Rᵃ)—<br>Rᵃ: Hydrogen Atom | =C(Rᵇ)—<br>Rᵇ: Hydrogen Atom | Methine | Methine | Methine | Single Bond | $(CR^{y_1}R^{y_1})_n$<br>n = 1<br>—CH₂— | COOH |

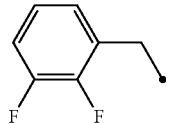

| Example 29 | —Q¹—A¹<br>Q¹: Methylene<br>A¹: 3-CF₃Ph | Double Bond | =C(Rᵃ)—<br>Rᵃ: Hydrogen Atom | =C(Rᵇ)—<br>Rᵇ: Hydrogen Atom | Methine | Methine | Methine | Single Bond | $(CR^{y_1}R^{y_1})_n$<br>n = 1<br>—CH₂— | COOH |

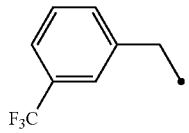

TABLE 10

| | R¹ | ---- | W¹ | W² | W³ | W⁴ | W⁵ | X | Y | Z |
|---|---|---|---|---|---|---|---|---|---|---|
| Example 30 | —Q¹—A¹<br>Q¹: Methylene<br>A¹: 4-CF₃Ph | Double Bond | =C(Rᵃ)—<br>Rᵃ: Hydrogen Atom | =C(Rᵇ)—<br>Rᵇ: Hydrogen Atom | Methine | Methine | Methine | Single Bond | (CR^(y1)R^(y1))ₙ<br>n = 1<br>—CH₂— | COOH |
| Example 31 | —Q¹—A¹<br>Q¹: Methylene<br>A¹: 2,4-Me₂Ph | Double Bond | =C(Rᵃ)—<br>Rᵃ: Hydrogen Atom | =C(Rᵇ)—<br>Rᵇ: Hydrogen Atom | Methine | Methine | Methine | Single Bond | (CR^(y1)R^(y1))ₙ<br>n = 1<br>—CH₂— | COOH |
| Example 32 | —Q¹—A¹<br>Q¹: Methylene<br>A¹: 2,5-Me₂Ph | Double Bond | =C(Rᵃ)—<br>Rᵃ: Hydrogen Atom | =C(Rᵇ)—<br>Rᵇ: Hydrogen Atom | Methine | Methine | Methine | Single Bond | (CR^(y1)R^(y1))ₙ<br>n = 1<br>—CH₂— | COOH |
| Example 33 | —Q¹—A¹<br>Q¹: Methylene<br>A¹: 3-MePh | Double Bond | =C(Rᵃ)—<br>Rᵃ: Hydrogen Atom | =C(Rᵇ)—<br>Rᵇ: Hydrogen Atom | Methine | Methine | Methine | Single Bond | (CR^(y1)R^(y1))ₙ<br>n = 1<br>—CH₂— | COOH |

TABLE 11

| | R¹ | ---- | W¹ | W² | W³ | W⁴ | W⁵ | X | Y | Z |
|---|---|---|---|---|---|---|---|---|---|---|
| Example 34 | —Q¹—A¹<br>Q¹: Methylene<br>A¹: 4-MePh | Double Bond | =C(Rᵃ)—<br>Rᵃ: Hydrogen Atom | =C(Rᵇ)—<br>Rᵇ: Hydrogen Atom | Methine | Methine | Methine | Single Bond | (CR^(y1)R^(y1))ₙ<br>n = 1<br>—CH₂— | COOH |
| Example 35 | —Q¹—A¹<br>Q¹: Methylene<br>A¹: 4-pyridyl | Double Bond | =C(Rᵃ)—<br>Rᵃ: Hydrogen Atom | =C(Rᵇ)—<br>Rᵇ: Hydrogen Atom | Methine | Methine | Methine | Single Bond | (CR^(y1)R^(y1))ₙ<br>n = 1<br>—CH₂— | COOH |
| Example 36 | —Q¹—A¹<br>Q¹: Methylene<br>A¹: 3-MeO—Ph | Double Bond | =C(Rᵃ)—<br>Rᵃ: Hydrogen Atom | =C(Rᵇ)—<br>Rᵇ: Hydrogen Atom | Methine | Methine | Methine | Single Bond | (CR^(y1)R^(y1))ₙ<br>n = 1<br>—CH₂— | COOH |

TABLE 11-continued

| Example | R¹ | ---- | W¹ | W² | W³ | W⁴ | W⁵ | X | Y | Z |
|---|---|---|---|---|---|---|---|---|---|---|
| Example 37 | —Q¹—A¹<br>Q¹: Methylene<br>A¹: 3-MeO—Ph<br>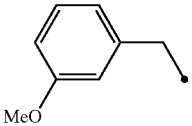 | Double Bond | =C(Rᵃ)—<br>Rᵃ: Hydrogen Atom | =C(Rᵇ)—<br>Rᵇ: Hydrogen Atom | Methine | Methine | Methine | Single Bond | (CR^η R^η')ₙ<br>n = 1<br>—CH₂— | COOH |

TABLE 12

| Example | R¹ | ---- | W¹ | W² | W³ | W⁴ | W⁵ | X | Y | Z |
|---|---|---|---|---|---|---|---|---|---|---|
| Example 38 | —Q¹—A¹<br>Q¹: Methylene<br>A¹: 4-MeO—Ph | Double Bond | =C(Rᵃ)—<br>Rᵃ: Hydrogen Atom | =C(Rᵇ)—<br>Rᵇ: Hydrogen Atom | Methine | Methine | Methine | Single Bond | (CR^η R^η')ₙ<br>n = 1<br>—CH₂— | COOH |
| Example 39 | —Q¹—A¹<br>Q¹: Methylene<br>A¹: 1-naphthyl-Ph | Double Bond | =C(Rᵃ)—<br>Rᵃ: Hydrogen Atom | =C(Rᵇ)—<br>Rᵇ: Hydrogen Atom | Methine | Methine | Methine | Single Bond | (CR^η R^η')ₙ<br>n = 1<br>—CH₂— | COOH |
| Example 40 | —Q¹—A¹<br>Q¹: Methylene<br>A¹: 2-naphthyl-Ph | Double Bond | =C(Rᵃ)—<br>Rᵃ: Hydrogen Atom | =C(Rᵇ)—<br>Rᵇ: Hydrogen Atom | Methine | Methine | Methine | Single Bond | (CR^η R^η')ₙ<br>n = 1<br>—CH₂— | COOH |
| Example 41 | —Q¹—A¹<br>Q¹: Methylene<br>A¹: 6-Cl-pyridine-3-yl | Double Bond | =C(Rᵃ)—<br>Rᵃ: Hydrogen Atom | =C(Rᵇ)—<br>Rᵇ: Hydrogen Atom | Methine | Methine | Methine | Single Bond | (CR^η R^η')ₙ<br>n = 1<br>—CH₂— | COOH |

TABLE 13

| Example | R¹ | ---- | W¹ | W² | W³ | W⁴ | W⁵ | X | Y | Z |
|---|---|---|---|---|---|---|---|---|---|---|
| Example 42 | —Q¹—A¹<br>Q¹: Methylene<br>A¹: 6-Me-pyridine-2-yl<br>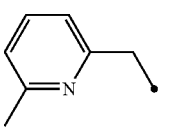 | Double Bond | =C(Rᵃ)—<br>Rᵃ: Hydrogen Atom | =C(Rᵇ)—<br>Rᵇ: Hydrogen Atom | Methine | Methine | Methine | Single Bond | (CR^η R^η')ₙ<br>n = 1<br>—CH₂— | COOH |

TABLE 13-continued

| | R¹ | ---- | W¹ | W² | W³ | W⁴ | W⁵ | X | Y | Z |
|---|---|---|---|---|---|---|---|---|---|---|
| Example 43 | —Q¹—A¹<br>Q¹: Methylene<br>A¹: biphenyl-2-yl<br>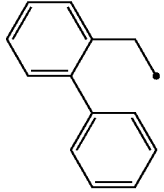 | Double Bond | =C(Rᵃ)—<br>Rᵃ: Hydrogen Atom | =C(Rᵇ)—<br>Rᵇ: Hydrogen Atom | Methine | Methine | Methine | Single Bond | $(CR^{y_1}R^{y_1})_n$<br>n = 1<br>—CH₂— | COOH |
| Example 44 | —Q¹—A¹<br>Q¹: Methylene<br>A¹: biphenyl-3-yl<br>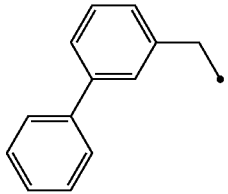 | Double Bond | =C(Rᵃ)—<br>Rᵃ: Hydrogen Atom | =C(Rᵇ)—<br>Rᵇ: Hydrogen Atom | Methine | Methine | Methine | Single Bond | $(CR^{y_1}R^{y_1})_n$<br>n = 1<br>—CH₂— | COOH |
| Example 45 | —Q¹—A¹<br>Q¹: Methylene<br>A¹: biphenyl-4-yl<br>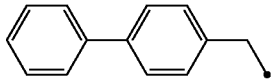 | Double Bond | =C(Rᵃ)—<br>Rᵃ: Hydrogen Atom | =C(Rᵇ)—<br>Rᵇ: Hydrogen Atom | Methine | Methine | Methine | Single Bond | $(CR^{y_1}R^{y_1})_n$<br>n = 1<br>—CH₂— | COOH |

TABLE 14

| | R¹ | ---- | W¹ | W² | W³ | W⁴ | W⁵ | X | Y | Z |
|---|---|---|---|---|---|---|---|---|---|---|
| Example 46 | —Q¹—A¹<br>Q¹: Methylene<br>A¹: 3-PhO—Ph<br>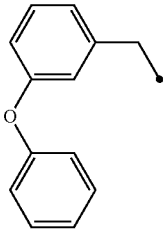 | Double Bond | =C(Rᵃ)—<br>Rᵃ: Hydrogen Atom | =C(Rᵇ)—<br>Rᵇ: Hydrogen Atom | Methine | Methine | Methine | Single Bond | $(CR^{y_1}R^{y_1})_n$<br>n = 1<br>—CH₂— | COOH |
| Example 47 | —Q¹—A¹<br>Q¹: —(CH₂)₃—<br>A¹: Ph<br>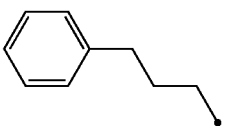 | Double Bond | =C(Rᵃ)—<br>Rᵃ: Hydrogen Atom | =C(Rᵇ)—<br>Rᵇ: Hydrogen Atom | Methine | Methine | Methine | Single Bond | $(CR^{y_1}R^{y_1})_n$<br>n = 1<br>—CH₂— | COOH |

TABLE 14-continued

| | R¹ | ---- | W¹ | W² | W³ | W⁴ | W⁵ | X | Y | Z |
|---|---|---|---|---|---|---|---|---|---|---|
| Example 48 | Lower alkyl group (isopropyl) | Double Bond | =C(R$^a$)— R$^a$: Hydrogen Atom | =C(R$^b$)— R$^b$: Hydrogen Atom | Methine | Methine | Methine | Single Bond | (CR$^{Yi}$R$^{Yi'}$)$_n$ n = 1 —CH$_2$— | COOH |
| Example 49 | Lower alkyl group (isobutyl) | Double Bond | =C(R$^a$)— R$^a$: Hydrogen Atom | =C(R$^b$)— R$^b$: Hydrogen Atom | Methine | Methine | Methine | Single Bond | (CR$^{Yi}$R$^{Yi'}$)$_n$ n = 1 —CH$_2$— | COOH |
| Example 50 | Lower alkyl group that may be substituted with a cycloalkyl group (cyclohexylmethyl) | Double Bond | =C(R$^a$)— R$^a$: Hydrogen Atom | =C(R$^b$)— R$^b$: Hydrogen Atom | Methine | Methine | Methine | Single Bond | (CR$^{Yi}$R$^{Yi'}$)$_n$ n = 1 —CH$_2$— | COOH |

TABLE 15

| | R¹ | ---- | W¹ | W² | W³ | W⁴ | W⁵ | X | Y | Z |
|---|---|---|---|---|---|---|---|---|---|---|
| Example 51 | —Q¹—A¹ Q¹: Methylene A¹: 2,6-Me$_2$Ph | Double Bond | =C(R$^a$)— R$^a$: Hydrogen Atom | =N— | Methine | Methine | Methine | Single Bond | Single Bond | COOH |
| Example 52 | —Q¹—A¹ Q¹: Methylene A¹: 2,6-Me$_2$Ph | Double Bond | =C(R$^a$)— R$^a$: Hydrogen Atom | =N— | Methine | Methine | Methine | Single Bond | (CR$^{Yi}$R$^{Yi'}$)$_n$ n = 1 —CH$_2$— | COOH |
| Example 53 | —Q¹—A¹ Q¹: Methylene A¹: 2,6-Me$_2$Ph | Double Bond | =N— | =C(R$^b$)— R$^b$: Hydrogen Atom | Methine | Methine | Methine | Single Bond | Single Bond | COOH |

TABLE 16

| | R¹ | ---- | W¹ | W² | W³ | W⁴ | W⁵ | X | Y | Z |
|---|---|---|---|---|---|---|---|---|---|---|
| Example 54 | —Q¹—A¹<br>Q¹: Methylene<br>A¹: 2,6-Me₂Ph<br>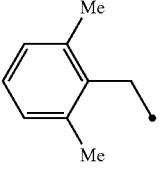 | Double Bond | =N— | =C(R$^b$)—<br>R$^b$:<br>Hydrogen Atom | Methine | Methine | Methine | Single Bond | (CR$^{Yi}$R$^{Yii}$)$_n$<br>n = 1<br>—CH₂— | COOH |
| Example 55 | —Q¹—A¹<br>Q¹: Methylene<br>A¹: 2,6-Me₂Ph<br>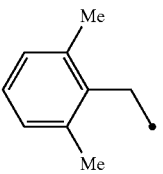 | Double Bond | =C(R$^a$)—<br>R$^a$:<br>Hydrogen Atom | =C(R$^b$)—<br>R$^b$:<br>Hydrogen Atom | Methine | Methine | Methine | Lower alkenylene<br>—CH₂=CH₂— | Single Bond | COOH |
| Example 56 | —Q¹—A¹<br>Q¹: Methylene<br>A¹: 2,6-Me₂Ph<br>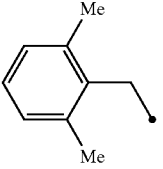 | Double Bond | =C(R$^a$)—<br>R$^a$:<br>Hydrogen Atom | =C(R$^b$)—<br>R$^b$:<br>Hydrogen Atom | Methine | Methine | Methine | Single Bond | (CR$^{Yi}$R$^{Yii}$)$_n$<br>n = 2<br>—(CH₂)₂— | COOH |

TABLE 17

| | R¹ | ---- | W¹ | W² | W³ | W⁴ | W⁵ | X | Y | Z |
|---|---|---|---|---|---|---|---|---|---|---|
| Example 57 | —Q¹—A¹<br>Q¹: Methylene<br>A¹: 2,6-Me₂Ph<br>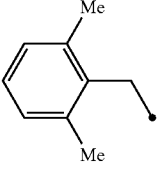 | Double Bond | =C(R$^a$)—<br>R$^a$:<br>Hydrogen Atom | =C(R$^b$)—<br>R$^b$:<br>Hydrogen Atom | Methine | Methine | Methine | Single Bond | (CR$^{Yi}$R$^{Yii}$)$_n$<br>n = 2<br>—CH(OH)CH₂—<br>R$^{Yi}$=OH | COOH |
| Example 58 | —Q¹—A¹<br>Q¹: Methylene<br>A¹: 2,6-Me₂Ph<br>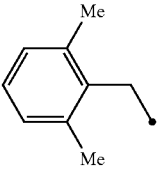 | Double Bond | =C(R$^a$)—<br>R$^a$:<br>Hydrogen Atom | =C(R$^b$)—<br>R$^b$:<br>Hydrogen Atom | Methine | Methine | Methine | Single Bond | (CR$^{Yi}$R$^{Yii}$)$_n$<br>n = 5<br>—(CH₂)₅— | COOH |

TABLE 18

| | R¹ | ---- | W¹ | W² | W³ | W⁴ | W⁵ | X | Y | Z |
|---|---|---|---|---|---|---|---|---|---|---|
| Example 59 | —Q¹—A¹<br>Q¹: Methylene<br>A¹: 2,6-Me₂Ph<br>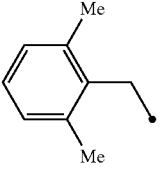 | Double Bond | =C(Rᵃ)—<br>Rᵃ: Hydrogen Atom | =C(Rᵇ)—<br>Rᵇ: Hydrogen Atom | Methine | Methine | Methine | carbonyl | $(CR^{Yi}R^{Yii})_n$<br>n = 2<br>—(CH₂)₂— | COOH |
| Example 60 | —Q¹—A¹<br>Q¹: Methylene<br>A¹: 2,6-Me₂Ph<br>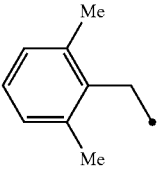 | Double Bond | =C(Rᵃ)—<br>Rᵃ: Hydrogen Atom | =C(Rᵇ)—<br>Rᵇ: Hydrogen Atom | Methine | Methine | Methine | Single Bond | $(CR^{Yi}R^{Yii})_n$<br>n = 3<br>—(CH₂)₃— | COOH |
| Example 61 | —Q¹—A¹<br>Q¹: Methylene<br>A¹: 2,6-Me₂Ph<br>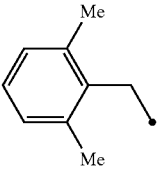 | Double Bond | =C(Rᵃ)—<br>Rᵃ: Hydrogen Atom | =C(Rᵇ)—<br>Rᵇ: Me | Methine | Methine | Methine | Single Bond | Single Bond | COOH |

TABLE 19

| | R¹ | ---- | W¹ | W² | W³ | W⁴ | W⁵ | X | Y | Z |
|---|---|---|---|---|---|---|---|---|---|---|
| Example 62 | —Q¹—A¹<br>Q¹: Methylene<br>A¹: 2,6-Me₂Ph<br>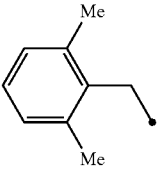 | Double Bond | =C(Rᵃ)—<br>Rᵃ: Hydrogen Atom | =C(Rᵇ)—<br>Rᵇ: | Methine | Methine | Methine | Single Bond | Single Bond | COO⁻K⁺ |
| Example 63 | —Q¹—A¹<br>Q¹: Methylene<br>A¹: 2,6-Me₂Ph<br>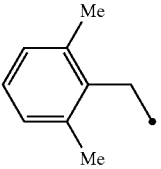 | Double Bond | =C(Rᵃ)—<br>Rᵃ: Hydrogen Atom | =C(Rᵇ)—<br>Rᵇ: Me | Methine | Methine | Methine | Single Bond | $(CR^{Yi}R^{Yii})_n$<br>n = 1<br>—CH₂— | OH |

TABLE 19-continued

| | R¹ | ---- | W¹ | W² | W³ | W⁴ | W⁵ | X | Y | Z |
|---|---|---|---|---|---|---|---|---|---|---|
| Example 64 | —Q¹—A¹<br>Q¹: Methylene<br>A¹: 2,6-Me₂Ph<br>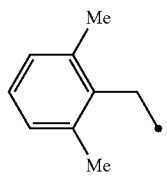 | Double Bond | $=C(R^a)$—<br>$R^a$:<br>Hydrogen Atom | $=C(R^b)$—<br>$R^b$: Me | Methine | Methine | Methine | Single Bond | $(CR^{Yi}R^{Yi})_n$<br>n = 1<br>—CH₂— | COOH |

TABLE 20

| | R¹ | ---- | W¹ | W² | W³ | W⁴ | W⁵ | X | Y | Z |
|---|---|---|---|---|---|---|---|---|---|---|
| Example 65 | —Q¹—A¹<br>Q¹: Methylene<br>A¹: 2,6-Me₂Ph<br>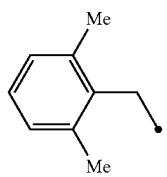 | Double Bond | $=C(R^a)$—<br>$R^a$:<br>Hydrogen Atom | $=C(R^b)$—<br>$R^b$: Me | Methine | Methine | Methine | Single Bond | $(CR^{Yi}R^{Yi})_n$<br>n = 1<br>—CH₂— | COO⁻K⁺ |
| Example 66 | —Q¹—A¹<br>Q¹: Methylene<br>A¹: 2,6-Me₂Ph<br>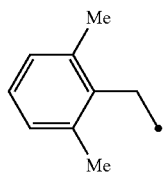 | Double Bond | =N— | $=C(R^b)$—<br>$R^b$: Me | Methine | Methine | Methine | Single Bond | $(CR^{Yi}R^{Yi})_n$<br>n = 1<br>—CH₂— | COOH |

TABLE 21

| | R¹ | ---- | W¹ | W² | W³ | W⁴ | W⁵ | X | Y | Z |
|---|---|---|---|---|---|---|---|---|---|---|
| Example 67 | —Q¹—A¹<br>Q¹: Methylene<br>A¹: Ph<br>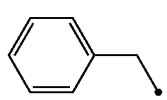 | Double Bond | $=C(R^a)$—<br>$R^a$:<br>Hydrogen Atom | $=C(R^b)$—<br>$R^b$: Cl | Methine | Methine | Methine | Single Bond | $(CR^{Yi}R^{Yi})_n$<br>n = 1<br>—CH₂— | COOH |
| Example 68 | —Q¹—A¹<br>Q¹: Methylene<br>A¹: 2,6-Me₂Ph<br>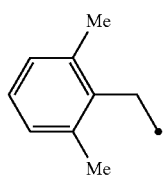 | Double Bond | $=C(R^a)$—<br>$R^a$:<br>Hydrogen Atom | $=C(R^b)$—<br>$R^b$: Cl | Methine | Methine | Methine | Single Bond | $(CR^{Yi}R^{Yi})_n$<br>n = 1<br>—CH₂— | COOH |

TABLE 21-continued

| | R¹ | ---- | W¹ | W² | W³ | W⁴ | W⁵ | X | Y | Z |
|---|---|---|---|---|---|---|---|---|---|---|
| Example 69 | —Q¹—A¹<br>Q¹: Methylene<br>A¹: 2,6-Me₂Ph | Double Bond | =C(Rᵃ)—<br>Rᵃ: Me | =C(Rᵇ)—<br>Rᵇ: Hydrogen Atom | Methine | Methine | Methine | Single Bond | Single Bond | COOH |

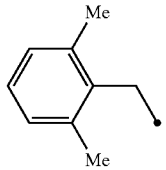

TABLE 22

| | R¹ | ---- | W¹ | W² | W³ | W⁴ | W⁵ | X | Y | Z |
|---|---|---|---|---|---|---|---|---|---|---|
| Example 70 | —Q¹—A¹<br>Q¹: Methylene<br>A¹: Ph | Double Bond | =C(Rᵃ)—<br>Rᵃ: Me | =C(Rᵇ)—<br>Rᵇ: Hydrogen Atom | Methine | Methine | Methine | Single Bond | Single Bond | COOH |

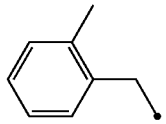

| Example 71 | —Q¹—A¹<br>Q¹: Methylene<br>A¹: 2-MePh | Double Bond | =C(Rᵃ)—<br>Rᵃ: Me | =C(Rᵇ)—<br>Rᵇ: Hydrogen Atom | Methine | Methine | Methine | Single Bond | Single Bond | COOH |

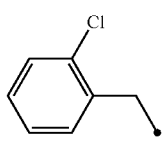

| Example 72 | —Q¹—A¹<br>Q¹: Methylene<br>A¹: 2-ClPh | Double Bond | =C(Rᵃ)—<br>Rᵃ: Me | =C(Rᵇ)—<br>Rᵇ: Hydrogen Atom | Methine | Methine | Methine | Single Bond | Single Bond | COOH |

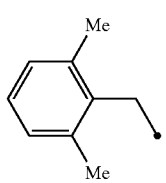

| Example 73 | —Q¹—A¹<br>Q¹: Methylene<br>A¹: 2,6-Me₂Ph | Double Bond | =C(Rᵃ)—<br>Rᵃ: CF₃ | =N— | Methine | Methine | Methine | Single Bond | Single Bond | COOH |

TABLE 23

| | R¹ | ---- | W¹ | W² | W³ | W⁴ | W⁵ | X | Y | Z |
|---|---|---|---|---|---|---|---|---|---|---|
| Example 74 | —Q¹—A¹<br>Q¹: Methylene<br>A¹: Ph | Single Bond | =C($R^{aa}$)($R^{ab}$)—<br>$R^{aa}$: H<br>$R^{ab}$: H | =C($R^{ba}$)($R^{bb}$)—<br>$R^{ba}$: H<br>$R^{bb}$: H | Methine | Methine | Methine | Single Bond | (CR$^{Yi}$R$^{Yi\prime}$)$_n$<br>n = 1<br>—CH$_2$— | COO⁻K⁺ |
| Example 75 | —Q¹—A¹<br>Q¹: Methylene<br>A¹: 2,6-Me$_2$Ph | Single Bond | =C($R^{aa}$)($R^{ab}$)—<br>$R^{aa}$: H<br>$R^{ab}$: H | =C($R^{ba}$)($R^{bb}$)—<br>$R^{ba}$: H<br>$R^{bb}$: H | Methine | Methine | Methine | Single Bond | (CR$^{Yi}$R$^{Yi\prime}$)$_n$<br>n = 1<br>—CH$_2$— | COOH |
| Example 76 | —Q¹—A¹<br>Q¹: Methylene<br>A¹: 2,6-Me$_2$Ph | Single Bond | =C($R^{aa}$)($R^{ab}$)—<br>$R^{aa}$: H<br>$R^{ab}$: H | =C($R^{ba}$)($R^{bb}$)—<br>$R^{ba}$: H<br>$R^{bb}$: H | Methine | Methine | Methine | Single Bond | (CR$^{Yi}$R$^{Yi\prime}$)$_n$<br>n = 1<br>—CH$_2$— | COO⁻K⁺ |
| Example 77 | —Q¹—A¹<br>Q¹: Methylene<br>A¹: 2,6-Me$_2$Ph | Single Bond | =C($R^{aa}$)($R^{ab}$)—<br>$R^{aa}$: H<br>$R^{ab}$: H | =C($R^{ba}$)($R^{bb}$)—<br>$R^{ba}$: H<br>$R^{bb}$: H | Methine | =C(Cl)— | Methine | Single Bond | (CR$^{Yi}$R$^{Yi\prime}$)$_n$<br>n = 1<br>—CH$_2$— | COOH |

TABLE 24

| | R¹ | ---- | W¹ | W² | W³ | W⁴ | W⁵ | X | Y | Z |
|---|---|---|---|---|---|---|---|---|---|---|
| Example 78 | —Q¹—A¹<br>Q¹: Methylene<br>A¹: 2,6-Me$_2$Ph | Single Bond | =C($R^{aa}$)($R^{ab}$)—<br>$R^{aa}$: H<br>$R^{ab}$: H | =C($R^{ba}$)($R^{bb}$)—<br>$R^{ba}$: Me<br>$R^{bb}$: H | Methine | Methine | Methine | Single Bond | (CR$^{Yi}$R$^{Yi\prime}$)$_n$<br>n = 1<br>—CH$_2$— | COOH |

TABLE 24-continued

| | R¹ | ---- | W¹ | W² | W³ | W⁴ | W⁵ | X | Y | Z |
|---|---|---|---|---|---|---|---|---|---|---|
| Example 79 | —Q¹—A¹<br>Q¹: Methylene<br>A¹: 2,6-Me₂Ph | Single Bond | =C(R$^{aa}$)(R$^{ab}$)—<br>R$^{aa}$: H<br>R$^{ab}$: H | =C(R$^{ba}$)(R$^{bb}$)—<br>R$^{ba}$: Me<br>R$^{bb}$: H<br>Chiral compound | Methine | Methine | Methine | Single Bond | (CR$^{y_1}$R$^{y_1}$)$_n$<br>n = 1<br>—CH₂— | COOH |
| Example 80 | —Q¹—A¹<br>Q¹: Methylene<br>A¹: 2,6-Me₂Ph | Single Bond | =C(R$^{aa}$)(R$^{ab}$)—<br>R$^{aa}$: H<br>R$^{ab}$: H | =C(R$^{ba}$)(R$^{bb}$)—<br>R$^{ba}$: Me<br>R$^{bb}$: Me | Methine | Methine | Methine | Single Bond | (CR$^{y_1}$R$^{y_1}$)$_n$<br>n = 1<br>—CH₂— | COOH |

TABLE 25

| | R¹ | ---- | W¹ | W² | W³ | W⁴ | W⁵ | X | Y | Z |
|---|---|---|---|---|---|---|---|---|---|---|
| Example 81 | —Q¹—A¹<br>Q¹: Methylene<br>A¹: 2,6-Me₂Ph | Single Bond | =C(R$^{aa}$)(R$^{ab}$)—<br>R$^{aa}$: H<br>R$^{ab}$: H | =C(R$^{ba}$)(R$^{bb}$)—<br>R$^{ba}$: H<br>R$^{bb}$: H | Methine | Methine | Methine | Single Bond | Single Bond | COOH |
| Example 82 | —Q¹—A¹<br>Q¹: Methylene<br>A¹: 2,6-Cl₂Ph | Double Bond | =C(R$^a$)—<br>R$^a$:<br>Hydrogen Atom | =C(R$^b$)—<br>R$^b$:<br>Methyl Group | Methine | Methine | Methine | Single Bond | (CR$^{y_1}$R$^{y_1}$)$_n$<br>n = 1<br>—CH₂— | COOH |
| Example 83 | —Q¹—A¹<br>Q¹: Methylene<br>A¹: 2,6-Cl₂Ph | Double Bond | =C(R$^a$)—<br>R$^a$:<br>Hydrogen Atom | =C(R$^b$)—<br>R$^b$:<br>Methyl Group | Methine | Methine | Methine | Single Bond | (CR$^{y_1}$R$^{y_1}$)$_n$<br>n = 1<br>—CH₂— | COO⁻K⁺ |

TABLE 26

| | R¹ | ---- | W¹ | W² | W³ | W⁴ | W⁵ | X | Y | Z |
|---|---|---|---|---|---|---|---|---|---|---|
| Example 84 | —Q¹—A¹<br>Q¹: Methylene<br>A¹: 2,3-Cl₂Ph | Double Bond | =C(Rᵃ)—<br>Rᵃ:<br>Hydrogen Atom | =C(Rᵇ)—<br>Rᵇ: Methyl Group | Methine | Methine | Methine | Single bond | (CRʸⁱRʸⁱ)ₙ<br>n = 1<br>—CH₂— | COOH |
| Example 85 | —Q¹—A¹<br>Q¹: Methylene<br>A¹: 2,5-Me₂Ph | Double Bond | =C(Rᵃ)—<br>Rᵃ:<br>Hydrogen Atom | =C(Rᵇ)—<br>Rᵇ: Methyl Group | Methine | Methine | Methine | Single Bond | (CRʸⁱRʸⁱ)ₙ<br>n = 1<br>—CH₂— | COOH |

TABLE 27

| | R¹ | ---- | W¹ | W² | W³ | W⁴ | W⁵ | X | Y | Z |
|---|---|---|---|---|---|---|---|---|---|---|
| Example 86 | —Q¹—A¹<br>Q¹: Methylene<br>A¹: 2-Cl-6-F-Ph | Double Bond | =C(Rᵃ)—<br>Rᵃ: Hydrogen Atom | =C(Rᵇ)—<br>Rᵇ: Methyl Group | Methine | Methine | Methine | Single Bond | (CRʸⁱRʸⁱ)ₙ<br>n = 1<br>—CH₂— | COOH |
| Example 87 | —Q¹—A¹<br>Q¹: Methylene<br>A¹: 2-Cl-Ph | Double Bond | =C(Rᵃ)—<br>Rᵃ: Hydrogen Atom | =C(Rᵇ)—<br>Rᵇ: Methyl Group | Methine | Methine | Methine | Single bond | (CRʸⁱRʸⁱ)ₙ<br>n = 1<br>—CH₂— | COOH |
| Example 88 | —Q¹—A¹<br>Q¹: Methylene<br>A¹: 6-Cl-benzo[d][1,3]dioxiole-5-yl | Double Bond | =C(Rᵃ)—<br>Rᵃ: Hydrogen Atom | =C(Rᵇ)—<br>Rᵇ: Methyl Group | Methine | Methine | Methine | Single bond | (CRʸⁱRʸⁱ)ₙ<br>n = 1<br>—CH₂— | COOH |

TABLE 27-continued

| | R¹ | ---- | W¹ | W² | W³ | W⁴ | W⁵ | X | Y | Z |
|---|---|---|---|---|---|---|---|---|---|---|
| Example 89 | —Q¹—A¹<br>Q¹: Methylene<br>A¹: 2,6-Cl₂Ph<br>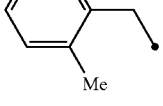 | Double Bond | =C(Rª)—<br>Rª: Hydrogen Atom | =C(R$^b$)—<br>R$^b$: Methyl Group | Methine | Methine | Methine | Single Bond | (CR$^{yi}$R$^{yi}$)$_n$<br>n = 2<br>—CH₂—CH₂— | COOH |

TABLE 28

| | R¹ | ---- | W¹ | W² | W³ | W⁴ | W⁵ | X | Y | Z |
|---|---|---|---|---|---|---|---|---|---|---|
| Example 90 | —Q¹—A¹<br>Q¹: Methylene<br>A¹: 2,6-Me₂Ph<br>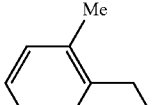 | Double Bond | =C(Rª)—<br>Rª: Hydrogen Atom | =C(R$^b$)—<br>R$^b$: Acetyl Group | Methine | Methine | Methine | Single Bond | Single Bond | COOH |
| Example 91 | —Q¹—A¹<br>Q¹: Methylene<br>A¹: 2,6-Me₂Ph<br>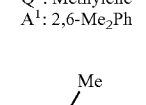 | Double Bond | =C(Rª)—<br>Rª: Hydrogen Atom | =C(R$^b$)—<br>R$^b$: Ethyl Group | Methine | Methine | Methine | Single Bond | Single Bond | COOH |
| Example 92 | —Q¹—A¹<br>Q¹: Methylene<br>A¹: 2,6-Me₂Ph | Double Bond | =C(Rª)—<br>Rª: Hydrogen Atom | =C(R$^b$)—<br>R$^b$: Isopropyl Group | Methine | Methine | Methine | Single Bond | Single Bond | COOH |
| Example 93 | —Q¹—A¹<br>Q¹: Methylene<br>A¹: 5-Cl-thiophene-2-yl<br>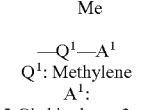 | Double Bond | =C(Rª)—<br>Rª: Hydrogen Atom | =C(R$^b$)—<br>R$^b$: Hydrogen Atom | Methine | Methine | Methine | Single Bond | (CR$^{yi}$R$^{yi}$)$_n$<br>n = 1<br>—CH₂— | COOH |

TABLE 29

| | R¹ | ---- | W¹ | W² | W³ | W⁴ | W⁵ | X | Y | Z |
|---|---|---|---|---|---|---|---|---|---|---|
| Example 94 | —Q¹—A¹<br>Q¹: Methylene<br>A¹: 2,6-Me₂Ph<br> | Double Bond | =C(Rᵃ)—<br>Rᵃ:<br>Hydrogen Atom | =C(Rᵇ)—<br>Rᵇ:<br>Chlorine Atom | Methine | Methine | Methine | Single Bond | Single Bond | 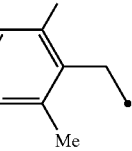 |
| Example 95 | —Q¹—A¹<br>Q¹: Methylene<br>A¹: 2,6-Me₂Ph<br>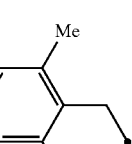 | Double Bond | =C(Rᵃ)—<br>Rᵃ:<br>Hydrogen Atom | =C(Rᵇ)—<br>Rᵇ:<br>Hydrogen Atom | —N= | Methine | Methine | Single Bond | Single Bond | COOH |
| Example 96 | —Q¹—A¹<br>Q¹: Methylene<br>A¹: 2,6-Me₂Ph<br>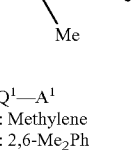 | Double Bond | =C(Rᵃ)—<br>Rᵃ:<br>Hydrogen Atom | =C(Rᵇ)—<br>Rᵇ:<br>Hydrogen Atom | Methine | Methine | —N= | Single Bond | Single Bond | COOH |

TABLE 30

| | R¹ | ---- | W¹ | W² | W³ | W⁴ | W⁵ | X | Y | Z |
|---|---|---|---|---|---|---|---|---|---|---|
| Example 97 | —Q¹—A¹<br>Q¹: Methylene<br>A¹: 2,6-Cl₂Ph | Double Bond | =N— | =C(Rᵇ)—<br>Rᵇ: Methyl Group | Methine | Methine | Methine | Single Bond | (CRʸʸRʸʸ)ₙ<br>n = 1<br>—CH₂— | COOH |
| Example 98 | —Q¹—A¹<br>Q¹: Methylene<br>A¹: 2,6-Cl₂Ph | Double Bond | =N— | =C(Rᵇ)—<br>Rᵇ: Methyl Group | Methine | Methine | Methine | Single Bond | (CRʸʸRʸʸ)ₙ<br>n = 1<br>—CH₂— | COO⁻K⁺ |

TABLE 30-continued

| | R$^1$ | ---- | W$^1$ | W$^2$ | W$^3$ | W$^4$ | W$^5$ | X | Y | Z |
|---|---|---|---|---|---|---|---|---|---|---|
| Example 99 | —Q$^1$—A$^1$<br>Q$^1$: Methylene<br>A$^1$: 2,3-Cl$_2$Ph | Double Bond | =N— | =C(R$^b$)—<br>R$^b$: Methyl Group | Methine | Methine | Methine | Single Bond | (CR$^{Yi}$R$^{Yi}$)$_n$<br>n = 1<br>—CH$_2$— | COOH |

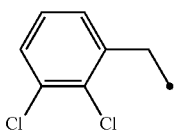

TABLE 31

| | R$^1$ | ---- | W$^1$ | W$^2$ | W$^3$ | W$^4$ | W$^5$ | X | Y | Z |
|---|---|---|---|---|---|---|---|---|---|---|
| Example 100 | —Q$^1$—A$^1$<br>Q$^1$: Methylene<br>A$^1$: 2,3-Cl$_2$Ph | Double Bond | =N— | =C(R$^b$)—<br>R$^b$: Methyl Group | Methine | Methine | Methine | Single Bond | (CR$^{Yi}$R$^{Yi}$)$_n$<br>n = 1<br>—CH$_2$— | COO$^-$K$^+$ |

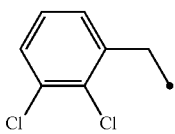

| | R$^1$ | ---- | W$^1$ | W$^2$ | W$^3$ | W$^4$ | W$^5$ | X | Y | Z |
|---|---|---|---|---|---|---|---|---|---|---|
| Example 101 | —Q$^1$—A$^1$<br>Q$^1$: Methylene<br>A$^1$: 2,5-Me$_2$Ph | Double Bond | =N— | =C(R$^b$)—<br>R$^b$: Methyl Group | Methine | Methine | Methine | Single Bond | (CR$^{Yi}$R$^{Yi}$)$_n$<br>n = 1<br>—CH$_2$— | COOH |

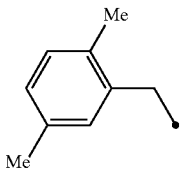

TABLE 32

| | R$^1$ | ---- | W$^1$ | W$^2$ | W$^3$ | W$^4$ | W$^5$ | X | Y | Z |
|---|---|---|---|---|---|---|---|---|---|---|
| Example 102 | —Q$^1$—A$^1$<br>Q$^1$: Methylene<br>A$^1$: 2-Cl-6-MePh | Double Bond | =N— | =C(R$^b$)—<br>R$^b$: Methyl Group | Methine | Methine | Methine | Single Bond | (CR$^{Yi}$R$^{Yi}$)$_n$<br>n = 1<br>—CH$_2$— | COOH |

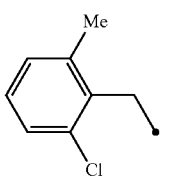

| | R$^1$ | ---- | W$^1$ | W$^2$ | W$^3$ | W$^4$ | W$^5$ | X | Y | Z |
|---|---|---|---|---|---|---|---|---|---|---|
| Example 103 | —Q$^1$—A$^1$<br>Q$^1$: Methylene<br>A$^1$: 2-Cl-6-MePh | Double Bond | =N— | =C(R$^b$)—<br>R$^b$: Methyl Group | Methine | Methine | Methine | Single Bond | (CR$^{Yi}$R$^{Yi}$)$_n$<br>n = 1<br>—CH$_2$— | COO$^-$K$^+$ |

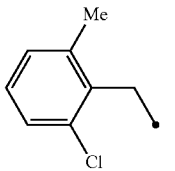

TABLE 32-continued

| | R¹ | ---- | W¹ | W² | W³ | W⁴ | W⁵ | X | Y | Z |
|---|---|---|---|---|---|---|---|---|---|---|
| Example 104 | —Q¹—A¹<br>Q¹: Methylene<br>A¹: 2-Cl-6-FPh | Double Bond | =N— | =C(R$^b$)—<br>R$^b$: Methyl Group | Methine | Methine | Methine | Single Bond | (CR$^{Yi}$R$^{Yi}$)$_n$<br>n = 1<br>—CH$_2$— | COOH |

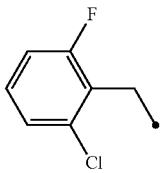

TABLE 33

| | R¹ | ---- | W¹ | W² | W³ | W⁴ | W⁵ | X | Y | Z |
|---|---|---|---|---|---|---|---|---|---|---|
| Example 105 | —Q¹—A¹<br>Q¹: Methylene<br>A¹: 3,5-dimethyl-isoxazole-4-yl | Double Bond | =N— | =C(R$^b$)—<br>R$^b$: Methyl Group | Methine | Methine | Methine | Single Bond | (CR$^{Yi}$R$^{Yi}$)$_n$<br>n = 1<br>—CH$_2$— | COOH |

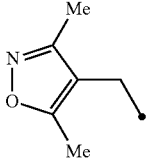

| | R¹ | ---- | W¹ | W² | W³ | W⁴ | W⁵ | X | Y | Z |
|---|---|---|---|---|---|---|---|---|---|---|
| Example 106 | —Q¹—A¹<br>Q¹: Methylene<br>A¹: 5-chloro benzo[b]thiophene-3-yl | Double Bond | =N— | =C(R$^b$)—<br>R$^b$: Methyl Group | Methine | Methine | Methine | Single Bond | (CR$^{Yi}$R$^{Yi}$)$_n$<br>n = 1<br>—CH$_2$— | COOH |

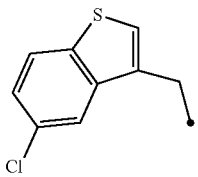

| | R¹ | ---- | W¹ | W² | W³ | W⁴ | W⁵ | X | Y | Z |
|---|---|---|---|---|---|---|---|---|---|---|
| Example 107 | —Q¹—A¹<br>Q¹: Methylene<br>A¹: Naphthalene-1-yl | Double Bond | =N— | =C(R$^b$)—<br>R$^b$: Methyl Group | Methine | Methine | Methine | Single Bond | (CR$^{Yi}$R$^{Yi}$)$_n$<br>n = 1<br>—CH$_2$— | COOH |

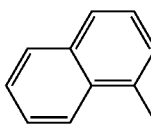

TABLE 34

| | R¹ | ---- | W¹ | W² | W³ | W⁴ | W⁵ | X | Y | Z |
|---|---|---|---|---|---|---|---|---|---|---|
| Example 108 | —Q¹—A¹<br>Q¹: Methylene<br>A¹: 2,4,6-Me$_3$Ph | Double Bond | =N— | =C(R$^b$)—<br>R$^b$: Methyl Group | Methine | Methine | Methine | Single Bond | (CR$^{Yi}$R$^{Yi}$)$_n$<br>n = 1<br>—CH$_2$— | COOH |

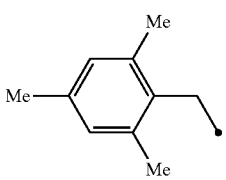

TABLE 34-continued

| | R¹ | ---- | W¹ | W² | W³ | W⁴ | W⁵ | X | Y | Z |
|---|---|---|---|---|---|---|---|---|---|---|
| Example 109 | —Q¹—A¹<br>Q¹: Methylene<br>A¹: 2-Cl-6-CNPh<br>(2-Cl-6-CN-phenylmethyl) | Double Bond | =N— | =C(R$^b$)—<br>R$^b$: Methyl Group | Methine | Methine | Methine | Single Bond | (CR$^{Y1}$R$^{Y1'}$)$_n$<br>n = 1<br>—CH$_2$— | COOH |
| Example 110 | —Q¹—A¹<br>Q¹: Methylene<br>A¹: 2-Cl-6-CNPh<br>(2-Cl-6-CN-phenylmethyl) | Double Bond | =N— | =C(R$^b$)—<br>R$^b$: Methyl Group | Methine | Methine | Methine | Single Bond | (CR$^{Y1}$R$^{Y1'}$)$_n$<br>n = 1<br>—CH$_2$— | COO⁻K⁺ |

TABLE 35

| | R¹ | ---- | W¹ | W² | W³ | W⁴ | W⁵ | X | Y | Z |
|---|---|---|---|---|---|---|---|---|---|---|
| Example 111 | —Q¹—A¹<br>Q¹: Methylene<br>A¹: 2,6-Cl$_2$Ph<br>(2,6-dichlorophenylmethyl) | Double Bond | =N— | =C(R$^b$)—<br>R$^b$:<br>Methyl Group | Methine | Methine | Methine | Single Bond | (CR$^{Y1}$R$^{Y1'}$)$_n$<br>n = 1,<br>R$^{Y1}$ = H,<br>R$^{Y1'}$ = Me<br>—CH(CH$_3$)— | COOH |
| Example 112 | —Q¹—A¹<br>Q¹: Methylene<br>A¹: 2,6-Cl$_2$Ph<br>(2,6-dichlorophenylmethyl) | Double Bond | =N— | =C(R$^b$)—<br>R$^b$:<br>Methyl Group | Methine | Methine | Methine | Single Bond | (CR$^{Y1}$R$^{Y1'}$)$_n$<br>n = 1,<br>R$^{Y1}$ = Me,<br>R$^{Y1'}$ = Me<br>—C(CH$_3$)$_2$— | COOH |
| Example 113 | —Q¹—A¹<br>Q¹: Methylene<br>A¹: 2,6-Cl$_2$Ph<br>(2,6-dichlorophenylmethyl) | Double Bond | =N— | =C(R$^b$)—<br>R$^b$:<br>Methyl Group | Methine | Methine | Methine | Single Bond | (CR$^{Y1}$R$^{Y1'}$)$_n$<br>n = 1,<br>R$^{Y1}$ = H,<br>R$^{Y1'}$ = Et<br>—CH(CH$_2$CH$_3$)— | COOH |

TABLE 36

| | $R^1$ | ---- | $W^1$ | $W^2$ | $W^3$ | $W^4$ | $W^5$ | X | Y | Z |
|---|---|---|---|---|---|---|---|---|---|---|
| Example 114 | —$Q^1$—$A^1$<br>$Q^1$: Ethylene<br>$A^1$: Ph<br>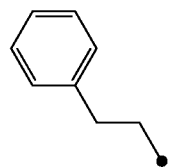 | Double Bond | =N— | =C($R^b$)—<br>$R^b$:<br>Methyl Group | Methine | Methine | Methine | Single Bond | $(CR^{yy}R^{yy})_n$<br>n = 1<br>—CH$_2$— | COOH |
| Example 115 | —$Q^1$—$A^1$<br>$Q^1$: Methylene<br>$A^1$: Quinoline-8-yl<br>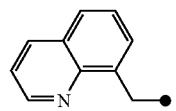 | Double Bond | =N— | =C($R^b$)—<br>$R^b$:<br>Methyl Group | Methine | Methine | Methine | Single Bond | $(CR^{yy}R^{yy})_n$<br>n = 1<br>—CH$_2$— | COOH |

TABLE 37

| | $R^1$ | ---- | $W^1$ | $W^2$ | $W^3$ | $W^4$ | $W^5$ | X | Y | Z |
|---|---|---|---|---|---|---|---|---|---|---|
| Example 116 | —$Q^1$—$A^1$<br>$Q^1$: Methylene<br>$A^1$: Quinoline-8-yl<br>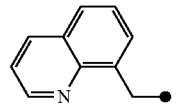 | Double Bond | =N— | =C($R^b$)—<br>$R^b$:<br>Methyl Group | Methine | Methine | Methine | Single Bond | $(CR^{yy}R^{yy})_n$<br>n = 1<br>—CH$_2$— | COO$^-$K$^+$ |
| Example 117 | —$Q^1$—$A^1$<br>$Q^1$: Methylene<br>$A^1$: 2,6-Me$_2$Ph<br>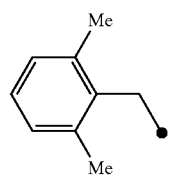 | Double Bond | =N— | =C($R^b$)—<br>$R^b$:<br>Methyl Group | Methine | Methine | Methine | Single Bond | Single bond | COOH |
| Example 118 | —$Q^1$—$A^1$<br>$Q^1$: Methylene<br>$A^1$: 2,6-Me$_2$Ph<br>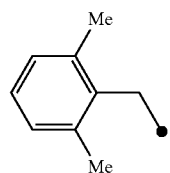 | Double Bond | =N— | =C($R^b$)—<br>$R^b$:<br>Methyl Group | Methine | Methine | Methine | Single Bond | Single Bond | COO$^-$K$^+$ |

TABLE 37-continued

| | R¹ | ---- | W¹ | W² | W³ | W⁴ | W⁵ | X | Y | Z |
|---|---|---|---|---|---|---|---|---|---|---|
| Example 119 | —Q¹—A¹<br>Q¹: Methylene<br>A¹: 2,6-Cl₂Ph<br>(2,6-dichlorobenzyl) | Double Bond | =N— | =C(R$^b$)—<br>R$^b$: Methyl Group | Methine | Methine | Methine | Single Bond | Single Bond | COOH |

TABLE 38

| | R¹ | ---- | W¹ | W² | W³ | W⁴ | W⁵ | X | Y | Z |
|---|---|---|---|---|---|---|---|---|---|---|
| Example 120 | —Q¹—A¹<br>Q¹: Methylene<br>A¹: 2,3-Cl₂Ph<br>(2,3-dichlorobenzyl) | Double Bond | =N— | =C(R$^b$)—<br>R$^b$: Methyl Group | Methine | Methine | Methine | Single Bond | Single Bond | COOH |
| Example 121 | —Q¹—A¹<br>Q¹: Methylene<br>A¹: 2,6-Me₂Ph<br>(2,6-dimethylbenzyl) | Double Bond | =N— | =C(R$^b$)—<br>R$^b$: Methyl Group | Methine | Methine | Methine | Single Bond | (CR$^{y1}$R$^{y1}$)$_n$<br>n = 2<br>—CH₂—CH₂— | COOH |
| Example 122 | —Q¹—A¹<br>Q¹: Methylene<br>A¹: 2,6-Cl₂Ph<br>(2,6-dichlorobenzyl) | Double Bond | =N— | =C(R$^b$)—<br>R$^b$: Methyl Group | Methine | Methine | Methine | Single Bond | (CR$^{y1}$R$^{y1}$)$_n$<br>n = 2<br>—CH₂—CH₂— | COOH |
| Example 123 | —Q¹—A¹<br>Q¹: Methylene<br>A¹: 2,6-Cl₂Ph<br>(2,6-dichlorobenzyl) | Double Bond | =N— | =C(R$^b$)—<br>R$^b$: Methyl Group | Methine | Methine | Methine | Single Bond | (CR$^{y1}$R$^{y1}$)$_n$<br>n = 2<br>—CH₂—CH₂— | COO⁻K⁺ |

TABLE 39

| | R¹ | ---- | W¹ | W² | W³ | W⁴ | W⁵ | X | Y | Z |
|---|---|---|---|---|---|---|---|---|---|---|
| Example 124 | —Q¹—A¹<br>Q¹: Methylene<br>A¹: 5-chlorobenzo[b]thiophene-3-yl<br>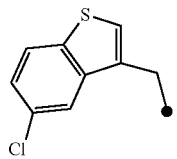 | Double Bond | =N— | =C(R$^b$)—<br>R$^b$:<br>Methyl Group | Methine | Methine | Methine | Single Bond | (CR$^{Y1}$R$^{Y1'}$)$_n$<br>n = 2<br>—CH$_2$—CH$_2$— | COOH |
| Example 125 | —Q¹—A¹<br>Q¹: Methylene<br>A¹: 2-Cl-6-CNPh<br>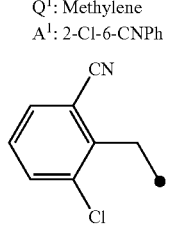 | Double Bond | =N— | =C(R$^b$)—<br>R$^b$:<br>Methyl Group | Methine | Methine | Methine | Single Bond | (CR$^{Y1}$R$^{Y1'}$)$_n$<br>n = 2<br>—CH$_2$—CH$_2$— | COOH |
| Example 126 | —Q¹—A¹<br>Q¹: Methylene<br>A¹: 2-Cl-6-CNPh<br>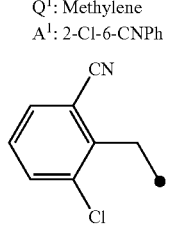 | Double Bond | =N— | =C(R$^b$)—<br>R$^b$:<br>Methyl Group | Methine | Methine | Methine | Single Bond | (CR$^{Y1}$R$^{Y1'}$)$_n$<br>n = 2<br>—CH$_2$—CH$_2$— | COO⁻K⁺ |

TABLE 40

| | R¹ | ---- | W¹ | W² | W³ | W⁴ | W⁵ | X | Y | Z |
|---|---|---|---|---|---|---|---|---|---|---|
| Example 127 | —Q¹—A¹<br>Q¹: Methylene<br>A¹: 2,6-Cl$_2$Ph<br>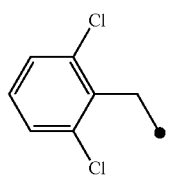 | Double Bond | =N— | =C(R$^b$)—<br>R$^b$:<br>Methyl Group | Methine | Methine | Methine | Single Bond | (CR$^{Y1}$R$^{Y1'}$)$_n$<br>n = 2,<br>R$^{Y1}$ = H,<br>R$^{Y1'}$ = OH,<br>R$^{Y2}$, R$^{Y2'}$ = H<br>—CH(OH)CH$_2$— | COOH |
| Example 128 | —Q¹—A¹<br>Q¹: Methylene<br>A¹: 2,6-Cl$_2$Ph<br>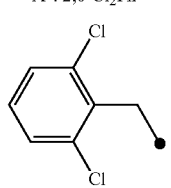 | Double Bond | =N— | =C(R$^b$)—<br>R$^b$:<br>Methyl Group | Methine | Methine | Methine | Single Bond | (CR$^{Y1}$R$^{Y1'}$)$_n$<br>n = 1,<br>R$^{Y1}$ = H,<br>R$^{Y1'}$ = OH<br>—CH(OH)— | COOH |

TABLE 40-continued

| | R¹ | ---- | W¹ | W² | W³ | W⁴ | W⁵ | X | Y | Z |
|---|---|---|---|---|---|---|---|---|---|---|
| Example 129 | —Q¹—A¹<br>Q¹: Methylene<br>A¹: 2,6-Cl₂Ph<br>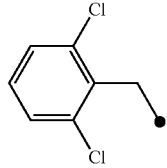 | Double Bond | =N— | =C(R$^b$)—<br>R$^b$:<br>Methyl Group | Methine | Methine | Methine | Single Bond | (CR$^{Y1}$R$^{Y1'}$)$_n$<br>n = 1,<br>R$^{Y1}$ = H,<br>R$^{Y1'}$ = OH<br>—CH(OH)— | COO⁻K⁺ |

TABLE 41

| | R¹ | ---- | W¹ | W² | W³ | W⁴ | W⁵ | X | Y | Z |
|---|---|---|---|---|---|---|---|---|---|---|
| Example 130 | —Q¹—A¹<br>Q¹: Methylene<br>A¹: 2,6-Cl₂Ph<br>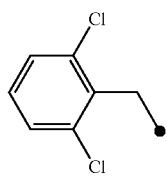 | Double Bond | =N— | =C(R$^b$)—<br>R$^b$:<br>Methyl Group | Methine | Methine | Methine | Carbonyl Group | (CR$^{Y1}$R$^{Y1'}$)$_n$<br>n = 2<br>—CH₂—CH₂— | COOH |
| Example 131 | —Q¹—A¹<br>Q¹: Methylene<br>A¹: 2,6-Cl₂Ph<br>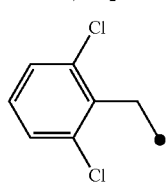 | Double Bond | =N— | =C(R$^b$)—<br>R$^b$:<br>Methyl Group | Methine | Methine | Methine | Single Bond | (CR$^{Y1}$R$^{Y1'}$)$_n$<br>n = 1<br>—CH₂— | CONH₂ |
| Example 132 | —Q¹—A¹<br>Q¹: Methylene<br>A¹: 2,6-Cl₂Ph<br>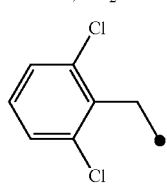 | Double Bond | =N— | =C(R$^b$)—<br>R$^b$:<br>Methyl Group | Methine | Methine | Methine | Single Bond | (CR$^{Y1}$R$^{Y1'}$)$_n$<br>n = 2<br>—CH₂—CH₂— | CONH₂ |

TABLE 42

| | R¹ | ---- | W¹ | W² | W³ | W⁴ | W⁵ | X | Y | Z |
|---|---|---|---|---|---|---|---|---|---|---|
| Example 133 | —Q¹—A¹<br>Q¹: Methylene<br>A¹: 2,6-Cl₂Ph<br>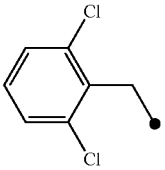 | Double Bond | =N— | =C(R$^b$)—<br>R$^b$:<br>Methyl Group | Methine | Methine | Methine | Single Bond | (CR$^{Yi}$R$^{Yi}$)$_n$<br>n = 3<br>—CH₂—CH₂—CH₂— | COOH |
| Example 134 | —Q¹—A¹<br>Q¹: Methylene<br>A¹: 2,6-Cl₂Ph<br>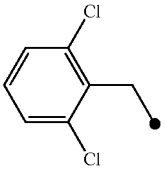 | Double Bond | =N— | =C(R$^b$)—<br>R$^b$:<br>Methyl Group | Methine | Methine | Methine | Single Bond | (CR$^{Yi}$R$^{Yi}$)$_n$<br>n = 1<br>—CH₂— | 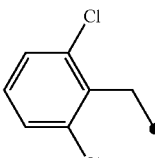 |
| Example 135 | —Q¹—A¹<br>Q¹: Methylene<br>A¹: 2,6-Cl₂Ph<br>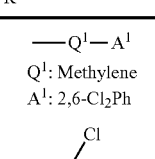 | Double Bond | =N— | =C(R$^b$)—<br>R$^b$:<br>Methyl Group | Methine | Methine | Methine | Single Bond | (CR$^{Yi}$R$^{Yi}$)$_n$<br>n = 2<br>—CH₂—CH₂— | 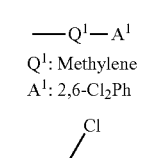 |

TABLE 43

| | R¹ | ---- | W¹ | W² | W³ | W⁴ | W⁵ | X | Y | Z |
|---|---|---|---|---|---|---|---|---|---|---|
| Example 136 | —Q¹—A¹<br>Q¹: Methylene<br>A¹: 2,6-Cl₂Ph<br>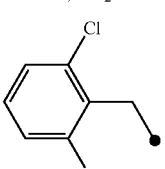 | Double Bond | =N— | =C(R$^b$)—<br>R$^b$:<br>Methyl Group | Methine | Methine | Methine | Single Bond | (CR$^{Yi}$R$^{Yi}$)$_n$<br>n = 1<br>—CH₂— | 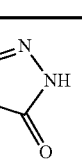<br>2-oxo-1,3,4-oxadiazolyl group |
| Example 137 | —Q¹—A¹<br>Q¹: Methylene<br>A¹: 2,6-Cl₂Ph<br>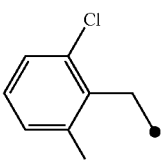 | Double Bond | =N— | =C(R$^b$)—<br>R$^b$:<br>Methyl Group | Methine | Methine | Methine | Single Bond | (CR$^{Yi}$R$^{Yi}$)$_n$<br>n = 1<br>—CH₂— | 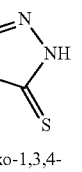<br>2-thioxo-1,3,4-oxadiazolyl group |

TABLE 43-continued

| | R¹ | ---- | W¹ | W² | W³ | W⁴ | W⁵ | X | Y | Z |
|---|---|---|---|---|---|---|---|---|---|---|
| Example 138 | —Q¹—A¹<br>Q¹: Methylene<br>A¹: 2,6-Cl₂Ph<br>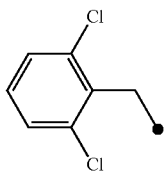 | Double Bond | =N— | =C(R$^b$)—<br>R$^b$:<br>Methyl Group | Methine | Methine | Methine | Oxygen Atom | $(CR^{\eta}R^{\eta})_n$<br>n = 1<br>—CH₂— | COOH |

TABLE 44

| | R¹ | ---- | W¹ | W² | W³ | W⁴ | W⁵ | X | Y | Z |
|---|---|---|---|---|---|---|---|---|---|---|
| Example 139 | —Q¹—A¹<br>Q¹: Methylene<br>A¹: 2,6-Cl₂Ph<br>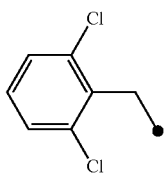 | Double Bond | =N— | =C(R$^b$)—<br>R$^b$:<br>Methyl Group | Methine | Methine | Methine | Single Bond | $(CR^{\eta}R^{\eta})_n$<br>n = 1<br>—CH₂— | SO₃H |
| Example 140 | —Q¹—A¹<br>Q¹: Methylene<br>A¹: 2,6-Cl₂Ph | Double Bond | =N— | =C(R$^b$)—<br>R$^b$:<br>Ethyl Group | Methine | Methine | Methine | Single Bond | $(CR^{\eta}R^{\eta})_n$<br>n = 1<br>—CH₂— | COOH |
| Example 141 | —Q¹—A¹<br>Q¹: Methylene<br>A¹: 2,6-Cl₂Ph<br>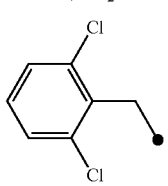 | Double Bond | =N— | =C(R$^b$)—<br>R$^b$:<br>Ethyl Group | Methine | Methine | Methine | Single Bond | $(CR^{\eta}R^{\eta})_n$<br>n = 1<br>—CH₂— | COO⁻K⁺ |

TABLE 45

| | R¹ | ---- | W¹ | W² | W³ | W⁴ | W⁵ | X | Y | Z |
|---|---|---|---|---|---|---|---|---|---|---|
| Example 142 | —Q¹—A¹<br>Q¹: Methylene<br>A¹: 2,6-Me₂Ph<br>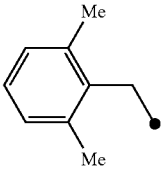 | Double Bond | =N— | =C(R$^b$)—<br>R$^b$:<br>Ethyl Group | Methine | Methine | Methine | Single Bond | (CR$^{Y1}$R$^{Y1}$)$_n$<br>n = 1<br>—CH₂— | COOH |
| Example 143 | —Q¹—A¹<br>Q¹: Methylene<br>A¹: 2,6-Me₂Ph<br>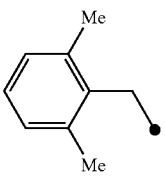 | Double Bond | =N— | =C(R$^b$)—<br>R$^b$:<br>Ethyl Group | Methine | Methine | Methine | Single Bond | Single Bond | COOH |
| Example 144 | —Q¹—A¹<br>Q¹: Methylene<br>A¹: 2,6-Cl₂Ph<br>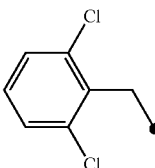 | Double Bond | =N— | =C(R$^b$)—<br>R$^b$:<br>Ethyl Group | Methine | Methine | Methine | Single Bond | Single Bond | COOH |

TABLE 46

| | R¹ | ---- | W¹ | W² | W³ | W⁴ | W⁵ | X | Y | Z |
|---|---|---|---|---|---|---|---|---|---|---|
| Example 145 | —Q¹—A¹<br>Q¹: Methylene<br>A¹: 2,6-Cl₂Ph<br>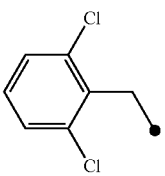 | Double Bond | =N— | =C(R$^b$)—<br>R$^b$:<br>Ethyl Group | Methine | Methine | Methine | Single Bond | (CR$^{Y1}$R$^{Y1}$)$_n$<br>n = 2<br>—CH₂—CH₂— | COOH |
| Example 146 | —Q¹—A¹<br>Q¹: Methylene<br>A¹: 2,6-Cl₂Ph<br>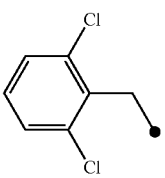 | Double Bond | =N— | =C(R$^b$)—<br>R$^b$:<br>Ethyl Group | Methine | Methine | Methine | Vinylene Group<br>—CH=CH— | Single Bond | COOH |

TABLE 46-continued

| | R¹ | ---- | W¹ | W² | W³ | W⁴ | W⁵ | X | Y | Z |
|---|---|---|---|---|---|---|---|---|---|---|
| Example 147 | —Q¹—A¹<br>Q¹: Methylene<br>A¹: 2,6-Me₂Ph<br>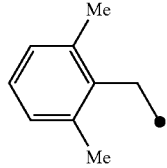 | Double Bond | =N— | =C(R$^b$)—<br>R$^b$:<br>Isopropyl Group | Methine | Methine | Methine | Single Bond | (CR$^{y_1}$R$^{y_1}$)$_n$<br>n = 1<br>—CH₂— | COOH |

TABLE 47

| | R¹ | ---- | W¹ | W² | W³ | W⁴ | W⁵ | X | Y | Z |
|---|---|---|---|---|---|---|---|---|---|---|
| Example 148 | —Q¹—A¹<br>Q¹: Methylene<br>A¹: 2,6-Cl₂Ph<br>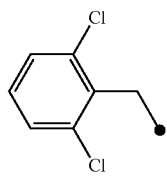 | Double Bond | =N— | =C(R$^b$)—<br>R$^b$:<br>Cyclopropyl Group | Methine | Methine | Methine | Single Bond | (CR$^{y_1}$R$^{y_1}$)$_n$<br>n = 1<br>—CH₂— | COOH |
| Example 149 | —Q¹—A¹<br>Q¹: Methylene<br>A¹: 2,6-Me₂Ph<br>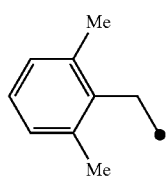 | Double Bond | =N— | =C(R$^b$)—<br>R$^b$:<br>Chlorine Atom | Methine | Methine | Methine | Single Bond | Single Bond | COOH |
| Example 150 | —Q¹—A¹<br>Q¹: Methylene<br>A¹: 2,6-Cl₂Ph<br>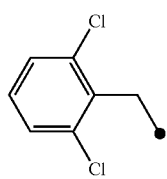 | Double Bond | =N— | =C(R$^b$)—<br>R$^b$:<br>Cyano Group | Methine | Methine | Methine | Single Bond | Single Bond | COOH |

TABLE 48

| | R¹ | ---- | W¹ | W² | W³ | W⁴ | W⁵ | X | Y | Z |
|---|---|---|---|---|---|---|---|---|---|---|
| Example 151 | —Q¹—A¹<br>Q¹: Methylene<br>A¹: 2,6-Cl₂Ph | Double Bond | =N— | =C(R$^b$)—<br>R$^b$: Methyl Group | Methine | Methine | —N= | Single Bond | Single Bond | COOH |
| Example 152 | —Q¹—A¹<br>Q¹: Methylene<br>A¹: 2,6-Cl₂Ph | Double Bond | =N— | =C(R$^b$)—<br>R$^b$: Methyl Group | Methine | Methine | —N= | Single Bond | (CR$^n$R$^m$)$_n$<br>n = 1<br>—CH₂— | (tetrazole) |
| Example 153 | —Q¹—A¹<br>Q¹: Methylene<br>A¹: 2,6-Cl₂Ph | Double Bond | =N— | =C(R$^b$)—<br>R$^b$: Methyl Group | Methine | Methine | —N= | Single Bond | Single Bond | COOH |

TABLE 49

| | R¹ | ---- | W¹ | W² | W³ | W⁴ | W⁵ | X | Y | Z |
|---|---|---|---|---|---|---|---|---|---|---|
| Example 154 | —Q¹—A¹<br>Q¹: Methylene<br>A¹: 2,6-Cl₂Ph | Double Bond | =N— | =C(R$^b$)—<br>R$^b$: Methyl Group | —N= | Methine | Methine | Single Bond | Single Bond | COO⁻K⁺ |
| Example 155 | —Q¹—A¹<br>Q¹: Methylene<br>A¹: 2,6-Cl₂Ph | Double Bond | =N— | =C(R$^b$)—<br>R$^b$: Methyl Group | —N= | Methine | Methine | Vinylene Group<br>—CH=CH— | Single Bond | COOH |

TABLE 49-continued

| | R¹ | ---- | W¹ | W² | W³ | W⁴ | W⁵ | X | Y | Z |
|---|---|---|---|---|---|---|---|---|---|---|
| Example 156 | —Q¹—A¹<br>Q¹: Methylene<br>A¹: 2,6-Cl₂Ph | Double Bond | =N— | =C(R$^b$)—<br>R$^b$:<br>Methyl Group | —N= | Methine | Methine | Single Bond | Single Bond | tetrazole (1H) |

TABLE 50

| | R¹ | ---- | W¹ | W² | W³ | W⁴ | W⁵ | X | Y | Z |
|---|---|---|---|---|---|---|---|---|---|---|
| Example 157 | —Q¹—A¹<br>Q¹: Methylene<br>A¹: 2,6-Cl₂Ph | Double Bond | =N— | =C(R$^b$)—<br>R$^b$:<br>Methyl Group | —N= | Methine | Methine | Single Bond | Single Bond | tetrazole K⁺ salt |
| Example 158 | —Q¹—A¹<br>Q¹: Methylene<br>A¹: 2,3-Cl₂Ph | Double Bond | =N— | =C(R$^b$)—<br>R$^b$:<br>Methyl Group | —N= | Methine | Methine | Single Bond | Single Bond | tetrazole (1H) |
| Example 159 | —Q¹—A¹<br>Q¹: Methylene<br>A¹: 2,3-Cl₂Ph | Double Bond | =N— | =C(R$^b$)—<br>R$^b$:<br>Methyl Group | —N= | Methine | Methine | Single Bond | Single Bond | tetrazole K⁺ salt |
| Example 160 | —Q¹—A¹<br>Q¹: Methylene<br>A¹: Cl-6-MePh | Double Bond | =N— | =C(R$^b$)—<br>R$^b$:<br>Methyl Group | —N= | Methine | Methine | Single Bond | Single Bond | tetrazole (1H) |

TABLE 51

| | R¹ | ---- | W¹ | W² | W³ | W⁴ | W⁵ | X | Y | Z |
|---|---|---|---|---|---|---|---|---|---|---|
| Example 161 | —Q¹—A¹<br>Q¹: Methylene<br>A¹: Cl-6-MePh<br>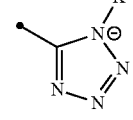 | Double Bond | =N— | =C(R$^b$)—<br>R$^b$:<br>Methyl Group | —N= | Methine | Methine | Single Bond | Single Bond |  |
| Example 162 | —Q¹—A¹<br>Q¹: Methylene<br>A¹: Naphthalene-1-yl<br> | Double Bond | =N— | =C(R$^b$)—<br>R$^b$:<br>Methyl Group | —N= | Methine | Methine | Single Bond | Single Bond | |
| Example 163 | —Q¹—A¹<br>Q¹: Methylene<br>A¹: 2,5-Me₂Ph | Double Bond | =N— | =C(R$^b$)—<br>R$^b$:<br>Methyl Group | —N= | Methine | Methine | Single Bond | Single Bond | |

TABLE 52

| | R¹ | ---- | W¹ | W² | W³ | W⁴ | W⁵ | X | Y | Z |
|---|---|---|---|---|---|---|---|---|---|---|
| Example 164 | —Q¹—A¹<br>Q¹: Methylene<br>A¹: 2-Cl-6-cyclopropyl Ph | Double Bond | =N— | =C(R$^b$)—<br>R$^b$:<br>Methyl Group | —N= | Methine | Methine | Single Bond | Single Bond | |

TABLE 52-continued

| | R¹ | ---- | W¹ | W² | W³ | W⁴ | W⁵ | X | Y | Z |
|---|---|---|---|---|---|---|---|---|---|---|
| Example 165 | —Q¹—A¹<br>Q¹: Methylene<br>A¹: 2-Cl-6-cyclopropyl Ph<br>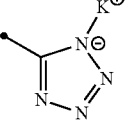 | Double Bond | =N— | =C(R$^b$)—<br>R$^b$: Methyl Group | —N= | Methine | Methine | Single Bond | Single Bond | 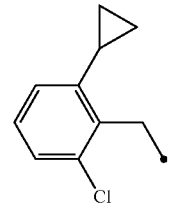 |
| Example 166 | —Q¹—A¹<br>Q¹: Methylene<br>A¹: 2,6-dicyclopropyl Ph<br>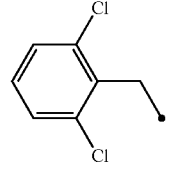 | Double Bond | =N— | =C(R$^b$)—<br>R$^b$: Methyl Group | —N= | Methine | Methine | Single Bond | Single Bond | 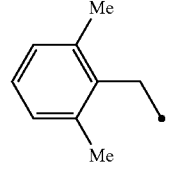 |

TABLE 53

| | R¹ | ---- | W¹ | W² | W³ | W⁴ | W⁵ | X | Y | Z |
|---|---|---|---|---|---|---|---|---|---|---|
| Example 167 | —Q¹—A¹<br>Q¹: Methylene<br>A¹: 2,6-Cl₂Ph | Double Bond | =N— | =C(R$^b$)—<br>R$^b$: Ethyl Group | —N= | Methine | Methine | Single Bond | Single Bond | COOH |
| Example 168 | —Q¹—A¹<br>Q¹: Methylene<br>A¹: 2,6-Me₂Ph | Double Bond | =N— | =C(R$^b$)—<br>R$^b$: Ethyl Group | —N= | Methine | Methine | Single Bond | Single Bond | COOH |

TABLE 53-continued

| | R¹ | ---- | W¹ | W² | W³ | W⁴ | W⁵ | X | Y | Z |
|---|---|---|---|---|---|---|---|---|---|---|
| Example 169 | —Q¹—A¹<br>Q¹: Methylene<br>A¹: 2,3-Cl₂Ph<br>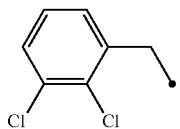 | Double Bond | =N— | =C(R$^b$)—<br>R$^b$: Ethyl Group | —N= | Methine | Methine | Single Bond | Single Bond | COOH |

TABLE 54

| | R¹ | ---- | W¹ | W² | W³ | W⁴ | W⁵ | X | Y | Z |
|---|---|---|---|---|---|---|---|---|---|---|
| Example 170 | —Q¹—A¹<br>Q¹: Methylene<br>A¹: Cl-6-MePh<br>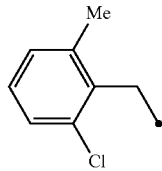 | Double Bond | =N— | =C(R$^b$)—<br>R$^b$: Ethyl Group | —N= | Methine | Methine | Single Bond | Single Bond | COOH |
| Example 171 | —Q¹—A¹<br>Q¹: Methylene<br>A¹: 2,6-Cl₂Ph<br>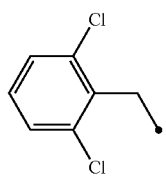 | Double Bond | =N— | =C(R$^b$)—<br>R$^b$: Ethyl Group | —N= | Methine | Methine | Single Bond | Single Bond | 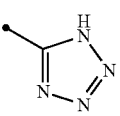 |
| Example 172 | —Q¹—A¹<br>Q¹: Methylene<br>A¹: 2,6-Cl₂Ph<br>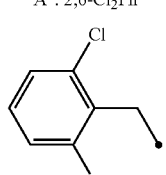 | Double Bond | =N— | =C(R$^b$)—<br>R$^b$: Chlorine Atom | —N= | Methine | Methine | Single Bond | Single Bond | COOH |

TABLE 55

| | R¹ | ---- | W¹ | W² | W³ | W⁴ | W⁵ | X | Y | Z |
|---|---|---|---|---|---|---|---|---|---|---|
| Example 173 | —Q¹—A¹<br>Q¹: Methylene<br>A¹: 2,6-Cl₂Ph<br>(2,6-dichlorobenzyl structure) | Double Bond | =N— | =C(R^b)—<br>R^b: Chlorine Atom | —N= | Methine | Methine | Single Bond | Single Bond | COO⁻K⁺ |
| Example 174 | —Q¹—A¹<br>Q¹: Methylene<br>A¹: Cl-6-MePh<br>(2-methyl-6-chlorobenzyl structure) | Double Bond | =N— | =C(R^b)—<br>R^b: Chlorine Atom | —N= | Methine | Methine | Single Bond | Single Bond | COOH |
| Example 175 | —Q¹—A¹<br>Q¹: Methylene<br>A¹: 2,6-Cl₂Ph<br>(2,6-dichlorobenzyl structure) | Double Bond | =N— | =C(R^b)—<br>R^b: Chlorine Atom | —N= | Methine | Methine | Single Bond | Single Bond | tetrazole (1H-tetrazol-5-yl) |

TABLE 56

| | R¹ | ---- | W¹ | W² | W³ | W⁴ | W⁵ | X | Y | Z |
|---|---|---|---|---|---|---|---|---|---|---|
| Example 176 | —Q¹—A¹<br>Q¹: Methylene<br>A¹: 2,6-Cl₂Ph<br>(2,6-dichlorobenzyl structure) | Double Bond | =N— | =C(R^b)—<br>R^b: Chlorine Atom | —N= | Methine | Methine | Single Bond | Single Bond | tetrazole K⁺ salt |
| Example 177 | —Q¹—A¹<br>Q¹: Methylene<br>A¹: Cl-6-MePh<br>(2-methyl-6-chlorobenzyl structure) | Double Bond | =N— | =C(R^b)—<br>R^b: Chlorine Atom | —N= | Methine | Methine | Single Bond | Single Bond | tetrazole (1H-tetrazol-5-yl) |

TABLE 56-continued

| | R¹ | ---- | W¹ | W² | W³ | W⁴ | W⁵ | X | Y | Z |
|---|---|---|---|---|---|---|---|---|---|---|
| Example 178 | —Q¹—A¹<br>Q¹: Methylene<br>A¹: Cl-6-MePh<br>(2-methyl-6-chlorophenyl-methylene) | Double Bond | =N— | =C(R^b)—<br>R^b: Chlorine Atom | —N= | Methine | Methine | Single Bond | Single Bond | tetrazolyl K⁺ salt |

TABLE 57

| | R¹ | ---- | W¹ | W² | W³ | W⁴ | W⁵ | X | Y | Z |
|---|---|---|---|---|---|---|---|---|---|---|
| Example 179 | —Q¹—A¹<br>Q¹: Methylene<br>A¹: 2,6-Cl₂Ph | Double Bond | =N— | =C(R^b)—<br>R^b: Methyl Group | Methine | =C—<br>OMe | Methine | Single Bond | Single Bond | COOH |
| Example 180 | —Q¹—A¹<br>Q¹: Methylene<br>A¹: 2,6-Cl₂Ph | Double Bond | =N— | =C(R^b)—<br>R^b: Methyl Group | Methine | =C—<br>OH | Methine | Single Bond | Single Bond | COOH |
| Example 181 | —Q¹—A¹<br>Q¹: Methylene<br>A¹: 2,6-Cl₂Ph | Double Bond | =N— | =C(R^b)—<br>R^b: Methyl Group | Methine | Methine | Methine | Single Bond | (CR^{Y1}R^{Y1'})ₙ<br>n = 2<br>—CH2CH(OH)—<br>R^{Y1}, R^{Y1'},<br>R^{Y2'} = H,<br>R^{Y2} = OH | COOH |

TABLE 58

| | R¹ | ---- | W¹ | W² | W³ | W⁴ | W⁵ | X | Y | Z |
|---|---|---|---|---|---|---|---|---|---|---|
| Example 182 | —Q¹—A¹<br>Q¹: Methylene<br>A¹: 2,6-Cl₂Ph | Double Bond | =N— | =C(R$^b$)—<br>R$^b$: Ethyl Group | Methine | Methine | Methine | Single Bond | Single Bond | (tetrazole) |
| Example 183 | —Q¹—A¹<br>Q¹: Methylene<br>A¹: 2,6-Cl₂Ph | Double Bond | =N— | =C(R$^b$)—<br>R$^b$: Methyl Group | Methine | Methine | Methine | Single Bond | (CR$^{Y1}$R$^{Y1'}$)$_n$<br>n = 1<br>—CF₂—<br>R$^{Y1}$ = R$^{Y1'}$ = F | COOH |
| Example 184 | —Q¹—A¹<br>Q¹: Methylene<br>A¹: 2,6-Cl₂Ph | Double Bond | =N— | =C(R$^b$)—<br>R$^b$: Methyl Group | Methine | Methine | Methine | Single Bond | (CR$^{Y1}$R$^{Y1'}$)$_n$<br>n = 1<br>—CF₂—<br>R$^{Y1}$ = R$^{Y1'}$ = F | COO⁻K⁺ |

TABLE 59

| | R¹ | ---- | W¹ | W² | W³ | W⁴ | W⁵ | X | Y | Z |
|---|---|---|---|---|---|---|---|---|---|---|
| Example 185 | —Q¹—A¹<br>Q¹: Methylene<br>A¹: 2-Cl-6-cyclopropyl Ph | Double Bond | =N— | =C(R$^b$)—<br>R$^b$: Methyl Group | Methine | Methine | Methine | Single Bond | (CR$^{Y1}$R$^{Y1'}$)$_n$<br>n = 2<br>—CH₂—CH₂— | COOH |

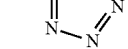

TABLE 59-continued

| | R¹ | ---- | W¹ | W² | W³ | W⁴ | W⁵ | X | Y | Z |
|---|---|---|---|---|---|---|---|---|---|---|
| Example 186 | —Q¹—A¹<br>Q¹: Methylene<br>A¹: 2,6-Me₂Ph<br>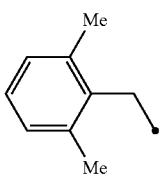 | Single Bond | —(C=O)— | =C(R$^{bc}$)—<br>R$^{bc}$:<br>Isopropyl Group | Methine | Methine | Methine | Single Bond | Single Bond | COOH |

Industrial Applicability

The compound represented by Formula (I) of the present invention and a pharmaceutically acceptable salt and ester of the compound have excellent URAT1 inhibitory action, and thus can reduce the blood uric acid level, and are useful as an agent for treating or preventing pathological conditions associated with the blood uric acid such as hyperuricemia, gouty node, acute gout arthritis, chronic gout arthritis, gouty kidney, urolithiasis, a renal function disorder, a coronary artery disease or an ischemic heart disease.

The invention claimed is:
1. A compound represented by the following formula:

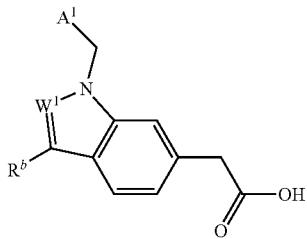

wherein A¹ represents an aryl group or a heteroaryl group substituted with one to three substituents selected from the <Substituent group L> described later (herein any two substituents adjacent to each other on the aryl group or the heteroaryl group may join together to form a lower alkylenedioxy group.);
W¹ represents —CH= or a nitrogen atom; R$^b$ represents a lower alkyl group, a cycloalkyl group, a halogen atom or a cyano group;
<Substituent group L>:
a halogen atom, a hydroxyl group, a nitro group, a cyano group, a formyl group, an amino group, a carboxyl group, a lower alkyl group, a halo-lower alkyl group, a cycloalkyl group, a lower alkoxy group, a halo-lower alkoxy group, a hydroxy lower alkyl group, a lower alkoxy lower alkyl group, a lower alkoxycarbonyl group, a lower alkanoyl group, a lower alkylthio group, a lower alkylsulfonyl group, a lower alkylamino group, a di-lower alkylamino group, a carbamoyl group, a mono-lower alkyl carbamoyl group, a di-lower alkyl carbamoyl group, a lower alkanoylamino group, a lower alkylsulfonylamino group, a lower alkoxycarbonylamino group, an aralkyl group, an aryloxy group, a heteroaryloxy group, and a lower alkenyl group;
or a pharmaceutically acceptable salt or ester of the compound.

2. A compound, or a pharmaceutically acceptable salt or ester of the compound, wherein the compound is any one of the following (b)-(j), (m) and (s):
(b) 2-[1-(2,6-dimethylbenzyl)-3-methyl-1H-indole-6-yl]acetic acid,
(c) 2-[1-(2,6-dimethylbenzyl)-3-methyl-1H-indazole-6-yl]acetic acid,
(d) 2-[3-chloro-1-(2,6-dimethylbenzyl)-1H-indole-6-yl]acetic acid,
(e) 2-[1-(2,6-dimethylbenzyl)-2,3-dihydro-1H-indole-6-yl]acetic acid,
(f) (3-RS)-2-[1-(2,6-dimethylbenzyl)-2,3-dihydro-3-methyl-1H-indole-6-yl]acetic acid,
(g) 2-[1-(2,6-dimethylbenzyl)-2,3-dihydro-3,3-dimethyl-1H-indole-6-yl]acetic acid,
(h) 2-[1-(2,6-dichlorobenzyl)-3-methyl-1H-indole-6-yl]acetic acid,
(i) 2-[1-(2,6-dichlorobenzyl)-3-methyl-1H-indazole-6-yl]acetic acid,
(j) 2-[1-(2-chloro-6-methylbenzyl)-3-methyl-1H-indazole-6-yl]acetic acid,
(m) 2-[1-(2,6-dichlorobenzyl)-3-ethyl-1H-indazole-6-yl]acetic acid, or
(s) [1-(2,6-dichlorobenzyl)-3-methyl-1H-indazole-6-yl]difluoroacetic acid.

3. A compound, which is
2-[1-(2,6-dimethylbenzyl)-3-methyl-1H-indole-6-yl]acetic acid, or a pharmaceutically acceptable salt or ester of the compound.

4. A compound, which is
2-[1-(2,6-dimethylbenzyl)-3-methyl-1H-indazole-6-yl]acetic acid, or a pharmaceutically acceptable salt or ester of the compound.

5. A compound, which is
2-[3-chloro-1-(2,6-dimethylbenzyl)-1H-indole-6-yl]acetic acid, or a pharmaceutically acceptable salt or ester of the compound.

6. A compound, which is
2-[1-(2,6-dimethylbenzyl)-2,3-dihydro-1H-indole-6-yl]acetic acid, or a pharmaceutically acceptable salt or ester of the compound.

7. A compound, which is
(3-RS)-2-[1-(2,6-dimethylbenzyl)-2,3-dihydro-3-methyl-1H-indole-6-yl]acetic acid, or a pharmaceutically acceptable salt or ester of the compound.

8. A compound, which is
2-[1-(2,6-dimethylbenzyl)-2,3-dihydro-3,3-dimethyl-1H-indole-6-yl]acetic acid, or a pharmaceutically acceptable salt or ester of the compound.

9. A compound, which is 2-[1-(2,6-dichlorobenzyl)-3-methyl-1H-indole-6-yl]acetic acid, or a pharmaceutically acceptable salt or ester of the compound.

10. A compound, which is 2-[1-(2,6-dichlorobenzyl)-3-methyl-1H-indazole-6-yl]acetic acid, or a pharmaceutically acceptable salt or ester of the compound.

11. A compound, which is 2-[1-(2-chloro-6-methylbenzyl)-3-methyl-1H-indazole-6-yl]acetic acid, or a pharmaceutically acceptable salt or ester of the compound.

12. A compound, which is 2-[1-(2,6-dichlorobenzyl)-3-ethyl-1H-indazole-6-yl]acetic acid, or a pharmaceutically acceptable salt or ester of the compound.

13. A compound, which is [1-(2,6-dichlorobenzyl)-3-methyl-1H-indazole-6-yl]difluoroacetic acid, or a pharmaceutically acceptable salt or ester of the compound.

14. A URAT1 inhibitor comprising the compound according to any one of claims 1, 6, 7, 8 and 13 or a pharmaceutically acceptable salt or ester of the compound.

15. An agent for reducing a uric acid level in blood, wherein the agent comprises the compound according to any one of claims 1, 6, 7, 8 and 13 or a pharmaceutically acceptable salt or ester of the compound.

16. A pharmaceutical composition comprising the compound according to any one of claims 1, 6, 7, 8 and 13 or a pharmaceutically acceptable salt or ester of the compound and a pharmaceutically acceptable carrier.

17. A compound represented by the following formula:

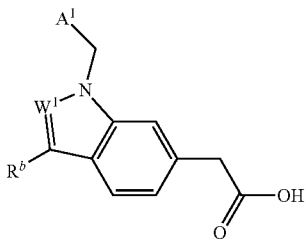

wherein $A^1$ represents an aryl group or a heteroaryl group, which is substituted with one to three substituents selected from the <Substituent group L> (herein any two substituents adjacent to each other on the aryl group or the heteroaryl group may join together to form a lower alkylenedioxy group.);

$W^1$ represents —CH= or a nitrogen atom; and $R^b$ represents a lower alkyl group, a cycloalkyl group, a halogen atom or a cyano group;

<Substituent group L>:

a halogen atom, a cyano group, a lower alkyl group, a halo-lower alkyl group, a cycloalkyl group, a lower alkoxy group, and an aryloxy group;

or a pharmaceutically acceptable salt or ester of the compound.

18. A compound represented by the following formula:

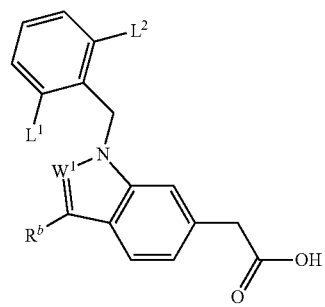

wherein $W^1$ represents —CH= or a nitrogen atom;

$R^b$ represents a lower alkyl group, a cycloalkyl group, a halogen atom or a cyano group; and $L^1$ and $L^2$ represent each independently a halogen atom, a cyano group, a lower alkyl group, a halo-lower alkyl group, a cycloalkyl group, a lower alkoxy group, or an aryloxy group;

or a pharmaceutically acceptable salt or ester of the compound.

* * * * *